(12) United States Patent
Kobayashi et al.

(10) Patent No.: US 8,580,147 B2
(45) Date of Patent: *Nov. 12, 2013

(54) LIQUID CRYSTAL COMPOUND, LIQUID CRYSTAL COMPOSITION AND LIQUID CRYSTAL DISPLAY DEVICE

(75) Inventors: Masahide Kobayashi, Chiba (JP); Junichi Yamashita, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/496,201

(22) PCT Filed: Sep. 2, 2010

(86) PCT No.: PCT/JP2010/065017
§ 371 (c)(1), (2), (4) Date: Mar. 14, 2012

(87) PCT Pub. No.: WO2011/033937
PCT Pub. Date: Mar. 24, 2011

(65) Prior Publication Data
US 2012/0168677 A1 Jul. 5, 2012

(30) Foreign Application Priority Data
Sep. 18, 2009 (JP) .................. 2009-216759

(51) Int. Cl.
C09K 19/12 (2006.01)
C09K 19/52 (2006.01)
C09K 19/06 (2006.01)
C09K 19/30 (2006.01)
C09K 19/00 (2006.01)

(52) U.S. Cl.
USPC .............. 252/299.66; 252/299.01; 252/299.6; 252/299.63; 428/1.1; 349/182

(58) Field of Classification Search
USPC ............... 252/299.01, 299.6, 299.63, 299.66; 428/1.1; 349/182
See application file for complete search history.

(56) References Cited

U.S. PATENT DOCUMENTS 8,501,038 B2 * 8/2013 Kobayashi ............... 252/299.66
2012/0018672 A1 * 1/2012 Kobayashi ............... 252/299.61

FOREIGN PATENT DOCUMENTS

| EP | 1346995 | 9/2003 |
| JP | 2002-193853 | 7/2002 |
| WO | 89/02425 | 3/1989 |
| WO | 89/08633 | 9/1989 |
| WO | 91/10936 | 7/1991 |
| WO | 98/23564 | 6/1998 |
| WO | 2010/082558 | 7/2010 |

* cited by examiner

*Primary Examiner* — Geraldina Visconti
(74) *Attorney, Agent, or Firm* — Jianq Chyun IP Office

(57) ABSTRACT

A liquid crystal compound represented by formula (1-1).

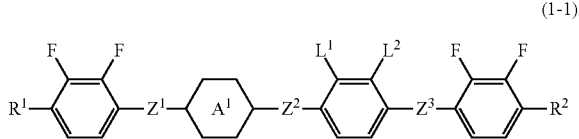

(1-1)

For example, $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^1$ is trans-1,4-cyclohexylene, 1,4-cyclohexenylene, 1,3-dioxane-2,5-diyl, pyrimidine-2,5-diyl or pyridine-2,5-diyl; $L^1$ and $L^2$ are independently hydrogen or fluorine, and at least one of them is fluorine; and $Z^1$, $Z^2$ and $Z^3$ are independently a single bond, —(CH$_2$)$_2$—, —CH═CH—, —C≡C—, —CH$_2$O—, —OCH$_2$—, —COO— or —OCO—.

20 Claims, No Drawings

LIQUID CRYSTAL COMPOUND, LIQUID CRYSTAL COMPOSITION AND LIQUID CRYSTAL DISPLAY DEVICE

CROSS-REFERENCE TO RELATED APPLICATION

This application is a 371 of international application of PCT application serial no. PCT/JP2010/065017, filed on Sep. 2, 2010, which claims the priority benefit of Japan application no. 2009-216759, filed on Sep. 18, 2009. The entirety of each of the above-mentioned patent applications is hereby incorporated by reference herein and made a part of this specification.

FIELD OF THE INVENTION

The invention relates to a liquid crystal compound, a liquid crystal composition and a liquid crystal display device. More specifically, the invention relates to a fluorobenzene derivative having fluorine at a lateral position, which is liquid crystalline, a liquid crystal composition including this compound and having a nematic phase, and a liquid crystal display device containing this composition.

DESCRIPTION OF RELATED ART

A liquid crystal display device typified by a liquid crystal display panel, a liquid crystal display module and so forth utilizes optical anisotropy, dielectric anisotropy and so forth, which are possessed by a liquid crystal compound (in this invention the term is used as a generic term for a compound having a liquid crystal phase such as a nematic phase or a smectic phase, and a compound having no liquid crystal phases but useful as a component of a liquid crystal composition). A variety of operating modes of this liquid crystal display device are known, such as a PC (phase change) mode, a TN (twisted nematic) mode, a STN (super twisted nematic) mode, a BTN (bistable twisted nematic) mode, a ECB (electrically controlled birefringence) mode, a OCB (optically compensated bend) mode, a IPS (in-plane switching) mode, a VA (vertical alignment) mode and a PSA (polymer sustained alignment).

In the operating mode, the ECB mode, the IPS mode, the VA mode and so forth utilize homeotropic orientation of liquid crystal molecules, and it is known that in particular the IPS mode and the VA mode are able to improve a limited viewing angle that is a disadvantage of a conventional display mode such as the TN mode or the STN mode.

A variety of liquid crystal compounds in which hydrogen on the benzene ring had been replaced by fluorine have conventionally been studied as a component of a liquid crystal composition having negative dielectric anisotropy, which can be used for liquid crystal display devices having these operating modes.

For example, the compounds (A) and (B), in which hydrogen on the benzene ring had been replaced by fluorine, were studied (see patent documents Nos. 1 and 2). However, these compounds did not have such a large negative dielectric anisotropy that satisfied market demand.

The compound (C) having fluorine-substituted benzene was also studied (see patent document No. 3). However, this compound did not have such a large negative dielectric anisotropy that satisfied market demand.

The quaterphenyl compound (D) having two fluorine-substituted benzenes was also studied (see patent document No. 4). However, this compound had a quite high melting point and a poor compatibility. The compound did not have such a large negative dielectric anisotropy that satisfied market demand.

The compound (E) having an ethylene bonding group and three fluorine-substituted benzene was also studied (see patent document No. 5). However, this compound (E) had a high melting point and a poor compatibility. The compound did not have such a large negative dielectric anisotropy that satisfied market demand.

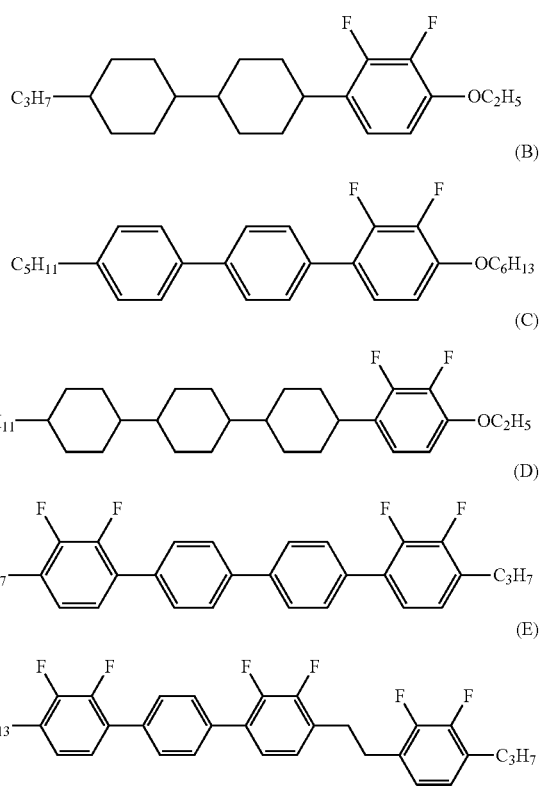

PRIOR ART

Patent Document

Patent document No. 1: JP H02-503441 A (1990).
Patent document No. 2: WO 1989-002425 A.
Patent document No. 3: JP 2002-193853 A.
Patent document No. 4: EP 1,346,995 A (2003).
Patent document No. 5: WO 1998-023564 A.

SUMMARY OF THE INVENTION

Means for Solving the Subject

In view of the circumstances described above, there are still subjects to be solved even in a liquid crystal display device having an operating mode such as an IPS mode or a VA mode in comparison with CRTs as a display device, and, for example, an improvement of the response speed, an improvement of the contrast and a decrease in the driving voltage are expected.

A display device operated in the IPS mode or the VA mode described above mainly contains a liquid crystal composition having negative dielectric anisotropy, and a liquid crystal compound included in this liquid crystal composition is required to have the following characteristics shown in items (1) to (8), in order to improve the characteristics of the display device. That is to say:

(1) being chemically stable and physically stable,
(2) having a high clearing point (transition temperature between a liquid crystal phase and an isotropic phase),
(3) having a low minimum temperature of a liquid crystal phase (a nematic phase, a smectic phase and so forth), especially of a nematic phase,
(4) having a small viscosity,
(5) having a suitable optical anisotropy,
(6) having a large negative dielectric anisotropy,
(7) having a suitable elastic constant $K_{33}$ ($K_{33}$: a bend elastic constant), and
(8) having an excellent compatibility with other liquid crystal compounds.

A voltage holding ratio can be increased when a composition including a chemically and physically stable liquid crystal compound, as described in item (1), is used for a display device.

The temperature range of a nematic phase can be increased in a composition that includes a liquid crystal compound having a high clearing point or a low minimum temperature of a liquid crystal phase as described in items (2) and (3), and thus the display device can be used in a wide temperature range.

When a composition that includes a compound having a small viscosity as described in item (4) and a compound having a large elastic constant $K_{33}$ as described in item (7) are used for a display device, the response speed can be improved. When a composition that includes a compound having a suitable optical anisotropy as described in item (5) is used for a display device, an improvement of the contrast in the display device can be expected. A device requires compositions having a small to large optical anisotropy, depending on the design of the device. Recently, a method for improving the response speed by means of a decreased cell thickness has been studied, whereby a liquid crystal composition having a large optical anisotropy is also required.

When a liquid crystal compound has a large negative dielectric anisotropy, the threshold voltage of the liquid crystal composition including this compound can be decreased. Hence, the driving voltage of a display device can be decreased and the electric power consumption can also be decreased, when the display device contains a composition that includes a compound having a large negative dielectric anisotropy as described in item (6). The driving voltage of a display device can be decreased and thus the electric power consumption can also be decreased, when a display device contains a composition that includes a compound having a small elastic constant $K_{33}$ as described in item (7).

A liquid crystal compound is generally used in the form of a composition prepared by mixing it with many other liquid crystal compounds in order to exhibit characteristics that are difficult to be attained by a single compound. Accordingly, it is desirable that a liquid crystal compound used for a display device has an excellent compatibility with other liquid crystal compounds and so forth, as described in item (8). Since the display device may also be used in a wide temperature range including a lower temperature than the freezing point, the compound that exhibits an excellent compatibility even at a low temperature may be desirable.

The first aim of the invention is to provide a liquid crystal compound having the stability to heat, light or the like, a wide temperature range of a nematic phase, a small viscosity, a large optical anisotropy and a suitable elastic constant $K_{33}$, and further having a large negative dielectric anisotropy and an excellent compatibility with other liquid crystal compounds.

The second aim of the invention is to provide a liquid crystal composition having the stability to heat, light and so forth, a small viscosity, a large optical anisotropy, a large negative dielectric anisotropy, a suitable elastic constant $K_{33}$ and a low threshold voltage, and further having a high maximum temperature of a nematic phase (the phase transition temperature between a nematic phase and an isotropic phase) and a low minimum temperature of a nematic phase by the inclusion of the compound.

The third aim of the invention is to provide a liquid crystal display device containing the composition described above and having a short response time, low electric power consumption, a low driving voltage, a large contrast and a wide temperature range in which the device can be used.

Means for Solving the Subject

As a result of earnest studies on these subjects, the inventors have found that in a specific structure including phenylene in which hydrogen on a benzene ring has been replaced by fluorine, a four-ring liquid crystal compound having three fluorine-substituted benzene at each end has the stability to heat, light or the like, a wide temperature range of a nematic phase, a small viscosity, a large optical anisotropy and a suitable elastic constant $K_{33}$, and further has a large negative dielectric anisotropy and an excellent compatibility with other liquid crystal compounds. The inventors have also found that a liquid crystal composition that includes the compound has the stability to heat, light or the like, a small viscosity, a large optical anisotropy, a suitable elastic constant $K_{33}$, a suitable and large dielectric anisotropy and a low threshold voltage, and further has a high maximum temperature of a nematic phase and a low minimum temperature of a nematic phase. The inventors have further found that a liquid crystal display device that contains the composition has a short response time, low electric power consumption, a low driving voltage, a large contrast ratio and a wide temperature range in which the device can be used. Thus, the inventors have completed the invention.

That is to say, the invention includes the contents described in the following items 1 to 20.

Item 1. A compound represented by formula (1-1).

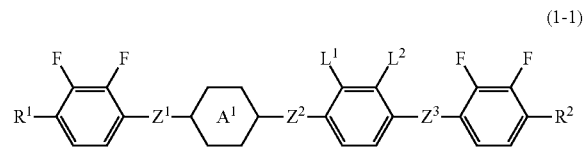

(1-1)

In formula (1-1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^1$ is trans-1,4-cyclohexylene, 1,4-cyclohexenylene, 1,3-dioxane-2,5-diyl, pyrimidine-2,5-diyl or pyridine-2,5-diyl;

$L^1$ and $L^2$ are independently hydrogen or fluorine, and at least one of them is fluorine; and $Z^1$, $Z^2$ and $Z^3$ are independently a single bond, —$(CH_2)_2$—, —CH=CH—, —C≡C—, —$CH_2O$—, —$OCH_2$—, —COO— or —OCO—.

Item 2. The compound according to item 1, wherein the compound is represented by formula (1-2).

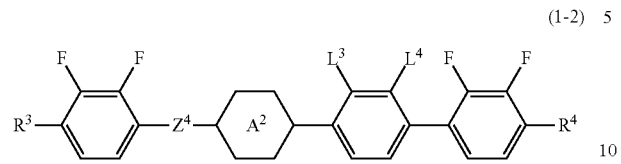
(1-2)

In formula (1-2), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^2$ is trans-1,4-cyclohexylene or 1,4-cyclohexenylene;

$L^3$ and $L^4$ are independently hydrogen or fluorine, and at least one of them is fluorine; and $Z^4$ is a single bond, —(CH$_2$)$_2$—, —CH=CH—, —C≡C—, —CH$_2$O—, —OCH$_2$—, —COO— or —OCO—.

Item 3. The compound according to item 1, wherein the compound is represented by formula (1-3).

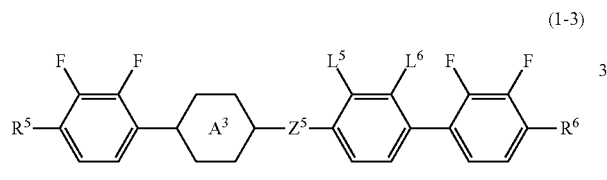
(1-3)

In formula (1-3), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^3$ is trans-1,4-cyclohexylene or 1,4-cyclohexenylene;

$L^5$ and $L^6$ are independently hydrogen or fluorine, and at least one of them is fluorine; and $Z^5$ is —(CH$_2$)$_2$—, —CH=CH—, —C≡C—, —CH$_2$O—, —OCH$_2$—, —COO— or —OCO—.

Item 4. The compound according to item 1, wherein the compound is represented by formula (1-4).

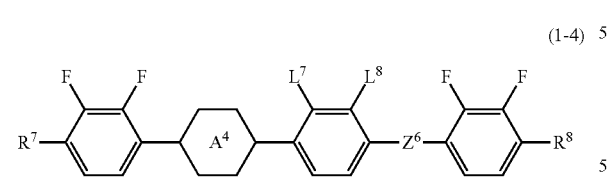
(1-4)

In formula (1-4), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^4$ is trans-1,4-cyclohexylene or 1,4-cyclohexenylene;

$L^7$ and $L^8$ are independently hydrogen or fluorine, and at least one of them is fluorine; and $Z^6$ is —(CH$_2$)$_2$—, —CH=CH—, —C≡C—, —CH$_2$O—, —OCH$_2$—, —COO— or —OCO—.

Item 5. The compound according to item 2, wherein the compound is represented by any one of formulas (1-5) and (1-6).

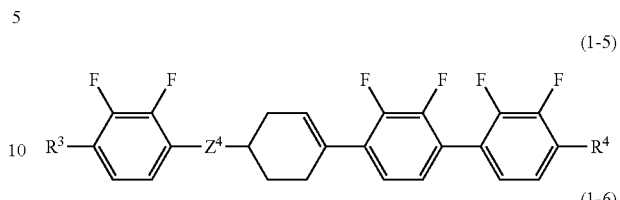
(1-5)

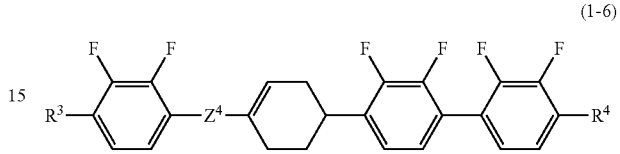
(1-6)

In formulas (1-5) and (1-6), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, —(CH$_2$)$_2$—, —CH$_2$O—, —OCH$_2$—, —COO— or —OCO—.

Item 6. The compound according to item 3, wherein the compound is represented by formula (1-7).

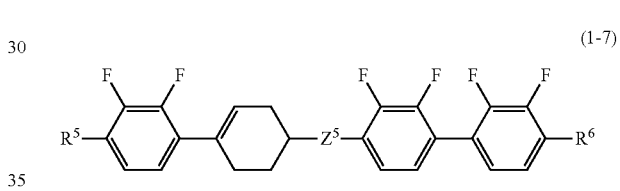
(1-7)

In formula (1-7), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is —(CH$_2$)$_2$—, —CH$_2$O—, —OCH$_2$—, —COO— or —OCO—.

Item 7. The compound according to item 4, wherein the compound is represented by any one of formulas (1-8) and (1-9).

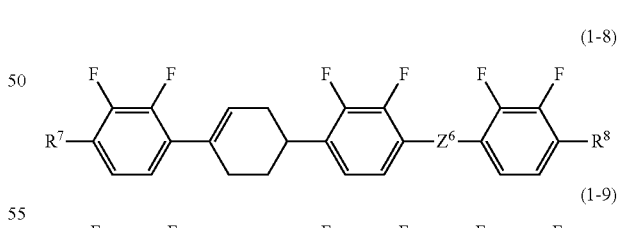
(1-8)

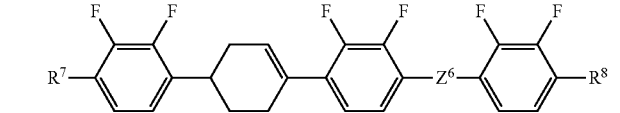
(1-9)

In formulas (1-8) and (1-9), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is —(CH$_2$)$_2$—, —CH$_2$O—, —OCH$_2$—, —COO— or —OCO—.

Item 8. The compound according to item 2, wherein the compound is represented by formula (1-10).

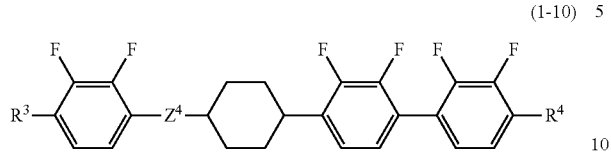
(1-10)

In formula (1-10), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, —$(CH_2)_2$—, —$CH_2O$—, —$OCH_2$—, —COO— or —OCO—.

Item 9. The compound according to item 3, wherein the compound is represented by formula (1-11).

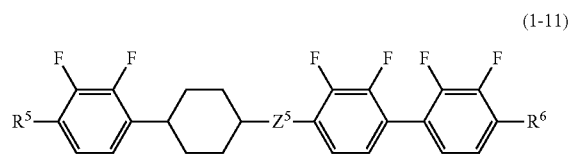
(1-11)

In formula (1-11), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is —$(CH_2)_2$—, —$CH_2O$—, —$OCH_2$—, —COO— or —OCO—.

Item 10. The compound according to item 4, wherein the compound is represented by formula (1-12).

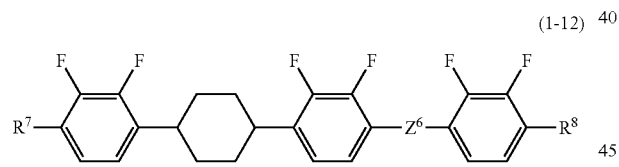
(1-12)

In formula (1-12), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is —$(CH_2)_2$—, —$CH_2O$—, —$OCH_2$—, —COO— or —OCO—.

Item 11. A liquid crystal composition including a compound according to any one of items 1 to 10.

Item 12. The liquid crystal composition according to item 11, further including at least one compound selected from the group of compounds represented by formulas (2), (3) and (4).

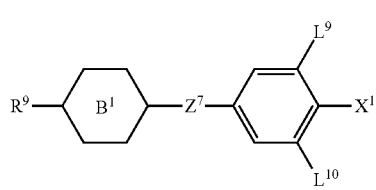
(2)

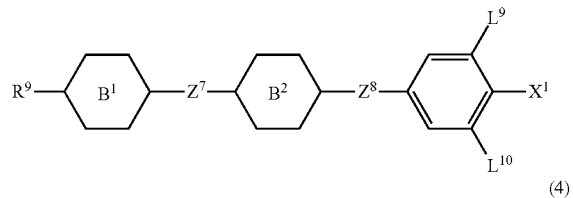
(3)

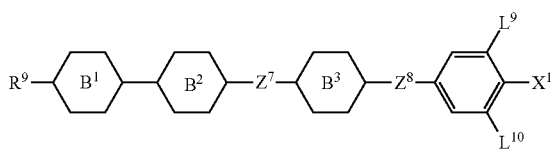
(4)

In formulas (2) to (4), $R^9$ is independently alkyl having 1 to 10 carbons or alkenyl having 2 to 10 carbons, and in the alkyl and the alkenyl, arbitrary hydrogen may be replaced by fluorine, and arbitrary —$CH_2$— may be replaced by —O—;

$X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

the ring $B^1$, the ring $B^2$ and the ring $B^3$ are independently 1,4-cyclohexylene, 1,3-dioxane-2,5-diyl, pyrimidine-2,5-diyl, 1-pyran-2,5-diyl, 1,4-phenylene, 2-fluoro-1,4-phenylene, 3-fluoro-1,4-phenylene or 3,5-difluoro-1,4-phenylene;

$Z^7$ and $Z^8$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^9$ and $L^{10}$ are independently hydrogen or fluorine.

Item 13. The liquid crystal composition according to item 11, further including at least one compound selected from the group of compounds represented by formula (5).

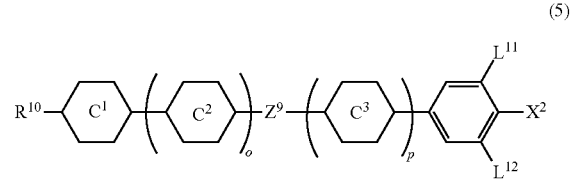
(5)

In formula (5), $R^{10}$ is alkyl having 1 to 10 carbons or alkenyl having 2 to 10 carbons, and in the alkyl and the alkenyl, arbitrary hydrogen may be replaced by fluorine, and arbitrary —$CH_2$— may be replaced by —O—;

$X^2$ is —C≡N or —C≡C—C≡N;

the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

$Z^9$ is —$(CH_2)_2$—, —COO—, —$CF_2O$—, —$OCF_2$—, —C≡C—, —$CH_2O$— or a single bond;

$L^{11}$ and $L^{12}$ are independently hydrogen or fluorine; and o is 0, 1 or 2, p is 0 or 1, and the sum of o and p is 0, 1, 2 or 3.

Item 14. The liquid crystal composition according to item 11, further including at least one compound selected from the group of compounds represented by formulas (6), (7), (8), (9), (10) and (11).

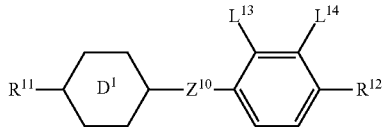 (6)

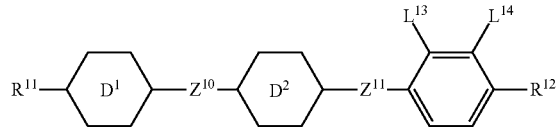 (7)

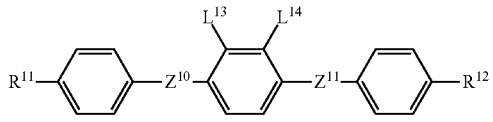 (8)

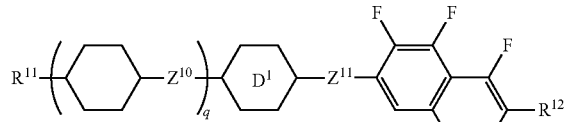 (9)

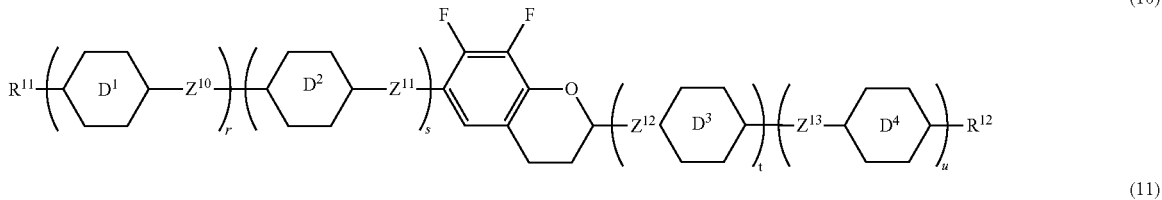 (10)

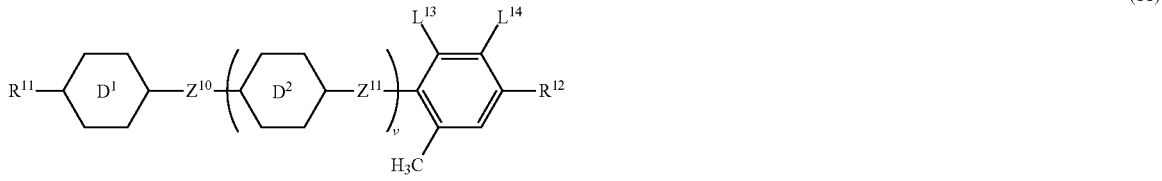 (11)

In formulas (6) to (11), $R^{11}$ and $R^{12}$ are independently alkyl having 1 to 10 carbons or alkenyl having 2 to 10 carbons, and in the alkyl and the alkenyl, arbitrary hydrogen may be replaced by fluorine, and arbitrary —$CH_2$— may be replaced by —O—;

the ring $D^1$, the ring $D^2$, the ring $D^3$ and the ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene;

$Z^{10}$, $Z^{11}$, $Z^{12}$ and $Z^{13}$ are independently —$(CH_2)_2$—, —COO—, —$CH_2O$—, —$OCF_2$—, —$OCF_2(CH_2)_2$— or a single bond;

$L^{13}$ and $L^{14}$ are independently fluorine or chlorine; and q, r, s, t, u and v are independently 0 or 1, and the sum of r, s, t and u is 1 or 2.

Item 15. The liquid crystal composition according to item 11, further including at least one compound selected from the group of compounds represented by formulas (12), (13) and (14).

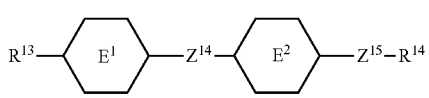 (12)

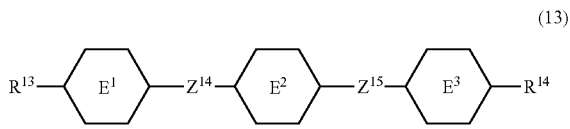 (13)

-continued

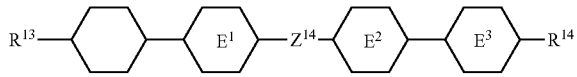 (14)

In formulas (12) to (14), $R^{13}$ and $R^{14}$ are independently alkyl having 1 to 10 carbons or alkenyl having 2 to 10 carbons, and in the alkyl and the alkenyl, arbitrary —$CH_2$— may be replaced by —O—;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —COO—, —$(CH_2)_2$—, —CH═CH— or a single bond.

Item 16. The liquid crystal composition according to item 12, further including at least one compound selected from the group of compounds represented by formula (5).

Item 17. The liquid crystal composition according to item 14, further including at least one compound selected from the group of compounds represented by formulas (12), (13) and (14).

Item 18. The liquid crystal composition according to any one of items 11 to 17, further including at least one optically active compound and/or at least one polymerizable compound.

Item 19. The liquid crystal composition according to any one of items 11 to 18, further including at least one antioxidant and/or at least one ultraviolet light absorber.

Item 20. A liquid crystal display device containing the liquid crystal composition according to any one of items 11 to 19.

Usage of the terms in this specification is as follows. A liquid crystal compound is a generic term for a compound having a liquid crystal phase such as a nematic phase or a smectic phase, and for a compound having no liquid crystal phases but useful as a component for a liquid crystal composition. The terms, a liquid crystal compound, a liquid crystal composition and a liquid crystal display device may be abbreviated to a compound, a composition and a device, respectively. A liquid crystal display device is a generic term for a liquid crystal display panel and a liquid crystal display module. The maximum temperature of a nematic phase is the phase transition temperature between a nematic phase and an isotropic phase, and may simply be abbreviated to a clearing point or the maximum temperature. The minimum temperature of the nematic phase may simply be abbreviated to the minimum temperature. The compound represented by formula (1) may be abbreviated to the compound (1). This abbreviation may apply to a compound represented by formula (2) and so forth. In formula (1) to formula (13), the symbols $B^1$, $D^1$, $E^1$ or the like surrounded by a hexagonal shape correspond to the ring $B^1$, the ring $D^1$, the ring $E^1$ or the like, respectively. The amount of a compound that is expressed as a percentage means a weight percentage (% by weight) based on the total weight of the composition. A plurality of symbols such as the ring $B^1$, $X^1$, the ring $C^2$ or the like were used in the same or different formulas, where these symbols may mean the same or different.

"Arbitrary" is used not only in cases where the position is arbitrary but also in cases where the number is arbitrary. However, it is not used in cases where the number is 0 (zero). The expression "arbitrary A may be replaced by B, C or D" includes cases where arbitrary A has been replaced by B, and arbitrary A has been replaced by C, and arbitrary A has been replaced by D, and also cases where a plurality of A have been replaced by at least two of B, C and/or D. For example, the expression "alkyl in which arbitrary —$CH_2$— may be replaced by —O— or —CH=CH—" includes alkyl, alkenyl, alkoxy, alkoxyalkyl, alkoxyalkenyl and alkenyloxyalkyl. Incidentally, it is undesirable in the invention that two successive —$CH_2$— are replaced by —O— to give —O—O—. It is also undesirable that terminal —$CH_2$— in alkyl has been replaced by —O—. The invention will be further explained below.

Effect of the Invention

The liquid crystal compound of the invention has the stability to heat, light or the like, a wide temperature range of a nematic phase, a small viscosity, a large optical anisotropy and a suitable elastic constant $K_{33}$ ($K_{33}$: a bend elastic constant), and further has a large negative dielectric anisotropy and an excellent compatibility with other liquid crystal compounds. The liquid crystal compound of the invention is a quite excellent in view of the fact that the maximum temperature of a nematic phase has a tendency not to decrease, and moreover the optical anisotropy has a tendency to increase without an increase in the viscosity.

The liquid crystal composition of the invention has a small viscosity, a large optical anisotropy, a suitable elastic constant $K_{33}$, a large negative dielectric anisotropy and a low threshold voltage, and further has a high maximum temperature of a nematic phase and a low minimum temperature of a nematic phase. In particular, the liquid crystal composition of the invention is effective in a device that requires a large optical anisotropy, since it has a large optical anisotropy.

The liquid crystal display device of the invention is characterized by containing this liquid crystal composition, and has a short response time, low electric power consumption, a small driving voltage, a large contrast ratio, a wide temperature range in which the device can be used. Thus, the liquid crystal display device can be used preferably for a display mode such as a PC mode, a TN mode, a STN mode, an ECB mode, an OCB mode, an IPS mode, a VA mode or a PSA mode. It can be suitably used especially for a liquid crystal display device having the IPS mode, the VA mode or the PSA mode.

DESCRIPTION OF THE EMBODIMENTS

The invention will be explained in more detail below.
Incidentally, in the following description, the amount of a compound that is expressed in a percentage means the weight percentage (% by weight) based on the total weight of the composition unless otherwise noted.
The Compound (1-1)
The liquid crystal compound of the invention has a structure represented by formula (1-1). Hereinafter the compound may be referred to as "the compound (1-1)."

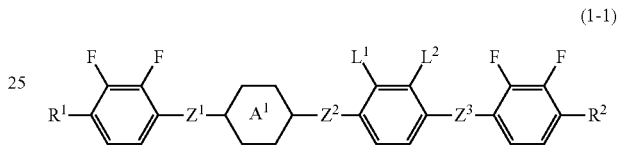

(1-1)

In formula (1-1), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

The ring $A^1$ is trans-1,4-cyclohexylene, 1,4-cyclohexenylene, 1,3-dioxane-2,5-diyl, pyrimidine-2,5-diyl or pyridine-2,5-diyl.

Incidentally, in this specification, the distinction of the compound structures according to the position of a double bond in 1,4-cyclohexenylene. Thus, the following two compound structures are allowable in the notation of 1,4-cyclohexenylene.

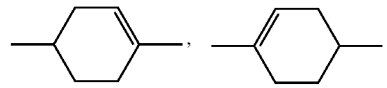

This rule applies to 1,3-dioxane-2,5-diyl and so forth.
$L^1$ and $L^2$ are independently hydrogen or fluorine, and at least one of them is fluorine; and $Z^1$, $Z^2$ and $Z^3$ are independently a single bond, —$(CH_2)_2$—, —CH=CH—, —C≡C—, —$CH_2$O—, —O$CH_2$—, —COO— or —OCO—.

The compound (1-1) has three 1,4-phenylene in which hydrogen at the 2- or 3-positions has been replaced by fluorine. The compound has a small viscosity, a suitable optical anisotropy, a suitable elastic constant $K_{33}$, a large negative dielectric anisotropy and an excellent compatibility with other liquid crystal compounds by having such a structure. It is particularly excellent in view of a large negative dielectric anisotropy without a decrease in the maximum temperature of a nematic phase and also without an increase in the viscosity.

In the formula, $R^1$ and $R^2$ are hydrogen, alkyl having 1 to 10 carbons or alkenyl having 2 to 10 carbons, alkoxy having 1 to 9 carbons, alkoxyalkyl having 2 to 9 carbons or alkenyloxy having 2 to 9 carbons, which are, for example, $CH_3(CH_2)_3$—, —$CH_2$—, $CH_3(CH_2)_2O$—, $CH_3$—O—$(CH_2)_2$—, $CH_3$—O—$CH_2$—O—, $H_2C$=CH—$(CH_2)_2$—, $CH_3$—CH=CH—$CH_2$— or $CH_3$—CH=CH—O—.

However, a group having adjacent oxygens, such as $CH_3$—O—O—$CH_2$—, or a group having adjacent double bond moieties, such as $CH_3$—CH=CH—CH=CH—, are undesirable in consideration of the stability of the compound.

It is desirable that the chain of carbon-carbon bonds in these groups is straight. When the chain of carbon-carbon bonds is straight, the temperature ranges of a liquid crystal phase can be increased and the viscosity can be decreased. When one of $R^1$ and $R^2$ is an optically active group, the compound is useful as a chiral dopant, and a reverse twisted domain which will occur in a liquid crystal display device can be prevented by the addition of the compound to a liquid crystal composition.

Desirable $R^1$ and $R^2$ are alkyl, alkoxy, alkoxyalkyl and alkenyl, and more desirable $R^1$ and $R^2$ are alkyl, alkoxy or alkenyl.

When $R^1$ and $R^2$ are alkyl, alkoxy or alkenyl, the temperature range of a liquid crystal phase in the liquid crystal compound can be increased.

A desirable configuration of —CH=CH— in the alkenyl depends on the position of the double bond.

A trans-configuration is desirable for the configuration of alkenyl having a double bond in the odd position, such as —CH=$CHCH_3$, —CH=$CHC_2H_5$, —CH=$CHC_3H_7$, —CH=$CHC_4H_9$, —$C_2H_4$—CH=$CHCH_3$ or —$C_2H_4$CH=$CHC_2H_5$.

On the other hand, a cis-configuration is desirable for the configuration of alkenyl having a double bond in the even position, such as —$CH_2$CH=$CHCH_3$, —$CH_2$CH=$CHC_2H_5$ or —$CH_2$CH=$CHC_3H_7$. An alkenyl compound possessing a desirable configuration described above has a wide temperature range of a liquid crystal phase, a large elastic constant ratio $K_{33}/K_{11}$ ($K_{33}$: a bend elastic constant, $K_{11}$: a splay elastic constant), and a decreased viscosity. When this liquid crystal compound is added to a liquid crystal composition, the maximum temperature ($T_{NI}$) of a nematic phase can be increased.

Specific examples of the alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ or —$C_{10}H_{21}$;

specific examples of the alkoxy include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ or —$OC_9H_{19}$;

specific examples of the alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$ or —$(CH_2)_5OCH_3$;

specific examples of the alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$ or —$(CH_2)_3$CH=$CH_2$, and specific examples of the alkenyloxy include —$OCH_2$CH=$CH_2$, —$OCH_2$CH=$CHCH_3$ or —$OCH_2$CH=$CHC_2H_5$.

In the specific examples of $R^1$ and $R^2$, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —$CH_2$CH=$CH_2$, —$CH_2$CH=$CHCH_3$, —$(CH_2)_2$CH=$CH_2$, —$CH_2$CH=$CHC_2H_5$, —$(CH_2)_2$CH=$CHCH_3$, —$(CH_2)_3$CH=$CH_2$, —$(CH_2)_3$CH=$CHC_2H_5$, —$(CH_2)_3$CH=$CHC_3H_7$, —$OCH_2$CH=$CH_2$, —$OCH_2$CH=$CHCH_3$ or —$OCH_2$CH=$CHC_2H_5$ is desirable, and —$CH_3$, —$C_2H_5$, —$C_3H_7$, —$OCH_3$, —$OC_2H_5$, —$OC_3H_7$, —$OC_4H_9$, —$(CH_2)_2$CH=$CH_2$, —$(CH_2)_2$CH=$CHCH_3$ or $(CH_2)_2$CH=$CHC_3H_7$ is more desirable.

The ring $A^1$ is trans-1,4-cyclohexylene, 1,4-cyclohexenylene, 1,3-dioxane-2,5-diyl, pyrimidine-2,5-diyl or pyridine-2,5-diyl.

In these rings, 1,4-cyclohexenylene and trans-1,4-cyclohexylene are more desirable, and trans-1,4-cyclohexylene is most desirable.

In particular, when at least one of these rings is trans-1,4-cyclohexylene, the viscosity is decreased, and when the liquid crystal compound is added to a liquid crystal composition, the maximum temperature of a nematic phase ($T_{NI}$) is increased.

$L^1$ and $L^2$ are each independently hydrogen or fluorine, and at least one of them is fluorine.

It is desirable that one of $L^1$ and $L^2$ is fluorine, since the melting point of the compound is decreased.

It is most desirable that all of $L^1$ and $L^2$ are fluorine, since the dielectric anisotropy of the compound is increased negatively.

$Z^1$, $Z^2$ and $Z^3$ are a single bond, —$(CH_2)_2$—, —CH=CH—, —C≡C—, —$CH_2$O—, —$OCH_2$—, —COO— or —OCO—.

It is desirable that $Z^1$, $Z^2$ and $Z^3$ are a single bond, —$(CH_2)_2$— or —CH=CH—, since the viscosity of the compound is decreased. It is more desirable that $Z^1$, $Z^2$ and $Z^3$ are —COO— or —OCO—, since the maximum temperature of a nematic phase ($T_{NI}$) of the compound is increased. It is further desirable that $Z^1$, $Z^2$ and $Z^3$ are —$CH_2$O— or —$OCH_2$—, since the dielectric anisotropy of the compound is increased negatively.

A single bond, —$(CH_2)_2$—, —$CH_2$O— or $OCH_2$— is desirable, and a single bond and —$(CH_2)_2$— are more desirable in consideration of the stability of the compound. When one of $Z^1$, $Z^2$ and $Z^3$ is —$(CH_2)_2$—, —CH=CH—, —C≡C—, —$CH_2$O—, —$OCH_2$—, —COO— or —OCO—, it is desirable that the other is a single bond, and it is more desirable that all of $Z^1$, $Z^2$ and $Z^3$ are a single bond in consideration of an increase in the maximum temperature of a nematic phase in the compound.

A trans-configuration is desirable in the configuration of other groups attached to the double bond, when $Z^1$, $Z^2$ and $Z^3$ are —CH=CH—. The temperature range of a liquid crystal phase of the liquid crystal compound is increased by the effect of such configuration, and the maximum temperature of a nematic phase ($T_{NI}$) is increased by the addition of the liquid crystal compound to a liquid crystal composition.

The temperature range of a liquid crystal phase is increased, the elastic constant ratio $K_{33}/K_{11}$ ($K_{33}$: a bend elastic constant, $K_{11}$: a splay elastic constant) is increased, and the viscosity of the compound is decreased when —CH=CH— is included in $Z^1$ and $Z^2$, and the maximum temperature of a nematic phase ($T_{NI}$) is increased when the liquid crystal compound is added to a liquid crystal composition.

Incidentally, the compound (1-1) may also contain isotopes such as $^2H$ (deuterium) and $^{13}C$ in a larger amount than the amount of the natural abundance, since such isotopes do not make a major difference in physical properties of the compound.

In the compound (1-1), it is possible to adjust physical properties, such as dielectric anisotropy, to desired values by suitably selecting $R^1$, $R^2$, the ring $A^1$, $Z^1$, $Z^2$ and, $Z^3$, $L^1$ and $L^2$.

Examples of desirable compounds among compounds represented by the compound (1-1) include the compounds (1-2) to (1-12).

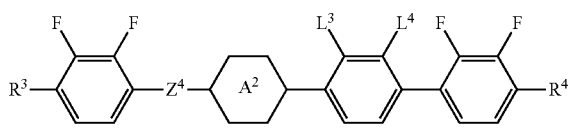
(1-2)

In formula (1-2), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^2$ is trans-1,4-cyclohexylene or 1,4-cyclohexenylene; $L^3$ and $L^4$ are independently hydrogen or fluorine, and at least one of them is fluorine; and $Z^4$ is a single bond, —$(CH_2)_2$—, —CH=CH—, —C≡C—, —$CH_2O$—, —$OCH_2$—, —COO— or —OCO—.

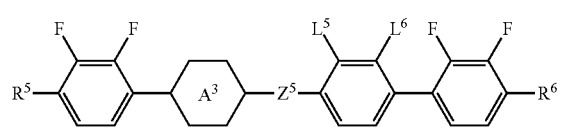
(1-3)

In formula (1-3), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^3$ is trans-1,4-cyclohexylene or 1,4-cyclohexenylene; $L^5$ and $L^6$ are independently hydrogen or fluorine, and at least one of them is fluorine; and $Z^5$ is —$(CH_2)_2$—, —CH=CH—, —$CH_2O$—, —$OCH_2$—, —COO— or —OCO—.

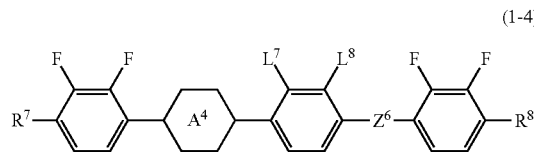
(1-4)

In formula (1-4), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^4$ is trans-1,4-cyclohexylene or 1,4-cyclohexenylene; $L^7$ and $L^8$ are independently hydrogen or fluorine, and at least one of them is fluorine; and $Z^6$ is —$(CH_2)_2$—, —CH=CH—, —$CH_2O$—, —$OCH_2$—, —COO— or —OCO—.

The compounds (1-2) to (1-4) are desirable in view of the stability to heat, light or the like, a lower minimum temperature of a liquid crystal phase, a higher maximum temperature of a nematic phase, a large optical anisotropy and a suitable elastic constant $K_{33}$ and a small viscosity. This is because they have three fluorine-substituted benzenes, and also a trans-1,4-cyclohexylene group or a 1,4-cyclohexenylene group, and have bonding groups asymmetrically in view of the structure of the whole compound.

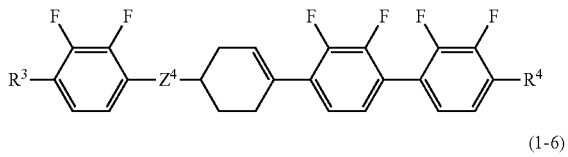
(1-5)

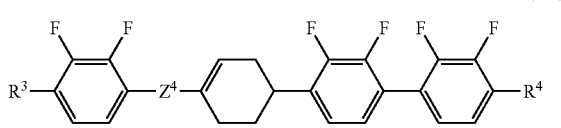
(1-6)

In formulas (1-5) and (1-6), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, —$(CH_2)_2$—, —$CH_2O$—, —$OCH_2$—, —COO— or —OCO—.

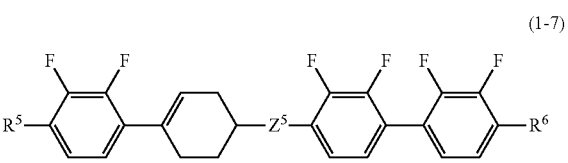
(1-7)

In formula (1-7), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is —$(CH_2)_2$—, —$CH_2O$—, —$OCH_2$—, —COO— or —OCO—.

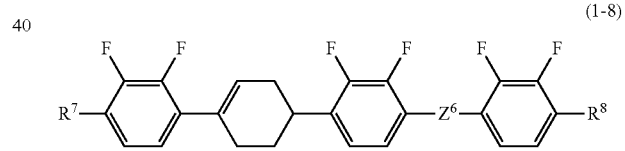
(1-8)

(1-9)

In formulas (1-8) and (1-9), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is —$(CH_2)_2$—, —$CH_2O$—, —$OCH_2$—, —COO— or —OCO—.

The compounds (1-8) and (1-9) are desirable in view of the stability to heat, light or the like, a lower minimum temperature of a liquid crystal phase, a higher maximum temperature of a nematic phase, a large optical anisotropy, a suitable elastic constant $K_{33}$ and a small viscosity. This is because they have three fluorine-substituted benzenes and also a 1,4-cyclohexenylene group, and have bonding groups asymmetrically in view of the structure of the whole compound.

(1-10)

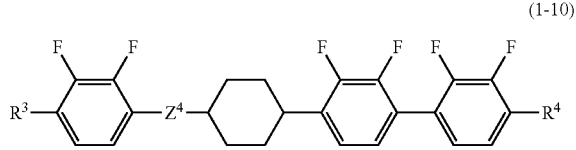

In formula (1-10), $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, —(CH$_2$)$_2$—, —CH$_2$O—, —OCH$_2$—, —COO— or —OCO—.

(1-11)

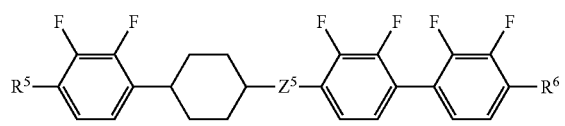

In formula (1-11), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is —(CH$_2$)$_2$—, —CH$_2$O—, —OCH$_2$—, —COO— or —OCO—.

(1-12)

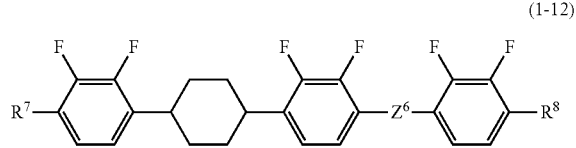

In formula (1-12), $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is —(CH$_2$)$_2$—, —CH$_2$O—, —OCH$_2$—, —COO— or —OCO—.

The compounds (1-11) and (1-12) are desirable in view of the stability to heat, light or the like, a lower minimum temperature of a liquid crystal phase, a higher maximum temperature of a nematic phase, a large optical anisotropy and a suitable elastic constant $K_{33}$ and a small viscosity. This is because they have three fluorine-substituted benzenes and also a trans-1,4-cyclohexylene group, and have bonding groups asymmetrically in view of the structure of the whole compound.

The compounds (1-2) to (1-12) have a large negative dielectric anisotropy, the stability to heat, light or the like, a wide temperature range of a nematic phase, a suitable optical anisotropy and a suitable elastic constant $K_{33}$. Among these, the compound where $Z^4$, $Z^5$ and $Z^6$ are —CH=CH— is desirable in view of a lower minimum temperature of a liquid crystal phase and a smaller viscosity nearly without a decrease in the maximum temperature of a nematic phase. The compound where $Z^4$, $Z^5$ and $Z^6$ are —COO— or —OCO— is more desirable in view of a high maximum temperature of a nematic phase. The compound where $Z^4$, $Z^5$ and $Z^6$ are —(CH$_2$)$_2$— is further desirable in view of a lower minimum temperature of a liquid crystal phase, a higher compatibility and a smaller viscosity. Further, the compound where $Z^4$, $Z^5$ and $Z^6$ are —CH$_2$O— or —OCH$_2$— is the most desirable in view of a larger negative dielectric anisotropy and a smaller viscosity.

When a liquid crystal compound has a structure shown by the compounds (1-2) to (1-12), it has a large negative dielectric anisotropy and an excellent compatibility with the other liquid crystal compounds. It also has the stability to heat, light or the like, a small viscosity, a large optical anisotropy and a suitable elastic constant $K_{33}$. A liquid crystal composition including the compound (1-1) is stable under conditions in which a liquid crystal display device is usually used, and this compound does not deposit its crystals (or its smectic phase) even when the composition is kept in storage at a low temperature.

Accordingly, the compound (1-1) can suitably utilized for a liquid crystal composition that is used for a liquid crystal display device having a display mode such as PC, TN, STN, ECB, OCB, IPS, VA or PSA, and utilized especially for a liquid crystal composition that is used for a liquid crystal display device having a display mode such as IPS, VA or PSA.

Preparation of the Compound (1-1)

The compound (1-1) can be synthesized by a suitable combination of techniques in synthetic organic chemistry. Methods of introducing objective terminal groups, rings and bonding groups into starting materials are described in books such as Organic Syntheses (John Wiley & Sons, Inc), Organic Reactions (John Wiley & Sons, Inc), Comprehensive Organic Synthesis (Pergamon Press) and New Experimental Chemistry Course (Shin Jikken Kagaku Kouza, in Japanese) (Maruzen Co., Ltd.).

Formation of the Bonding Group $Z^1$, $Z^2$ or $Z^3$

One example of methods for forming the bonding group $Z^1$, $Z^2$ or $Z^3$ is shown. Schemes for forming the bonding groups are illustrated as follows. In the schemes, MSG$^1$ or MSG$^2$ is a monovalent organic group. A plurality of the MSG$^1$ (or MSG$^2$) used in the schemes may mean the same or different. The compounds (1A) to (1E) correspond to the compound (1-1).

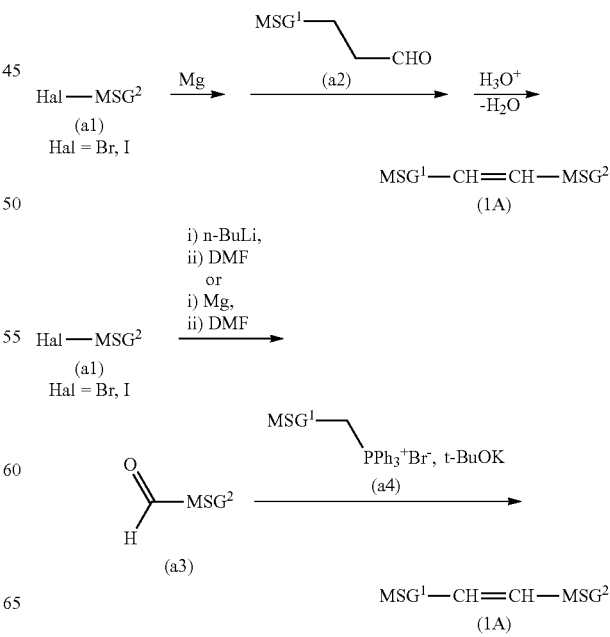

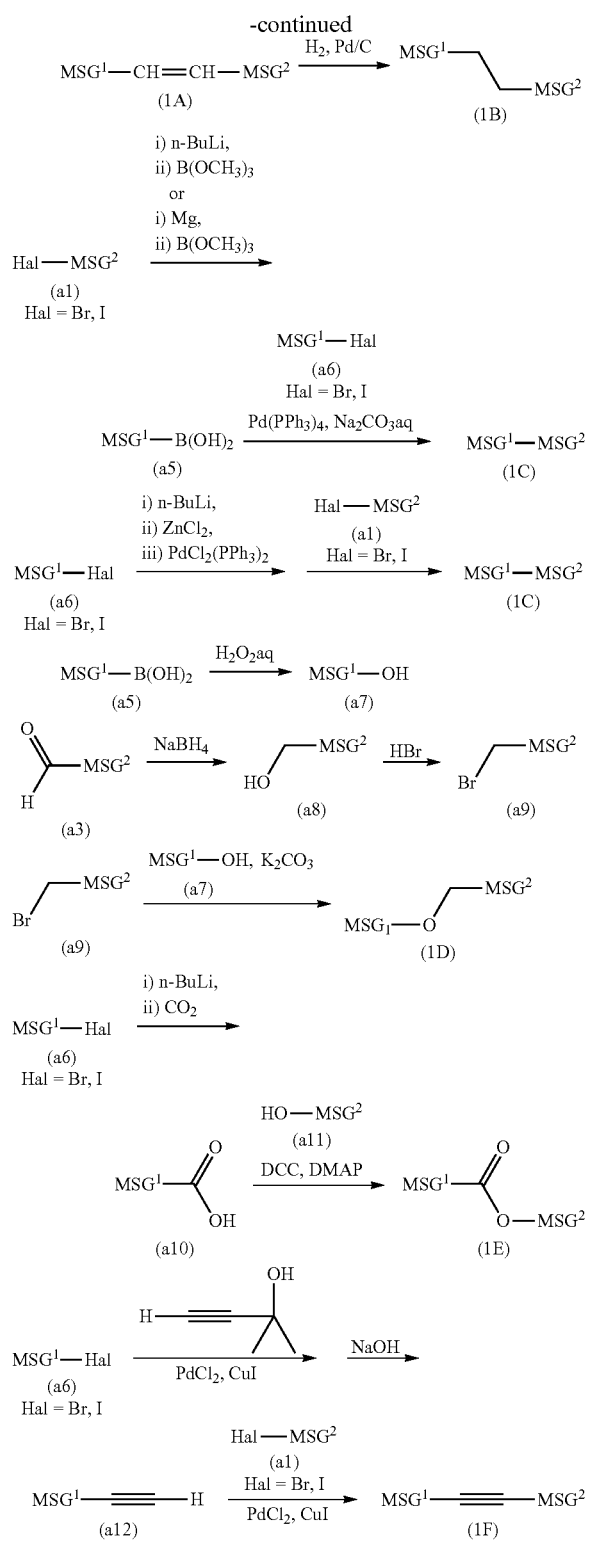

resulting alcohol derivative in the presence of an acid catalyst such as p-toluenesulfonic acid or the like.

The organohalogen compound (a1) is allowed to react with butyllithium or magnesium, and then with a formamide such as N,N-dimethylformamide (DMF) to give the aldehyde derivative (a3). Then, the compound (1A) having a corresponding double bond can be prepared by the reaction of the resulting the aldehyde (a3) with a phosphorus ylide prepared by the treatment of the phosphonium salt (a4) with a base such as potassium t-butoxide. Incidentally, the cis-isomer is isomerized to the trans-isomer by the known method when the trans-isomer is requested, since the cis-isomer may be formed in this reaction depending on the reaction conditions.

Formation of —$(CH_2)_2$—

The compound (1B) can be prepared by the hydrogenation of the compound (1A) in the presence of a catalyst such as palladium on carbon (Pd/C).

Formation of a Single Bond

A Grignard reagent or a lithium salt is prepared by the reaction of the organohalogen compound (a1) with magnesium or butyllithium. The dihydroxyborane derivative (a5) is prepared by the reaction of the Grignard reagent or the lithium salt thus prepared with a boric acid ester such as trimethyl borate, and then by the hydrolysis of the product in the presence of an acid such as hydrochloric acid. The compound (1C) can be prepared by the reaction of the dihydroxyborane derivative (a5) with the organohalogen compound (a6) in the presence of a catalyst, for example, of an aqueous carbonate solution and tetrakis(triphenylphosphine)palladium [Pd(PPh$_3$)$_4$].

The compound (1C) can also be prepared by the reaction of the organohalogen compound (a6) having a monovalent organic group MSG$^1$ with butyl lithium and further with zinc chloride, and then by the reaction of the resulting compound with the compound (a1) in the presence, for example, of a bistriphenylphosphinedichloropalladium [Pd(PPh$_3$)$_2$Cl$_2$] catalyst.

Formation of —$CH_2O$— or —$OCH_2$—

The oxidation of the dihydroxyborane derivative (a5) with an oxidizing agent such as hydrogen peroxide gives the alcohol derivative (a7). In a separate run, the reduction of the aldehyde derivative (a3) with a reducing agent such as sodium borohydride gives the alcohol derivative (a8). The halogenation of the resulting alcohol derivative (a8) with hydrobromic acid or the like gives the organohalogen compound (a9). The compound (1D) can be prepared by the reaction of the resulting alcohol derivative (a8) with the organohalogen compound (a9) in the presence of potassium carbonate or the like.

Formation of —COO— or —OCO—

The compound (a6) is allowed to react with n-butyllithium and then with carbon dioxide, giving the carboxylic acid derivative (a10). The compound (1E) having —COO— can be prepared by the dehydration of the carboxylic acid derivative (a10) and the phenol derivative (a11) in the presence of DDC (1,3-dicyclohexylcarbodiimide) and DMAP (4-dimethylaminopyridine). The compounds having —OCO— can also be prepared according to this method.

Formation of —C≡C—

The compound (a6) is allowed to react with 2-methyl-3-butyn-2-ol in the presence of a catalyst of dichloropalladium and a copper halide, and the product is deprotected under basic conditions to give the compound (a12). The compound (a12) is allowed to react with the compound (a1) in the presence of a catalyst of dichloropalladium and a copper halide to give the compound (1F).

Formation of a Double Bond

The organohalogen compound (a1) having a monovalent organic group MSG$^2$ is allowed to react with magnesium to give a Grignard reagent. The reaction of the resulting Grignard reagent or a lithium salt with the aldehyde derivative (a2) gives a corresponding alcohol derivative. The corresponding compound (1A) can be prepared by the dehydration of the Formation of the Ring $A^1$ Starting materials are commercially available, or methods for their syntheses are well known with regard to rings, such as trans-1,4-cyclohexylene, cyclohexene-1,4-diyl, 1,3-dioxane-2,5-diyl, pyrimidine-2,5-diyl and pyridine-2,5-diyl.

Method for the Production of the Compound (1-1)

Examples of the production for the compound (1-1) will be shown below.

The Liquid Crystal Composition

The liquid crystal composition of the invention will be explained below. This liquid crystal composition is characterized by including at least one of the compounds (1-1) as a component. The composition may include two or more of the compounds (1-1), or may be composed of the compound (1-1) alone. When the liquid crystal composition of the invention is prepared, its components can be selected, for example,

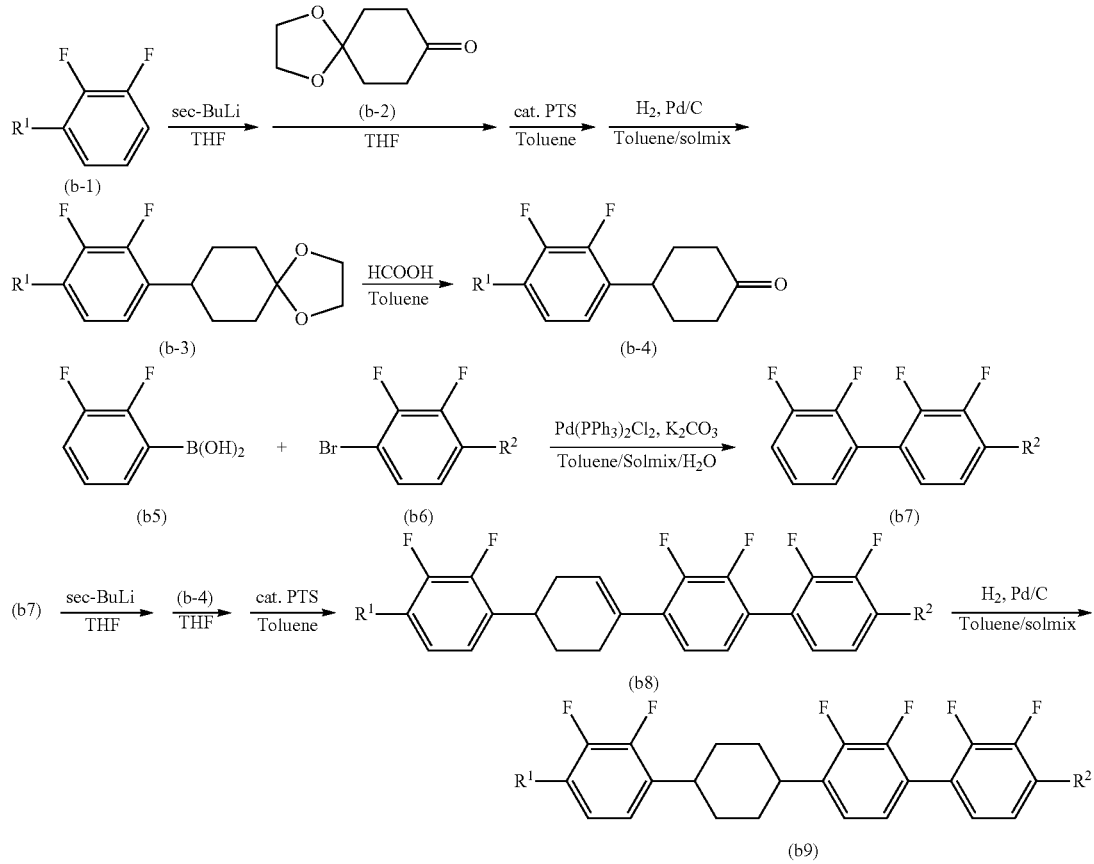

First, the difluorobenzene derivative (b1) was allowed to react with sec-BuLi to give a lithium salt. The reaction of carbonyl derivative (b2) with the lithium salt, and the dehydration reaction of the resulting alcohol derivative in the presence of an acid catalyst such as p-toluenesulfonic acid, and then the hydrogenation of the product in the presence of a catalyst such as Pd/C give the compound (b3). The resulting compound (b3) is allowed to react with formic acid or the like to give the carbonyl derivative (b4). Separately, the difluorophenylboronic acid (b5) is allowed to react with the bromodifluorobenzene derivative (b6) in the presence of a catalyst such as potassium carbonate and Pd(PPh$_3$)$_2$Cl$_2$ or the like to give the compound (b7).

The compound (b7) obtained in the above procedure is allowed to react with sec-BuLi to give a lithium salt. The reaction of the lithium salt with the carbonyl derivative (b4), and then the dehydration reaction of the resulting alcohol derivative in the presence of an acid catalyst such as p-toluenesulfonic acid give the compound (b8), which is one example of the compound (1-1) of the invention. Hydrogenation in the presence of a catalyst such as Pd/C gives the compound (b9), which is one example of the compound (1-1) of the invention.

by taking into consideration the dielectric anisotropy of the compound (1-1). The liquid crystal composition in which the components have been selected has a small viscosity, a large negative dielectric anisotropy, a suitable elastic constant $K_{33}$ and a low threshold voltage, and also has a high maximum temperature of a nematic phase (the phase transition temperature between a nematic phase and an isotropic phase) and a low minimum temperature of a nematic phase.

The Liquid Crystal Composition (1)

The liquid crystal composition of the invention should include a compound represented by formula (1) of the invention as a component A. The composition may include the component A only. The composition may include the component A and another component that is not specifically described in this specification. The liquid crystal compositions of the invention, which have a variety of characteristics, can be provided by the addition of a component selected from the components B, C, D and E, these of which will be shown below, to the component A.

Desirable components that will be added to the component A are the component B that is at least one compound selected from the group of compounds represented by formulas (2), (3) and (4), and/or the component C that is at least one compound selected from the group of compounds represented by formula (5) described above, and/or the component D that is at least one compound selected from the group of compounds represented by formulas (6), (7), (8), (9), (10) and (11). Further, the threshold voltage, the temperature range of a liquid crystal phase, the refractive index anisotropy, the dielectric anisotropy, the viscosity and so forth can be adjusted by the addition of the component E that is at least one compound selected from the group of compounds represented by formulas (12), (13) and (14).

In each component of the liquid crystal composition, which is used in the invention, there are no major differences in physical properties even if the component is an analogue composed of any isotope of the element.

In the component B described above, desirable examples of the compound (2) include formulas (2-1) to (2-16), desirable examples of the compound (3) include formulas (3-1) to (3-112), and desirable examples of the compound (4) include formulas (4-1) to (4-54).

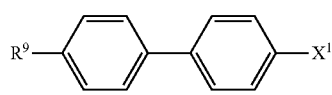
(2-1)

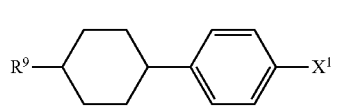
(2-2)

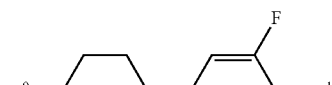
(2-3)

(2-4)

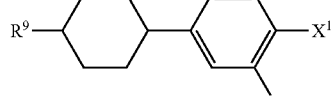
(2-5)

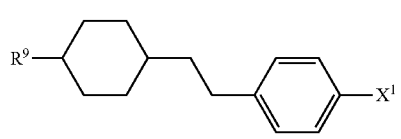
(2-6)

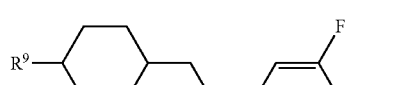
(2-7)

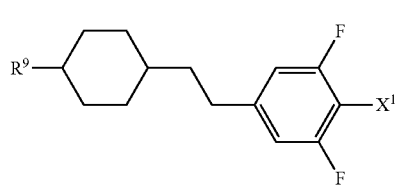

-continued

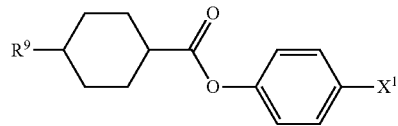
(2-8)

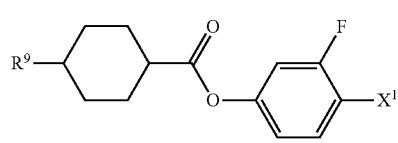
(2-9)

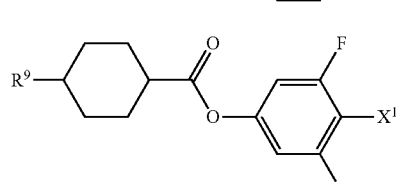
(2-10)

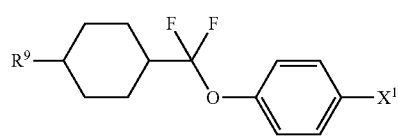
(2-11)

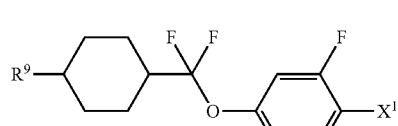
(2-12)

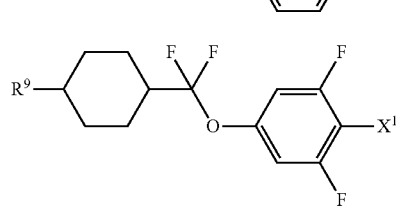
(2-13)

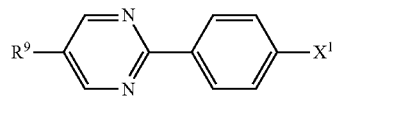
(2-14)

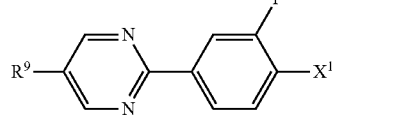
(2-15)

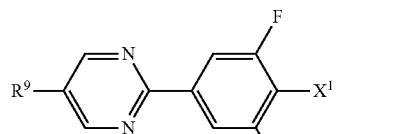
(2-16)

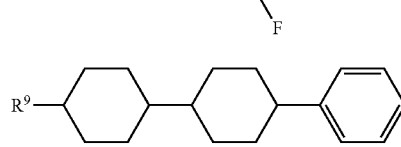
(3-1)

(3-2)

(3-3) 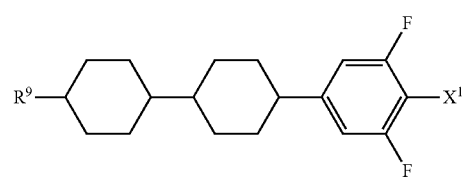
(3-4) 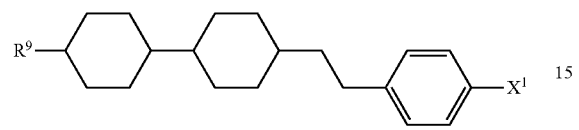
(3-5) 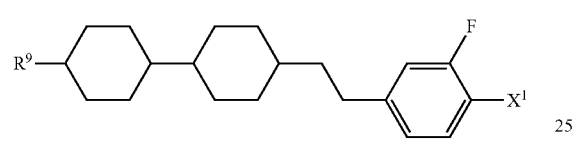
(3-6) 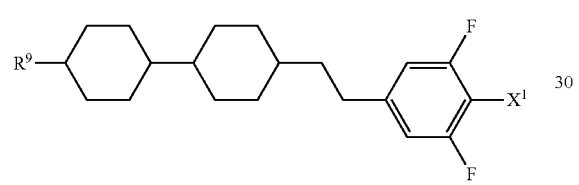
(3-7) 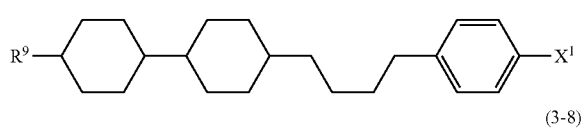
(3-8) 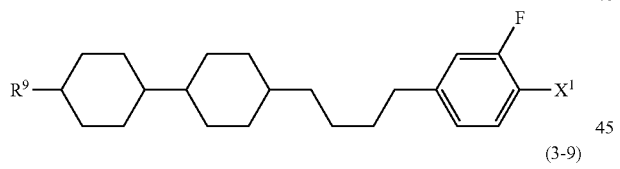
(3-9) 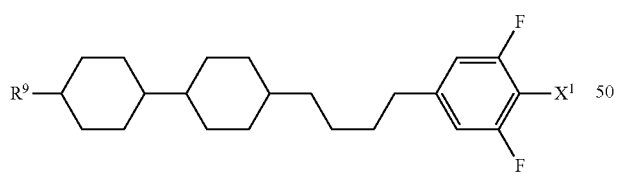
(3-10) 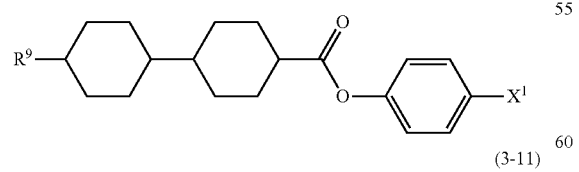
(3-11) 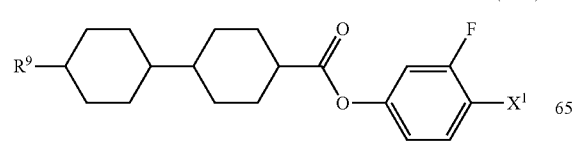
(3-12) 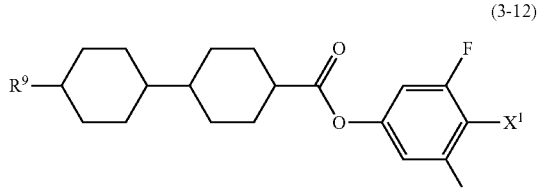
(3-13) 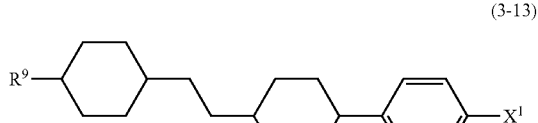
(3-14) 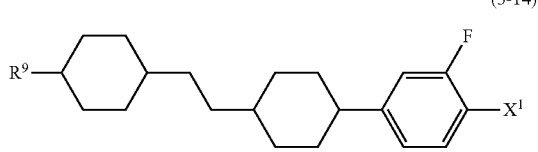
(3-15) 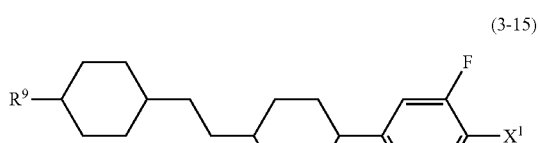
(3-16) 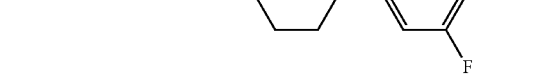
(3-17) 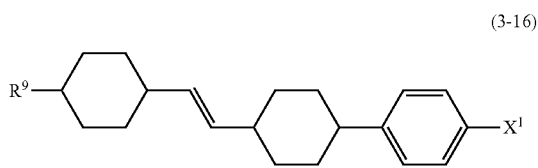
(3-18) 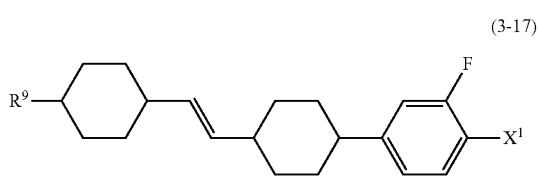
(3-19) 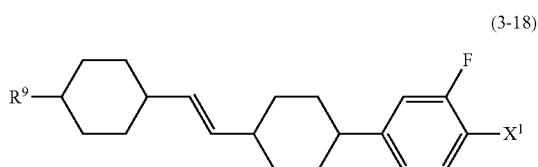
(3-20) 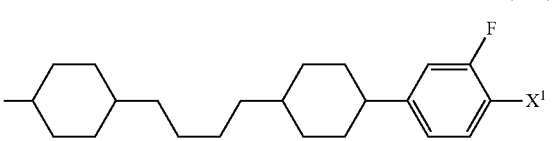

(3-21)
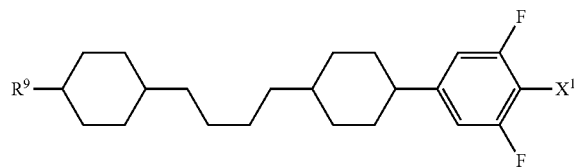
(3-22)
(3-23)
(3-24)
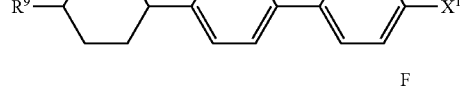
(3-25)
(3-26)
(3-27)
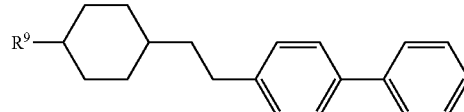
(3-28)
(3-29)
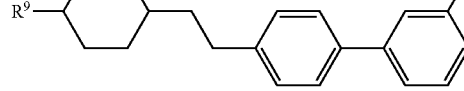
(3-30)
(3-31)
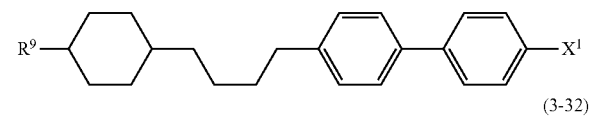
(3-32)
(3-33)
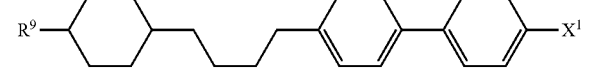
(3-34)
(3-35)
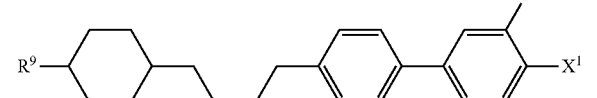
(3-36)
(3-37)
(3-38)
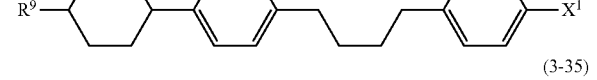
(3-39)
(3-40)
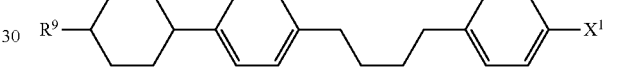

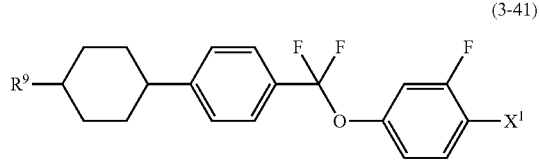 (3-41)
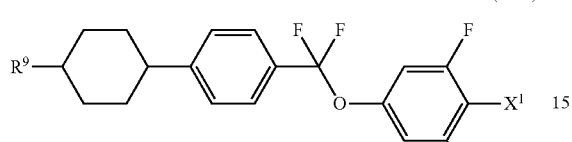 (3-42)
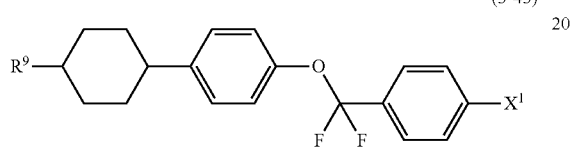 (3-43)
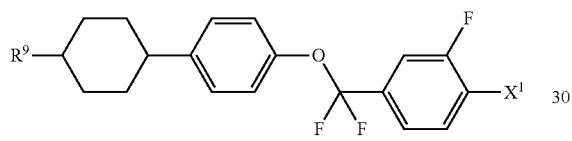 (3-44)
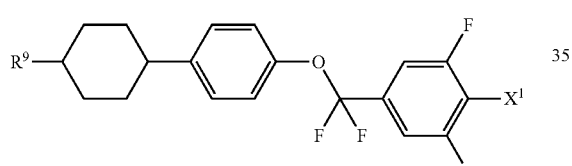 (3-45)
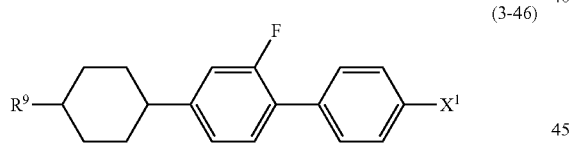 (3-46)
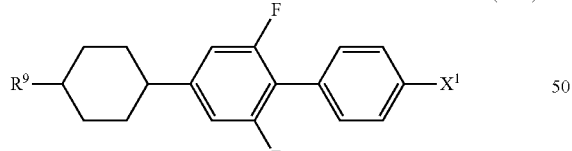 (3-47)
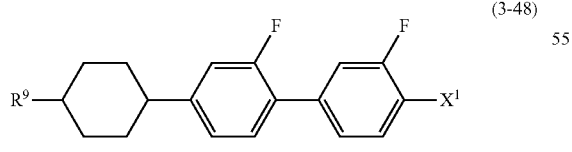 (3-48)
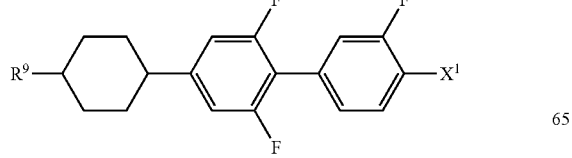 (3-49)
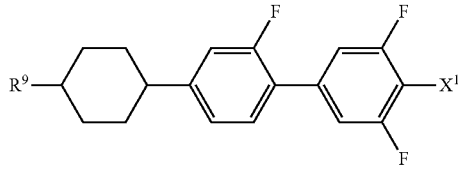 (3-50)
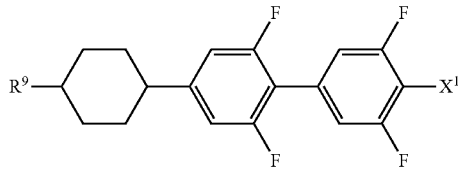 (3-51)
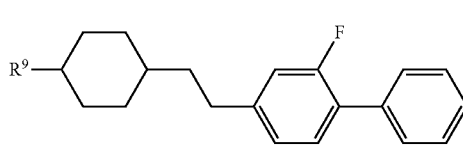 (3-52)
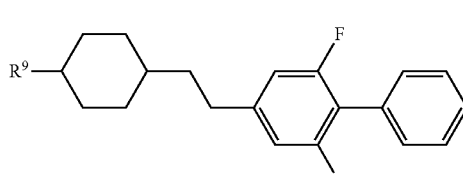 (3-53)
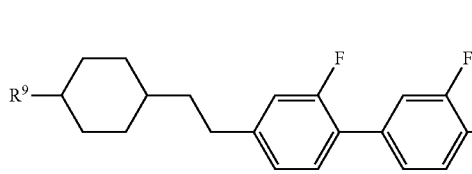 (3-54)
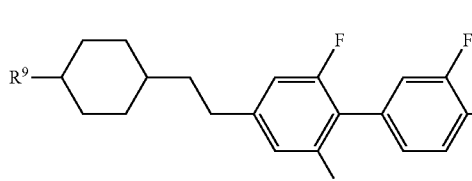 (3-55)
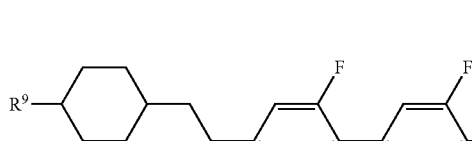 (3-56)
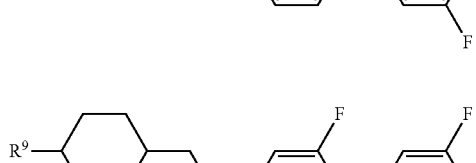 (3-57)

(3-58) 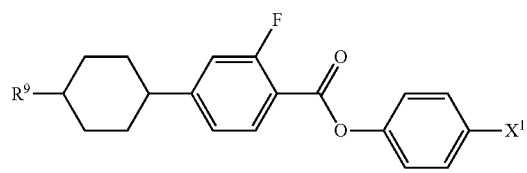
(3-59) 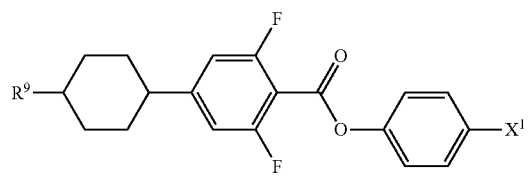
(3-60) 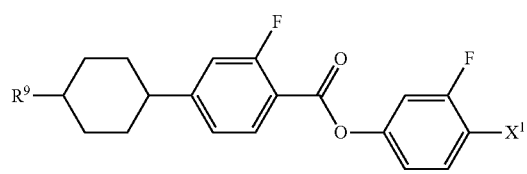
(3-61) 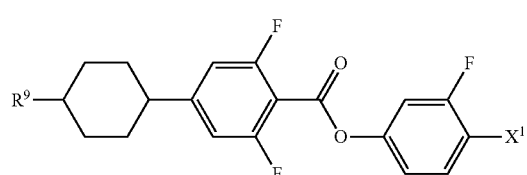
(3-62) 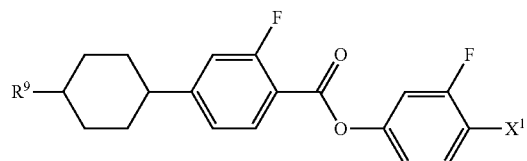
(3-63) 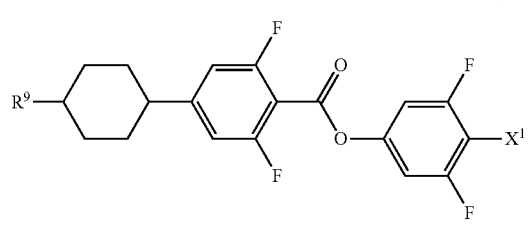
(3-64) 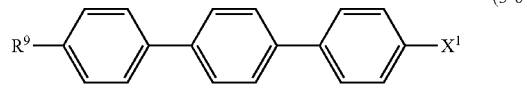
(3-65) 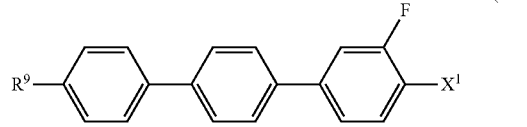
(3-66) 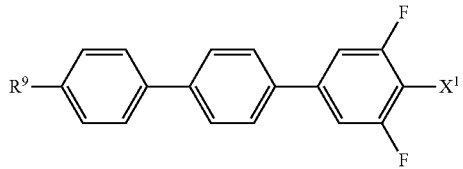
(3-67) 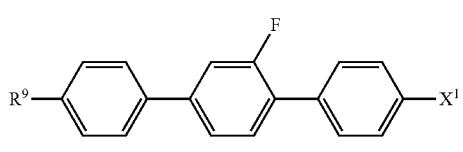
(3-68) 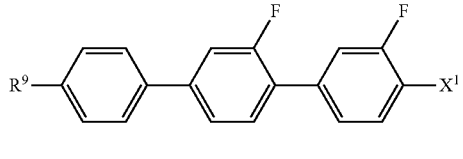
(3-69) 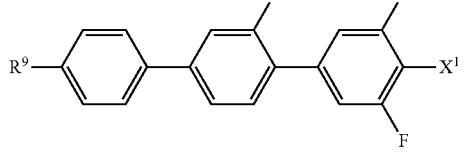
(3-70) 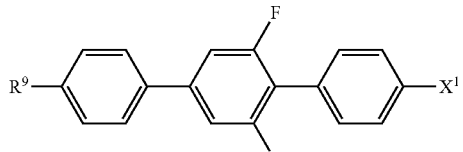
(3-71) 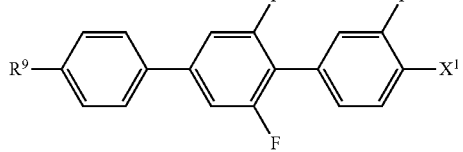
(3-72) 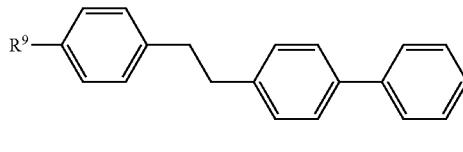
(3-73) 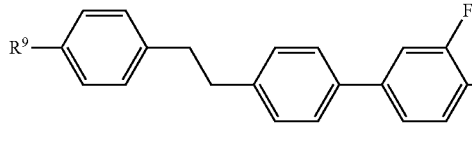
(3-74) 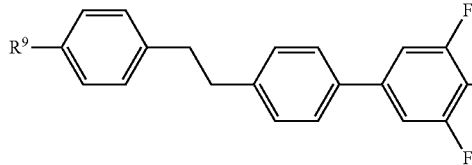

(3-75) 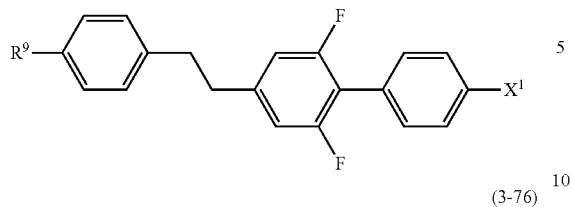
(3-76) 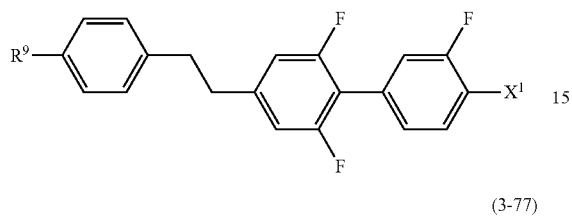
(3-77) 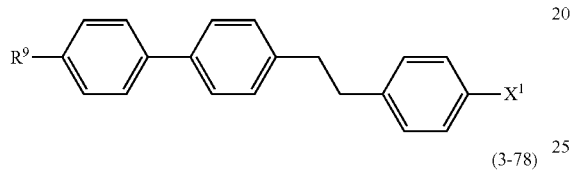
(3-78) 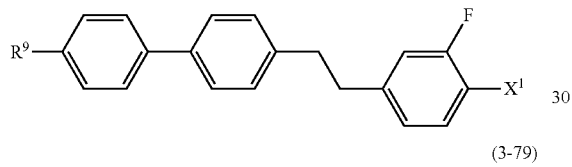
(3-79) 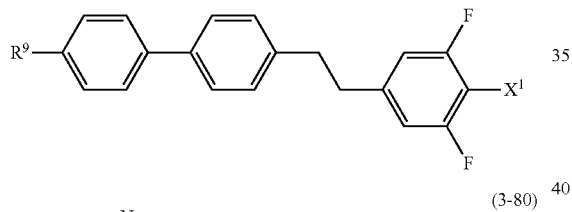
(3-80) 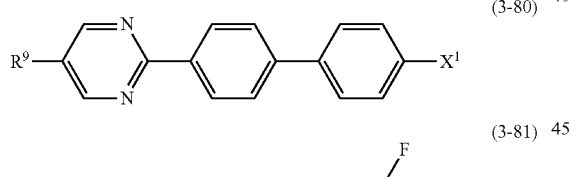
(3-81) 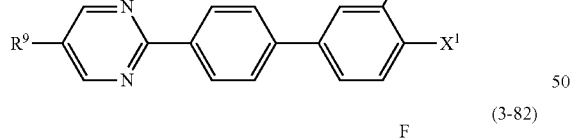
(3-82) 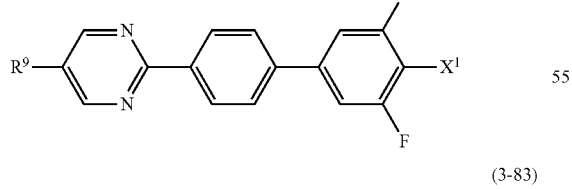
(3-83) 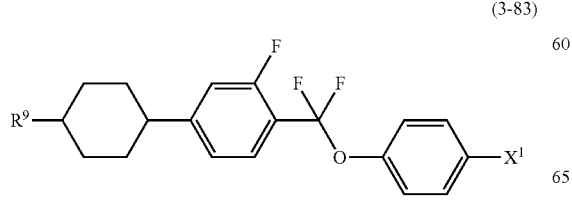
(3-84) 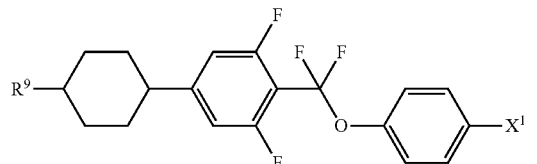
(3-85) 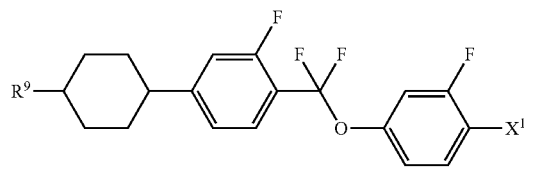
(3-86) 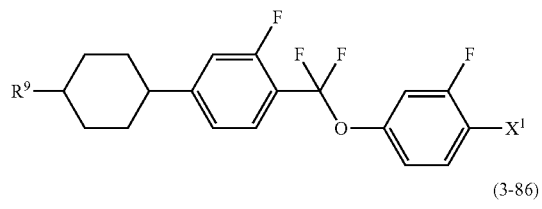
(3-87) 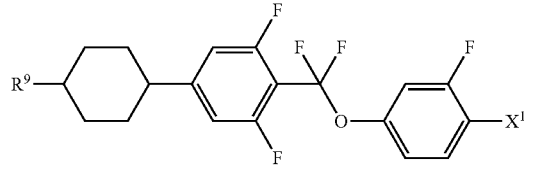
(3-88) 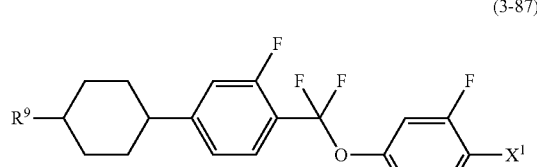
(3-89) 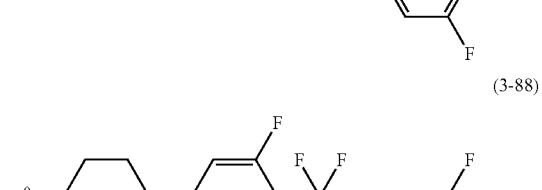
(3-90) 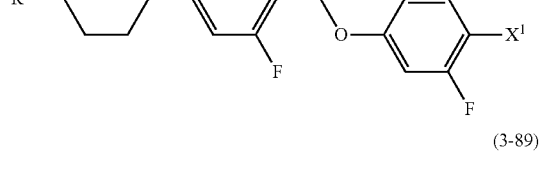
(3-91) 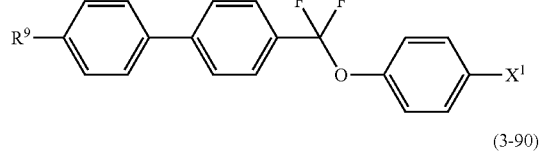
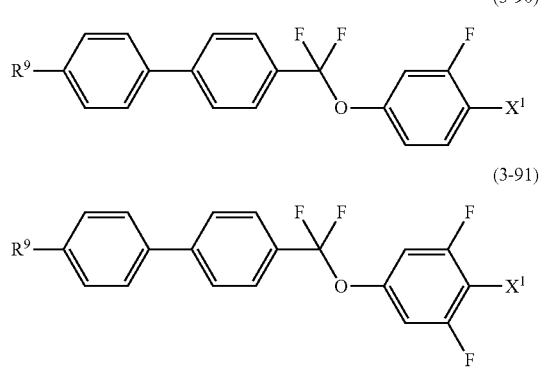

-continued (3-92)

(3-93)

(3-94)

(3-95)

(3-96)

(3-97)

(3-98)

(3-99)

-continued (3-100)

(3-101)

(3-102)

(3-103)

(3-104)

(3-105)

(3-106)

(3-107)

(3-108)

(3-109)

(3-110)
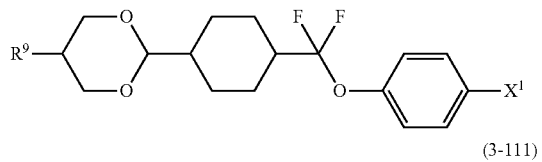
(3-111)
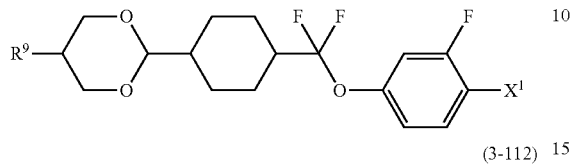
(3-112)
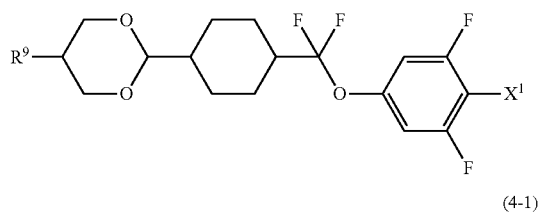
(4-1)
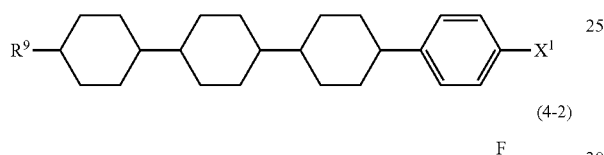
(4-2)
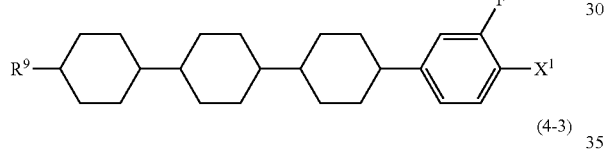
(4-3)
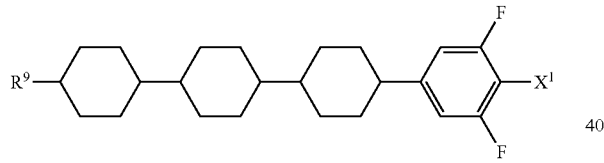
(4-4)
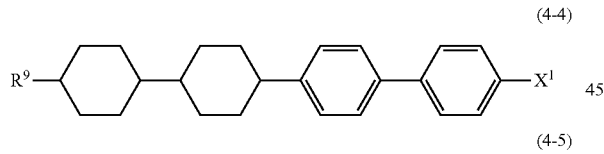
(4-5)
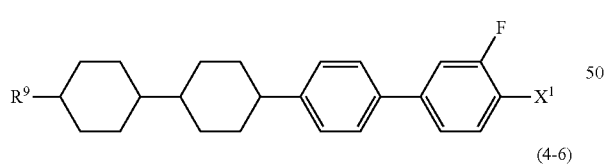
(4-6)
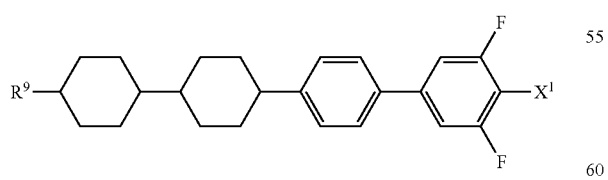
(4-7)

(4-8)
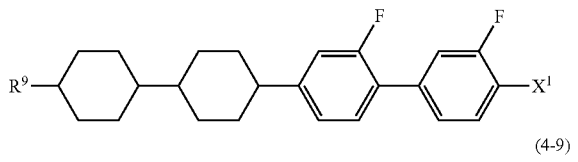
(4-9)
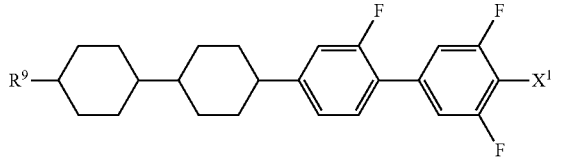
(4-10)
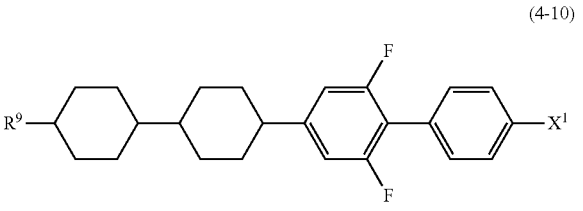
(4-11)
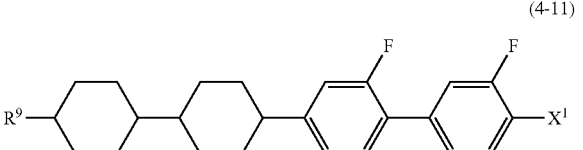
(4-12)
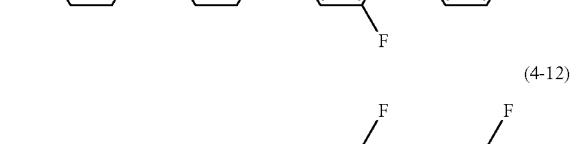
(4-13)
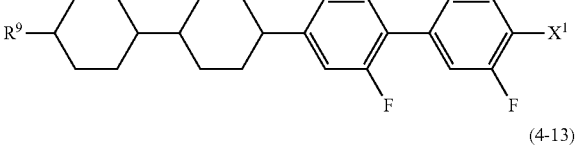
(4-14)
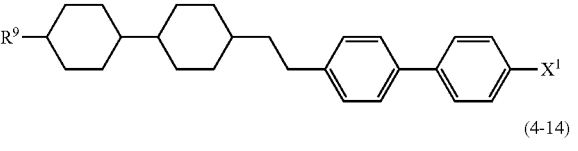
(4-15)
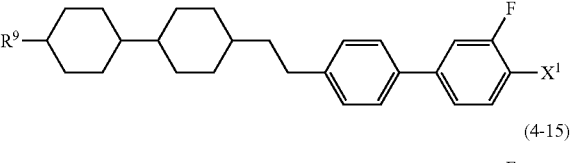
(4-16)
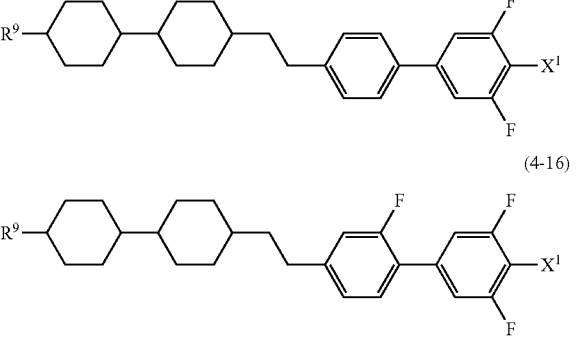

(4-17)
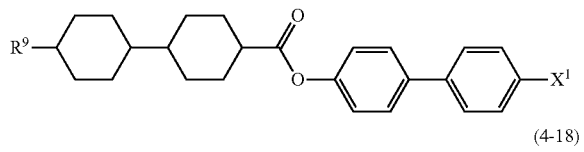
(4-18)
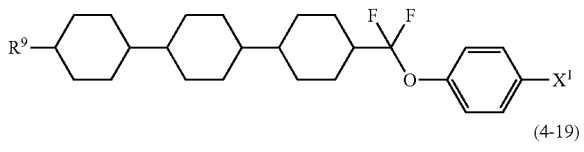
(4-19)
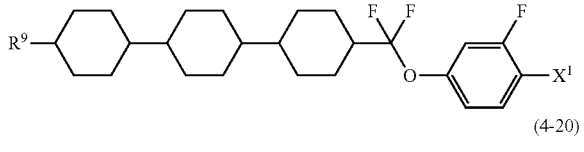
(4-20)
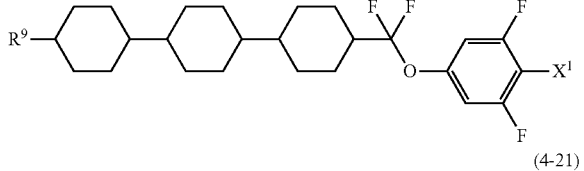
(4-21)
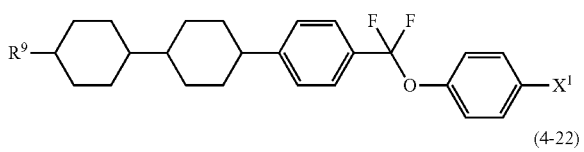
(4-22)

(4-23)
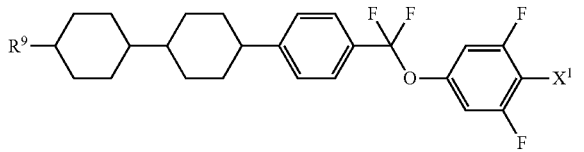
(4-24)
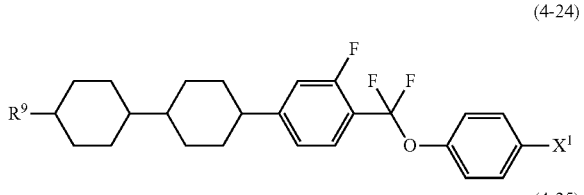
(4-25)
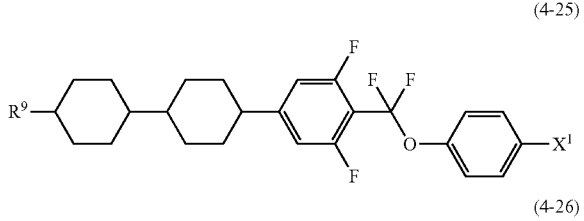
(4-26)
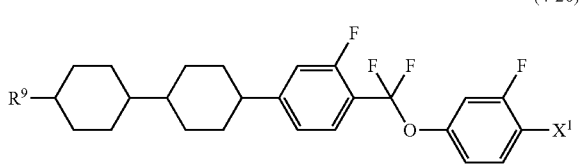
(4-27)
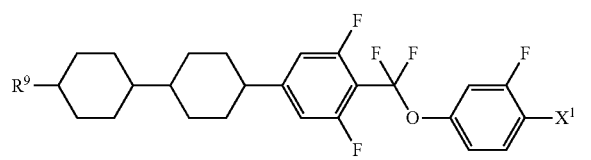
(4-28)

(4-29)
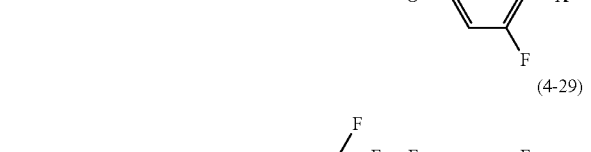
(4-30)
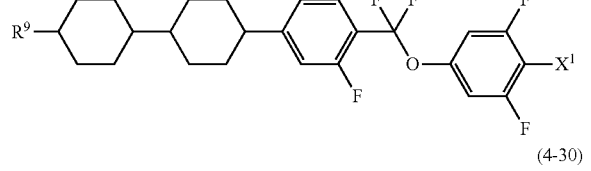
(4-31)
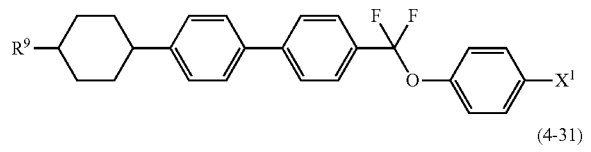
(4-32)

(4-33)
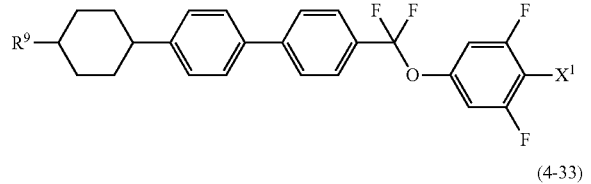
(4-34)
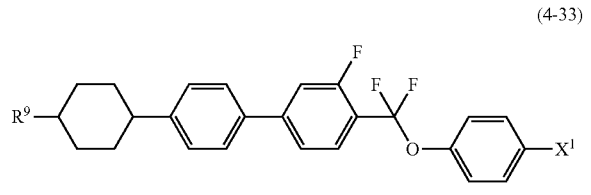
(4-35)
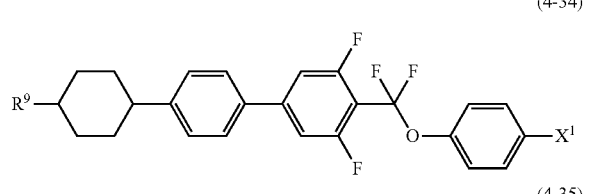
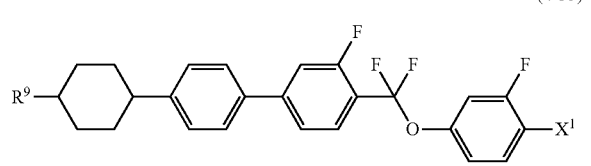

(4-36)
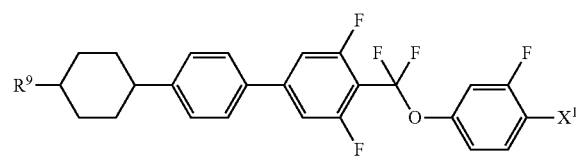
(4-37)
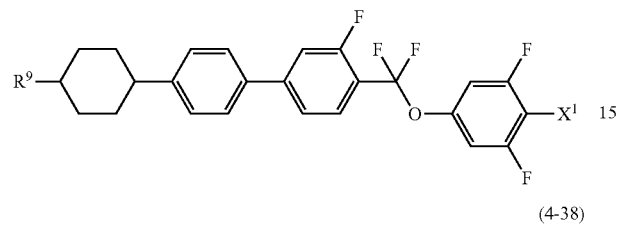
(4-38)
(4-39)
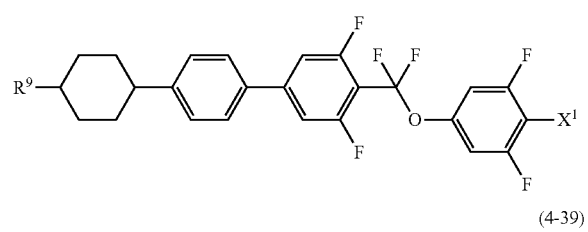
(4-40)
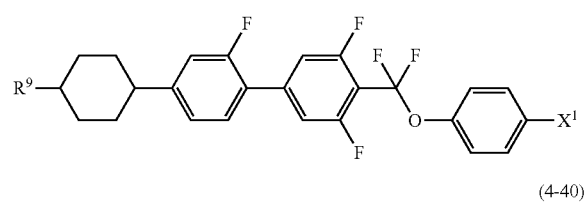
(4-41)
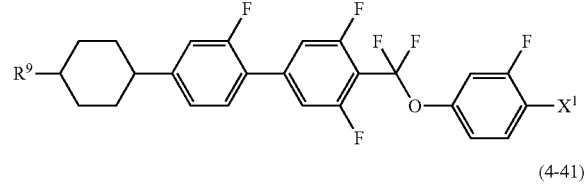
(4-42)
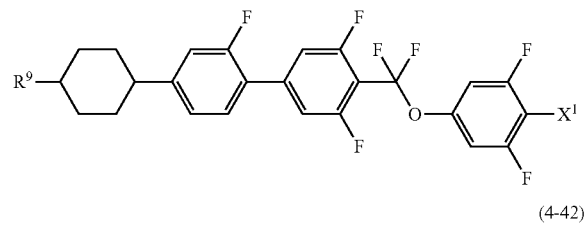
(4-43)

(4-44)
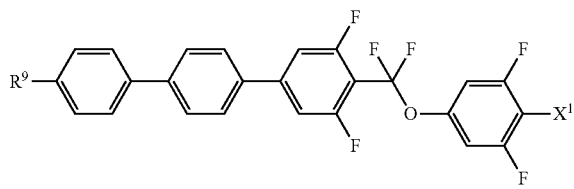
(4-45)
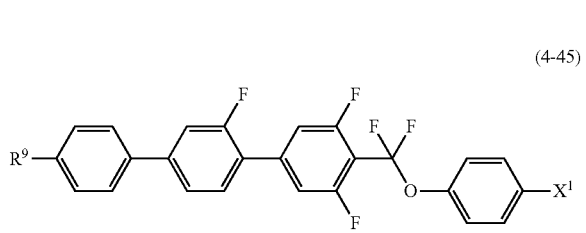
(4-46)
(4-47)
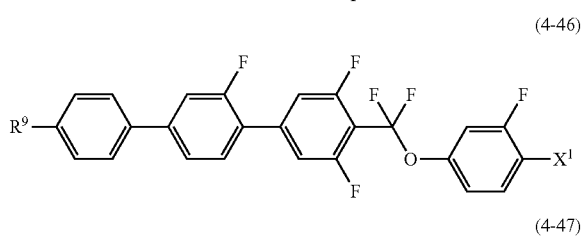
(4-48)
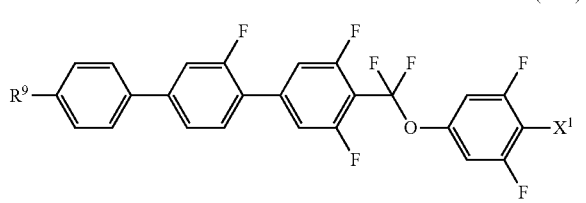
(4-49)
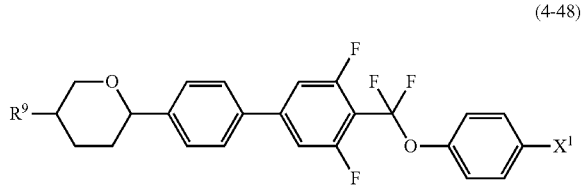
(4-50)
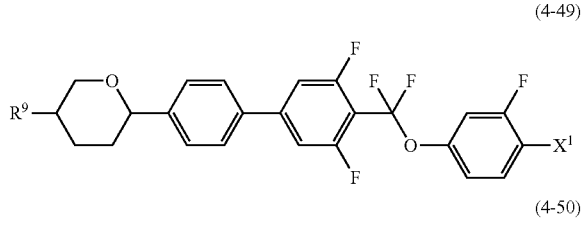
(4-51)
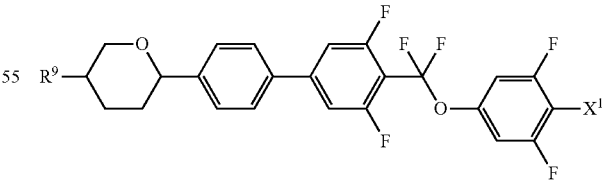
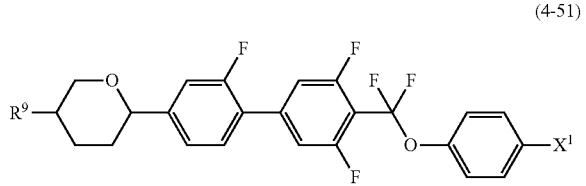

(4-52)
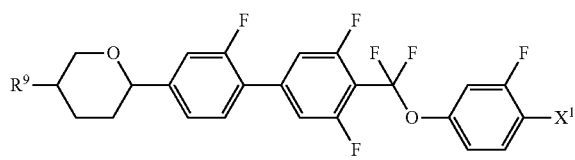

(4-53)
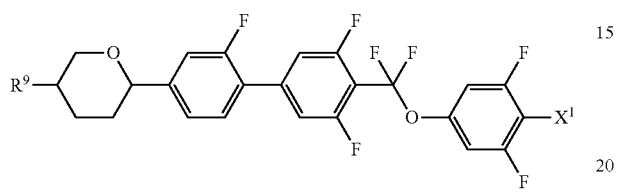

(4-54)
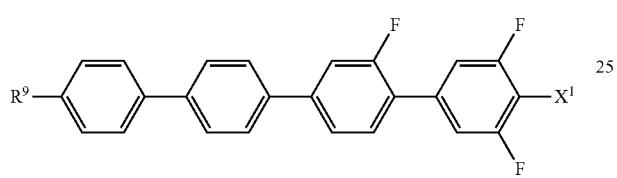

In the formulas, $R^9$ and $X^1$ have the same meanings as described above.

These compounds represented by formulas (2) to (4), that is the component B, are used in the preparation of the liquid crystal composition for use in a TFT mode and a PSA mode, since they have positive dielectric anisotropy and an especially excellent thermal or chemical stability. The content of the component B in the liquid crystal composition of the invention is suitably in the range of 1% to 99% by weight, preferably in the range of 10% to 97% by weight, and more preferably 40% to 95% by weight based on the total weight of the liquid crystal composition. The viscosity can be adjusted by a further addition of the compounds (12) to (14) (the component E).

Desirable examples of the compound represented by formula (5), that is the component C, include formulas (5-1) to (5-64).

(5-1)
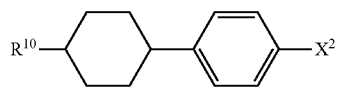

(5-2)
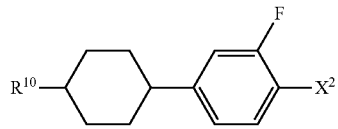

(5-3)
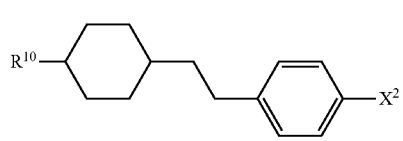

(5-4)
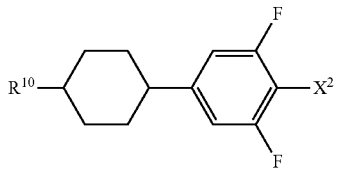

(5-5)
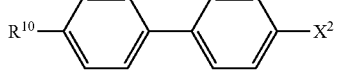

(5-6)
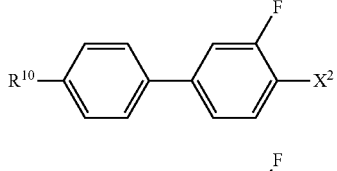

(5-7)
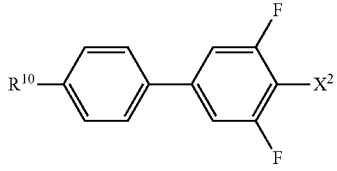

(5-8)
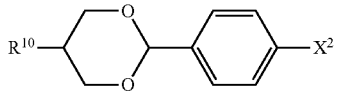

(5-9)
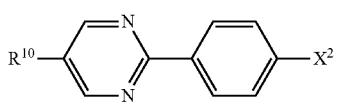

(5-10)
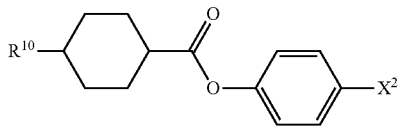

(5-11)
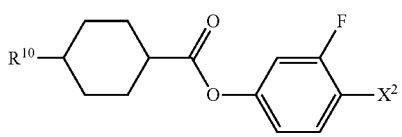

(5-12)
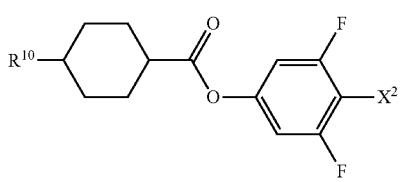

(5-13)
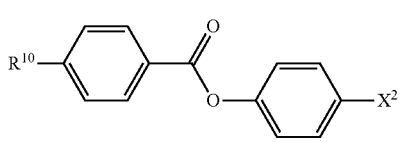

(5-14)
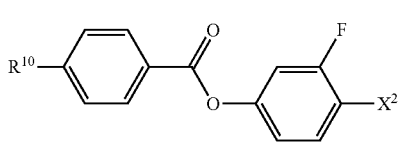

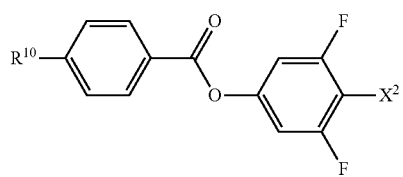 (5-15)
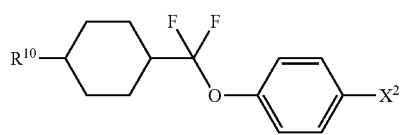 (5-16)
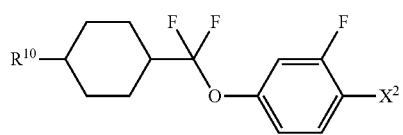 (5-17)
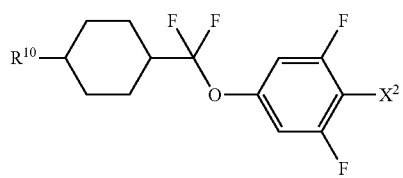 (5-18)
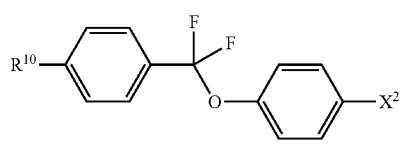 (5-19)
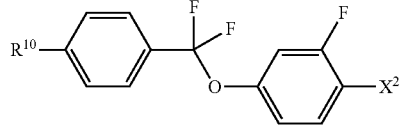 (5-20)
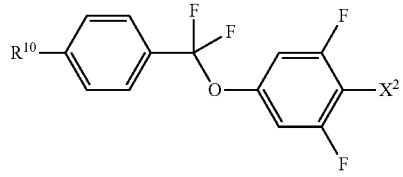 (5-21)
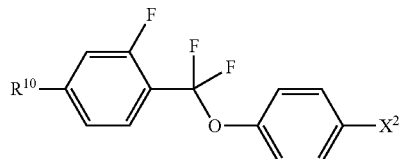 (5-22)
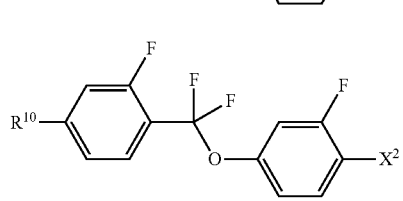 (5-23)
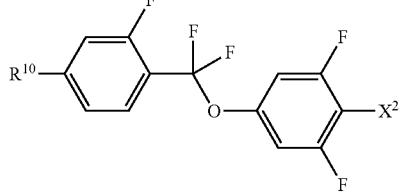 (5-24)
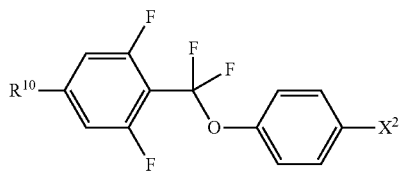 (5-25)
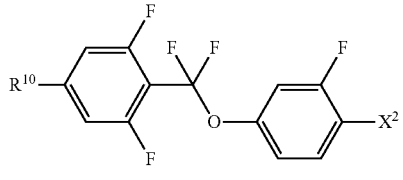 (5-26)
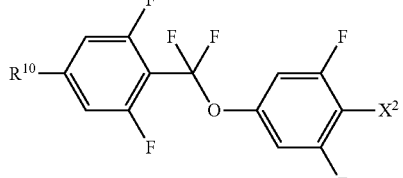 (5-27)
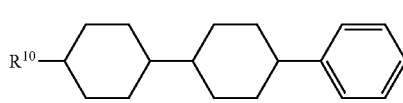 (5-28)
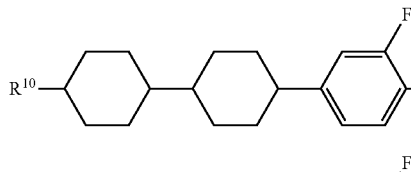 (5-29)
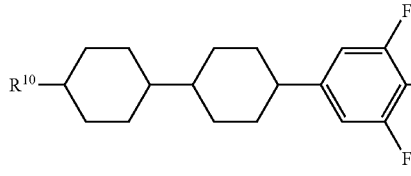 (5-30)
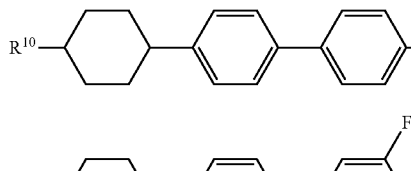 (5-31)
(5-32)
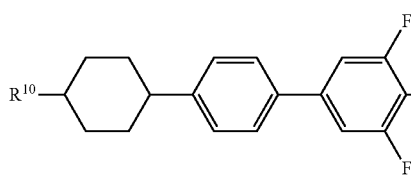 (5-33)

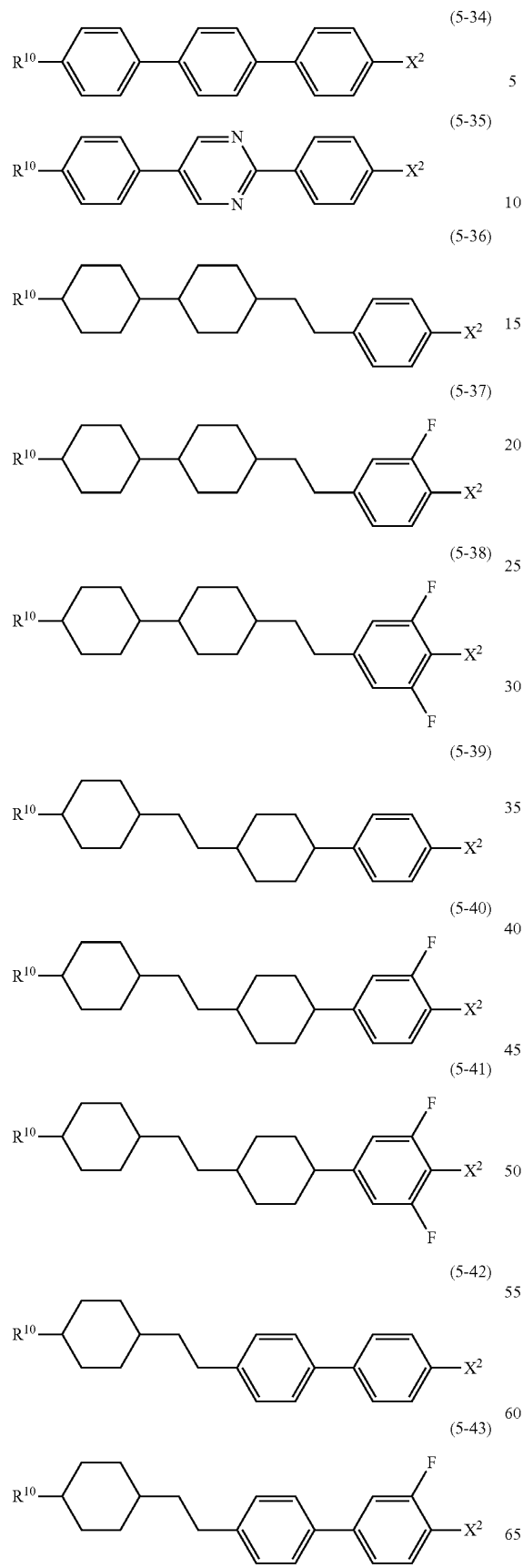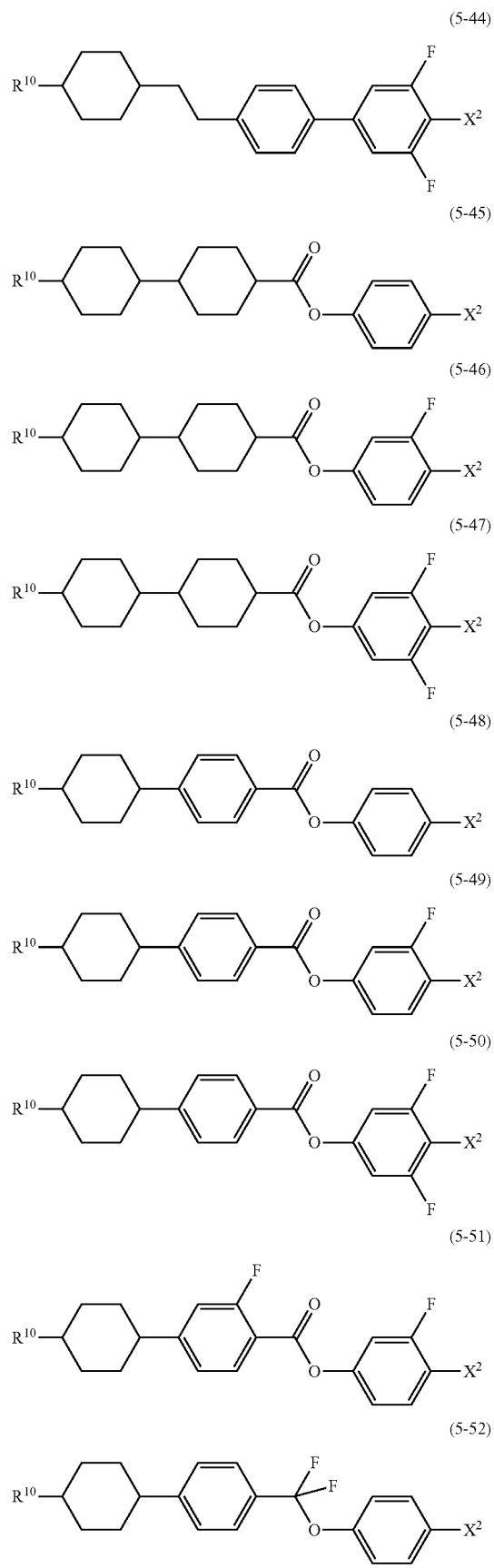

(5-53)
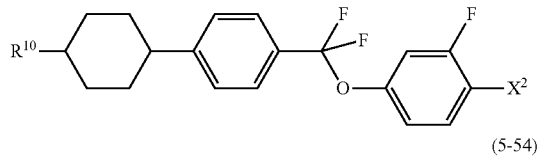

(5-54)
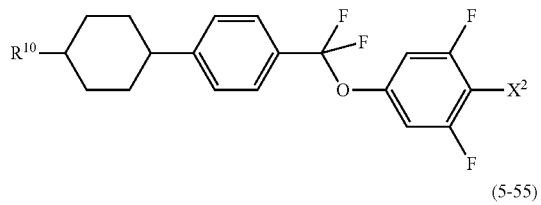

(5-55)

(5-56)
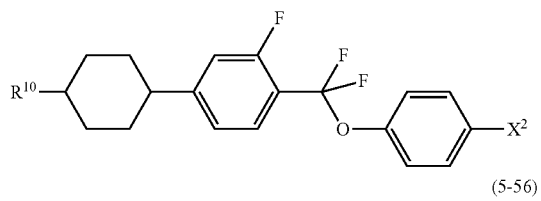

(5-57)
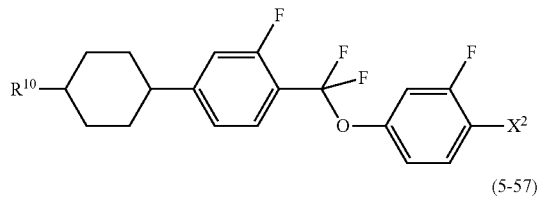

(5-58)
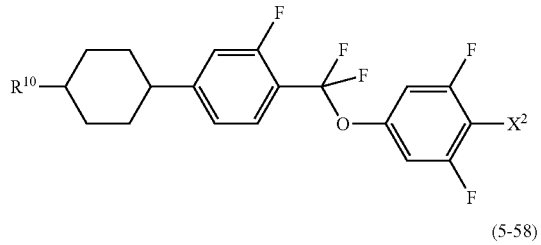

(5-59)

(5-60)
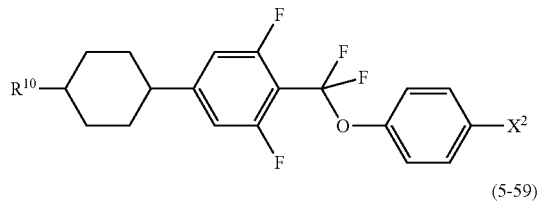

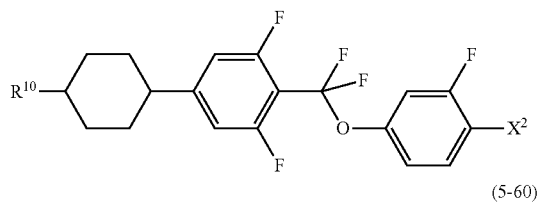

(5-61)
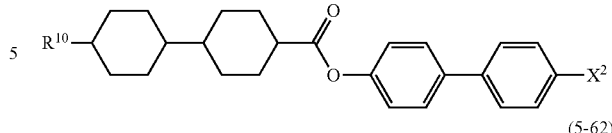

(5-62)
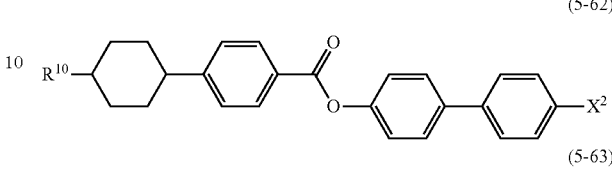

(5-63)
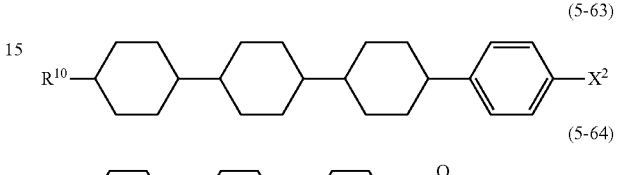

(5-64)
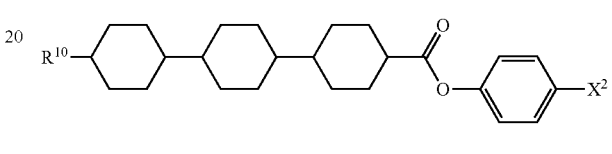

In the formulas, $R^{10}$ and $X^2$ have the same meanings as described above.

In formula (5), the two rings $C^2$ may mean the same or different when o is 2.

The compound represented by formula (5), that is the component C, is mainly used in the preparation of the liquid crystal composition for use in a STN mode, a TN mode and a PSA mode, since the dielectric anisotropy is positive and the value is quite large. The threshold voltage of the composition can be decreased by the addition of the component C. The viscosity can be adjusted, the refractive index anisotropy can be adjusted, and the temperature range of a liquid crystal phase can be increased. Furthermore, the component C can also be utilized for an improvement of the steepness.

The content of the component C is suitably in the range of 0.1% to 99.9% by weight, preferably in the range of 10% to 97% by weight, and more preferably in the range of 40% to 95% by weight in the preparation of the liquid crystal composition for use in a STN or TN mode. The threshold voltage, the temperature range of a liquid crystal phase, the refractive index anisotropy, the dielectric anisotropy, the viscosity and so forth can be adjusted by the addition of a component which will be described below.

The component D, that is at least one compound selected from the group of compounds represented by formulas (6) to (11), is desirable in the preparation of the liquid crystal composition having negative dielectric anisotropy for use in a VA (vertical alignment) mode, a PSA (polymer sustained alignment) mode and so forth.

Desirable examples of the compounds represented by formulas (6) to (11) (the component D) include formulas (6-1) to (6-6), formulas (7-1) to (7-15), formulas (8-1), formulas (9-1) to (9-3), formulas (10-1) to (10-11) and formulas (11-1) to (11-10).

(6-1)
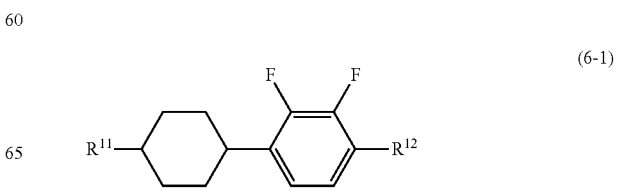

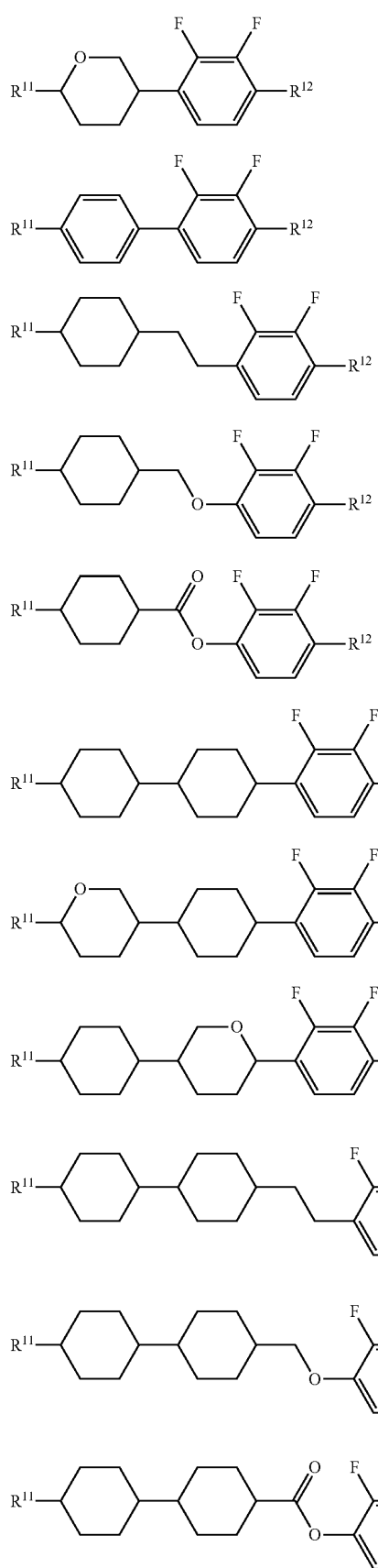
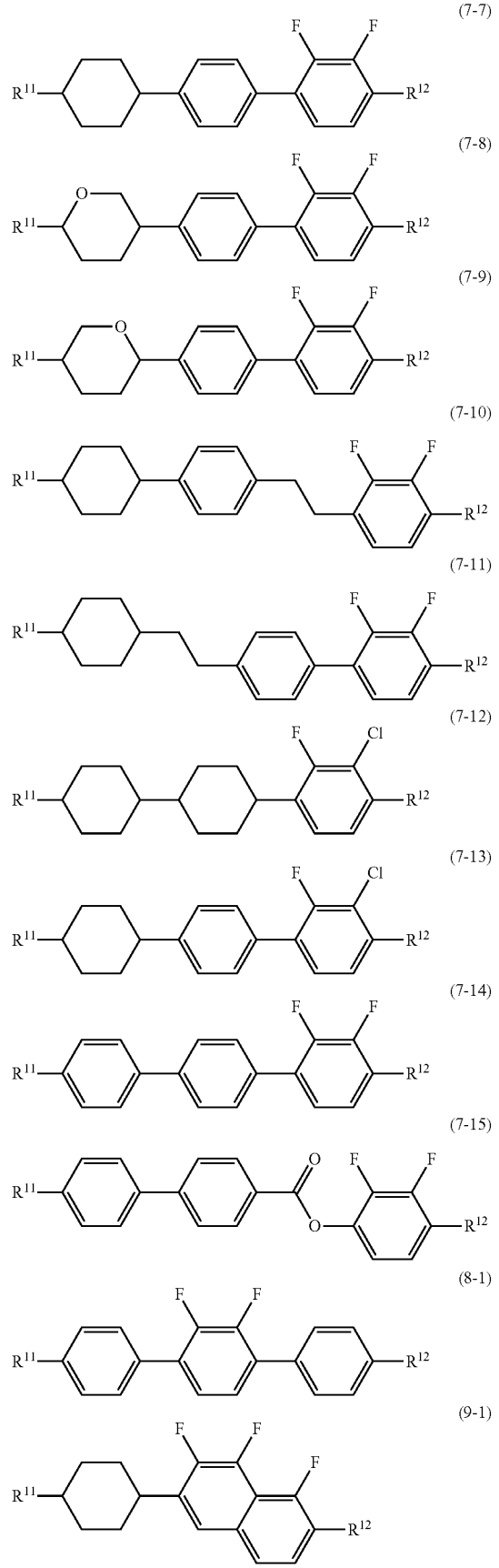

(9-2)
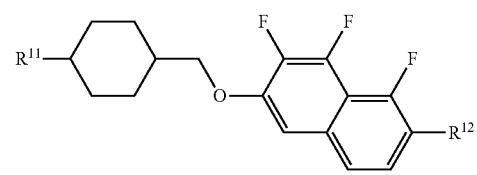
(9-3)
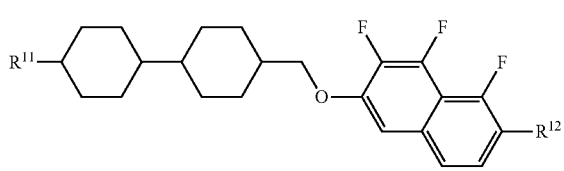
(10-1)
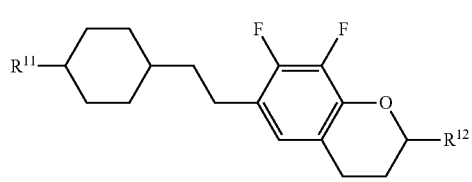
(10-2)
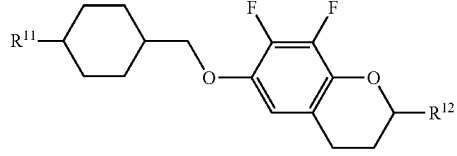
(10-3)
(10-4)
(10-5)
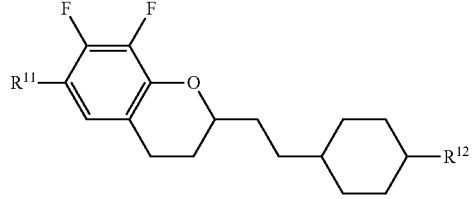
(10-6)
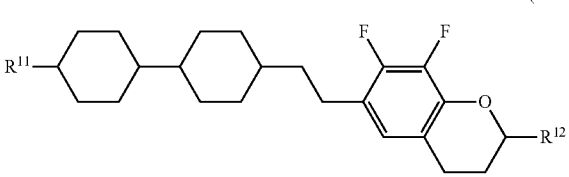
(10-7)
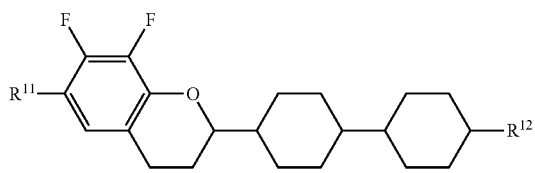
(10-8)
(10-9)
(10-10)
(10-11)
(11-1)
(11-2)
(11-3)
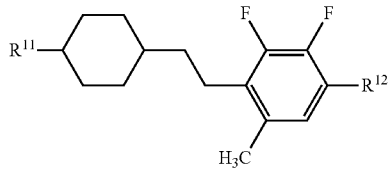

-continued

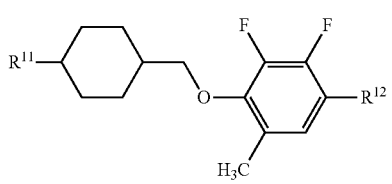 (11-4)

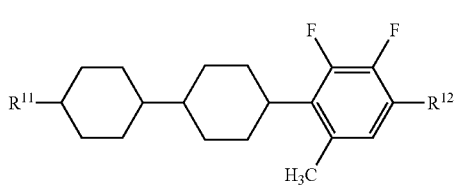 (11-5)

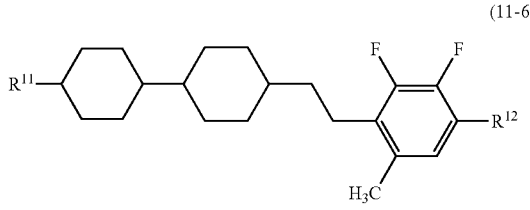 (11-6)

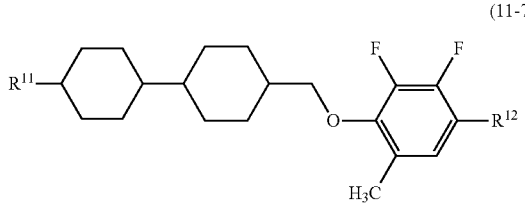 (11-7)

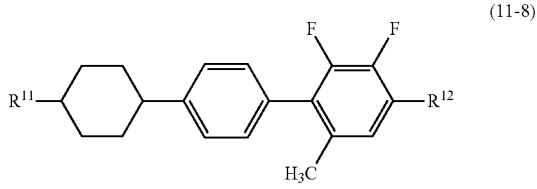 (11-8)

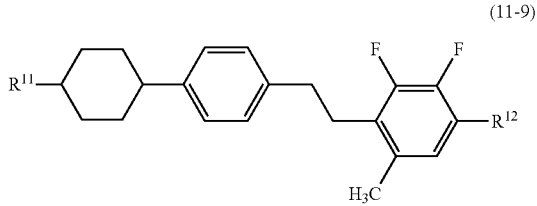 (11-9)

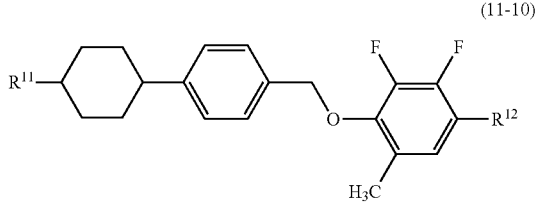 (11-10)

In the formulas, $R^{11}$ and $R^{12}$ have the same meanings as described above.

The compounds of the component D are mainly used in the liquid crystal composition having negative dielectric anisotropy for use in a VA mode and a PSA mode. As the content of the component D is increased, the threshold voltage of the composition decreases, however, the viscosity increases. Accordingly, it is desirable that the content of the component D decreases as long as the required value of the threshold voltage is satisfied. On the other hand, there are cases where sufficient voltage drive may not be attained in the content less than 40% by weight, since the absolute value of the dielectric anisotropy is about 5.

The compound represented by formula (6) among the component D is effective mainly in adjusting the threshold voltage, adjusting the viscosity, or adjusting the refractive index anisotropy, since it is a two-ring compound. The compounds represented by formulas (7) and (8) are effective in increasing the clearing point, increasing the temperature range of a nematic phase, decreasing the threshold voltage or increasing the refractive index anisotropy for instance, since it is a three-ring compound. The compounds represented by formulas (9), (10) and (11) are effective in decreasing the threshold voltage for instance.

The content of the component D is preferably in the range of 40% or more, and more preferably in the range of 50% to 95% by weight based on the total amount of the composition, in the preparation of the composition for use in a VA and PSA mode. The elastic constant can be adjusted and the voltage-transmission curve of the composition can be adjusted by the addition of the component D. It is desirable that the content of the component D is 30% by weight or less based on the total amount of the composition when the component D is added to a composition having positive dielectric anisotropy.

Desirable examples of the compounds represented by formulas (12), (13) and (14) (the component E) include formulas (12-1) to (12-11), formulas (13-1) to (13-19) and formulas (14-1) to (14-6), respectively.

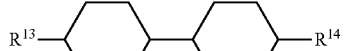 (12-1)

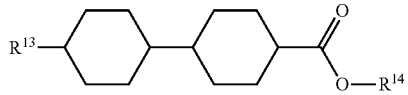 (12-2)

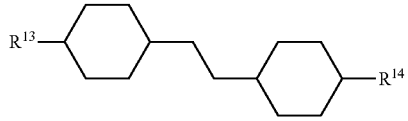 (12-3)

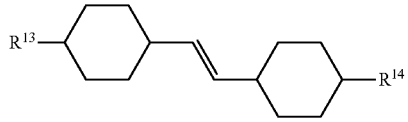 (12-4)

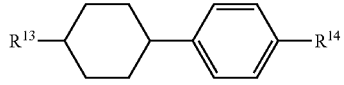 (12-5)

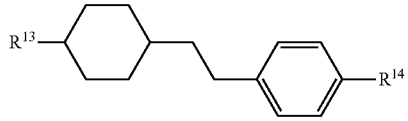 (12-6)

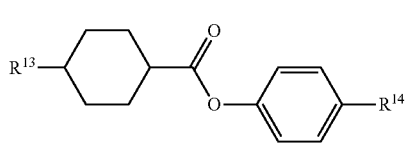 (12-7)

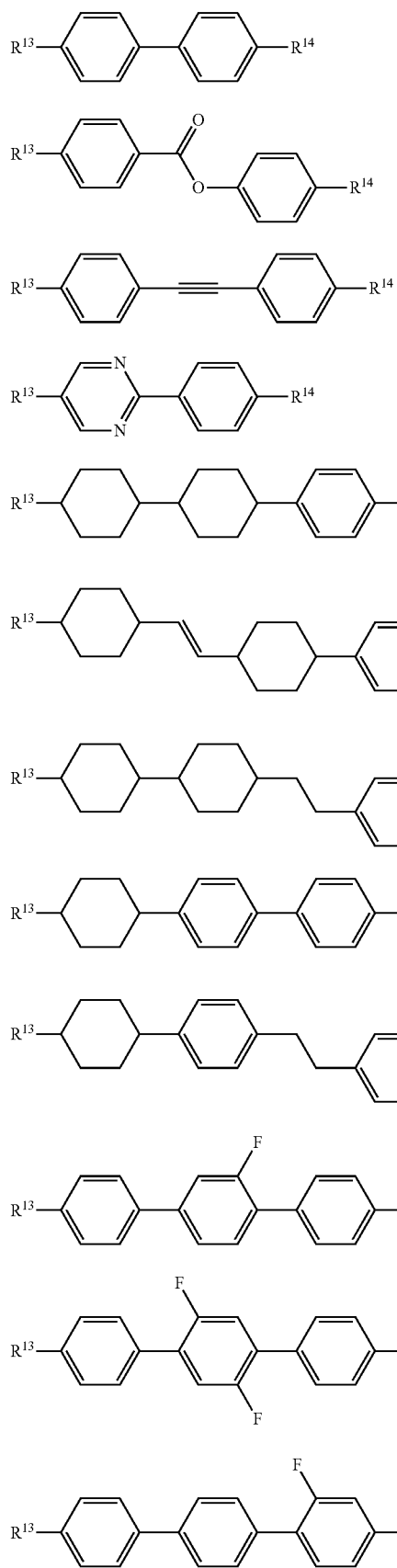
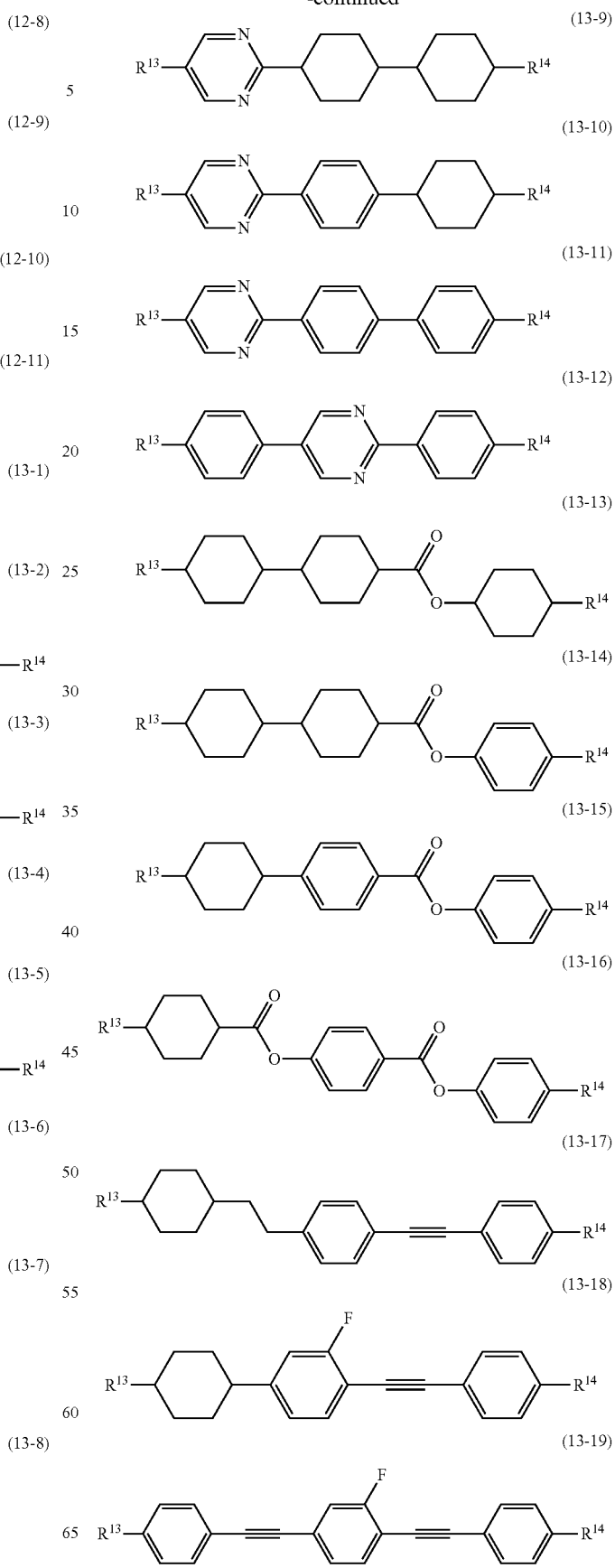

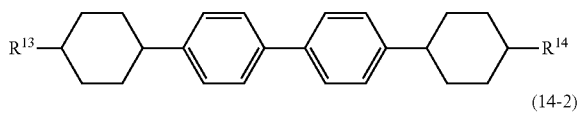
(14-1)

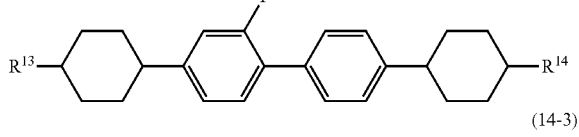
(14-2)

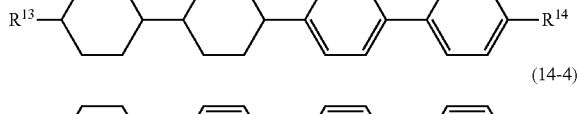
(14-3)

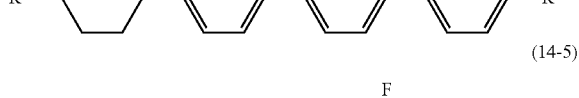
(14-4)

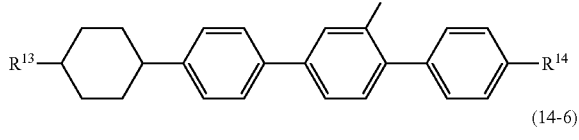
(14-5)

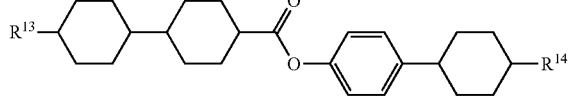
(14-6)

In the formulas, $R^{13}$ and $R^{14}$ have the same meanings as described above.

The compounds represented by formulas (12) to (14) (the component E) are close to neutral, since the absolute value of the dielectric anisotropy is small. The compound represented by formula (12) is effective mainly in adjusting the viscosity or adjusting the refractive index anisotropy, and the compounds represented by formulas (13) and (14) are effective in increasing the temperature range of a nematic phase that is caused by an increase in the clearing point for instance, or adjusting the refractive index anisotropy.

As the content of the component E is increased, the viscosity of the liquid crystal composition decreases, however the threshold voltage increases. Accordingly, it is desirable that the content increases as long as the required value of the threshold voltage of the liquid crystal composition is satisfied. The content of the component E is preferably 30% by weight or more, and more preferably 50% by weight or more based on the total amount of the composition, in the preparation of the liquid crystal composition for use in a TFT mode or a PSA mode. The content of the component E is preferably 30% by weight or more, and more preferably 40% by weight or more based on the total amount of the composition, in the preparation of the liquid crystal composition for use in a TN mode, a STN mode or a PSA mode.

It is desirable that the liquid crystal composition of the invention includes at least one of compounds represented by formula (1) of the invention in the range of 0.1% to 99% by weight for exhibiting excellent characteristics.

The liquid crystal composition of the invention is generally prepared according to known methods such as the mutual dissolution of necessary components at a high temperature, for example. An additive that is well known to a person skilled in the art may be added to the composition depending on its intended use. For example, a liquid crystal composition of the invention including an optically active compound, or including a polymerizable compound and a polymerization initiator, those of which will be described below, or a liquid crystal composition for use in a GH mode, to which a dye is added, can be prepared. The additive is generally well known to a person skilled in the art, and is described in the literature and so forth in detail.

In the liquid crystal composition of the invention, one or more optically active compounds of the invention may be added to the liquid crystal composition of the invention which is descried above.

A known chiral dopant is added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

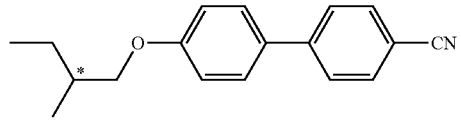
(Op-1)

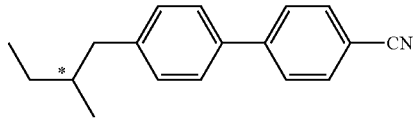
(Op-2)

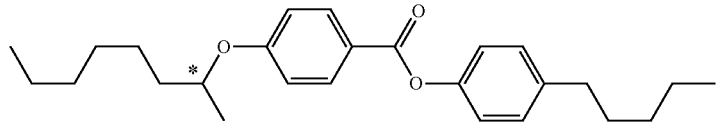
(Op-3)

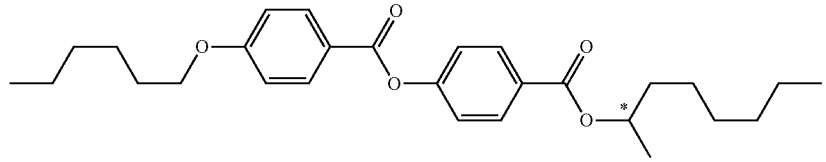
(Op-4)

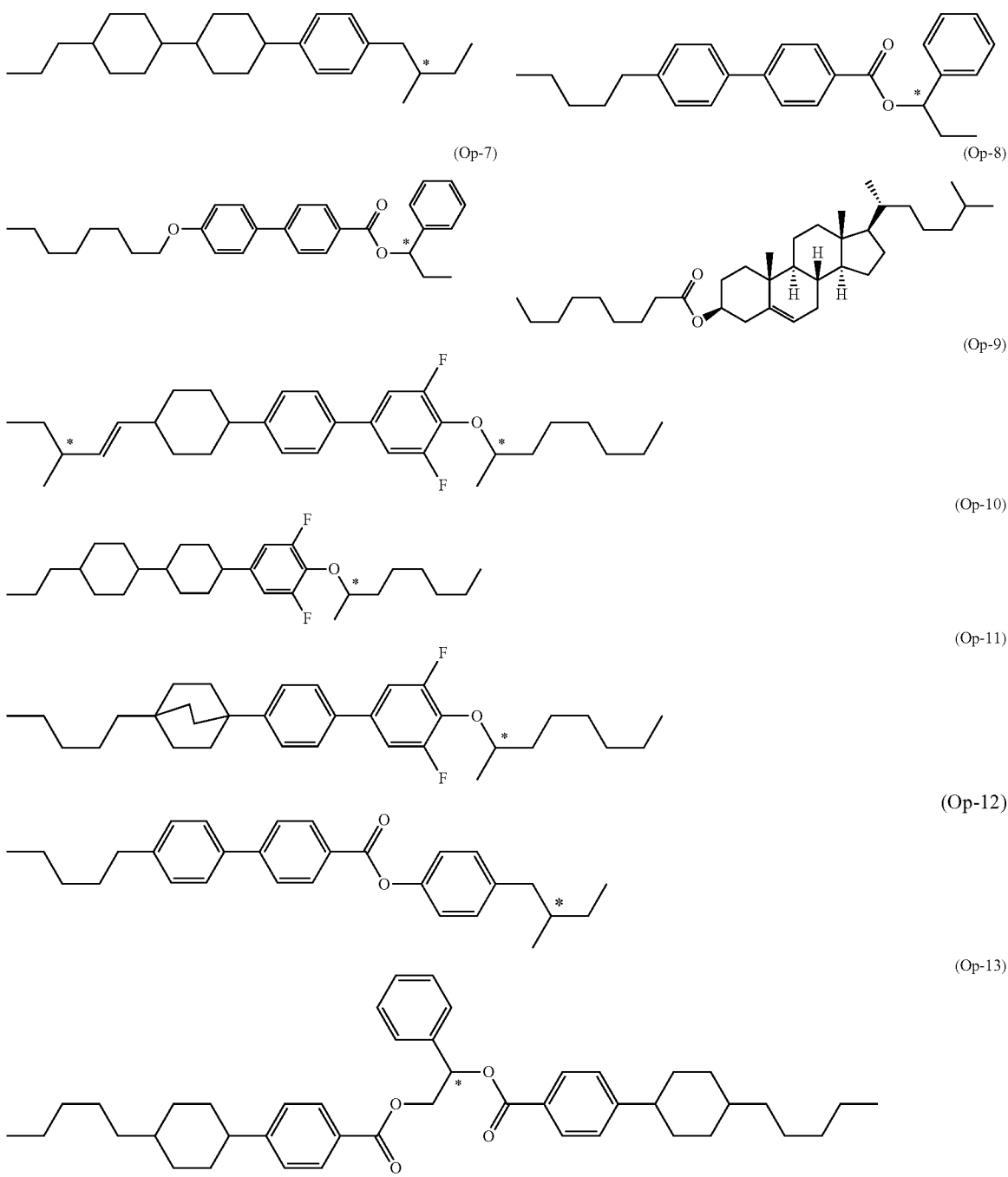

A helical pitch can be adjusted by the addition of this optically active compound to the liquid crystal composition of the invention. It is desirable to adjust the helical pitch to the range of 40 micrometers to 200 micrometers in a liquid crystal composition for use in a TFT mode and a TN mode. It is desirable to adjust the helical pitch to the range of 6 micrometers to 20 micrometers in a liquid crystal composition for use in a STN mode. It is desirable to adjust the helical pitch to the range of 1.5 micrometers to 4 micrometers for use in a BTN (bistable twisted nematic) mode. Two or more optically active compounds may be added for the purpose of adjusting the temperature dependence of the helical pitch.

The liquid crystal composition of the invention can be used as a liquid crystal composition for use in a GH mode by the addition of a dichroic dye such as a merocyanine, stylyl, azo, azomethine, azoxy, quinophthalone, anthraquinone or tetrazine compound.

The liquid crystal composition of the invention can be used for a NCAP-device prepared by micro-encapsulating nematic liquid crystals, and for a polymer-distributed liquid crystal display device (PDLCD) prepared by forming a three-dimensional network polymer in liquid crystals, such as a polymer network liquid crystal display device (PNLCD), and also for use in an ECB (electrically controlled birefringence) mode or a DS mode.

The liquid crystal composition of the invention can be used as a liquid crystal composition for use in a PSA (polymer sustained alignment) mode by the addition of a polymerizable compound. Examples of the polymerizable compound include compounds having polymerizable groups such as acrylates, methacrylates, vinyl compounds, vinyloxy compounds, propenyl ethers, epoxy compounds, vinyl ketones and oxetanes. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature. For example, Irgacure 651 (registered trademark), Irgacure 184 (registered trademark) or Darocure 1173 (registered trademark) (Ciba Japan K. K.), each of which is a photo-initiator, is suitable for radical polymerization.

Method for Preparing the Liquid Crystal Composition

When each of component compounds in the liquid crystal composition of the invention is a liquid, for example, the composition is prepared by mixing and shaking the compounds. When solids are included, the composition is prepared by mixing each compound, and then shaking after the compounds have been heated and liquefied. Moreover, the liquid crystal composition of the invention can also be prepared according to other known methods.

Characteristics of the Liquid Crystal Composition

The temperature range of the nematic phase is wide in the liquid crystal composition of the invention, since the maximum temperature of a nematic phase can be adjusted to 70° C. or higher and the minimum temperature of the nematic phase can be adjusted to −20° C. or lower. Accordingly, the liquid crystal display device containing this liquid crystal composition can be used in a wide temperature range.

In the liquid crystal composition of the invention, the optical anisotropy can arbitrarily be adjusted to the range, for example, of 0.10 to 0.13, and also to the range of 0.05 to 0.18, by suitably selecting each component, for instance.

In the liquid crystal composition of the invention, the liquid crystal composition having the dielectric anisotropy normally in the range of −5.0 to −2.0, and the dielectric anisotropy preferably in the range of −4.5 to −2.5 can be obtained. The liquid crystal composition having dielectric anisotropy in the range of −4.5 to −2.5 can be suitably used for a liquid crystal display device which operates by means of the IPS and VA modes.

The Liquid Crystal Display Device

The liquid crystal composition of the invention can be used not only for the liquid crystal display devices having operating modes such as PC, TN, STN, OCB and PSA modes which are driven by means of an AM mode, but also for liquid crystal display devices having operating modes such as PC, TN, STN, OCB, VA and IPS modes which are driven by means of a passive matrix (PM) mode.

The liquid crystal display devices having the AM mode and the PM mode can be applied to any of liquid crystal displays and so forth that have a reflection type, a transmission type, and a semi-transmission type.

Moreover, the liquid crystal composition of the invention can also be used for a dynamic scattering (DS) mode-device containing the liquid crystal composition to which a conducting agent is added, and a nematic curvilinear aligned phase (NCAP) device containing the liquid crystal composition microencapsulated, and a polymer dispersed (PD) device having a three-dimensional network polymer formed in the liquid crystal composition, for example, a polymer network (PN) device.

Since the liquid crystal composition of the invention has the characteristics described above, it can be suitably used for the liquid crystal display device having an AM mode which is driven by means of an operating mode such as the VA, IPS or PSA mode, wherein the liquid crystal composition having negative dielectric anisotropy is used, especially for the liquid crystal display device having the AM mode which is driven by means of the VA mode.

Incidentally, the direction of an electric field is perpendicular to liquid crystal layers in a liquid crystal display device which is driven by means of the TN mode, the VA mode or the like. On the other hand, the direction of an electric field is parallel to liquid crystal layers in a liquid crystal display device which is driven by means of the IPS mode or the like. The structure of the liquid crystal display device which is driven by means of the VA mode is reported by K. Ohmuro, S. Kataoka, T. Sasaki and Y. Koike, SID '97 Digest of Technical Papers, 28, 845 (1997), and the structure of the liquid crystal display device which is driven by means of the IPS mode is reported in WO 1991-010936 A (patent family: U.S. Pat. No. 5,576,867).

EXAMPLES

Examples of the Compound (1-1)

The invention will be explained below in more detail. However, the invention is not limited to the examples. The term "%" means "% by weight," unless otherwise noted.

Analytical methods will be explained first, since the resulting compounds herein were identified on the basis of nuclear magnetic resonance spectra obtained by means of $^1$H-NMR analysis, gas chromatograms obtained by means of gas chromatography (GC) analysis and so forth.

$^1$H-NMR Analysis

A model DRX-500 apparatus (made by Bruker BioSpin Corporation) was used for measurement. Samples prepared in the examples and so forth were dissolved in deuterated solvents such as $CDCl_3$ in which the samples were soluble, and the measurement was carried out under the conditions of room temperature, thirty-two times of accumulation and 500 MHz. In the explanation of the resulting nuclear magnetic resonance spectra, the symbols s, d, t, q, quip, sex, m and br stand for a singlet, a doublet, a triplet, a quartet, a quintet, a sextet, a multiplet and line-broadening, respectively. Tetramethylsilane (TMS) was used as the standard reference material for the zero point of the chemical shift (δ values).

GC Analysis

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 300° C.

A sample was dissolved in toluene to give a 1% by weight solution, and then 1 microliter of the resulting solution was injected into the sample injector.

Chromatopac Model C-R6A made by Shimadzu Corporation or its equivalent was used as a recorder. The resulting gas chromatogram showed the retention time of the peaks and the values of the peak areas corresponding to the component compounds.

Chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used. This is because there is no significant difference among the correction coefficients of the liquid crystal compounds as components. An internal standard method using gas chromatograms is used in order to determine the composition ratio of the liquid crystal compounds in the liquid crystal composition more accurately by means of the gas chromatograms. Each liquid crystal compound (test-component) weighed accurately in a fixed amount and a liquid crystal compound serving as a standard (standard reference material) are analyzed simultaneously by means of gas chromatography, and the relative intensity is calculated in advance from the ratio of the peak area of the test-component to that of the standard reference material. Then, the composition ratio of the liquid crystal compounds in the liquid crystal composition can be determined more accurately by means of the gas-chromatographic analysis using the correction method based on the relative intensity of the peak area of each component to that of the standard reference material.

Samples for Measurement of physical property values in liquid crystal compounds and so forth Two kinds of samples are used for measuring physical property values of a liquid crystal compound: one is the compound itself, and the other is a mixture of the compound and mother liquid crystals.

In the latter case using a sample in which the compound is mixed with mother liquid crystals, the measurement is carried out according to the following method. First, the sample is prepared by mixing 15% by weight of the liquid crystal compound obtained and 85% by weight of the mother liquid crystals. Then, extrapolated values are calculated from the measured values of the resulting sample by means of an extrapolation method based on the following formula. The extrapolated values are regarded as physical property values of this compound.

(Extrapolated value)=[100×(Measured value of sample)−(% by weight of mother liquid crystals)×(Measured value of mother liquid crystals)]/(% by weight of liquid crystal compound)

When a smectic phase or crystals deposits even at this ratio of the liquid crystal compound to the mother liquid crystals at 25° C., the ratio of the liquid crystal compound to the mother liquid crystals is changed in the order of (10% by weight:90% by weight), (5% by weight:95% by weight) and (1% by weight:99% by weight). Physical property values of the sample are measured at the ratio in which the smectic phase or the crystals have not deposited at 25° C. Extrapolated values are determined according to the above equation, and regards as physical property values of the liquid crystal compound.

There are a variety of mother liquid crystals used for measurement and, for example, the formulation of the mother liquid crystals (i) is shown below.

The Mother Liquid Crystals (i):

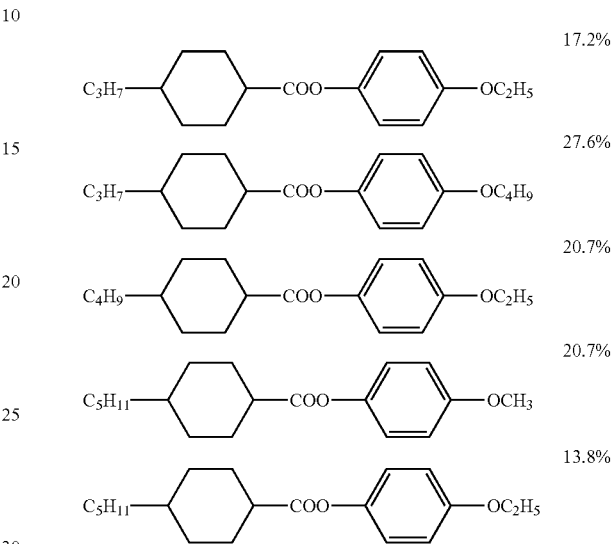

Incidentally, in the case where physical property values of a liquid crystal composition were measured, the liquid crystal composition itself was used as a sample.

Methods for measurement of physical property values of a liquid crystal compound and so forth Physical property values were measured according to the following methods. Most of the measurement methods are those described in the Standard of Electronic Industries Association of Japan, EIAJ•ED-2521A, or those with some modifications. No TFT was attached to a TN device or a VA device used for measurement.

Among measured values, the values obtained from a liquid crystal compound itself as a sample and the values obtained from a liquid crystal composition itself as a sample, were described here as experimental data. When a sample was prepared by mixing the compound with mother liquid crystals, the values calculated from a measured value according to the extrapolation method were described here as extrapolated values.

Phase Structure and Transition Temperature (° C.)

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope while the compound was heated at the rate of 3° C. per minute, and the kinds of phases were specified.

(2) A sample was heated and then cooled at a rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation, and thus the phase transition temperature was determined.

Hereinafter, the symbol C stood for crystals, which were expressed by $C_1$ or $C_2$ when the kinds of crystals were distinguishable. The symbols S and N stood for a smectic phase and a nematic phase, respectively. The symbol I stood for a liquid (isotropic). When a smectic B phase and a smectic A phase were distinguishable in the smectic phases, they were expressed as $S_B$ and $S_A$, respectively. Phase transition temperatures were expressed, for example, as "C 50.0 N 100.0 I", which means that the phase transition temperature from crystals to a nematic phase (CN) is 50.0° C., and the phase transition temperature from the nematic phase to a liquid (NI) is 100.0° C. The same applied to the other descriptions.

Maximum Temperature of a Nematic Phase ($T_{NI}$; ° C.)

A sample (a liquid crystal composition, a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. The maximum temperature of a nematic phase meant a temperature measured when part of the sample began to change from a nematic phase to an isotropic liquid. Hereinafter, the maximum temperature of a nematic phase may simply be abbreviated to "the maximum temperature."

Compatibility at Low Temperatures

Samples were prepared by mixing a liquid crystal compound with mother liquid crystals so that the amount of the liquid crystal compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals or a smectic phase had been deposited.

Viscosity (Bulk Viscosity; η; Measured at 20° C.; mPa·s)

It is characterized that as viscosity (bulk viscosity) is decreased, response time decreases.

An E-type viscometer was used for measurement.

Viscosity (Rotational Viscosity; η; Measured at 25° C.; mPa·s)

It is characterized that as viscosity (rotational viscosity) is decreased, response time decreases.

Measurement was carried out according to the method described in M. Imai, et al., Molecular Crystals and Liquid Crystals, Vol. 259, p. 37 (1995). A sample (a liquid crystal composition, a liquid crystal composition, or a mixture of a liquid crystal compound and mother liquid crystals) was put in a VA device in which the distance between the two glass substrates (cell gap) was 20 micrometers. A voltage in the range of 30 V to 50 V was applied stepwise with an increment of 1 volt to the device. After a period of 0.2 second with no voltage, a voltage was applied repeatedly under the conditions of only one rectangular wave (rectangular pulse; 0.2 second) and no voltage (2 seconds). The peak current and the peak time of the transient current generated by the applied voltage were measured. The value of rotational viscosity was obtained from the measured values and the calculating equation (8) on page 40 of the paper presented by M. Imai, et al. Incidentally, the value of the dielectric anisotropy necessary for the present calculation was obtained by the method described below, under the heading "Dielectric Anisotropy."

Optical Anisotropy (Refractive Index Anisotropy; Δn; Measured at 25° C.)

Measurement was carried out using an Abbe refractometer with a polarizing plate attached to the ocular, using light at a wavelength of 589 nanometers at 25° C. The surface of the main prism was rubbed in one direction, and then a sample (a liquid crystal composition, a liquid crystal composition, or a mixture of a liquid crystal compound and mother liquid crystals) was placed on the main prism. The refractive index (n∥) was measured when the direction of the polarized light was parallel to that of the rubbing. The refractive index (n⊥) was measured when the direction of polarized light was perpendicular to that of the rubbing. The value of the optical anisotropy (Δn) was calculated from the equation: Δn=n∥−n⊥.

Dielectric Anisotropy (Δ∈; Measured at 25° C.)

Dielectric anisotropy was measured by the following method.

An ethanol (20 mL) solution of octadecyltriethoxysilane (0.16 mL) was applied to well-washed glass substrates. The glass substrates were rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film formed on the glass substrates, a TN device in which the distance between the two glass substrates was 9 micrometers and the twist angle was 80 degrees was assembled.

A sample (a liquid crystal composition, a liquid crystal composition, or a mixture of a liquid crystal compound and mother liquid crystals) was put in the resulting VA device, a voltage of 0.5 V (1 kHz, sine waves) was applied to the sample, and then the dielectric constant (∈∥) in the major axis direction of the liquid crystal molecules was measured.

The sample (the liquid crystal composition, or the mixture of the liquid crystal compound and the mother liquid crystals) was put in the resulting TN device, a voltage of 0.5 V (1 kHz, sine waves) was applied to the sample, and then the dielectric constant (∈⊥) in the minor axis direction of the liquid crystal molecules was measured.

The value of the dielectric anisotropy was calculated from the equation of Δ∈=∈∥−∈⊥.

Voltage Holding Ratio (VHR; Measured at 25° C.; %)

A TN device used for measurement had a polyimide-alignment film and the distance between the two glass substrates (cell gap) was 6 micrometers. A sample (a liquid crystal composition, or a mixture of a liquid crystal compound and mother liquid crystals) was put in the device, and then the device was sealed with an adhesive polymerizable on irradiation with ultraviolet light. The TN device was charged by applying pulse voltage (60 microseconds at 5 V). Decreasing voltage was measured for 16.7 milliseconds with a High Speed Voltmeter, and the area A between a voltage curve and a horizontal axis in a unit period was measured. The area B was an area without the decrease. The voltage holding ratio was the percentage of the area A to the area B.

Elastic Constant ($K_{11}$ and $K_{33}$; Measured at 25° C.)

An elastic constant measurement system Model EC-1 made by Toyo Corporation was used for measurement. A sample was put in a homeotropic cell in which the distance between the two glass substrates (cell gap) was 20 micrometers. An electric charge of 20 volts to 0 volts was applied to the cell, and the electrostatic capacity and the applied voltage were measured. The measured values of the electrostatic capacity (C) and the applied voltage (V) were fitted to equation (2.98) and equation (2.101) in page 75 of the "Ekisho Debaisu Handobukku" (Liquid Crystal Device Handbook, in English; The Nikkan Kogyo Shimbun, Ltd.) and the value of the elastic constant was obtained from equation (2.100).

Example 1

Preparation of 4-(trans-4-(2,3-difluoro-4-(hexyloxy)phenyl)cyclohex-1-enyl)-4'-ethoxy-2,2',3,3'-tetrafluorobiphenyl (No. 27)

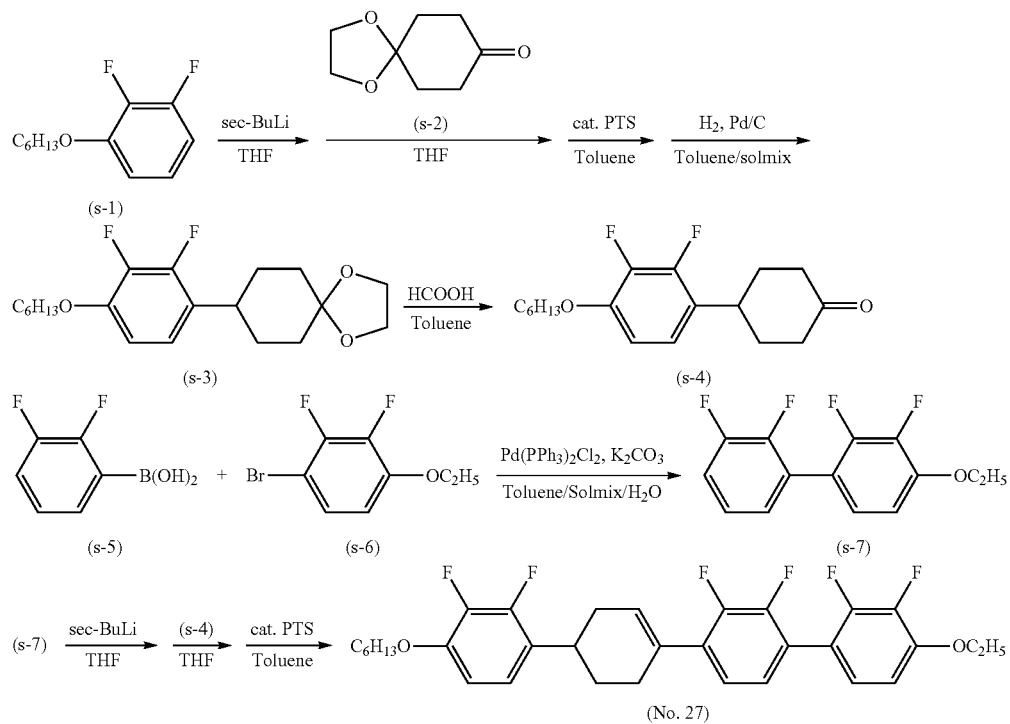

First Step:

1,2-Difluoro-3-hexyloxybenzene (s-1) (100.0 g) and THF (1,000 ml) were placed in a reaction vessel under an atmosphere of nitrogen, and cooled to −74° C. sec-Butyllithium (1.00M; n-hexane and cyclohexane solution; 357 ml) was added dropwise in the temperature range of −74° C. to −70° C., and the stirring was continued for another 2 hours. 1,4-Dioxaspiro[4.5]decan-8-one (s-2) (72.9 g) in a THF (500 ml) solution was added dropwise in the temperature range of −75° C. to −70° C., and the stirring was continued for 8 hours while the mixture was allowed to return to 25° C. The resulting reaction mixture was poured into a vessel containing an aqueous solution of ammonium chloride (1,000 ml) and ethyl acetate (1,000 ml) and mixed with them. The mixture was then allowed to stand until it had separated into organic and aqueous layers, and the extraction was carried out. The resulting organic layers were separated, and washed with water, a saturated aqueous solution of sodium hydrogencarbonate and water, and then dried over anhydrous magnesium sulfate. The solvent was distilled off under reduced pressure. p-Toluenesulfonic acid (4.5 g) and toluene (300 ml) were mixed with the residue, and the mixture was heated to reflux for 2 hours, while distilled water was removed. After the reaction solution had been cooled to 30° C., water (500 ml) and toluene (900 ml) were added and mixed with it. The mixture was then allowed to stand until it had separated into two layers of organic and aqueous layers, and the extraction into an organic layer was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent. The product was dissolved in a mixed solvent of toluene (250 ml) and Solmix A-11 (250 ml), and Pd/C (0.5 g) was added. The mixture was stirred at room temperature under a hydrogen atmosphere until hydrogen absorption had ceased. After the completion of the reaction, Pd/C was removed, and the solvent was distilled off. The resulting residue was purified by column chromatography using silica gel as a stationary phase powder and toluene as an eluent, and further purified by recrystallization from heptane and dried to give 8-(2,3-difluoro-4-hexyloxyphenyl)-1,4-dioxaspiro[4.5]decane (s-3) (144.5 g). The yield based on the compound (s-1) was 87.3%.

Second Step:

The compound (s-3) (144.5 g), formic acid (87%; 188.0 ml) and toluene (400 ml) were mixed, and the mixture was heated to reflux for 2 hours. After the reaction solution had been cooled to 30° C., water (500 ml) and toluene (1,000 ml) were added and mixed with it. The mixture was then allowed to stand until it had separated into two layers of organic and aqueous layers, and the extraction into an organic layer was carried out. The resulting organic layers were separated, and washed with water, a saturated aqueous solution of sodium hydrogencarbonate and water, and then dried over anhydrous magnesium sulfate. The solvent was distilled off under reduced pressure. The resulting residue was purified by column chromatography using silica gel as a stationary phase powder and toluene as an eluent and further purified by recrystallization from heptane and dried to give 1-(2,3-difluoro-4-hexyloxyphenyl)-cyclohexan-4-one (s-4) (123.0 g). The yield based on the compound (s-3) was 97.2%.

Third Step:

4-Bromo-2,3-difluoroethoxybenzene (s-5) (45.2 g), 2,3-difluorophenyllboronic acid (s-6) (36.1 g), potassium carbonate (79.1 g), Pd(Ph$_3$P)$_2$Cl$_2$ (4.0 g), toluene (200 ml), Solmix A-11 (200 ml) and water (200 ml) were placed in a reaction vessel under an atmosphere of nitrogen, and heated to reflux for 2 hours. After the reaction solution had been cooled to 25° C., it was poured into water (200 ml) and toluene (200 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and a mixed solvent of toluene and heptane (toluene:heptane=2:1 by volume) as an eluent, and further purified by recrystallization from Solmix A-11 and dried to give 4-ethoxy-2,2',3,3'-tetrafluoro-1,1'-biphenyl (s-7) (40.1 g). The yield based on the compound (s-5) was 77.8%.

Fourth Step:

The compound (s-7) (10.0 g) and THF (200 ml) were placed in a reaction vessel under an atmosphere of nitrogen, and cooled to −74° C. sec-Butyllithium (1.00M; n-hexane and cyclohexane solution; 44 ml) was added dropwise in the temperature range of −74° C. to −70° C., and the stirring was continued for another 2 hours. The compound (s-4) (11.5 g) in a THF (100 ml) solution was added dropwise in the temperature range of −75° C. to −70° C., and the stirring was continued for 8 hours while the mixture was allowed to return to 25° C. The resulting reaction mixture was poured into a vessel containing an aqueous solution of ammonium chloride (300 ml) and ethyl acetate (300 ml) and mixed with them. The mixture was then allowed to stand until it had separated into organic and aqueous layers, and the extraction was carried out. The resulting organic layers were separated, and washed with water, a saturated aqueous solution of sodium hydrogencarbonate and water, and then dried over anhydrous magnesium sulfate. The solvent was distilled off under reduced pressure. p-Toluenesulfonic acid (0.67 g) and toluene (300 ml) were mixed with the residue, and the mixture was heated to reflux for 2 hours, while distilled water was removed. After the reaction solution had been cooled to 30° C., water (300 ml) and toluene (500 ml) were added and mixed with it. The mixture was then allowed to stand until it had separated into two layers of organic and aqueous layers, and the extraction into an organic layer was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent. The product was further purified by recrystallization from a mixed solvent of ethyl acetate and Solmix A-11 (ethyl acetate:Solmix A-11=2:1 by volume) and dried to give 4-(trans-4-(2,3-difluoro-4-(hexyloxy)phenyl)cyclohex-1-enyl)-4'-ethoxy-2, 2',3,3'-tetrafluorobiphenyl (No. 27) (16.3 g). The yield based on the compound (s-7) was 79.5%.

The chemical shift (δ, ppm) in $^1$H-NMR analysis was described below, and the resulting compound was identified as 4-(trans-4-(2,3-difluoro-4-(hexyloxy)phenyl)cyclohex-1-enyl)-4'-ethoxy-2,2',3,3'-tetrafluorobiphenyl (No. 27). The solvent for measurement was CDCl$_3$.

Chemical shift (δ ppm): 7.07 (m, 3H), 6.91 (t, 1H), 6.81 (t, 1H), 6.71 (t, 1H), 6.12 (m, 1H), 4.17 (q, 2H), 4.02 (q, 2H), 3.22 (m, 1H), 2.70-2.59 (m, 1H), 2.59-2.44 (m, 2H), 2.38-2.30 (m, 1H), 2.08-2.01 (m, 1H), 2.01-1.91 (m, 1H), 1.81 (quin, 2H), 1.51-1.43 (m, 5H), 1.34 (m, 4H) and 0.91 (t, 3H).

Transition temperature was expressed in terms of the measured values of the compound itself. Maximum temperature (T$_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 27) were as follows.

Transition temperature: C 103.9 N 207.7 I.

T$_{NI}$=169.3° C., Δ∈=−10.55, Δn=0.205.

Example 2

Preparation of 4-(trans-4-(2,3-difluoro-4-(hexyloxy)phenyl)cyclohexyl)-4'-ethoxy-2,2',3,3'-tetrafluorobiphenyl (No. 7)

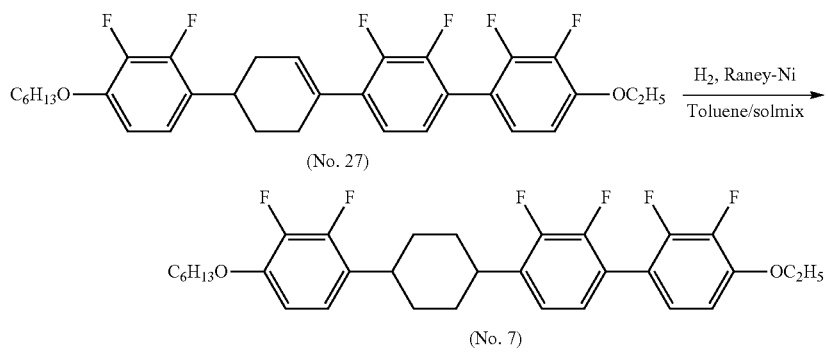

First Step:

The compound (No. 27) (14.4 g) was dissolved in a mixed solvent of toluene (150 ml) and Solmix A-11 (150 ml), to which Raney nickel (1.44 g) was added. The mixture was stirred at room temperature under a hydrogen atmosphere until hydrogen absorption had ceased. After the completion of the reaction, Raney nickel was removed, and the solvent was distilled off. The resulting residue was purified by column chromatography using silica gel as a stationary phase powder and a mixed solvent of heptane and toluene (heptane:toluene=1:2 by volume) as an eluent and further purified by recrystallization from a mixed solvent of ethyl acetate and Solmix A-11 (ethyl acetate:Solmix=1:2 by volume) and dried to give 4-(trans-4-(2,3-difluoro-4-(hexyloxy)phenyl)cyclohexyl)-4'-ethoxy-2,2',3,3'-tetrafluorobiphenyl (No. 7) (6.1 g). The yield based on the compound (No. 27) was 42.3%.

The chemical shift (δ, ppm) in $^1$H-NMR analysis was described below, and the resulting compound was identified as 4-(trans-4-(2,3-difluoro-4-(hexyloxy)phenyl)cyclohexyl)-4'-ethoxy-2,2',3,3'-tetrafluorobiphenyl (No. 7). The solvent for measurement was CDCl$_3$.

Chemical shift (δ ppm): 7.11-7.02 (m, 3H), 6.90 (td, 1H), 6.81 (td, 2H), 6.70 (td, 1H), 6.78 (td, 1H), 4.16 (q, 2H), 4.02 (t, 2H), 3.02 (m, 1H), 2.91 (m, 1H), 2.03 (m, 4H), 1.82 (quin, 2H), 1.77-1.62 (m, 4H), 1.51-1.43 (m, 5H), 1.38-1.31 (m, 4H) and 0.91 (t, 3H).

Transition temperature was expressed in terms of the measured values of the compound itself. Maximum temperature (T$_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 7) were as follows.

Transition temperature: C 116.4 N 239.0 I.
T$_{NI}$=175.6° C., Δ∈=−7.95, Δn=0.180.

Example 3

Preparation of 4-(2-(trans-4-(2,3-difluoro-4-(hexyloxy)phenyl)cyclohexyl)ethyl)-4'-ethoxy-2,2',3,3'-tetrafluorobiphenyl (No. 267)

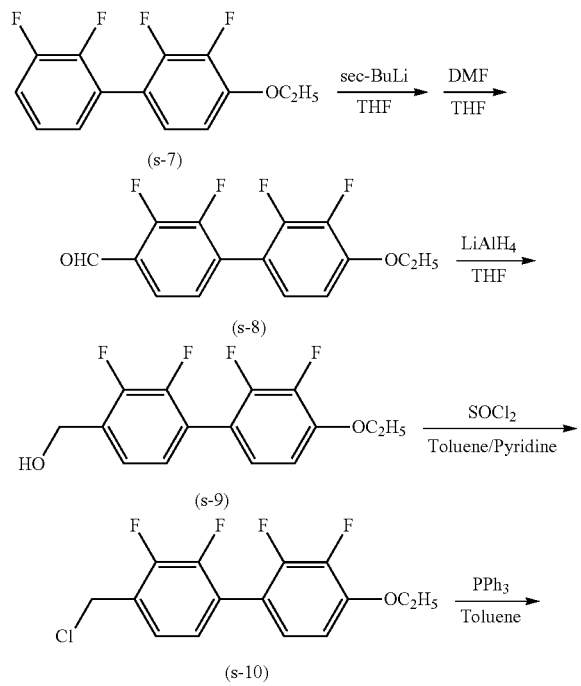

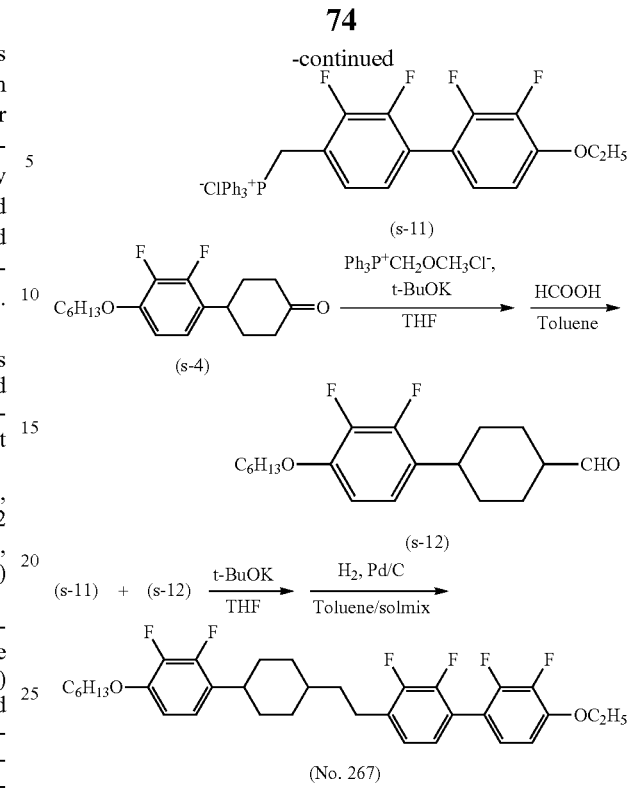

First Step:

4-Ethoxy-2,2',3,3'-tetrafluoro-1,1'-biphenyl (s-7) (28.0 g) and THF (500 ml) were placed in a reaction vessel under an atmosphere of nitrogen, and cooled to −74° C. sec-Butyllithium (1.00M; n-hexane and cyclohexane solution; 109 ml) was added dropwise in the temperature range of −74° C. to −70° C., and the stirring was continued for another 2 hours. N,N-Dimethylformamide (8.0 g) in a THF (200 ml) solution was added dropwise in the temperature range of −75° C. to −70° C., and the stirring was continued for 8 hours while the mixture was allowed to return to 25° C. The resulting reaction mixture was poured into a vessel containing a 1N-HCl aqueous solution (300 ml) and ethyl acetate (300 ml) and mixed with them. The mixture was then allowed to stand until it had separated into organic and aqueous layers, and the extraction was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent and further purified by recrystallization from a mixed solvent of THF and heptane (THF:heptane=1:5 by volume) and dried to give 4'-ethoxy-2,2',3,3'-tetrafluoro-1,1'-biphenyl-4-carboxaldehyde (s-8) (28.0 g). The yield based on the compound (s-7) was 90.6%.

Second Step:

Lithium aluminum hydride (0.76 g) was dispersed in THF (100 ml). The compound (s-8) (10.0 g) was added dropwise to the dispersion in the temperature range of −20° C. to −10° C., and the stirring was continued in this temperature range for another 2 hours. After the completion of reaction had been confirmed by means of GC analysis, ethyl acetate and a saturated aqueous solution of ammonia were successively added to the reaction mixture under ice-cooling, and the deposits were removed by filtration through Celite. The filtrate was extracted with ethyl acetate. The resulting organic layers were washed successively with water and brine, and then dried over anhydrous magnesium sulfate. The product was purified by recrystallization from heptane and dried and concentrated under reduced pressure to give (4'-ethoxy-2,2', 3,3'-tetrafluoro-1,1'-biphenyl-4-yl)methanol (s-9) (9.9 g). The yield based on the compound (s-8) was 98.3%.

Third Step:

The compound (s-9) (9.9 g), toluene (100 ml) and pyridine (0.1 ml) were placed in a reaction vessel under an atmosphere of nitrogen, and stirred at 45° C. for 1 hour. Thionyl chloride (2.9 ml) was added in the temperature range of 45° C. to 55° C., and the mixture was heated to reflux for 2 hours. After the reaction solution had been cooled to 25° C., it was poured into water (200 ml) and toluene (200 ml) and mixed with them. The mixture was then allowed to stand until it had separated into two layers of organic and aqueous layers, and the extraction into an organic layer was carried out. The resulting organic layers were separated, and washed with a saturated aqueous solution of sodium hydrogencarbonate twice and water three times, and then dried over anhydrous magnesium sulfate. The resulting solution was concentrated under reduced pressure. The resulting residue was purified by column chromatography using silica gel as a stationary phase powder and a mixed solvent of toluene and heptane (toluene:heptane=1:1 by volume) as an eluent and further purified by recrystallization from Solmix A-11 and dried to give 4-chloromethyl-4'-ethoxy-2,2',3,3'-tetrafluoro-1,1'-biphenyl (s-10) (8.6 g). The yield based on the compound (s-9) was 81.6%.

Fourth Step:

The compound (s-10) (8.6 g), toluene (100 ml) and triphenylphosphine (14.2 g) were placed in a reaction vessel under an atmosphere of nitrogen, and heated to reflux for 1 hour. After the reaction solution had been cooled to 25° C., the deposits were filtered and washed with toluene three times, washing away the unreacted starting materials, and the resulting colorless solids were dried to give ((4'-ethoxy-2,2',3,3'-tetrafluoro-1,1'-biphenyl-4-yl)methyl)triphenylphosphonium chloride (s-11) (11.8 g). The yield based on the compound (s-10) was 75.3%.

Fifth Step:

Well-dried methoxymethyltriphenylphosphonium chloride (39.8 g) and THF (500 ml) were mixed under an atmosphere of nitrogen, which was cooled to −30° C. Potassium t-butoxide (t-BuOK; 13.0 g) was added in two portions in the temperature range of −30° C. to −20° C. After 30 minutes of stirring at −20° C., the compound (s-4) (30 g) dissolved in THF (100 ml) was added dropwise in the temperature range of −30 to −20° C. The reaction mixture was stirred at −10° C. for 30 minutes, and it was poured into a mixture of water (200 ml) and toluene (200 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and toluene as an eluent. The resulting eluent as concentrated under reduced pressure to give 2,3-difluoro-1-(hexyloxy)-4-(4-(methoxymethylene) cyclohexyl)benzene. Formic acid (87%; 38.9 g) and toluene (200 ml) were added to the product, and the mixture was heated to reflux for 2 hours. After the reaction solution had been cooled to 30° C., water (100 ml) and toluene (200 ml) were added and mixed with it. The mixture was then allowed to stand until it had separated into two layers of organic and aqueous layers, and the extraction into an organic layer was carried out. The resulting organic layers were separated, and washed with water, a saturated aqueous solution of sodium hydrogencarbonate and water, and then dried over anhydrous magnesium sulfate. The solvent was distilled off under reduced pressure to give pale yellow solids. The residue was dissolved in toluene (100 ml), and added to a mixture cooled to 7° C. of sodium hydroxide (95%; 0.5 g) and methanol (400 ml), and the mixture was stirred at 10° C. for 2 hours. A 2N aqueous solution of sodium hydroxide (200 ml) was added, and the mixture was stirred at 5° C. for 2 hours. The resulting reaction mixture was poured into a mixture of water (500 ml) and toluene (500 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The solvent was distilled off under reduced pressure. The resulting residue was concentrated and purified by column chromatography using silica gel as a stationary phase powder and toluene as an eluent and dried to give trans-4-(2,3-difluorophenyl-4-hexyloxy)-cyclohexanecarboxaldehyde (s-12) (28.8 g). The yield based on the compound (s-4) was 81.6%.

Sixth Step:

Well-dried ((4'-ethoxy-2,2',3,3'-tetrafluoro-1,1'-biphenyl-4-yl)methyl)triphenyl phosphonium chloride (s-11) (5.0 g) and THF (100 ml) were mixed under an atmosphere of nitrogen, which was cooled to −10° C. Potassium t-butoxide (t-BuOK; 0.97 g) was added in two portions in the temperature range of −10° C. to −5° C. After 60 minutes of stirring at −10° C., the compound (s-12) (2.3 g) dissolved in THF (30 ml) was added dropwise in the temperature range of −10 to −5° C. After 30 minutes of stirring at 0° C., the reaction mixture was poured into water (100 ml) and toluene (50 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and toluene as an eluent, and the resulting eluent as concentrated under reduced pressure. The residue was dissolved in a mixed solvent of toluene (150 ml) and Solmix A-11 (150 ml), and Pd/C (0.1 g) was added. The mixture was stirred at room temperature under a hydrogen atmosphere until hydrogen absorption had ceased. After the completion of the reaction, Pd/C was removed, and the solvent was distilled off. The resulting residue was purified by recrystallization from a mixed solvent of ethyl acetate and Solmix A-11 (ethyl acetate:Solmix=1:4 by volume) to give 4-(2-(trans-4-(2,3-difluoro-4-(hexyloxy)phenyl)cyclohexyl)ethyl)-4'-ethoxy-2,2',3,3'-tetrafluorobiphenyl (No. 267) (1.4 g). The yield based on the compound (s-12) was 34.0%.

The chemical shift (δ, ppm) in $^1$H-NMR analysis was described below, and the resulting compound was identified as 4-(2-(trans-4-(2,3-difluoro-4-(hexyloxy)phenyl)cyclohexypethyl)-4'-ethoxy-2,2',3,3'-tetrafluorobiphenyl (No. 267). The solvent for measurement was $CDCl_3$.

Chemical shift (δ ppm): 6.99 (m, 3H), 6.82 (m, 2H), 6.65 (t, 1H), 4.17 (q, 2H), 4.01 (t, 2H), 2.73 (m, 3H), 1.95 (m, 2H), 1.88 (m, 2H), 1.80 (quin, 2H), 1.60 (q, 2H), 1.52-1.42 (m, 7H), 1.42-1,30(m, 5H), 1.21-1, 12(m, 2H) and 0.91 (t, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 267) were as follows.

Transition temperature: C 109.8 N 184.6 I.
$T_{NI}$=165.6° C., $\Delta\varepsilon$=−8.17, $\Delta n$=0.149.

Example 4

Preparation of 4-(trans-4-(2,3-difluoro-4-(hexyloxy)phenethyl)cyclohexyl)-4'-ethoxy-2,2',3,3'-tetrafluorobiphenyl (No. 67)

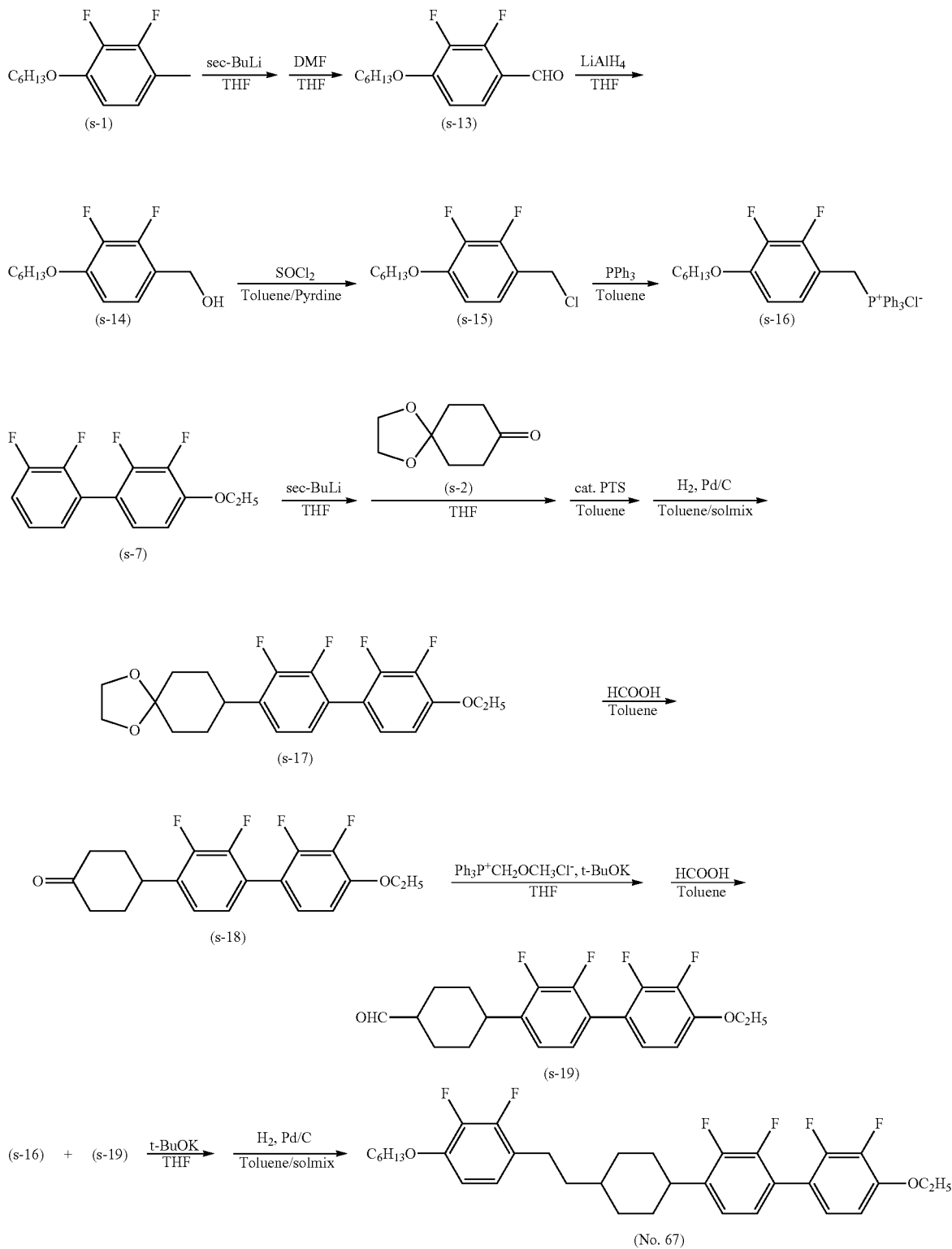

First Step:

2,3-Difluorohexyloxybenzene (s-1) (28.0 g) and THF (500 ml) were placed in a reaction vessel under an atmosphere of nitrogen, and cooled to −74° C. sec-Butyllithium (1.00M; n-hexane and cyclohexane solution; 109 ml) was added dropwise in the temperature range of −74° C. to −70° C., and the stirring was continued for another 2 hours. N,N-Dimethylformamide (8.0 g) in a THF (200 ml) solution was added dropwise in the temperature range of −75° C. to −70° C., and the stirring was continued for 8 hours while the mixture was allowed to return to 25° C. The resulting reaction mixture was poured into a vessel containing a 1N-HCl aqueous solution (300 ml) and ethyl acetate (300 ml) and mixed with them. The mixture was then allowed to stand until it had separated into organic and aqueous layers, and the extraction was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent, and further purified by recrystallization from a mixed solvent of THF and heptane (THF:heptane=1:5 by volume) and dried to give 2,3-difluoro-4-hexyloxybenzenecarboxaldehyde (s-13) (28.0 g). The yield based on the compound (s-1) was 90.6%.

Second Step:

Lithium aluminum hydride (0.76 g) was dispersed in THF (100 ml). The compound (s-13) (10.0 g) was added dropwise to the dispersion in the temperature range of −20° C. to −10° C., and the stirring was continued in this temperature range for another 2 hours. After the completion of reaction had been confirmed by means of GC analysis, ethyl acetate and a saturated aqueous solution of ammonia were successively added to the reaction mixture under ice-cooling, and the deposits were removed by filtration through Celite. The filtrate was extracted with ethyl acetate. The resulting organic layers were successively washed with water and brine, and then dried over anhydrous magnesium sulfate. The product was purified by recrystallization from heptane and dried and concentrated under reduced pressure to give (2,3-difluoro-4-hexyloxy)benzyl alcohol (s-14) (9.9 g). The yield based on the compound (s-13) was 98.3%.

Third Step:

The compound (s-14) (9.9 g), toluene (100 ml) and pyridine (0.1 ml) were placed in a reaction vessel under an atmosphere of nitrogen, and heated at 45° C. for 1 hour. Thionyl chloride (2.9 ml) was added in the temperature range of 45° C. to 55° C., and the mixture was heated to reflux for 2 hours. After the reaction solution had been cooled to 25° C., it was poured into water (200 ml) and toluene (200 ml) and mixed with them. The mixture was then allowed to stand until it had separated into two layers of organic and aqueous layers, and the extraction into an organic layer was carried out. The resulting organic layers were separated, and washed with a saturated aqueous solution of sodium hydrogencarbonate twice and water three times, and then dried over anhydrous magnesium sulfate. The resulting solution was concentrated under reduced pressure. The resulting residue was purified by column chromatography using silica gel as a stationary phase powder and a mixed solvent of toluene and heptane (toluene:heptane=1:1 by volume) as an eluent, and further purified by recrystallization from Solmix A-11 and dried to give (4-chloromethyl-2,3-difluoro)hexyloxybenzene (s-15) (8.6 g). The yield based on the compound (s-14) was 81.6%.

Fourth Step:

The compound (s-15) (8.6 g), toluene (100 ml) and triphenylphosphine (14.2 g) were placed in a reaction vessel under an atmosphere of nitrogen, and heated to reflux for 1 hour. After the reaction solution had been cooled to 25° C., the deposits were filtered and washed with toluene three times, washing away the unreacted starting materials, and the resulting colorless solids were dried to give (2,3-difluoro-4-hexyloxybenzyl)triphenylphosphonium chloride (s-16) (11.8 g). The yield based on the compound (s-15) was 75.3%.

Fifth Step:

4-Ethoxy-2,2',3,3'-tetrafluoro-1,1'-biphenyl (s-7) (8.0 g) and THF (100 ml) were placed in a reaction vessel under an atmosphere of nitrogen, and cooled to −74° C. sec-Butyllithium (1.00M; n-hexane and cyclohexane solution; 31 ml) was added dropwise in the temperature range of −74° C. to −70° C., and the stirring was continued for another 2 hours. 1,4-Dioxaspiro[4.5]decan-8-one (s-2) (4.9 g) in a THF (50 ml) solution was added dropwise in the temperature range of −75° C. to −70° C., and the stirring was continued for 8 hours while the mixture was allowed to return to 25° C. The resulting reaction mixture was poured into a vessel containing a 1N-HCl aqueous solution (100 ml) and ethyl acetate (100 ml) and mixed with them. The mixture was then allowed to stand until it had separated into organic and aqueous layers, and the extraction was carried out. The resulting organic layers were separated, and washed with a saturated aqueous solution of sodium hydrogencarbonate and water, and then dried over anhydrous magnesium sulfate. The solvent was distilled off under reduced pressure. p-Toluenesulfonic acid (0.27 g) and toluene (100 ml) were added and the mixture was heated to reflux for 2 hours, while distilled water was removed. After the reaction solution had been cooled to 30° C., water (200 ml) and toluene (100 ml) were added and mixed with it. The mixture was then allowed to stand until it had separated into two layers of organic and aqueous layers, and the extraction into an organic layer was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent. The product was dissolved in a mixed solvent of toluene (100 ml) and Solmix A-11 (100 ml), and Pd/C (0.1 g) was added. The mixture was stirred at room temperature under a hydrogen atmosphere until hydrogen absorption had ceased. After the completion of the reaction, Pd/C was removed, and the solvent was distilled off. The resulting residue was purified by column chromatography using silica gel as a stationary phase powder and toluene as an eluent, and further purified by recrystallization from heptane and dried to give 8-(4'-ethoxy-2,2',3,3'-tetrafluorobiphenyl-4-yl)-1,4-dioxaspiro[4.5]decane (s-17) (6.5 g). The yield based on the compound (7) was 53.2%.

Sixth Step:

The compound (s-17) (6.5 g), formic acid (87%; 7.3 ml) and toluene (100 ml) were mixed, and the mixture was heated to reflux for 2 hours. After the reaction solution had been cooled to 30° C., water (100 ml) and toluene (100 ml) were added and mixed with it. The mixture was then allowed to stand until it had separated into two layers of organic and aqueous layers, and the extraction into an organic layer was carried out. The resulting organic layers were separated, and washed with water, a saturated aqueous solution of sodium hydrogencarbonate and water, and then dried over anhydrous magnesium sulfate. The solvent was distilled off under reduced pressure. The resulting residue was purified by column chromatography using silica gel as a stationary phase powder and toluene as an eluent, and further purified by recrystallization from heptane and dried to give 4-(4'-ethoxy- 2,2',3,3'-tetrafluorobiphenyl-4-yl)cyclohexanone (s-18) (5.8 g). The yield based on the compound (s-17) was 99.5%.

Seventh Step:

Well-dried methoxymethyltriphenylphosphonium chloride (6.5 g) and THF (100 ml) were mixed under an atmosphere of nitrogen, which was cooled to −30° C. Potassium t-butoxide (t-BuOK; 2.1 g) was added in two portions in the temperature range of −30° C. to −20° C. After 30 minutes of stirring at −20° C., the compound (s-18) (5.8 g) dissolved in THF (50 ml) was added dropwise in the temperature range of −30 to −20° C. After 30 minutes of stirring at −10° C., the reaction mixture was poured into a mixture of water (200 ml) and toluene (200 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and toluene as an eluent. The resulting solution was concentrated under reduced pressure. Formic acid (87%; 38.9 g) and toluene (200 ml) were added and the mixture was heated reflux for 2 hours. After the reaction solution had been cooled to 30° C., water (100 ml) and toluene (200 ml) were added and mixed with it. The mixture was then allowed to stand until it had separated into two layers of organic and aqueous layers, and the extraction into an organic layer was carried out. The resulting organic layers were separated, and washed with water, a saturated aqueous solution of sodium hydrogencarbonate and water, and then dried over anhydrous magnesium sulfate. The solvent was distilled off under reduced pressure to give pale yellow solids. The residue was dissolved in toluene (50 ml), and added to a mixture cooled to 7° C. of sodium hydroxide (95%; 0.5 g) and methanol (200 ml), and the stirring was continued at 10° C. for 2 hours. A 2N aqueous solution of sodium hydroxide (100 ml) was added at 5° C., and the stirring was continued for another 2 hours. The resulting reaction mixture was poured into a mixture of water (100 ml) and toluene (100 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The solvent was distilled off under reduced pressure. The resulting residue was concentrated and purified by column chromatography using silica gel as a stationary phase powder and toluene as an eluent and dried to give trans-4-(4'-ethoxy-2,2',3,3'-tetrafluorobiphenyl-4-yl)cyclohexanecarboxaldehyde (s-19) (6.0 g). The yield based on the compound (s-18) was 96.1%.

Eighth Step:

Well-dried (2,3-difluoro-4-hexyloxybenzyl)triphenylphosphonium chloride (s-16) (4.6 g) and THF (100 ml) were mixed under an atmosphere of nitrogen, which was cooled to −10° C. Potassium t-butoxide (t-BuOK; 1.0 g) was added in the temperature range of −10° C. to −5° C. After 60 minutes of stirring at −10° C., the compound (s-19) (2.8 g) dissolved in THF (30 ml) was added dropwise in the temperature range of −10 to −5° C. After 30 minutes of stirring at 0° C., the reaction mixture was poured into a mixture of water (100 ml) and toluene (100 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and toluene as an eluent, and the eluent was concentrated under reduced pressure. The residue was dissolved in a mixed solvent of toluene (100 ml) and Solmix A-11 (100 ml), and Pd/C (0.1 g) was added. The mixture was stirred at room temperature under a hydrogen atmosphere until hydrogen absorption had ceased. After the completion of the reaction, Pd/C was removed, and the solvent was distilled off. The resulting residue was purified by recrystallization from a mixed solvent of ethyl acetate and Solmix A-11 (ethyl acetate:Solmix=1:4 by volume) to give trans-4-(4-(2,3-difluoro-4-(hexyloxy)phenethyl)cyclohexyl)-4'-ethoxy-2,2',3,3'-tetrafluorobiphenyl (No. 67) (1.9 g). The yield based on the compound (s-19) was 42.4%.

The chemical shift (δ, ppm) in $^1$H-NMR analysis was described below, and the resulting compound was identified as trans-4-(4-(2,3-difluoro-4-(hexyloxy)phenethyl)cyclohexyl)-4'-ethoxy-2,2',3,3'-tetrafluorobiphenyl (No. 67). The solvent for measurement was $CDCl_3$.

Chemical shift (δ ppm): 7.05 (m, 3H), 6.82 (m, 2H), 6.68 (t, 1H), 4.18 (q, 2H), 4.03 (t, 2H), 2.91 (m, 1H), 2.66 (t, 2H), 1.96 (m, 4H), 1.82 (quin, 2H), 1.58-1.43 (m, 9H), 1.36 (m, 5H), 1.24-1.14 (m, 2H) and 0.92 (t, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 67) were as follows.

Transition temperature: C 78.9 N 192.2 I.

$T_{NI}$=165.9° C., Δ∈=−9.87, Δn=0.175.

Example 5

Preparation of trans-4-(4-((2,3-difluoro-4-(hexyloxy)phenoxy)methyl)cyclohexyl)-4'-ethoxy-2,2',3,3'-tetrafluorobiphenyl (No. 107)

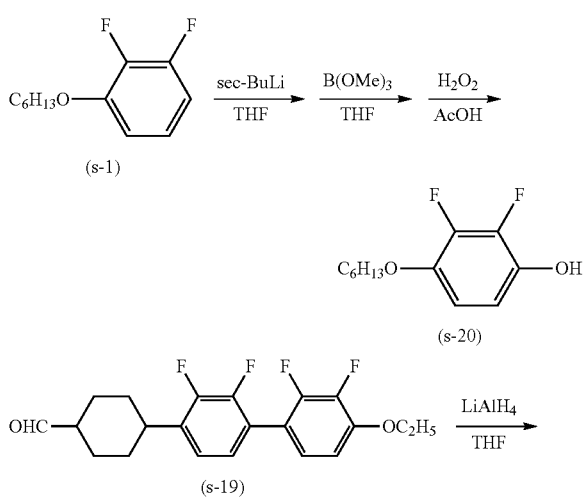

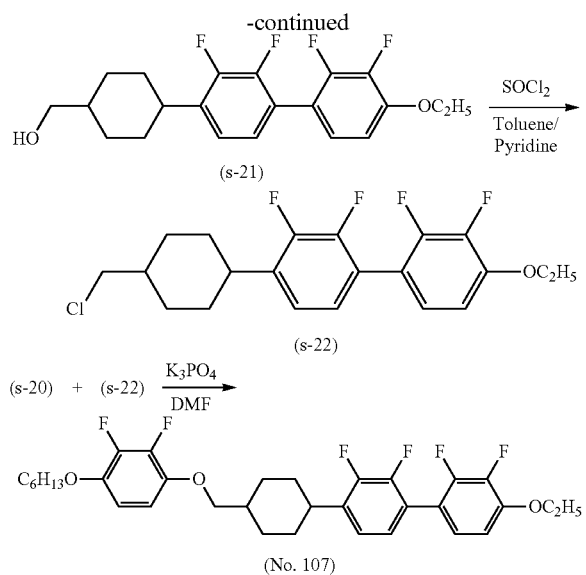

First Step:

1,2-Difluoro-3-hexyloxybenzene (s-1) (17.8 g) and THF (500 ml) were placed in a reaction vessel under an atmosphere of nitrogen, and cooled to −74° C. n-Butyllithium (1.57M; n-hexane and cyclohexane solution; 58.0 ml) was added dropwise in the temperature range of −74° C. to −70° C., and the stirring was continued for another 2 hours. Trimethyl borate (9.5 g) in a THF (50 ml) solution was added dropwise in the temperature range of −74° C. to −65° C., and the stirring was continued for 8 hours while the mixture was allowed to return to 25° C. The reaction mixture was poured into a vessel containing 1N-hydrochloric acid (100 ml) and ice-water (500 ml) and mixed with them. Ethyl acetate (300 ml) was added, and mixture was then allowed to stand until it had separated into organic and aqueous layers, and the extraction was carried out. The resulting organic layers were separated, and washed successively with water, a saturated aqueous solution of sodium hydrogencarbonate and brine, and then dried over anhydrous magnesium sulfate. The solvent was distilled off under reduced pressure. The residue and acetic acid (100 ml) were placed in a reaction vessel at room temperature under an atmosphere of nitrogen, and an aqueous solution of hydrogen peroxide (31%; 10.1 ml) was added dropwise in the temperature range of 25° C. to 30° C., and the stirring was continued for another 2 hours. The reaction mixture was poured into a vessel containing an aqueous solution of sodium hydrogen sulfite (100 ml) and ethyl acetate (300 ml) and mixed with them. The mixture was then allowed to stand until it had separated into organic and aqueous layers, and the extraction was carried out. The resulting organic layers were separated, and washed successively with water and brine, and then dried over anhydrous magnesium sulfate. The solvent was distilled off under reduced pressure to give 1,2-difluoro-3-hexyloxyphenol (s-20) (12.8 g). The yield based on the compound (s-1) was 66.6%.

Second Step:

Lithium aluminum hydride (0.20 g) was dispersed in THF (100 ml). The compound (s-19) (3.0 g) was added dropwise to the dispersion in the temperature range of −20° C. to −10° C., and the stirring was continued in this temperature range for another 2 hours. After the completion of reaction had been confirmed by means of GC analysis, ethyl acetate and a saturated aqueous solution of ammonia were added successively to the reaction mixture under ice-cooling, and the deposits were removed by filtration through Celite. The filtrate was extracted with ethyl acetate. The resulting organic layers were washed successively with water and brine, and then dried over anhydrous magnesium sulfate, and further purified by recrystallization from heptane and dried and concentrated under reduced pressure to give (trans-4-(4'-ethoxy-2,2',3,3'-tetrafluorobiphenyl-4-yl)cyclohexyl)methanol (s-21) (2.7 g). The yield based on the compound (s-19) was 89.5%.

Third Step:

The compound (s-21) (2.7 g), toluene (50 ml) and pyridine (0.1 ml) were placed in a reaction vessel under an atmosphere of nitrogen, and stirred at 45° C. for 1 hour. Thionyl chloride (0.56 ml) was added in the temperature range of 45° C. to 55° C., and the mixture was heated to reflux for 2 hours. After the reaction solution had been cooled to 25° C., it was poured into water (100 ml) and toluene (100 ml) and mixed with them. The mixture was then allowed to stand until it had separated into two layers of organic and aqueous layers, and the extraction into an organic layer was carried out. The resulting organic layers were separated, and washed with a saturated aqueous solution of sodium hydrogencarbonate twice and water three times, and then dried over anhydrous magnesium sulfate. The resulting solution was concentrated under reduced pressure. The resulting residue was purified by column chromatography using silica gel as a stationary phase powder and a mixed solvent of toluene and heptane (toluene:heptane=1:1 by volume) as an eluent, and further purified by recrystallization from Solmix A-11 and dried to give (trans-4-(4-(chloromethyl)cyclohexyl)-4'-ethoxy-2,2',3,3'-tetrafluorobiphenyl (s-22) (2.6 g). The yield based on the compound (s-21) was 91.9%.

Fourth Step:

1,2-Difluoro-3-hexyloxyphenol (s-20) (1.8 g) and tripotassium phosphate (K$_3$PO$_4$; 13.8 g) were added to DMF (100 ml) under an atmosphere of nitrogen, and the mixture was stirred at 80° C. The compound (s-22) (2.6 g) was added, and the mixture was stirred at 80° C. for 7 hours. After the reaction solution had been cooled to 30° C., the solids were separated by filtration, and toluene (100 ml) and water (100 ml) were added and mixed with the filtrate. The mixture was then allowed to stand until it had separated into two layers of organic and aqueous layers, and the extraction into an organic layer was carried out. The resulting organic layers were separated, and washed with brine, and then dried over anhydrous magnesium sulfate. The solvent was distilled off under reduced pressure. The resulting residue was purified by column chromatography using silica gel as a stationary phase powder and a mixed solvent of heptane and toluene (heptane:toluene=1:2 by volume) as an eluent, and further purified by recrystallization from a mixed solvent of Solmix A-11 and heptane (Solmix A-11:heptane=1:2 by volume) and dried to give trans-4-(4-((2,3-difluoro-4-(hexyloxy)phenoxy)methyl)cyclohexyl)-4'-ethoxy-2,2',3,3'-tetrafluorobiphenyl (No. 107)1.2 g). The yield based on the compound (s-22) was 31.1%.

The chemical shift (δ, ppm) in $^1$H-NMR analysis was described below, and the resulting compound was identified as trans-4-(4-((2,3-difluoro-4-(hexyloxy)phenoxy)methyl)cyclohexyl)-4'-ethoxy-2,2',3,3'-tetrafluorobiphenyl (No. 107). The solvent for measurement was CDCl$_3$.

Chemical shift (δ ppm): 7.05 (m, 3H), 6.81 (t, 1H), 6.63 (d, 2H), 4.17 (q, 2H), 3.98 (t, 2H), 3.84 (d, 2H), 2.93 (m, 1H), 2.07 (m, 2H), 1.99 (m, 2H), 1.92 (m, 1H), 1.79 (quin, 2H), 1.64-1.42 (m, 7H), 1.38-1.24 (m, 6H) and 0.91 (t, 3H).

Transition temperature was expressed in terms of the measured values of the compound itself. Maximum temperature ($T_{NI}$), dielectric anisotropy ($\Delta\varepsilon$) and optical anisotropy ($\Delta n$) were expressed in terms of extrapolated values calculated from the measured values of the sample, in which the compound was mixed with the mother liquid crystals (i), according to the extrapolation method described above. The physical property values of the compound (No. 107) were as follows.

Transition temperature: C 89.3 N 185.2 I.
$T_{NI}$=165.6° C., $\Delta\varepsilon$=−9.26, $\Delta n$=0.179.

Example 6

Preparation of 1-(2,3-difluoro-4-(hexyloxy)phenethyl)-4-(4-(4-ethoxy-2,3-difluorophenyl)cyclohex-1-enyl)-2,3-difluorobenzene (No. 487)

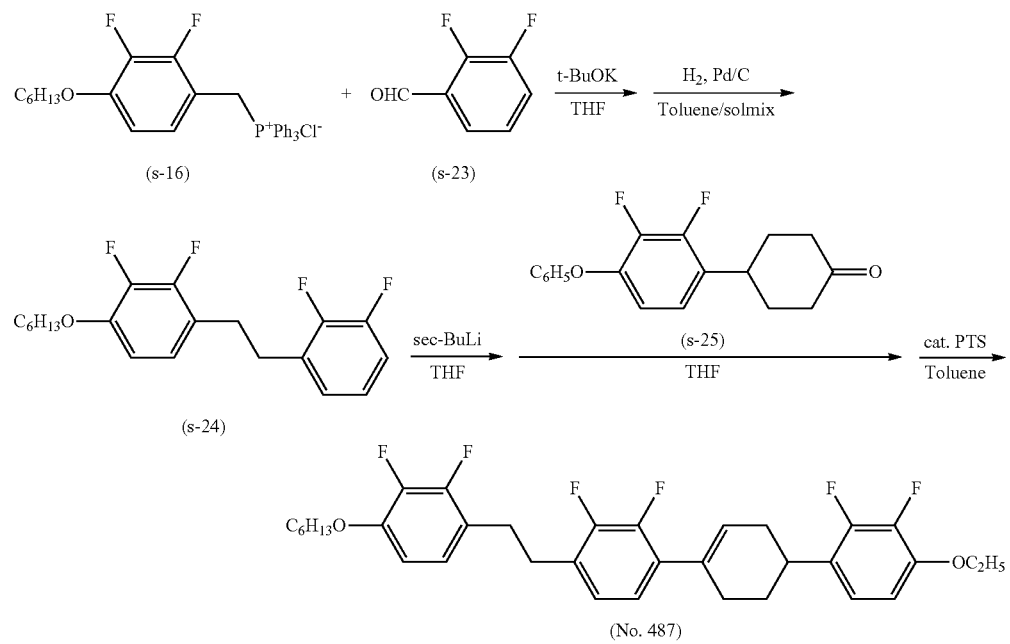

First Step:
Well-dried (2,3-difluoro-4-hexyloxybenzyl)triphenylphosphonium chloride (s-16) (7.5 g) and THF (100 ml) were mixed under an atmosphere of nitrogen, which was cooled to −10° C. Potassium t-butoxide (t-BuOK; 1.6 g) was added in the temperature range of −10° C. to −5° C. After 60 minutes of stirring at −10° C., 2,3-difluorobenzaldehyde (s-23) (1.9 g) dissolved in THF (30 ml) was added dropwise in the temperature range of −10 to −5° C. After 30 minutes of stirring at 0° C., the reaction mixture was poured into a mixture of water (100 ml) and toluene (100 ml) and mixed with them. The mixture was then allowed to stand until it had separated into two layers of organic and aqueous layers, and the extraction into an organic layer was carried out. The resulting organic layers were separated, and washed with water, and then dried over anhydrous magnesium sulfate. The resulting solution was concentrated under reduced pressure. The resulting residue was purified by column chromatography using silica gel as a stationary phase powder and toluene as an eluent, and the eluent was concentrated under reduced pressure. The residue was dissolved in a mixed solvent of toluene (100 ml) and Solmix A-11 (100 ml), and Pd/C (0.1 g) was added. The mixture was stirred at room temperature under a hydrogen atmosphere until hydrogen absorption had ceased. After the completion of the reaction, Pd/C was removed, and the solvent was distilled off. The resulting residue was purified by recrystallization from a mixed solvent of ethyl acetate and Solmix A-11 (ethyl acetate:Solmix=1:4 by volume) to give 1-(2,3-difluorophenethyl)-2,3-difluoro-4-(hexyloxy)benzene (s-24) (3.6 g). The yield based on the compound (s-23) was 76.0%.

Second Step:
1-(2,3-Difluorophenethyl)-2,3-difluoro-4-(hexyloxy)benzene (s-24) (3.6 g) and THF (100 ml) were placed in a reaction vessel under an atmosphere of nitrogen, and cooled to −74° C. sec-Butyllithium (1.00M; n-hexane and cyclohexane solution; 12 ml) was added dropwise in the temperature range of −74° C. to −70° C., and the stirring was continued for another 2 hours. 1-(2,3-Difluoro-4-ethoxyphenyl)-cyclohexan-4-one (s-25) (2.6 g) in a THF (50 ml) solution was added dropwise in the temperature range of −75° C. to −70° C., and the stirring was continued for 8 hours while the mixture was allowed to return to 25° C. The resulting reaction mixture was poured into a vessel containing a 1N-HCl aqueous solution (100 ml) and ethyl acetate (100 ml) and mixed with them. The mixture was then allowed to stand until it had separated into organic and aqueous layers, and the extraction was carried out. The resulting organic layers were separated, and washed with a saturated aqueous solution of sodium hydrogencarbonate and water, and then dried over anhydrous magnesium sulfate. The solvent was distilled off under reduced pressure. p-Toluenesulfonic acid (0.19 g) and toluene (100 ml) were added, and the mixture was heated to reflux for 2 hours, while distilled water was removed. After the reaction solution had been cooled to 30° C., water (200 ml) and toluene (100 ml) were added and mixed with it. The mixture was then allowed to stand until it had separated into two layers of organic and aqueous layers, and the extraction into an organic layer was carried out. The resulting organic layers were separated, and washed with a saturated aqueous solution of sodium hydrogencarbonate and water, and then dried over anhydrous magnesium sulfate. The resulting solution was purified by column chromatography using silica gel as a stationary phase powder and toluene as an eluent, and further purified by recrystallization from a mixed solvent of Solmix A-11 and heptane (Solmix A-11:heptane=1:2 by volume) and dried to give 1-(2,3-difluoro-4-(hexyloxy)phenethyl)-4-(4-(4-ethoxy-2,3-difluorophenyl)cyclohex-1-enyl)-2,3-difluorobenzene (No. 487) (3.1 g). The yield based on the compound (s-24) was 33.8%.

The chemical shift (δ, ppm) in $^1$H-NMR analysis was described below, and the resulting compound was identified as 1-(2,3-difluoro-4-(hexyloxy)phenethyl)-4-(4-(4-ethoxy-2,3-difluorophenyl)cyclohex-1-enyl)-2,3-difluorobenzene (No. 487). The solvent for measurement was CDCl$_3$.

Chemical shift (δ ppm): 6.90 (t, 2H), 6.81 (t, 1H), 6.76 (t, 1H), 6.70 (t, 1H), 6.63 (td, 1H), 6.03 (m, 1H), 4.11 (q, 2H), 4.00 (t, 2H), 3.19 (m, 1H), 2.91 (m, 4H), 2.65-2.39 (m, 3H), 2.35-2.26 (m, 1H), 2.04-1.98 (m, 1H), 1.98-1.88 (m, 1H), 1.80 (quin, 2H), 1.45 (m, 5H), 1.34 (m, 4H) and 0.91 (t, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 487) were as follows.

Transition temperature: C 81.8 N 148.1 I.
$T_{NI}$=133.9° C., Δ∈=−9.04, Δn=0.174.

Example 7

A variety of compounds were prepared using starting materials corresponding to them according to the procedure shown in Examples 1 to 6, and they were confirmed as objective compounds.

4'-(4-(2,3-Difluoro-4-(hexyloxy)phenyl)cyclohex-1-enyl)-4-ethoxy-2,2',3-trifluorobiphenyl (No. 33)

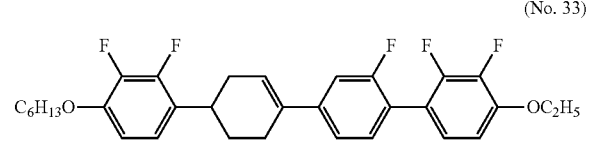

(No. 33)

The chemical shift (δ, ppm) in $^1$H-NMR analysis was described below, and the resulting compound was identified as 4'-(4-(2,3-difluoro-4-(hexyloxy)phenyl)cyclohex-1-enyl)-4-ethoxy-2,2',3-trifluorobiphenyl (No. 33). The solvent for measurement was CDCl$_3$.

Chemical shift (δ ppm): 7.31 (t, 1H), 7.26 (m, 1H), 7.20 (d, 1H), 7.06 (td, 1H), 6.90 (td, 1H), 6.80 (td, 1H), 6.70 (td, 1H), 6.29 (m, 1H), 4.17 (q, 2H), 4.02 (t, 2H), 3.18 (m, 1H), 2.66-2.50 (m, 3H), 2.38-2.29 (m, 1H), 2.12-2.04 (m, 1H), 1.99-1.90 (m, 1H), 1.81 (quin, 2H), 1.52-1.43 (m, 5H), 1.34 (m, 4H) and 0.91 (t, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 33) were as follows.

Transition temperature: C 108.9 S$_A$ 136.2 N 214.2 I.
$T_{NI}$=178.6° C., Δ∈=−8.54, Δn=0.219.

4'-(trans-4-(2,3-Difluoro-4-(hexyloxy)phenyl)cyclohexyl)-4-ethoxy-2,2',3-trifluorobiphenyl (No. 13)

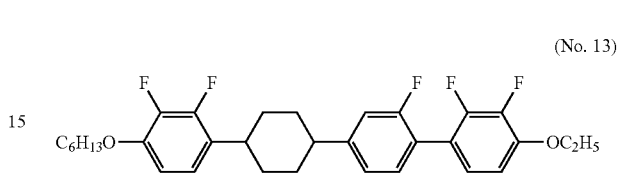

(No. 13)

The chemical shift (δ, ppm) in $^1$H-NMR analysis was described below, and the resulting compound was identified as 4'-(trans-4-(2,3-difluoro-4-(hexyloxy)phenyl)cyclohexyl)-4-ethoxy-2,2',3-trifluorobiphenyl (No. 13). The solvent for measurement was CDCl$_3$.

Chemical shift (δ ppm): 7.30 (t, 1H), 7.09 (d, 1H), 7.03 (m, 2H), 6.89 (td, 1H), 6.80 (td, 1H), 6.70 (td, 1H), 4.16 (q, 2H), 4.02 (t, 2H), 2.88 (m, 1H), 2.64 (m, 1H), 2.10-1.96 (m, 4H), 1.81 (quin, 2H), 1.65 (m, 4H), 1.52-1.43 (m, 5H), 1.34 (m, 4H) and 0.91 (t, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 13) were as follows.

Transition temperature: C 101.4 S$_A$ 121.4 N 232.7 I.
$T_{NI}$=170.6° C., Δ∈=−8.85, Δn=0.201.

4'-(4-(2,3-Difluoro-4-(hexyloxy)phenyl)cyclohex-1-enyl)-4-ethoxy-2,3,3'-trifluorobiphenyl (No. 38)

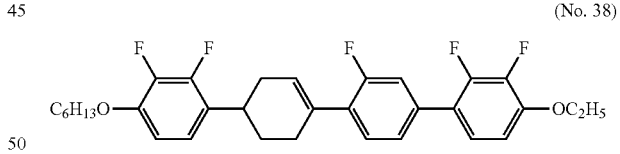

(No. 38)

The chemical shift (δ, ppm) in $^1$H-NMR analysis was described below, and the resulting compound was identified as 4'-(4-(2,3-difluoro-4-(hexyloxy)phenyl)cyclohex-1-enyl)-4-ethoxy-2,3,3'-trifluorobiphenyl (No. 38). The solvent for measurement was CDCl$_3$.

Chemical shift (δ ppm): 7.32 (t, 1H), 7.25 (d, 2H), 7.21 (d, 1H), 7.11 (t, 1H), 6.91 (t, 1H), 6.80 (t, 1H), 6.70 (t, 1H), 6.08 (m, 1H), 4.16 (q, 2H), 4.02 (t, 2H), 3.20 (m, 1H), 2.64 (m, 1H), 2.51 (m, 2H), 2.33 (m, 1H), 2.06-1.91 (m, 2H), 1.81 (quin, 2H), 1.52-1.43 (m, 4H), 1.38-1.30 (m, 4H) and 0.90 (m, 3H).

Transition temperature was expressed in terms of the measured values of the compound itself. Maximum temperature ($T_{NI}$), dielectric anisotropy (Δ∈) and optical anisotropy (Δn) were expressed in terms of extrapolated values calculated from the measured values of the sample, in which the compound was mixed with the mother liquid crystals (i), according to the extrapolation method described above. The physical property values of the compound (No. 38) were as follows.

Transition temperature: C 106.3 N 218.6 I.

$T_{NI}$=180.6° C., $\Delta\varepsilon$=−8.64, $\Delta n$=0.226.

4'-(trans-4-(2,3-Difluoro-4-(hexyloxy)phenyl)cyclo-hexyl)-4-ethoxy-2,3,3'-trifluorobiphenyl (No. 18)

(No. 18)

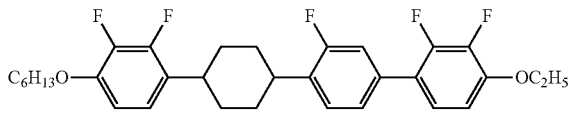

The chemical shift (δ, ppm) in ¹H-NMR analysis was described below, and the resulting compound was identified as 4'-(trans-4-(2,3-difluoro-4-(hexyloxy)phenyl)cyclohexyl)-4-ethoxy-2,3,3'-trifluorobiphenyl (No. 18). The solvent for measurement was CDCl$_3$.

Chemical shift (δ ppm): 7.30 (t, 1H), 7.09 (d, 1H), 7.03 (m, 2H), 6.89 (td, 1H), 6.80 (td, 1H), 6.70 (td, 1H), 4.16 (q, 2H), 4.02 (t, 2H), 2.88 (m, 1H), 2.64 (m, 1H), 2.10-1.96 (m, 4H), 1.81 (quin, 2H), 1.65 (m, 4H), 1.52-1.43 (m, 5H) and 1.34 (m, 4H) and 0.91 (t, 3H).

Transition temperature was expressed in terms of the measured values of the compound itself. Maximum temperature ($T_{NI}$), dielectric anisotropy ($\Delta\varepsilon$) and optical anisotropy ($\Delta n$) were expressed in terms of extrapolated values calculated from the measured values of the sample, in which the compound was mixed with the mother liquid crystals (i), according to the extrapolation method described above. The physical property values of the compound (No. 18) were as follows.

Transition temperature: C 121.0 N 247.2 I.

$T_{NI}$=189.6° C., 4E=−7.31, $\Delta n$=0.193.

4-Butoxy-4'-(trans-4-(4-ethoxy-2,3-difluorophenyl)cyclohexylmethoxy)-2,3,3'-trifluorobiphenyl (No. 357)

(No. 357)

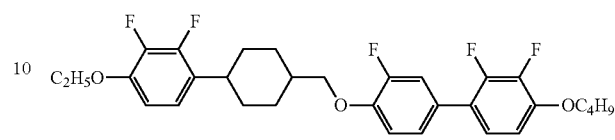

The chemical shift (δ, ppm) in ¹H-NMR analysis was described below, and the resulting compound was identified as 4-butoxy-4'-(trans-4-(4-ethoxy-2,3-difluorophenyl)cyclohexylmethoxy)-2,3,3'-trifluorobiphenyl (No. 357). The solvent for measurement was CDCl$_3$.

Chemical shift (δ ppm): 7.25 (d, 1H), 7.21 (d, 1H), 7.03 (m, 2H), 6.85 (td, 1H), 6.78 (td, 1H), 6.68 (td, 1H), 4.13-4.06 (m, 4H), 3.92 (d, 2H), 2.82 (tt, 1H), 2.07 (m, 2H), 1.95 (m, 2H), 1.83 (m, 2H), 1.58-1.48 (m, 5H), 1.44 (t, 3H), 1.34-1.23 (m, 2H) and 1.00 (t, 3H).

Transition temperature was expressed in terms of the measured values of the compound itself. Maximum temperature ($T_{NI}$), dielectric anisotropy ($\Delta\varepsilon$) and optical anisotropy ($\Delta n$) were expressed in terms of extrapolated values calculated from the measured values of the sample, in which the compound was mixed with the mother liquid crystals (i), according to the extrapolation method described above. The physical property values of the compound (No. 357) were as follows.

Transition temperature: C 119.0 N 204.1 I.

$T_{NI}$=181.6° C., $\Delta\varepsilon$=−7.95, $\Delta n$=0.190.

Example 8

The compound (No. 1) to the compound (No. 700) shown below can be synthesized by synthetic methods similar to those described in Examples 1 to 7. Attached data were measured in accordance with the methods described above. The measured values of the compound itself were used for the transition temperature, and the values converted from the measured values of the sample, in which the compound was mixed with the mother liquid crystals (i), by means of the extrapolation method described above were used for the maximum temperature ($T_{NI}$), the dielectric anisotropy ($\Delta\varepsilon$) and the optical anisotropy ($\Delta n$).

| No. |  |
| --- | --- |
| 1 | 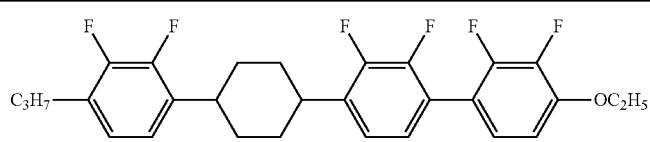 |
| 2 | 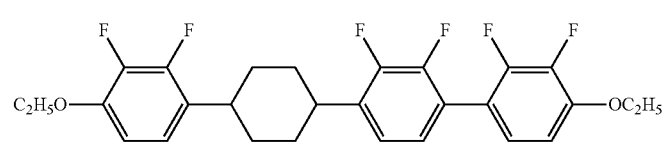 |

-continued
| No. | |
|---|---|
| 3 | 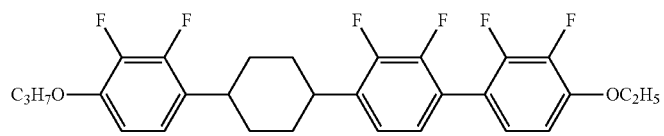 |
| 4 | 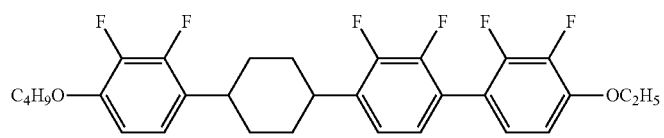 |
| 5 | 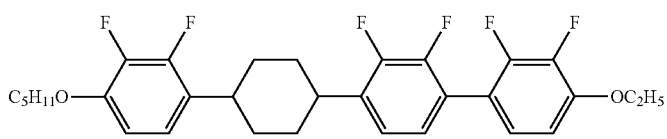 |
| 6 | 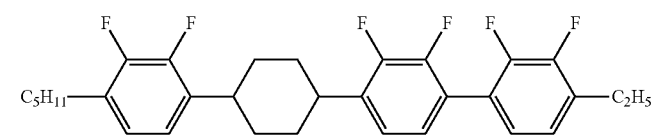 |
| 7 | 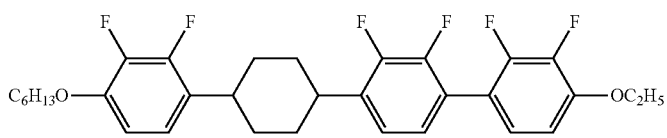 |
C 116.4 N 239.0 I
$T_{NI}$; 175.6° C., Δ ε; -7.95, Δ n; 0.180
| 8 | 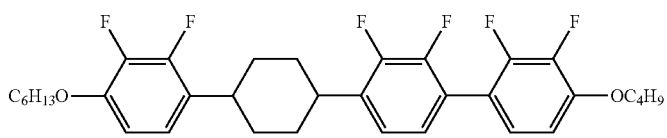 |
|---|---|
| 9 | 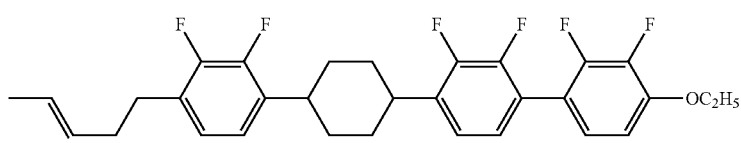 |
| 10 | 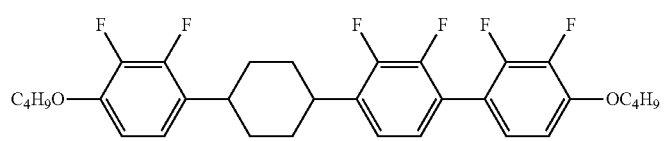 |
| 11 | 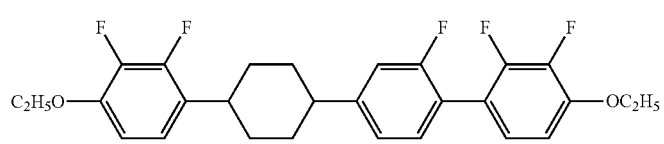 |
| 12 | 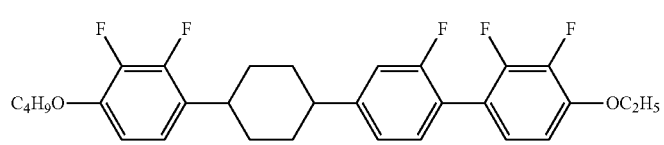 |

-continued
| No. | |
|---|---|
| 13 | 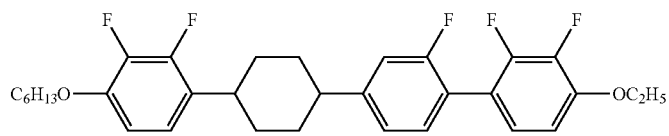 <br> C 101.4 S$_A$ 121.4 N 232.7 I <br> T$_{NI}$; 170.6° C., Δ ε; -8.85, Δ n; 0.201 |
| 14 | 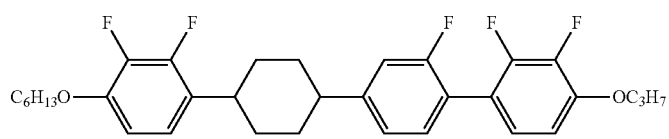 |
| 15 | 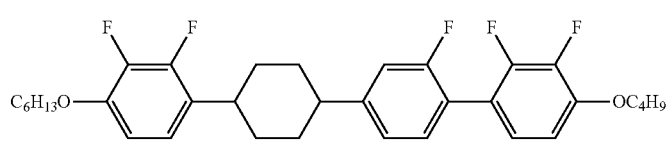 |
| 16 | 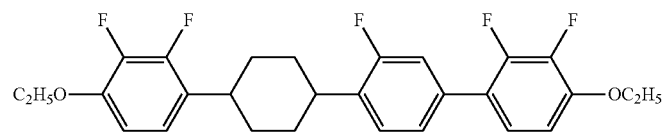 |
| 17 | 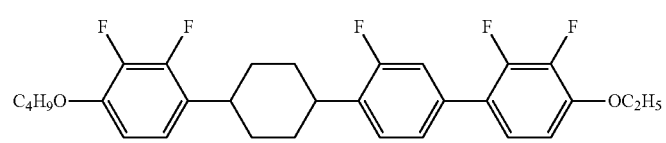 |
| 18 | 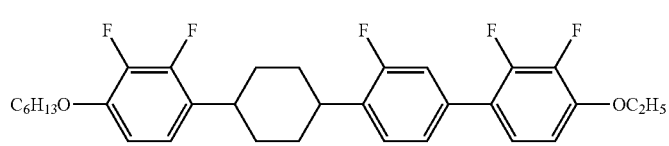 <br> C 121.0 N 247.2 I <br> T$_{NI}$; 189.6° C., Δ ε; -7.31, Δ n; 0.193 |
| 19 | 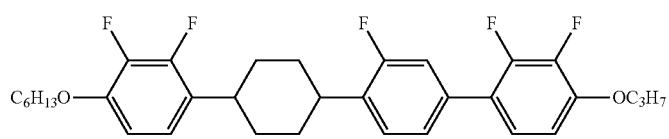 |
| 20 | 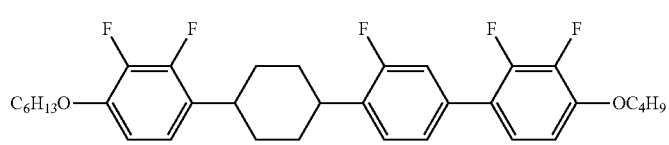 |
| 21 | 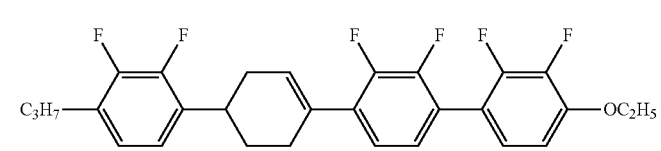 |
| 22 | 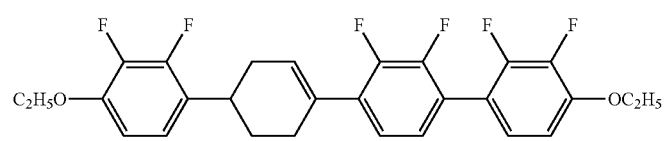 |

-continued
| No. | |
|---|---|
| 23 | 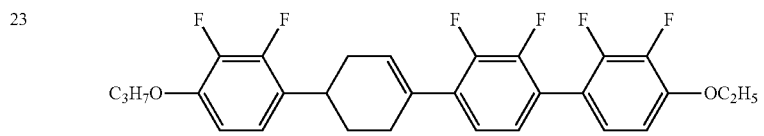 |
| 24 | 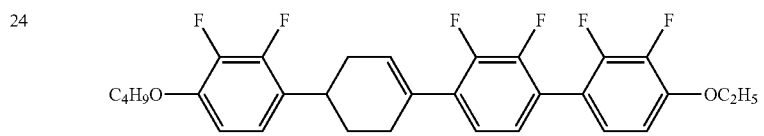 |
| 25 | 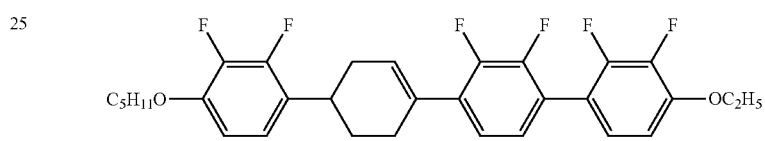 |
| 26 | 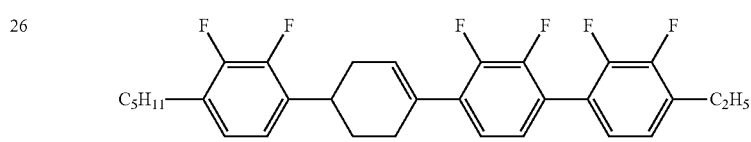 |
| 27 | 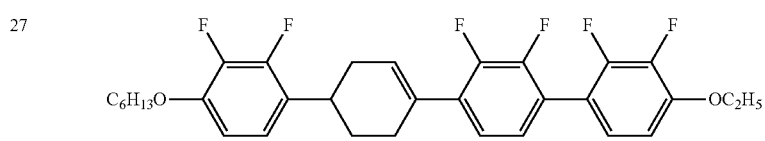<br>C 103.9 N 207.7 I<br>$T_{NI}$; 169.3° C., Δ ε; -10.55, Δ n; 0.205 |
| 28 | 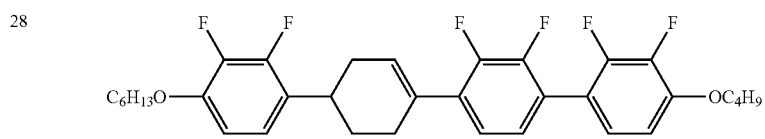 |
| 29 | 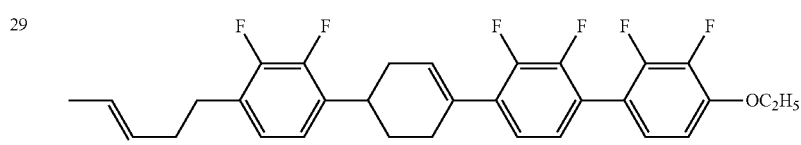 |
| 30 | 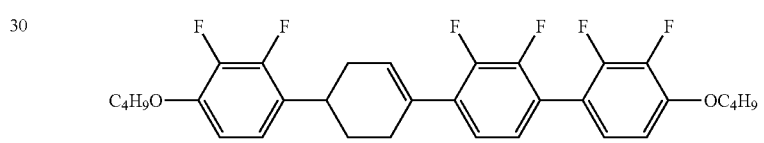 |
| 31 | 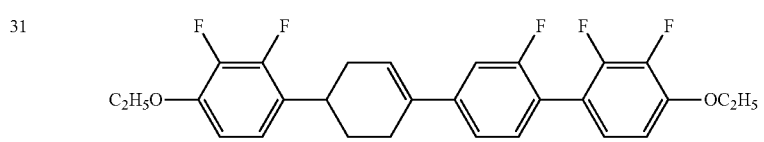 |
| 32 | 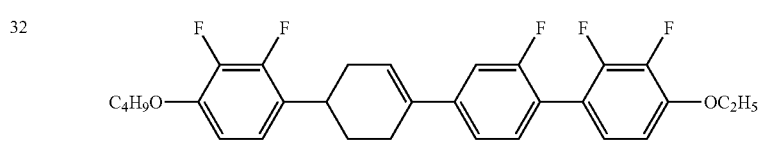 |

-continued
| No. | |
|---|---|
| 33 | 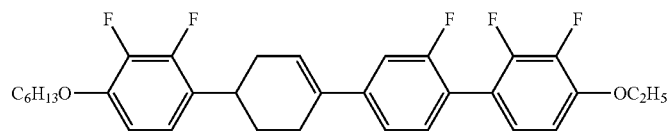<br>C 108.9 S$_A$ 136.2 N 214.2 I<br>T$_{NI}$; 178.6° C., Δ ε; -8.54, Δ n; 0.219 |
| 34 | 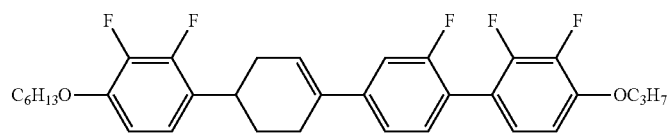 |
| 35 | 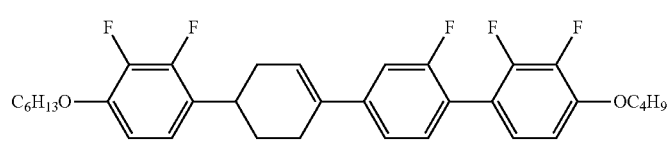 |
| 36 | 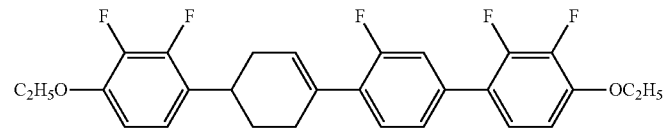 |
| 37 | 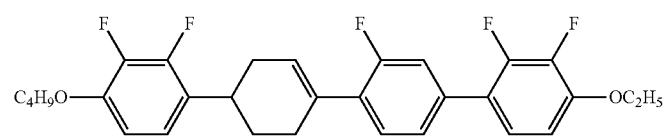 |
| 38 | 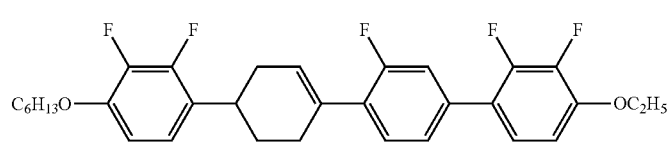<br>C 106.3 N 218.6 I<br>T$_{NI}$; 180.6° C., Δ ε; -8.64, Δ n; 0.226 |
| 39 | 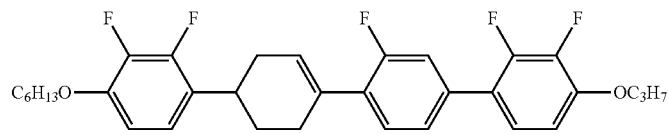 |
| 40 | 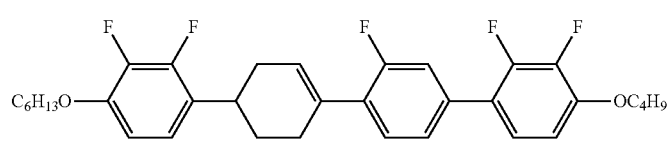 |
| 41 | 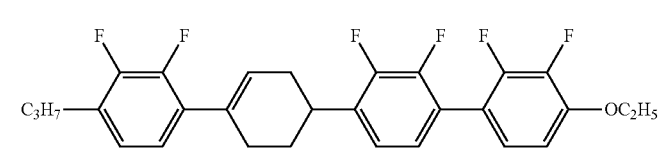 |
| 42 | 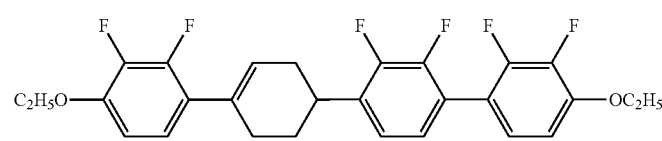 |

-continued
| No. | |
|---|---|
| 43 | 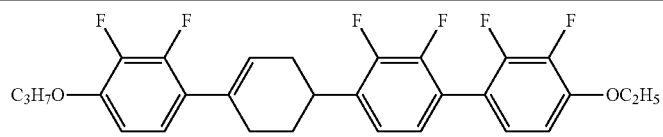 |
| 44 | 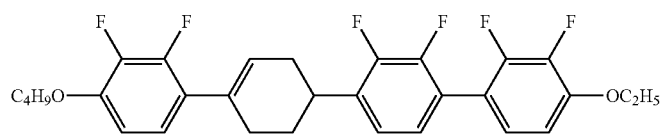 |
| 45 | 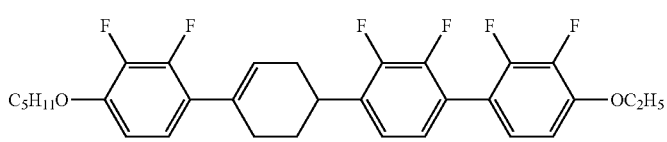 |
| 46 | 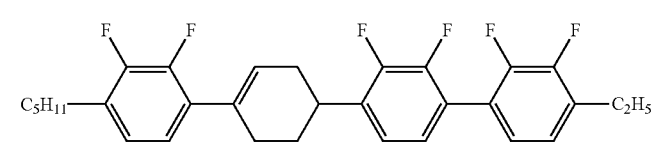 |
| 47 | 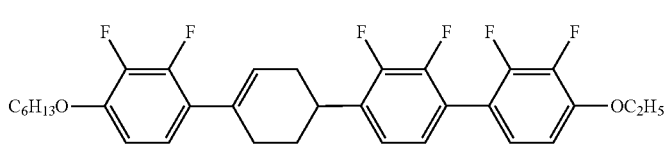 |
| 48 | 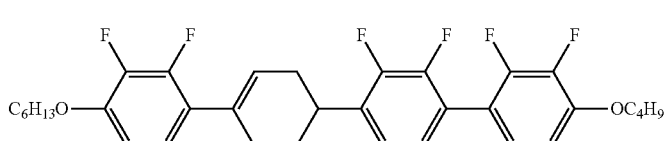 |
| 49 | 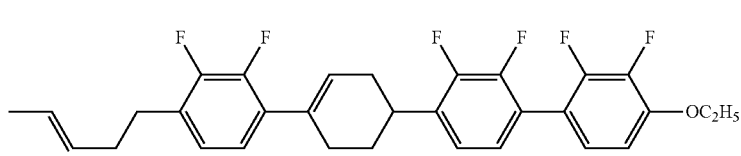 |
| 50 | 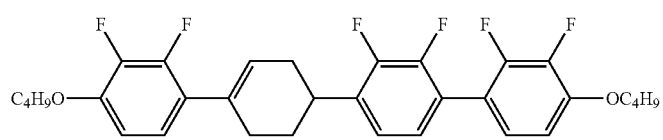 |
| 51 | 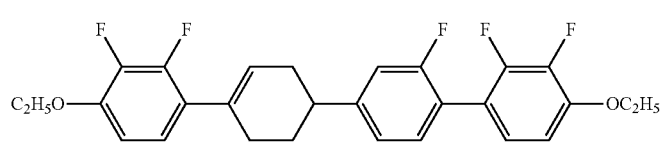 |
| 52 | 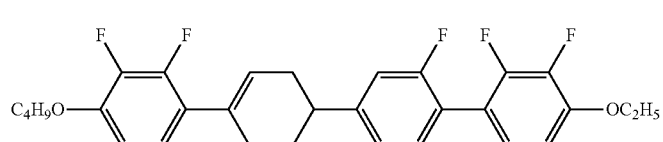 |
| 53 | 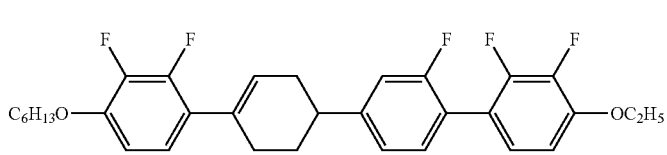 |

| No. | |
|---|---|
| 54 | C₆H₁₃O–[2,3-F₂-Ph]–[cyclohexenyl]–[2-F-Ph]–[2,3-F₂-Ph]–OC₃H₇ |
| 55 | C₆H₁₃O–[2,3-F₂-Ph]–[cyclohexenyl]–[2-F-Ph]–[2,3-F₂-Ph]–OC₄H₉ |
| 56 | C₂H₅O–[2,3-F₂-Ph]–[cyclohexenyl]–[2-F-Ph]–[2,3-F₂-Ph]–OC₂H₅ |
| 57 | C₄H₉O–[2,3-F₂-Ph]–[cyclohexenyl]–[2-F-Ph]–[2,3-F₂-Ph]–OC₂H₅ |
| 58 | C₆H₁₃O–[2,3-F₂-Ph]–[cyclohexenyl]–[2-F-Ph]–[2,3-F₂-Ph]–OC₂H₅ |
| 59 | C₆H₁₃O–[2,3-F₂-Ph]–[cyclohexenyl]–[2-F-Ph]–[2,3-F₂-Ph]–OC₃H₇ |
| 60 | C₆H₁₃O–[2,3-F₂-Ph]–[cyclohexenyl]–[2-F-Ph]–[2,3-F₂-Ph]–OC₄H₉ |
| 61 | C₃H₇–[2,3-F₂-Ph]–CH₂CH₂–[cyclohexyl]–[2,3-F₂-Ph]–[2,3-F₂-Ph]–OC₂H₅ |
| 62 | C₂H₅O–[2,3-F₂-Ph]–CH₂CH₂–[cyclohexyl]–[2,3-F₂-Ph]–[2,3-F₂-Ph]–OC₂H₅ |
| 63 | C₃H₇O–[2,3-F₂-Ph]–CH₂CH₂–[cyclohexyl]–[2,3-F₂-Ph]–[2,3-F₂-Ph]–OC₂H₅ |

-continued
| No. | |
|---|---|
| 64 | 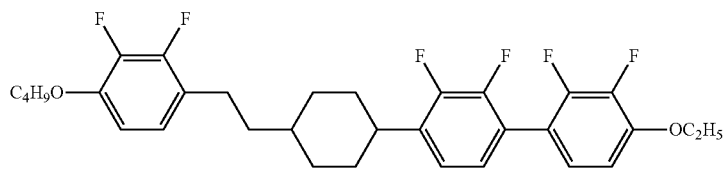 |
| 65 | 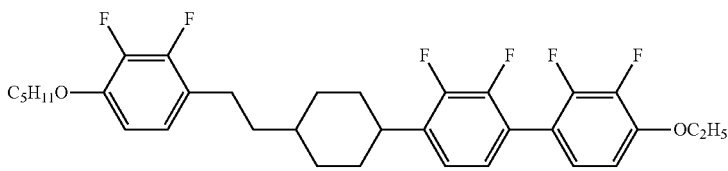 |
| 66 | 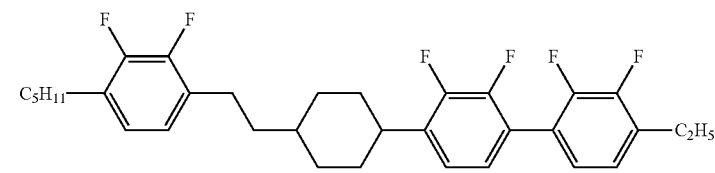 |
| 67 | 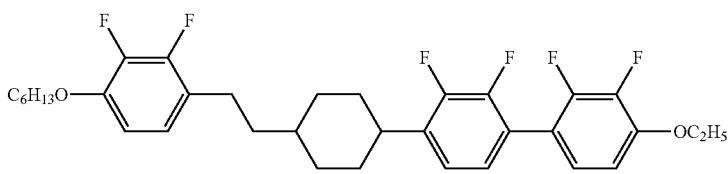
C 78.9 N 192.2 I
$T_{NI}$; 165.9° C., Δ ε; -9.87, Δ n; 0.175 |
| 68 | 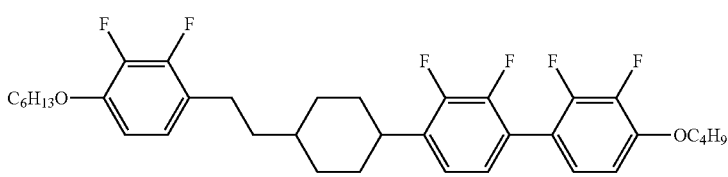 |
| 69 | 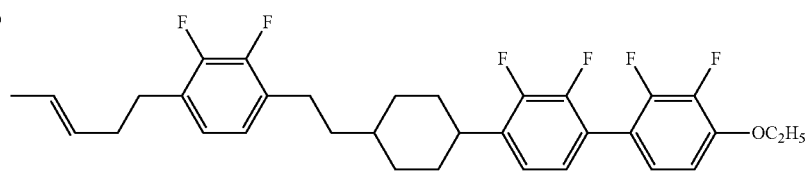 |
| 70 | 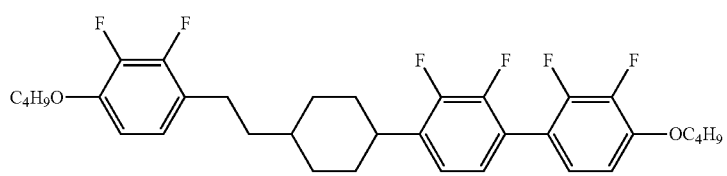 |
| 71 | 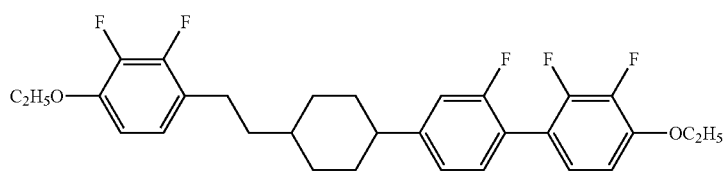 |

-continued
| No. | |
|---|---|
| 72 | 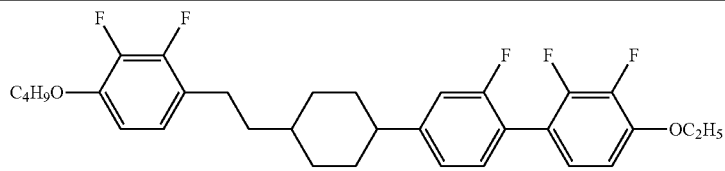 |
| 73 | 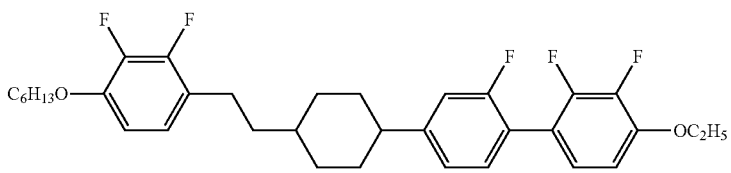 |
| 74 | 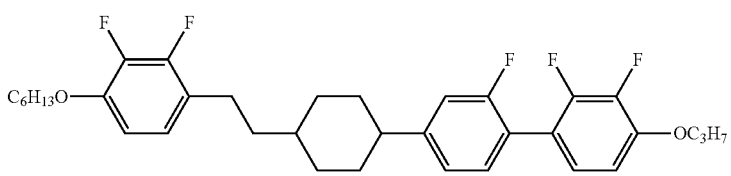 |
| 75 | 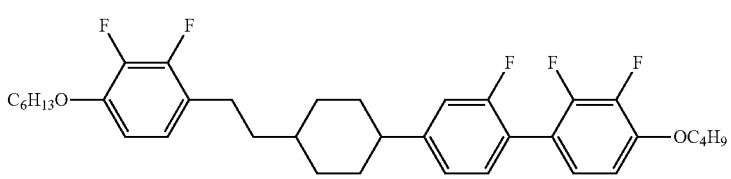 |
| 76 | 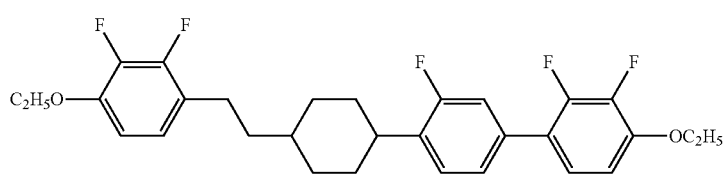 |
| 77 | 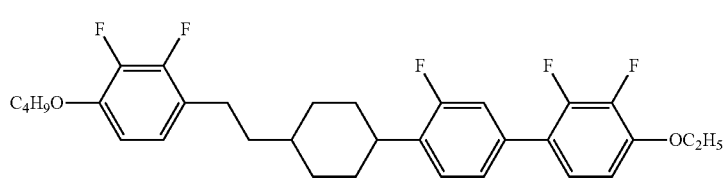 |
| 78 | 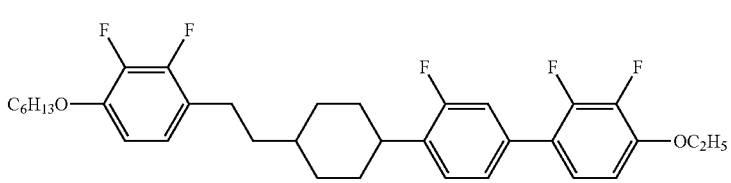 |
| 79 | 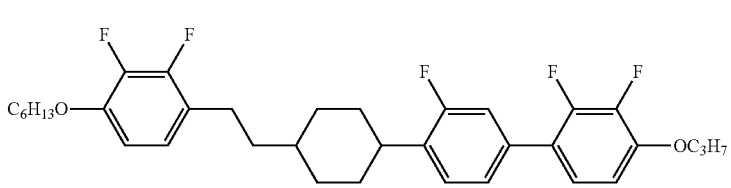 |
| 80 | 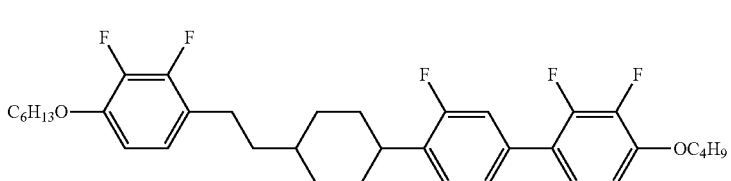 |

-continued
| No. | |
|---|---|
| 81 | 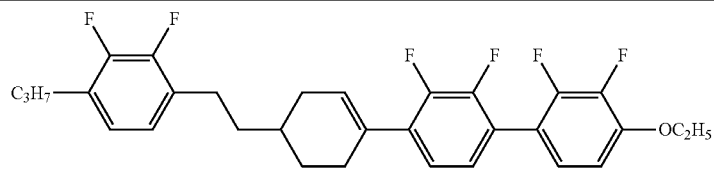 |
| 82 | 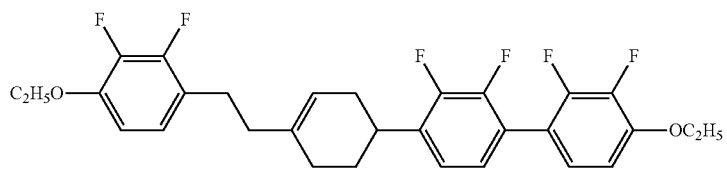 |
| 83 | 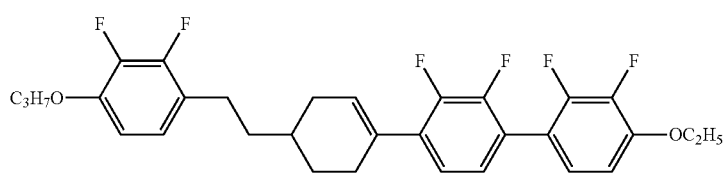 |
| 84 | 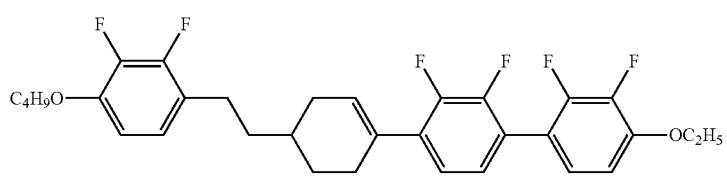 |
| 85 | 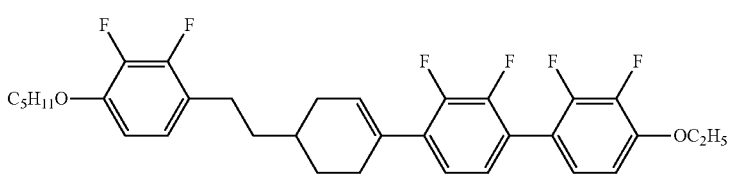 |
| 86 | 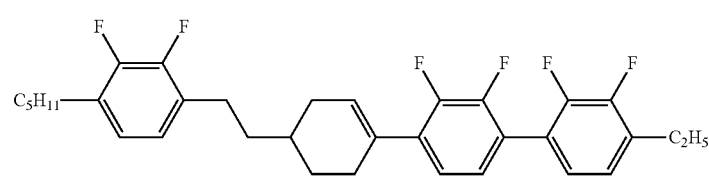 |
| 87 | 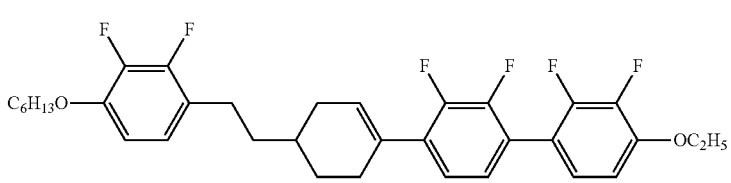 |
| 88 | 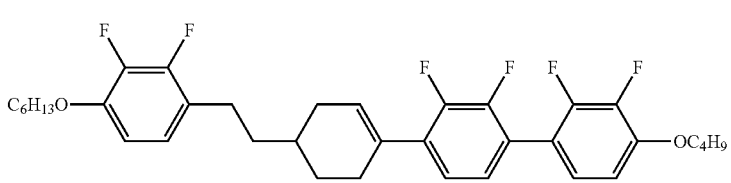 |
| 89 | 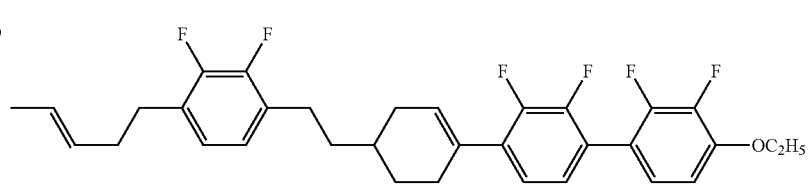 |

-continued
| No. | |
|---|---|
| 90 | 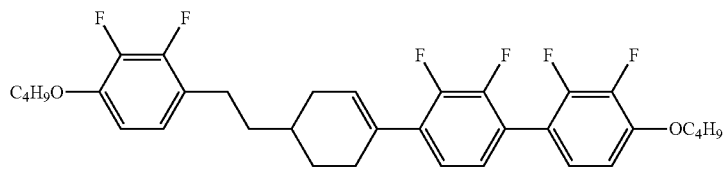 |
| 91 | 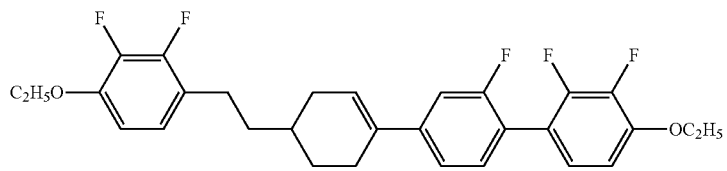 |
| 92 | 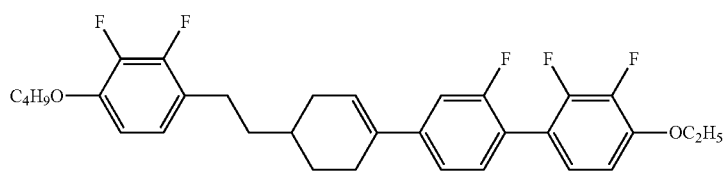 |
| 93 | 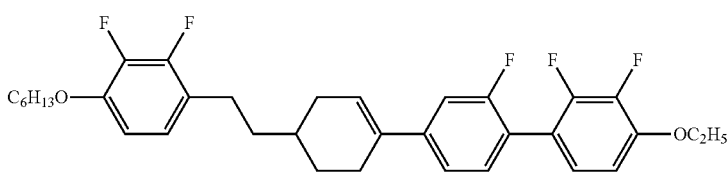 |
| 94 | 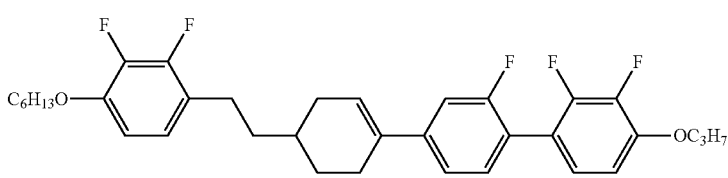 |
| 95 | 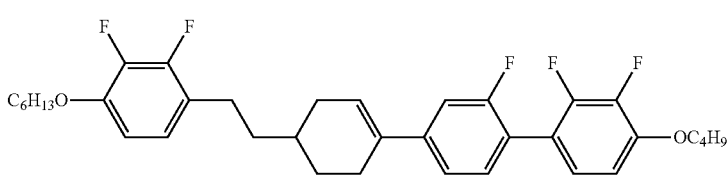 |
| 96 | 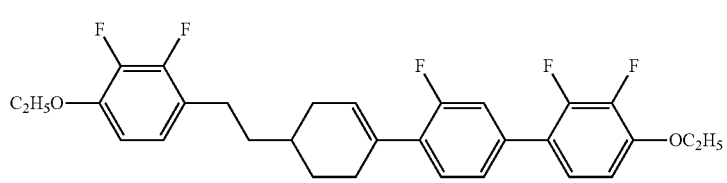 |
| 97 | 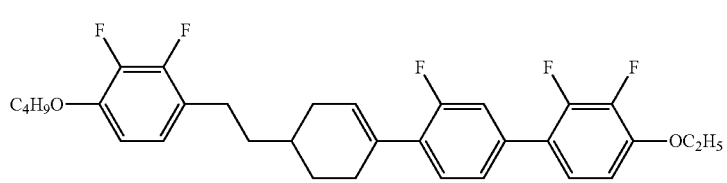 |
| 98 | 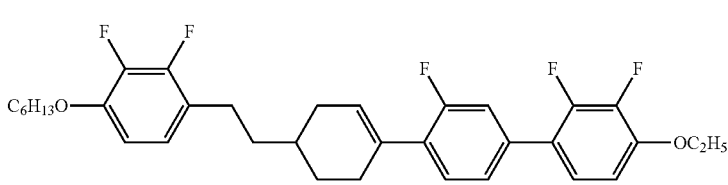 |

-continued
| No. | |
|---|---|
| 99 | 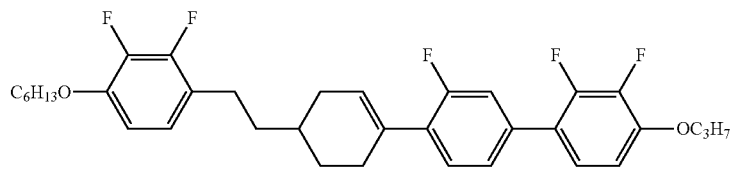 |
| 100 | 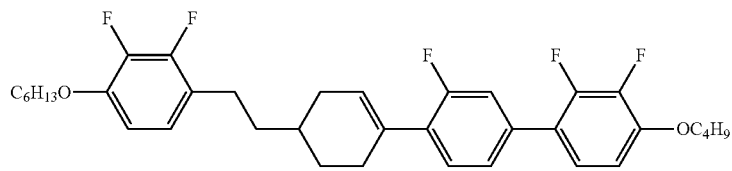 |
| 101 | 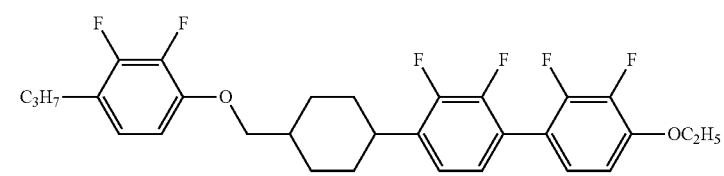 |
| 102 | 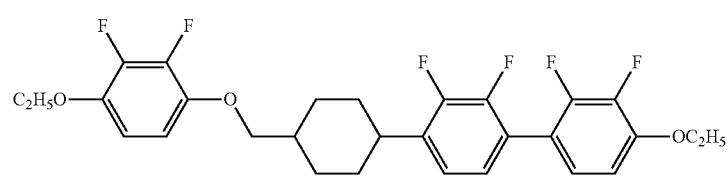 |
| 103 | 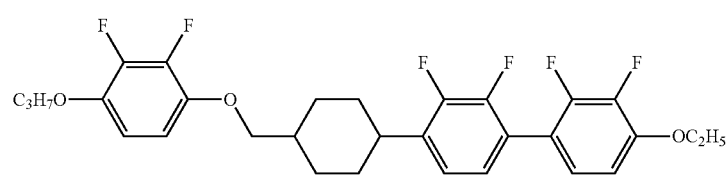 |
| 104 | 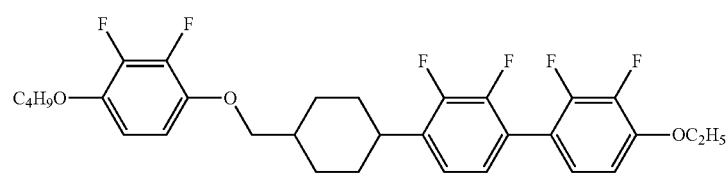 |
| 105 | 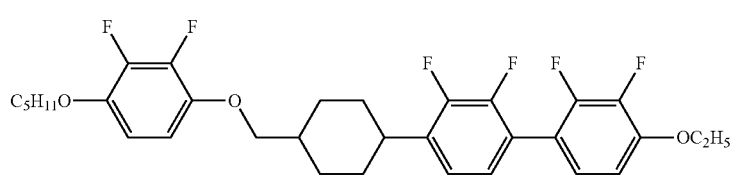 |
| 106 | 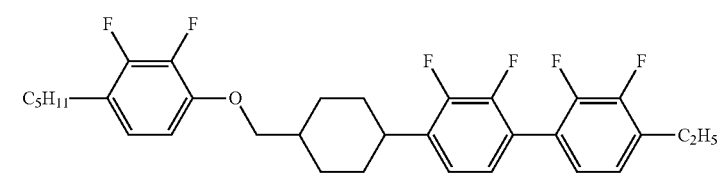 |

| No. | |
|---|---|
| 107 | 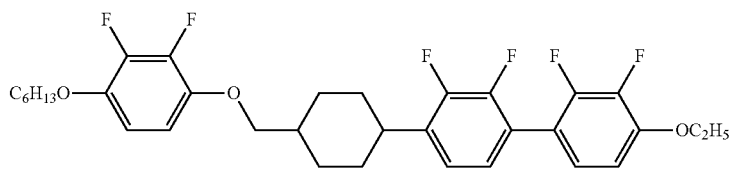
C 89.3 N 185.2 I
T$_{NI}$; 165.6° C., Δ ε; -9.26, Δ n; 0.179 |
| 108 | 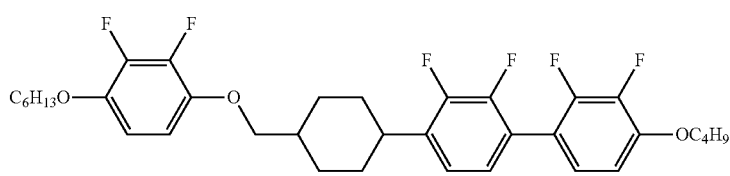 |
| 109 | 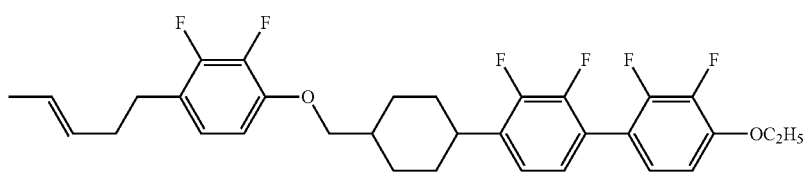 |
| 110 | 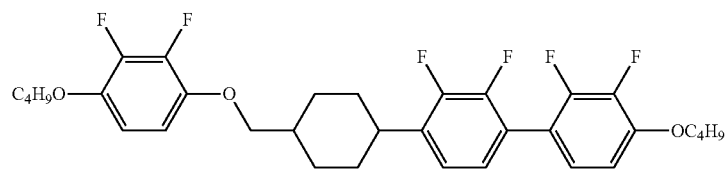 |
| 111 | 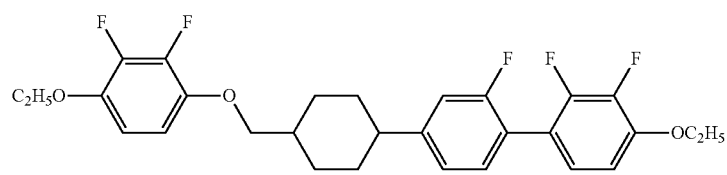 |
| 112 | 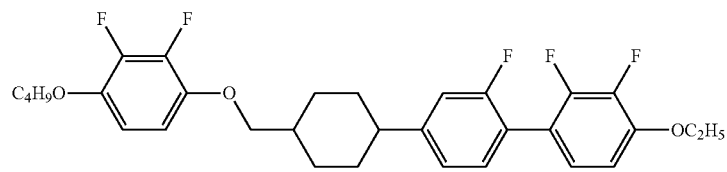 |
| 113 | 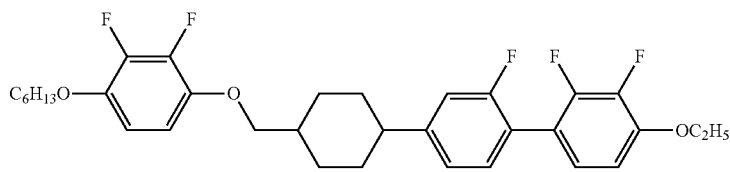 |
| 114 | 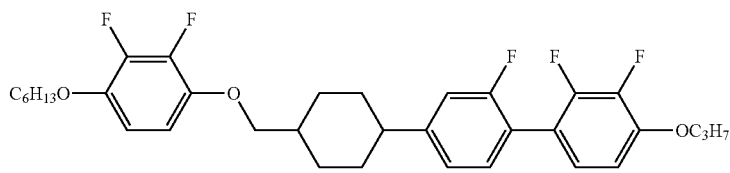 |

-continued
| No. | |
|---|---|
| 115 | 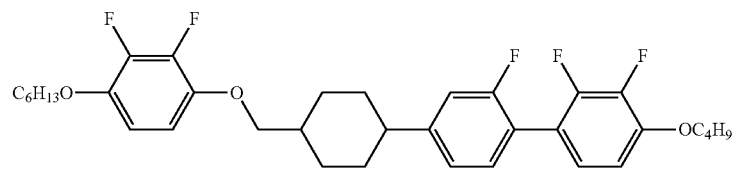 |
| 116 | 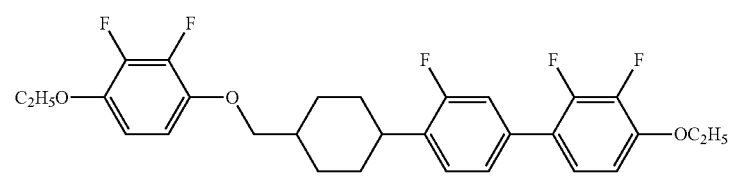 |
| 117 | 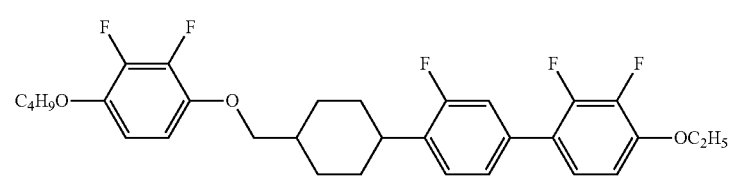 |
| 118 | 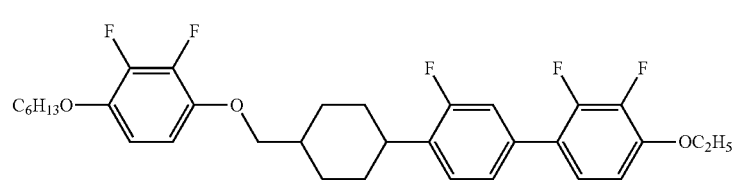 |
| 119 | 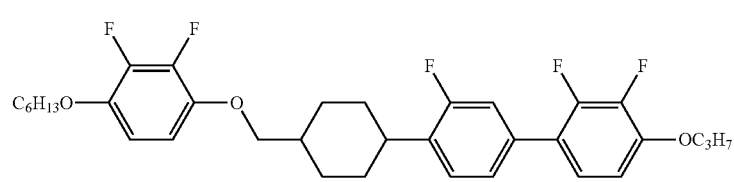 |
| 120 | 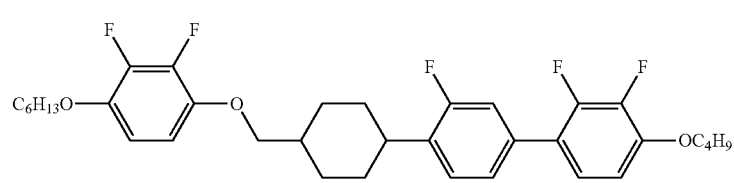 |
| 121 | 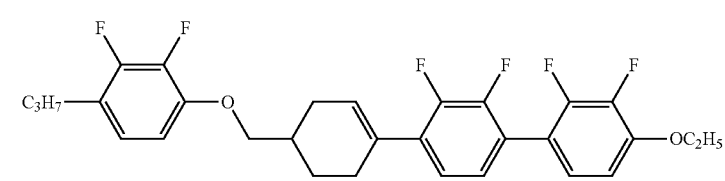 |
| 122 | 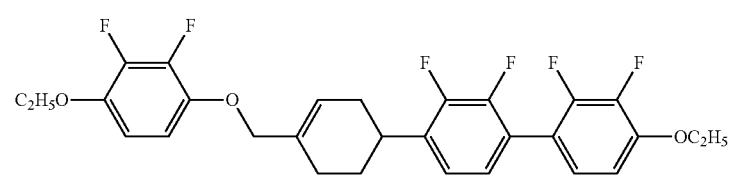 |
| 123 | 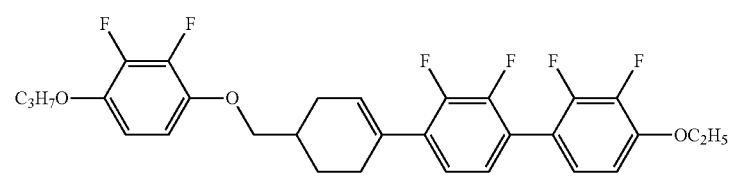 |

-continued
| No. | |
|---|---|
| 124 | 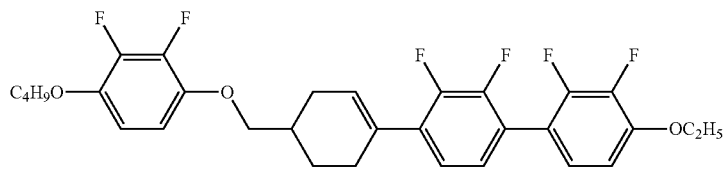 |
| 125 | 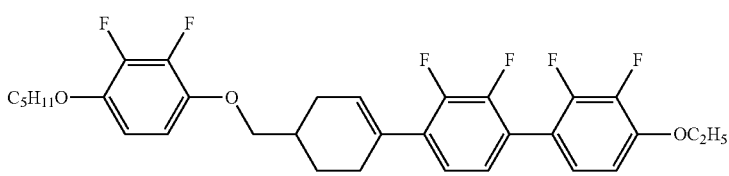 |
| 126 | 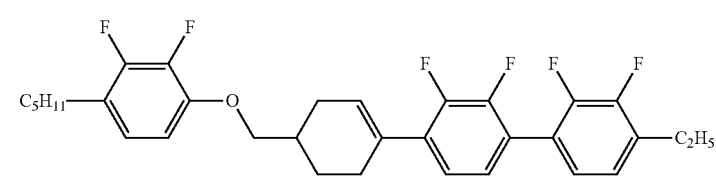 |
| 127 | 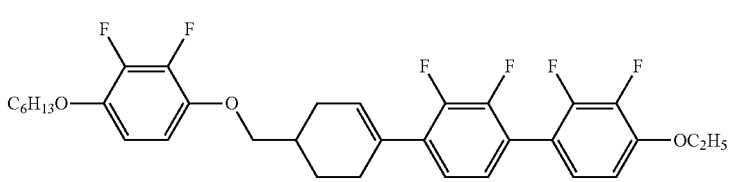 |
| 128 | 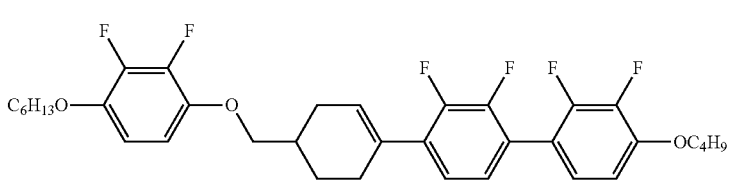 |
| 129 | 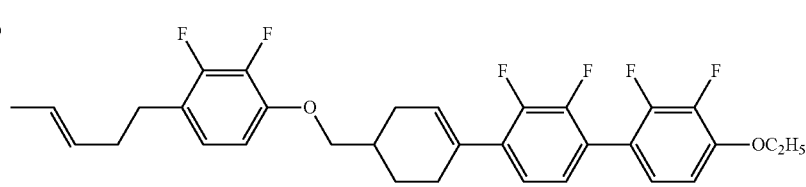 |
| 130 | 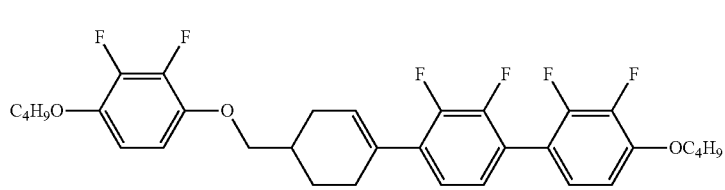 |
| 131 | 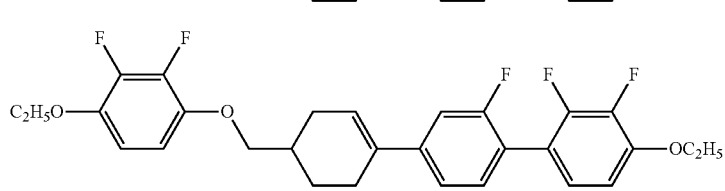 |
| 132 | 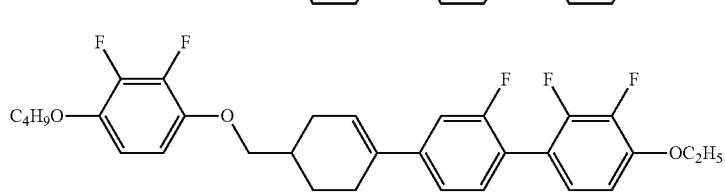 |

-continued
| No. | |
|---|---|
| 133 | 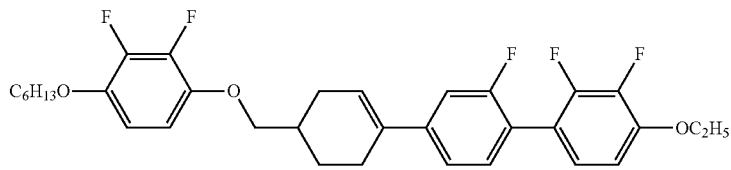 |
| 134 | 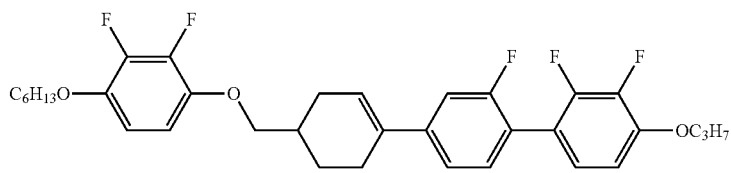 |
| 135 | 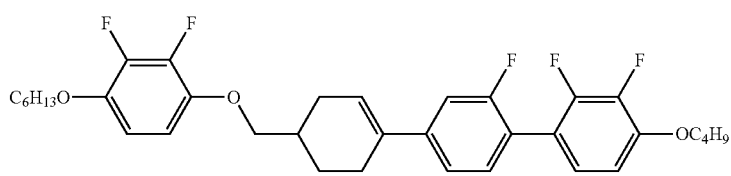 |
| 136 | 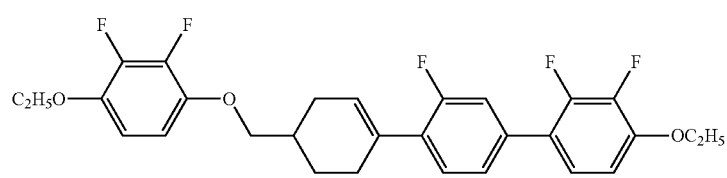 |
| 137 | 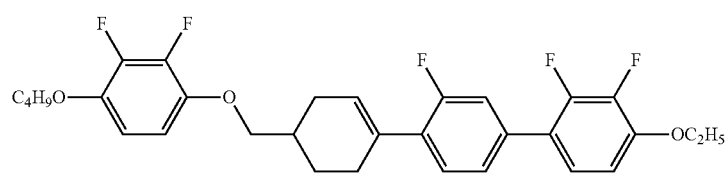 |
| 138 | 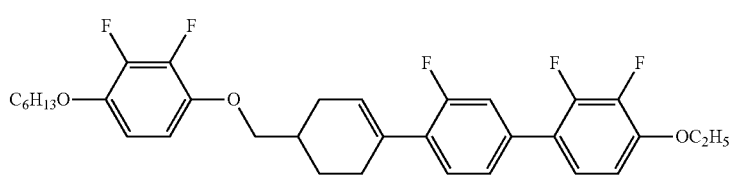 |
| 139 | 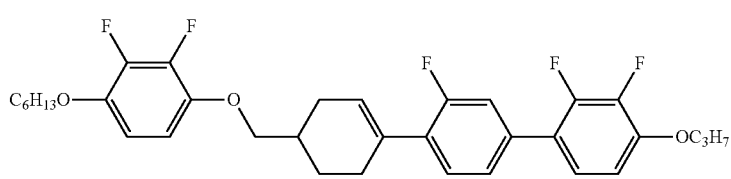 |
| 140 | 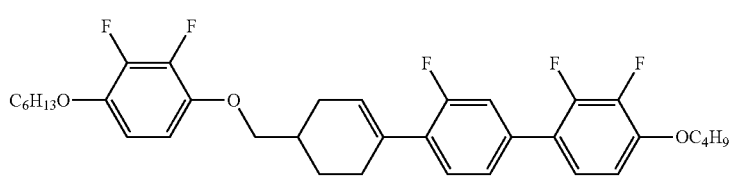 |
| 141 | 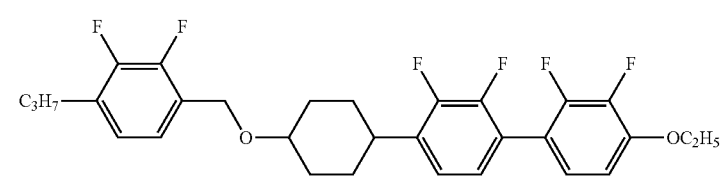 |

| No. | |
|---|---|
| 142 | 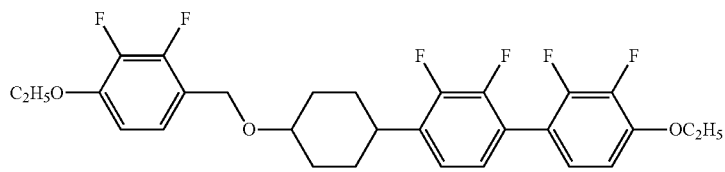 |
| 143 | 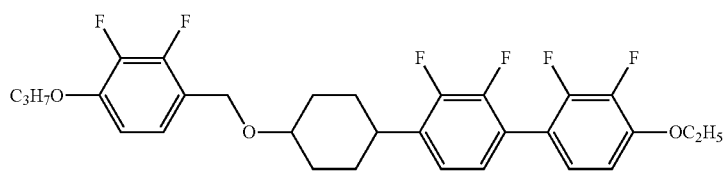 |
| 144 | 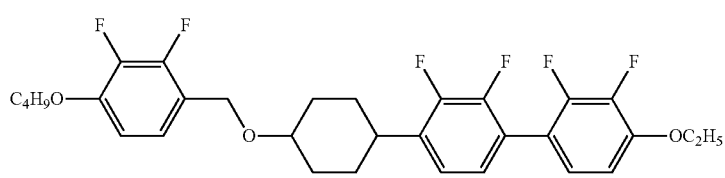 |
| 145 | 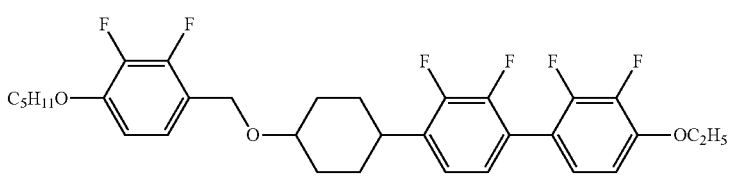 |
| 146 | 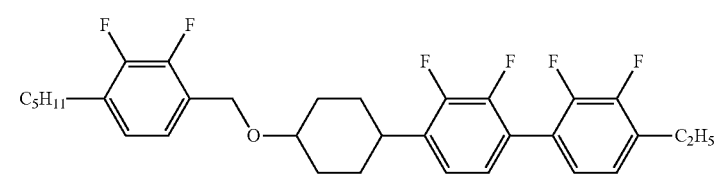 |
| 147 | 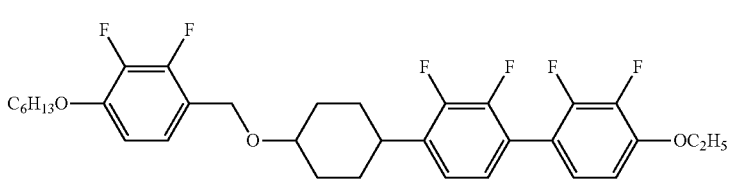 |
| 148 | 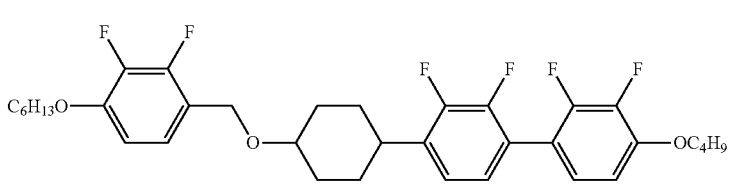 |
| 149 | 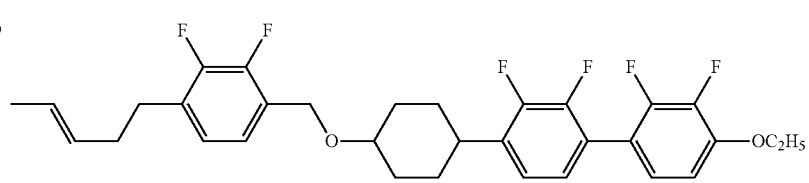 |
| 150 | 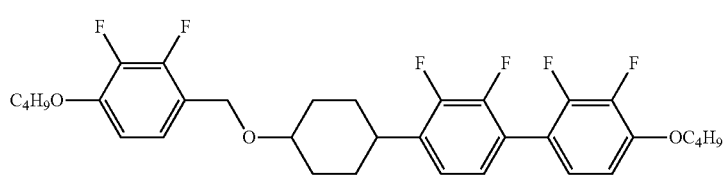 |

-continued
| No. | |
|---|---|
| 151 | 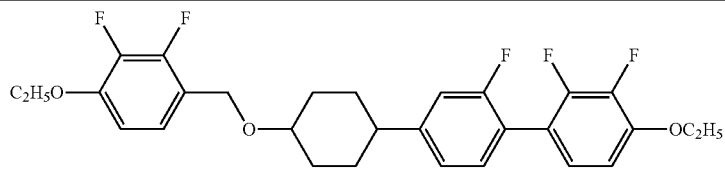 |
| 152 | 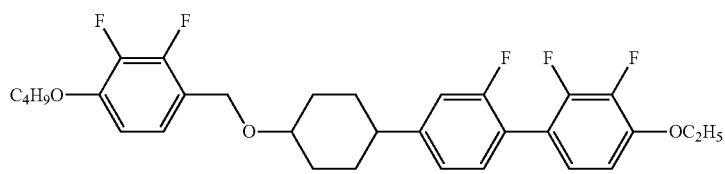 |
| 153 | 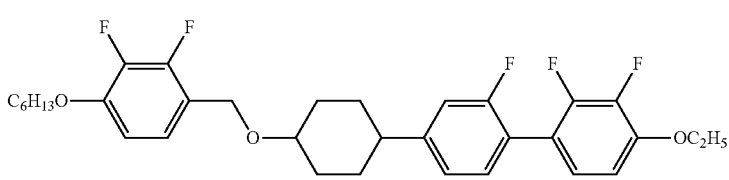 |
| 154 | 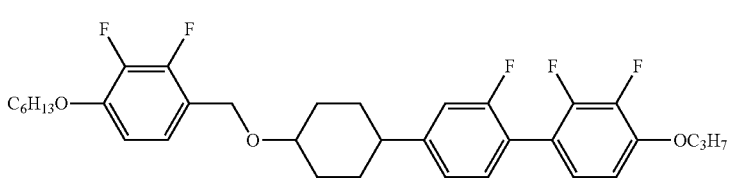 |
| 155 | 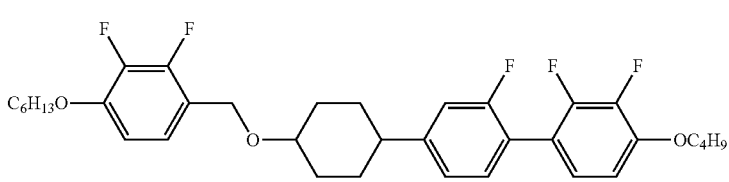 |
| 156 | 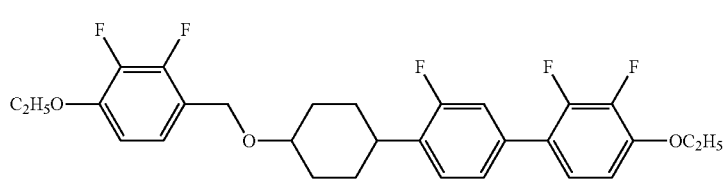 |
| 157 | 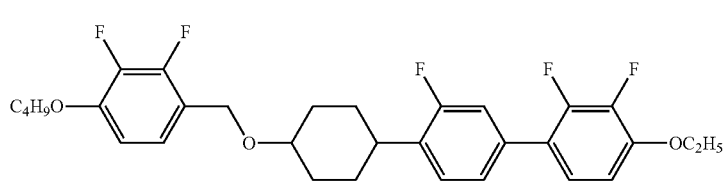 |
| 158 | 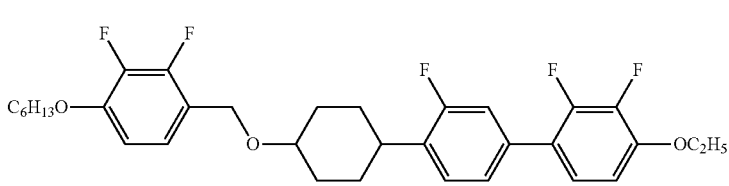 |
| 159 | 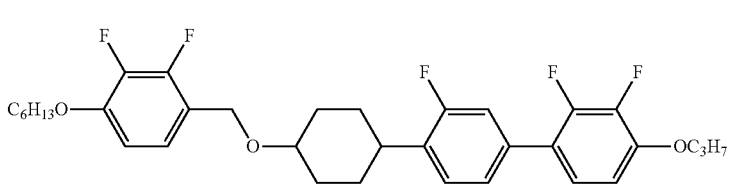 |

-continued
| No. | |
|---|---|
| 160 | 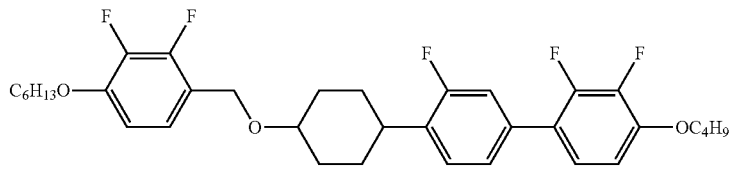 |
| 161 | 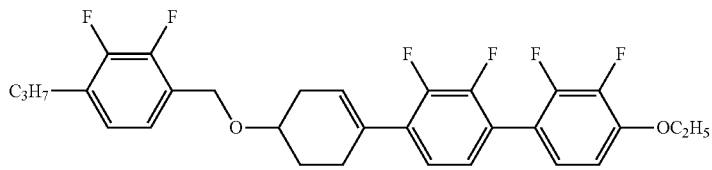 |
| 162 | 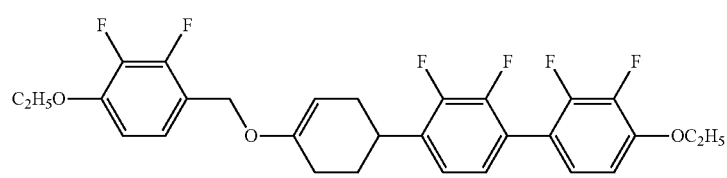 |
| 163 | 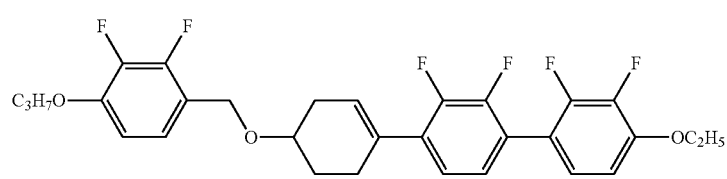 |
| 164 | 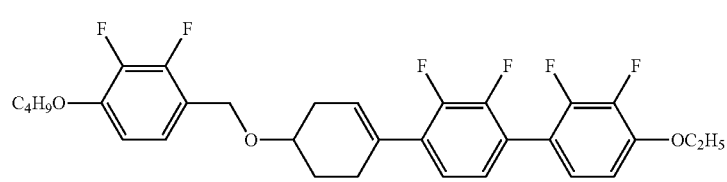 |
| 165 | 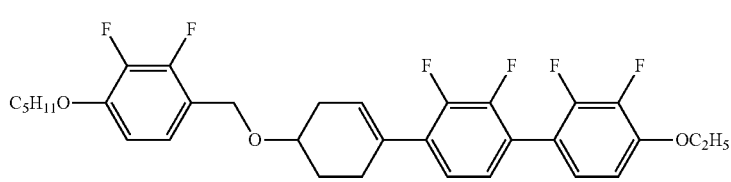 |
| 166 | 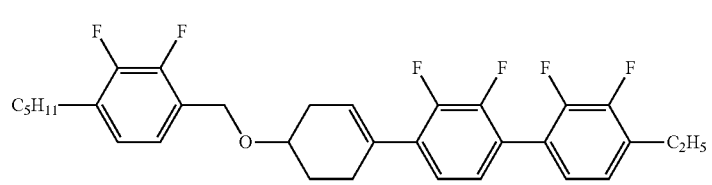 |
| 167 | 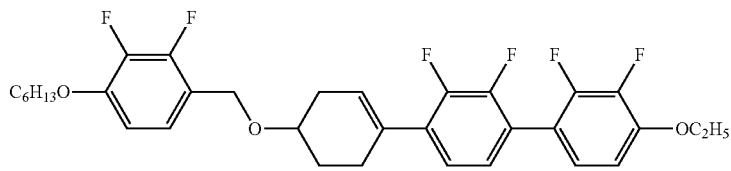 |
| 168 | 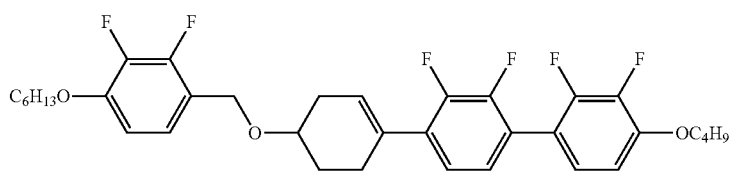 |

-continued
| No. | |
|---|---|
| 169 | 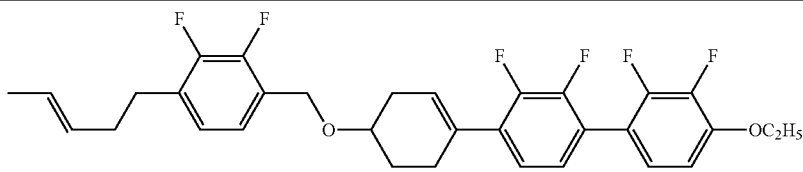 |
| 170 | 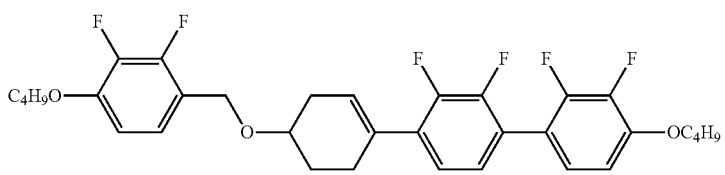 |
| 171 | 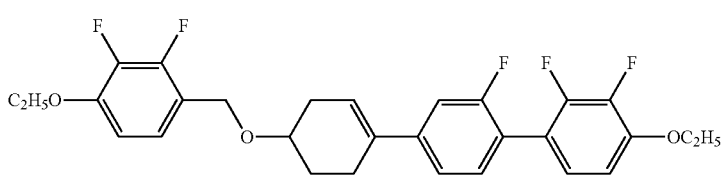 |
| 172 | 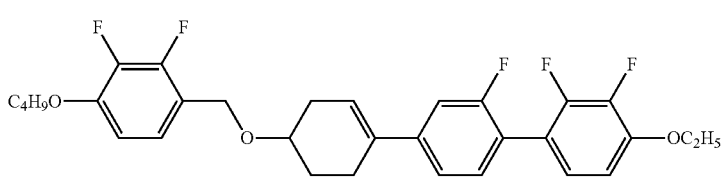 |
| 173 | 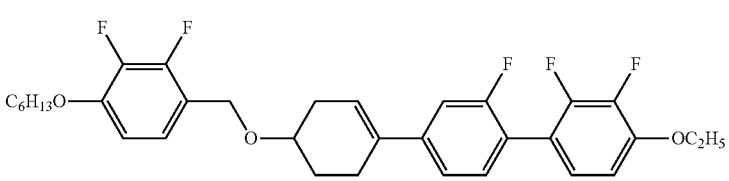 |
| 174 | 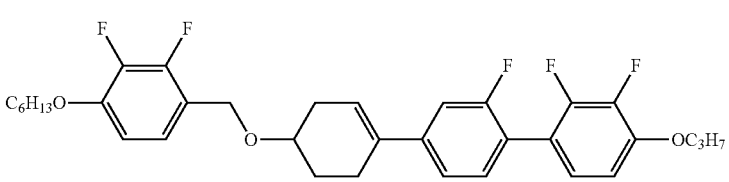 |
| 175 | 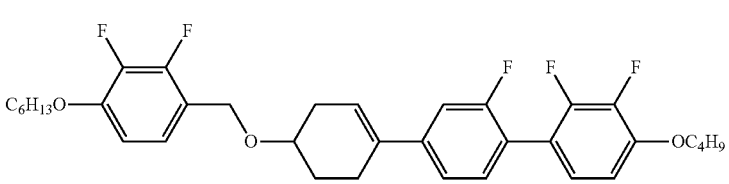 |
| 176 | 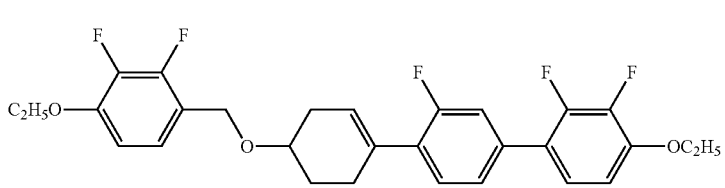 |
| 177 | 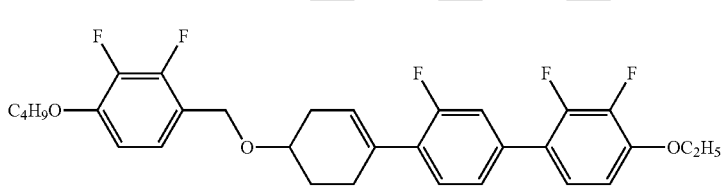 |

-continued
| No. | |
|---|---|
| 178 | 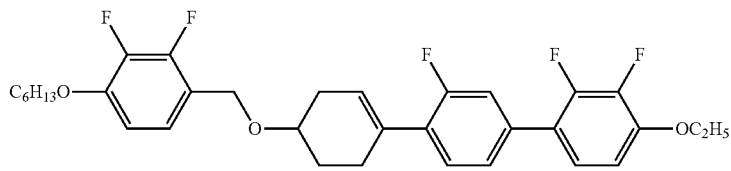 |
| 179 | 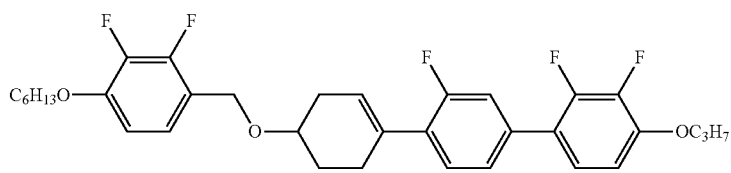 |
| 180 | 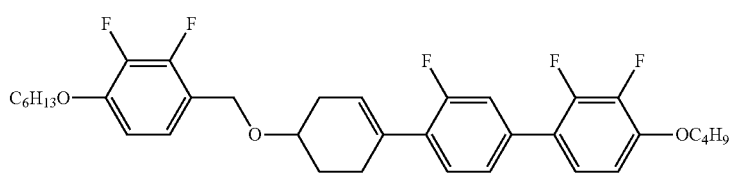 |
| 181 | 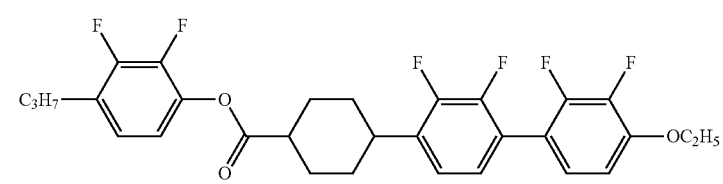 |
| 182 | 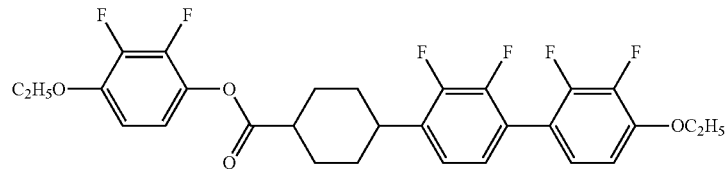 |
| 183 | 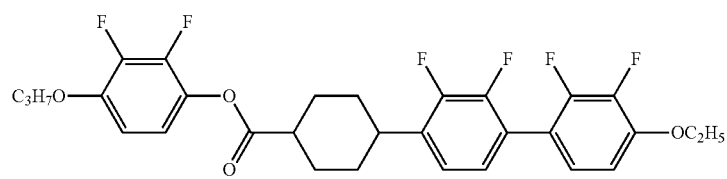 |
| 184 | 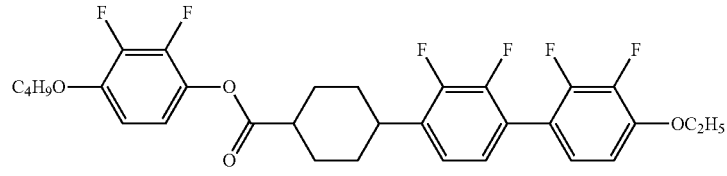 |
| 185 | 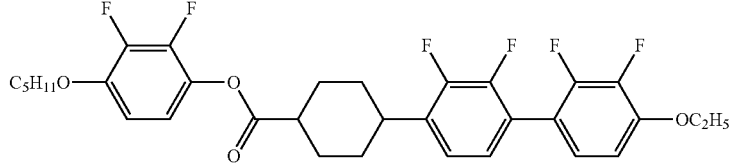 |
| 186 | 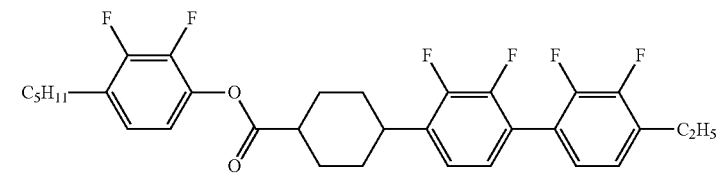 |

| No. | |
|---|---|
| 187 | 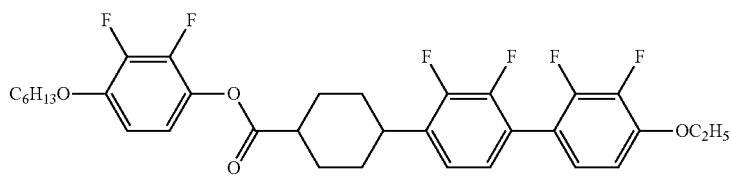 |
| 188 | 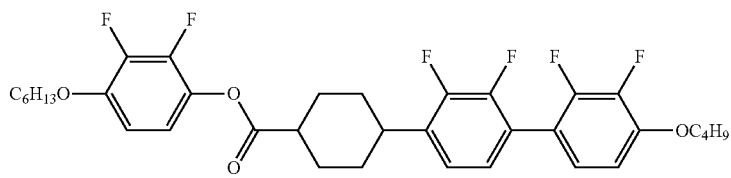 |
| 189 | 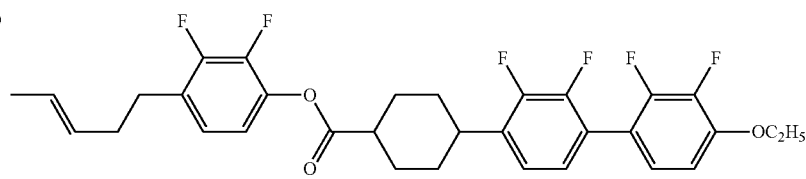 |
| 190 | 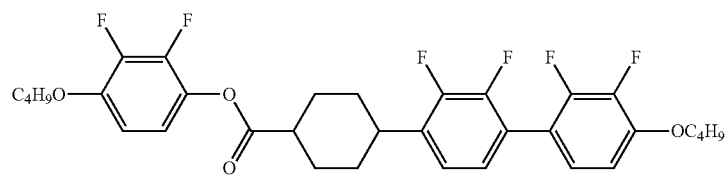 |
| 191 | 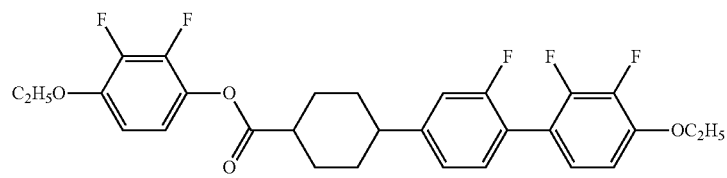 |
| 192 | 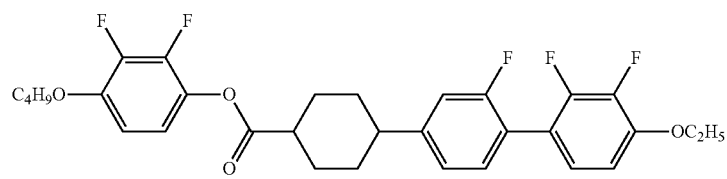 |
| 193 | 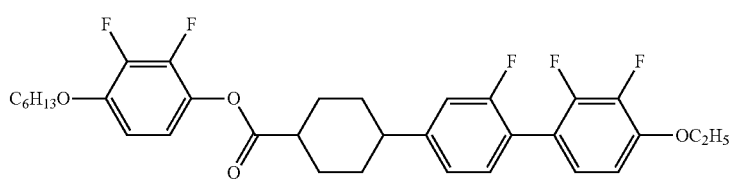 |
| 194 | 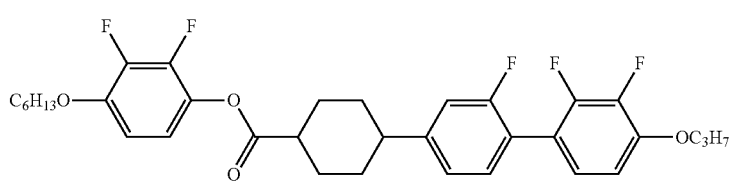 |

| No. | |
|---|---|
| 195 | 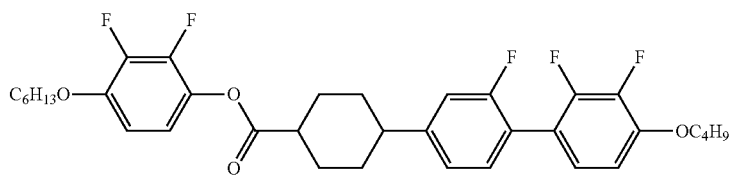 |
| 196 | 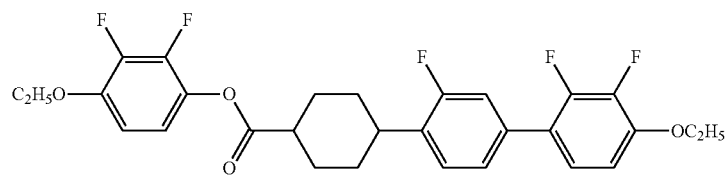 |
| 197 | 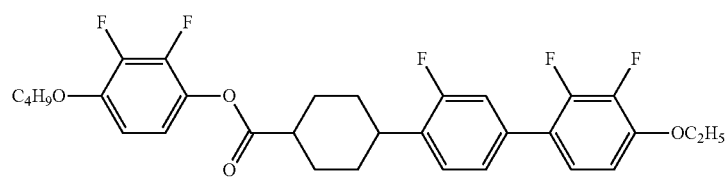 |
| 198 | 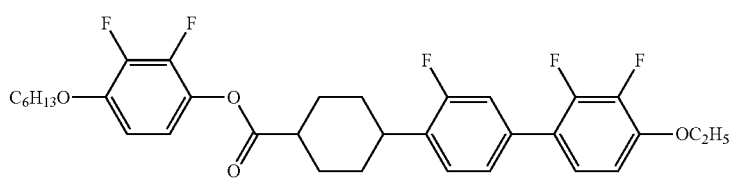 |
| 199 | 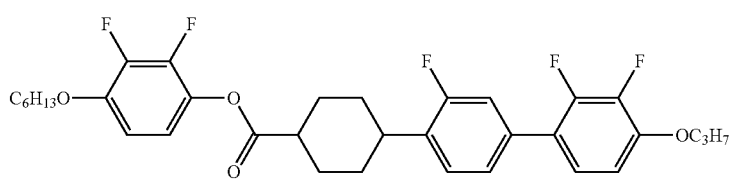 |
| 200 | 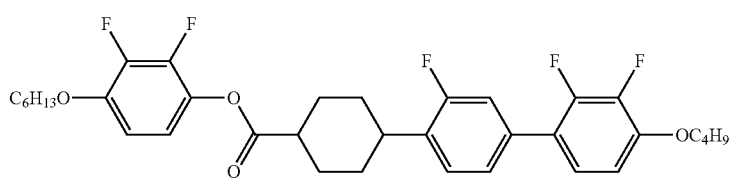 |
| 201 | 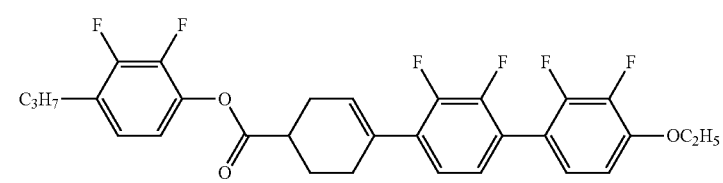 |
| 202 | 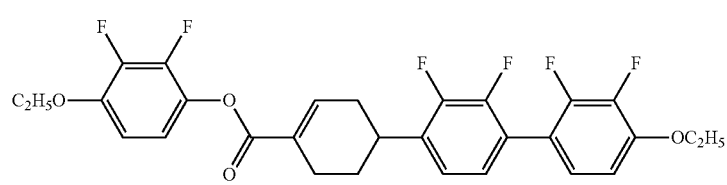 |

| No. | |
|---|---|
| 203 | 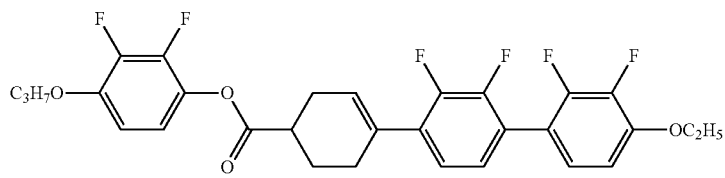 |
| 204 | 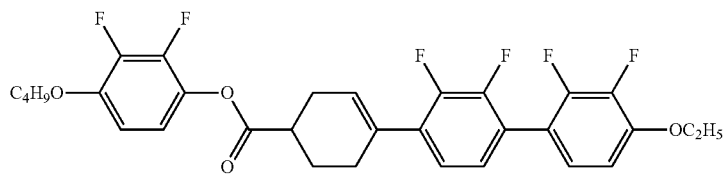 |
| 205 | 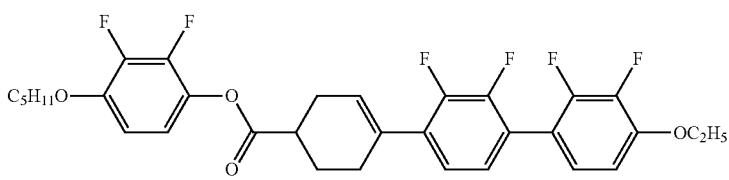 |
| 206 | 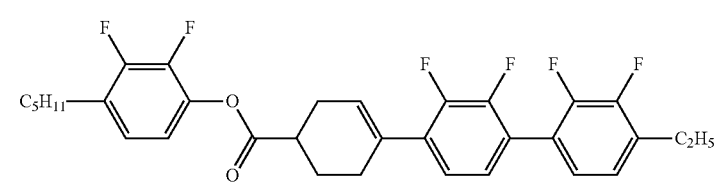 |
| 207 | 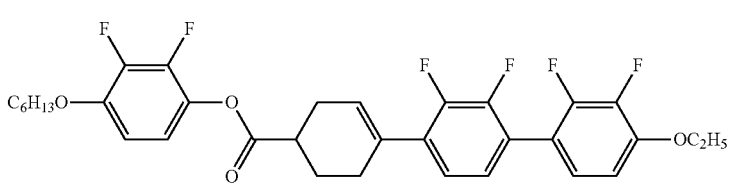 |
| 208 | 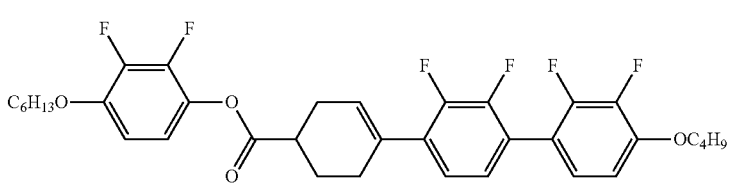 |
| 209 | 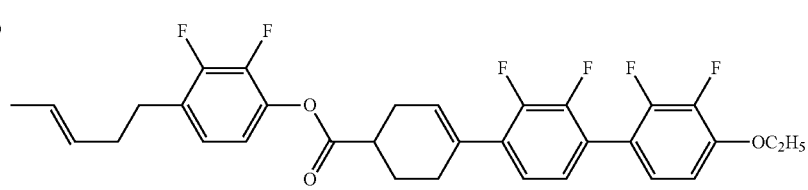 |
| 210 | 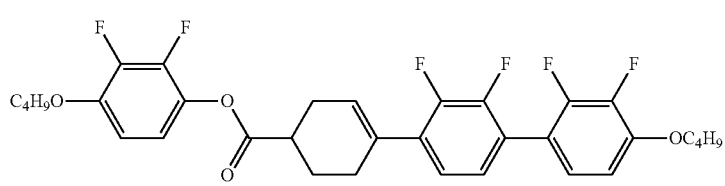 |

-continued
| No. | |
|---|---|
| 211 | 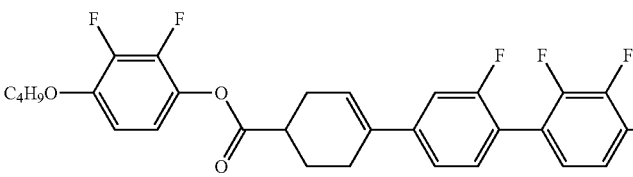 |
| 212 | 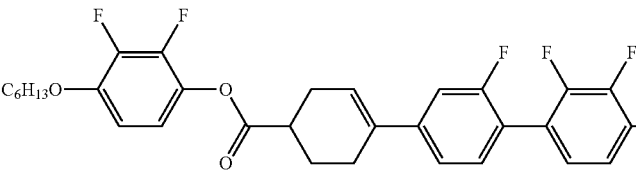 |
| 213 | 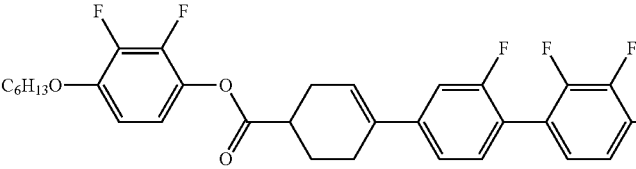 |
| 214 | 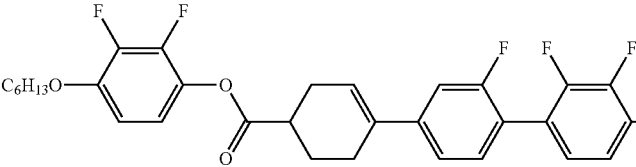 |
| 215 | 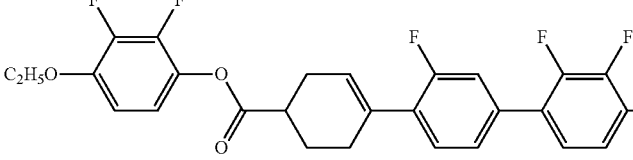 |
| 216 | 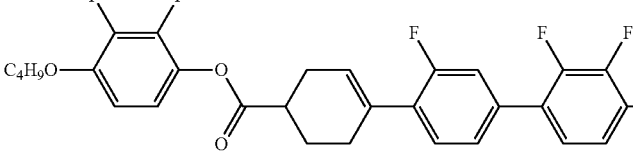 |
| 217 | 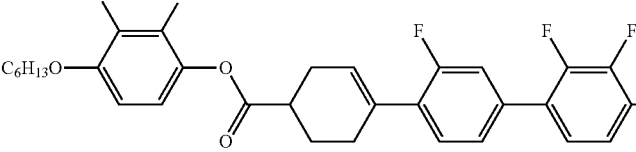 |
| 218 | |

-continued
| No. | |
|---|---|
| 219 | 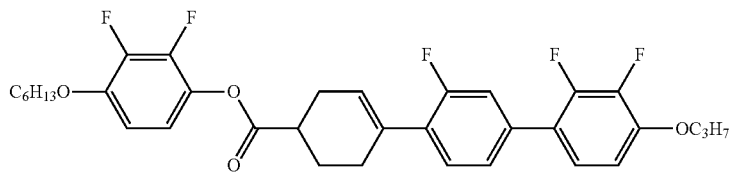 |
| 220 | 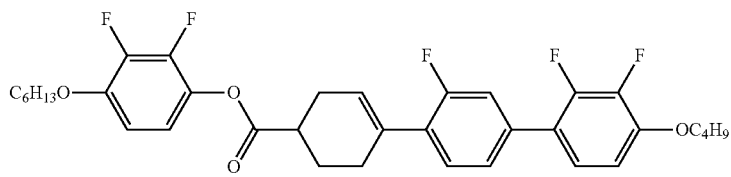 |
| 221 | 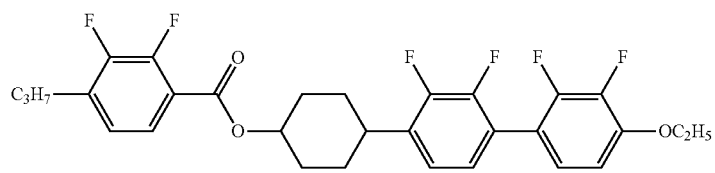 |
| 222 | 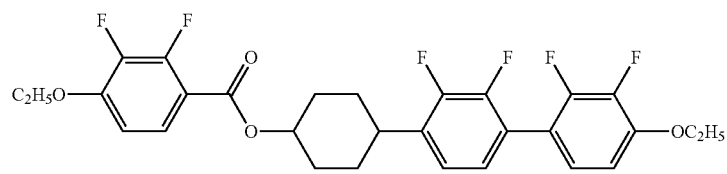 |
| 223 | 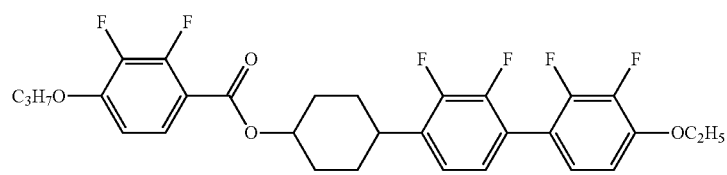 |
| 224 | 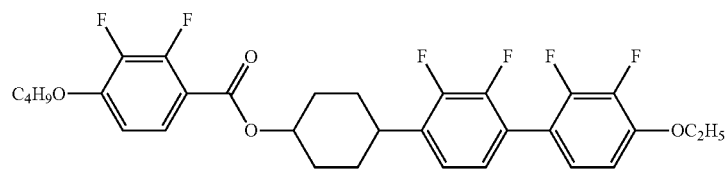 |
| 225 | 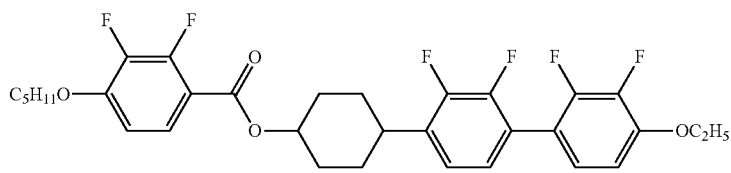 |
| 226 | 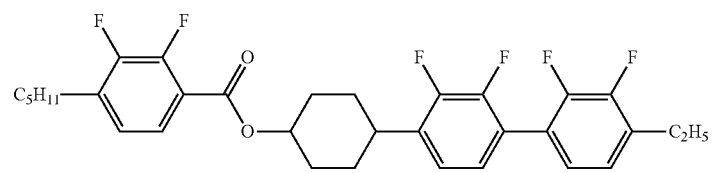 |
| 227 | 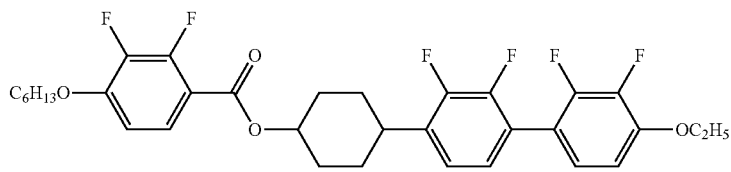 |

-continued
| No. | |
|---|---|
| 228 | 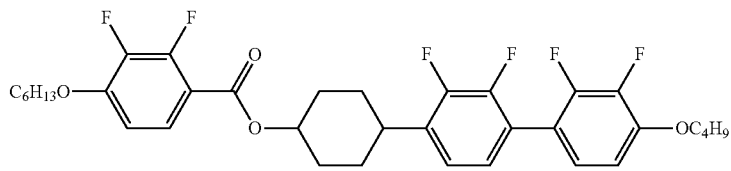 |
| 229 | 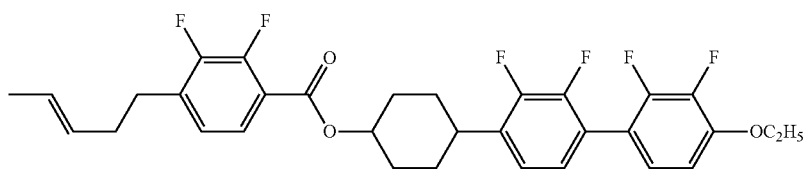 [SMILES: C/C=C/CCc1ccc(C(=O)OC2CCC(c3ccc(-c4ccc(OCC)c(F)c4F)c(F)c3F)CC2)c(F)c1F] |
| 230 | 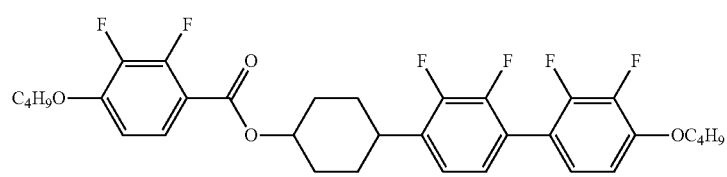 |
| 231 | 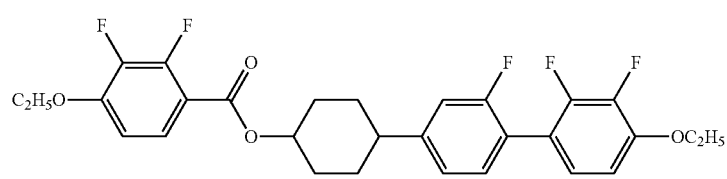 |
| 232 | 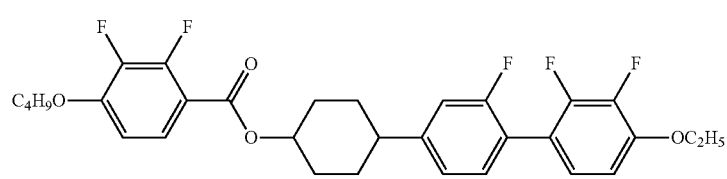 |
| 233 | 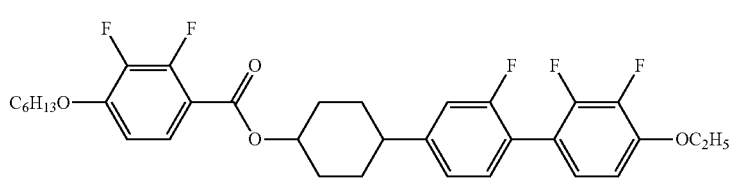 |
| 234 | 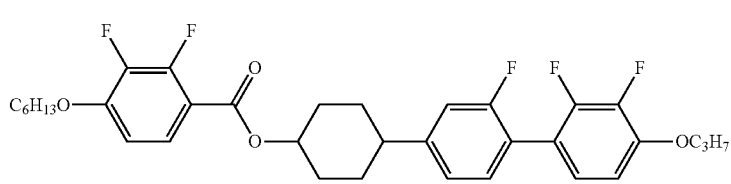 |
| 235 | 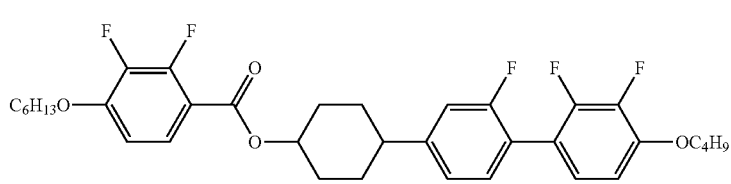 |
| 236 | 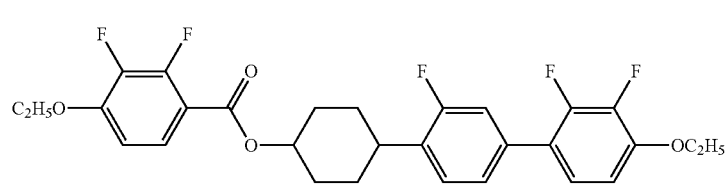 |

| No. | |
|---|---|
| 237 | 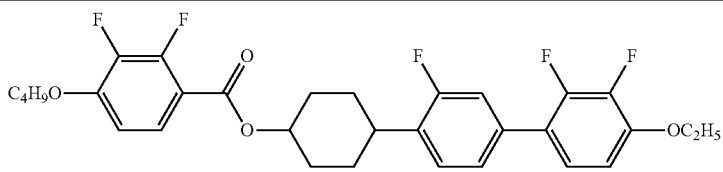 |
| 238 | 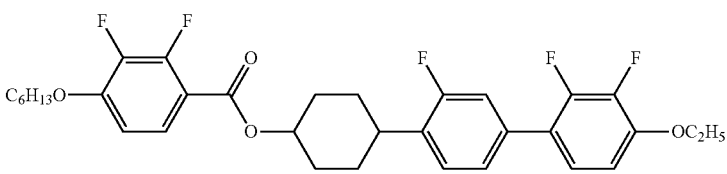 |
| 239 | 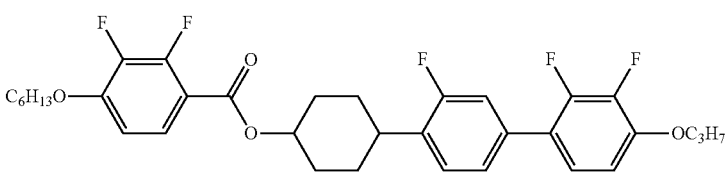 |
| 240 | 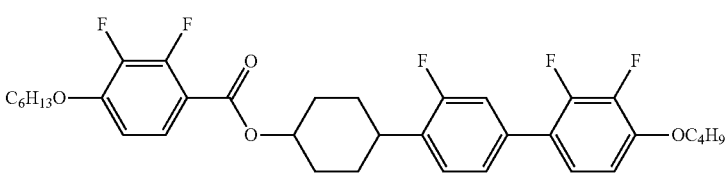 |
| 241 | 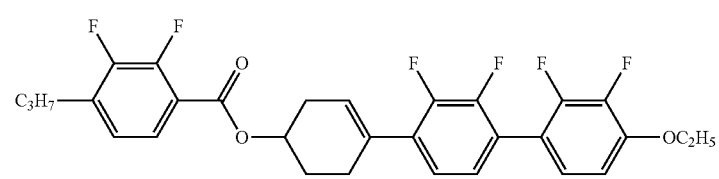 |
| 242 | 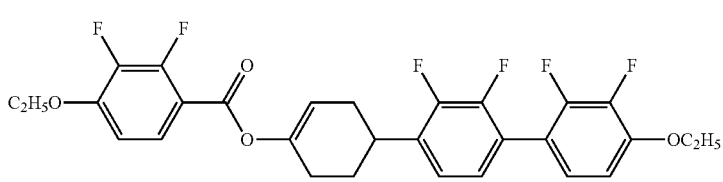 |
| 243 | 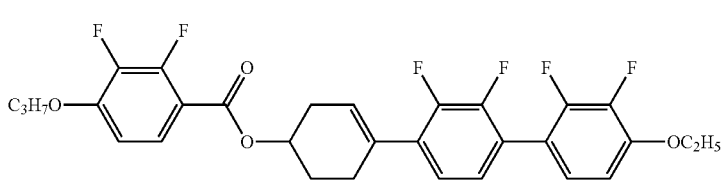 |
| 244 | 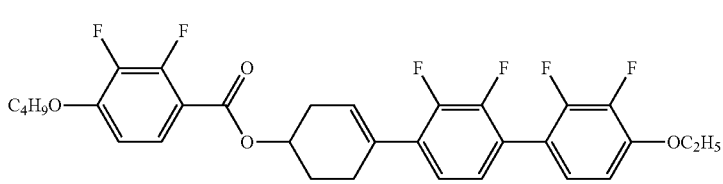 |
| 245 | 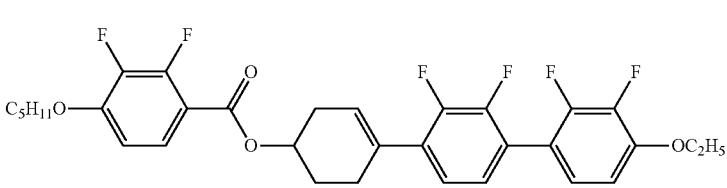 |

-continued
| No. | |
|---|---|
| 246 | 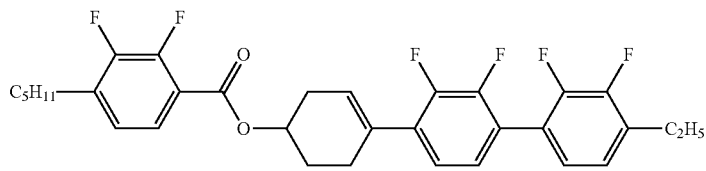 |
| 247 | 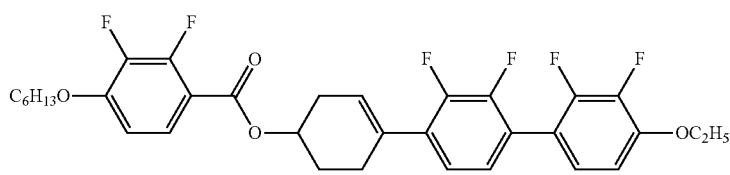 |
| 248 | 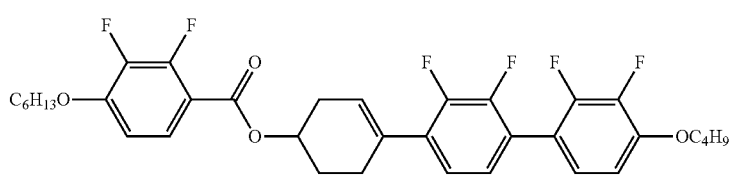 |
| 249 | 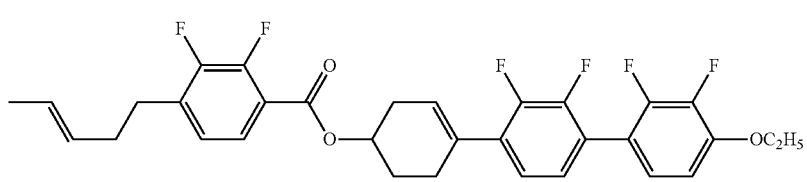 |
| 250 | 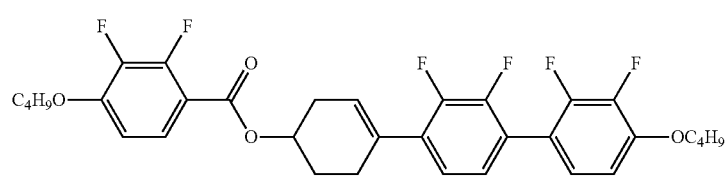 |
| 251 | 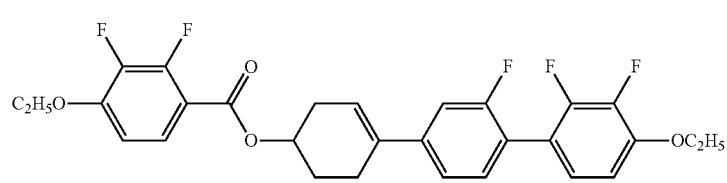 |
| 252 | 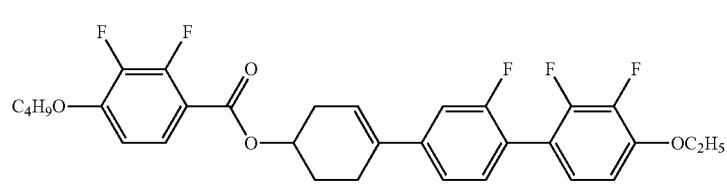 |
| 253 | 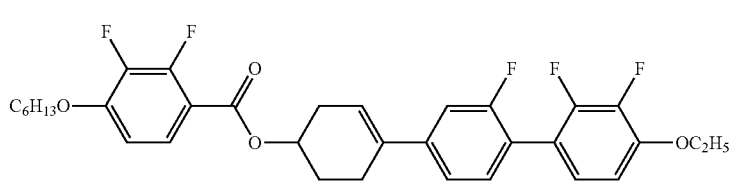 |
| 254 | 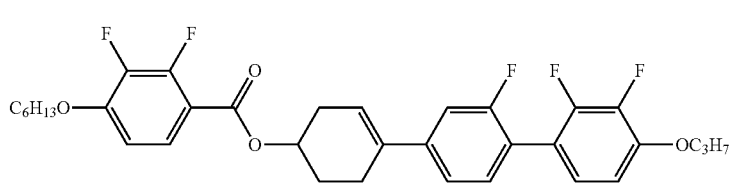 |

-continued
| No. | |
|---|---|
| 255 | 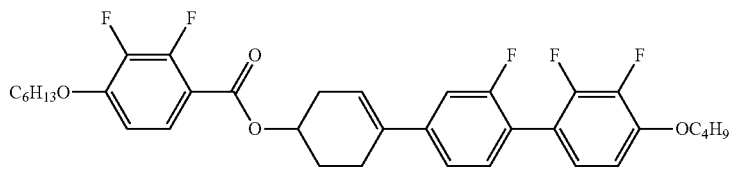 |
| 256 | 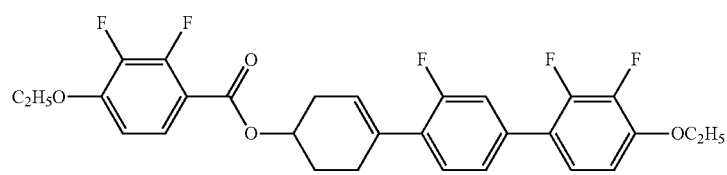 |
| 257 | 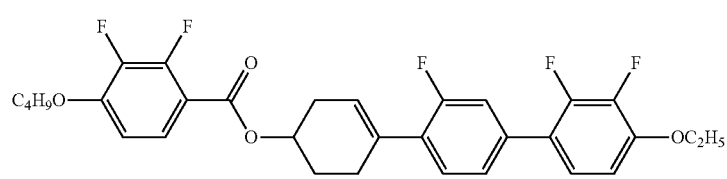 |
| 258 | 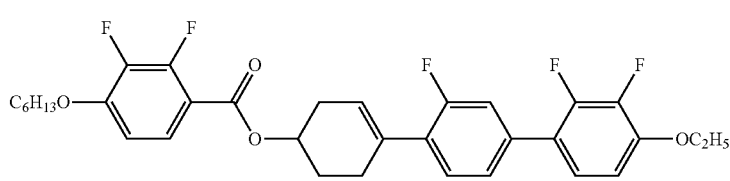 |
| 259 | 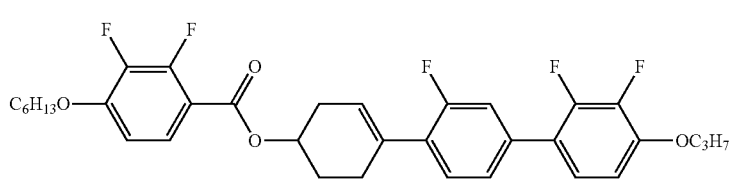 |
| 260 | 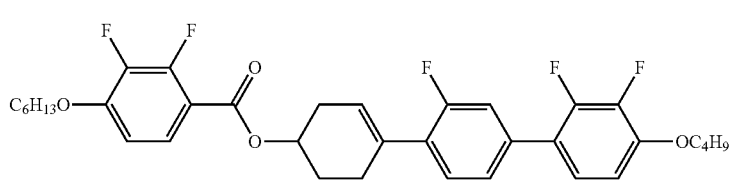 |
| 261 | 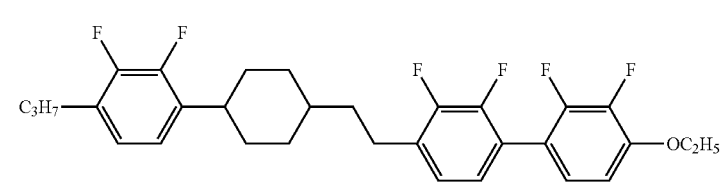 |
| 262 | 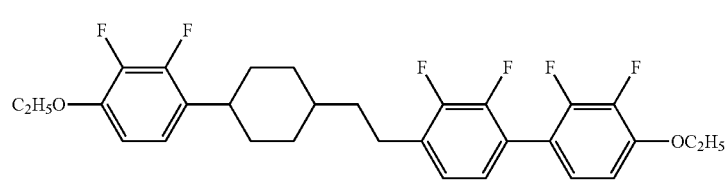 |
| 263 | 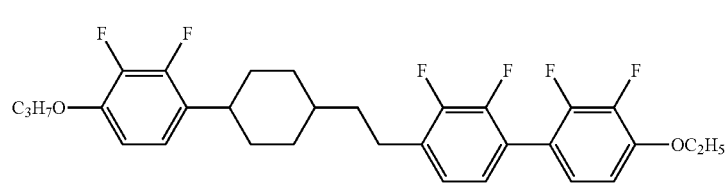 |

| No. | |
|---|---|
| 264 | 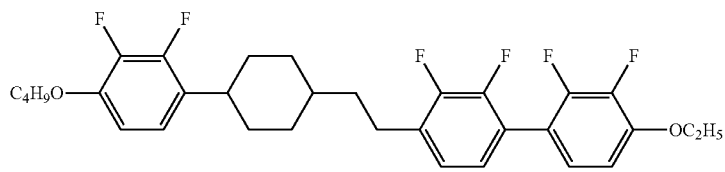 |
| 265 | 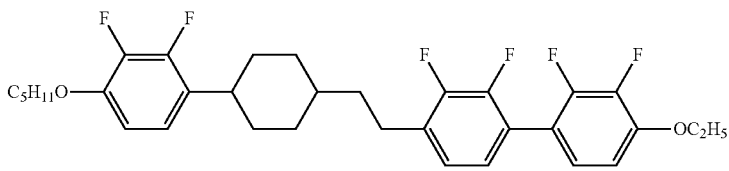 |
| 266 | 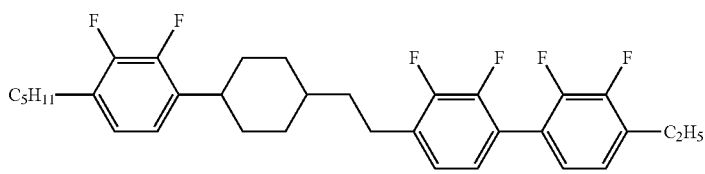 |
| 267 | 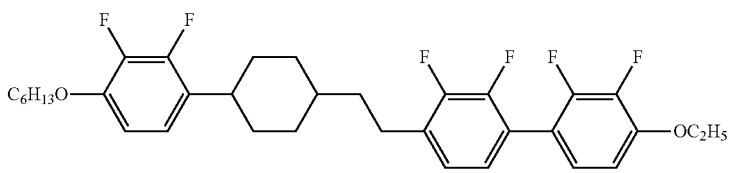 C 109.8 N 184.6 I<br>$T_{NI}$; 165.6° C., Δ ε; -8.17, Δ n; 0.149 |
| 268 | 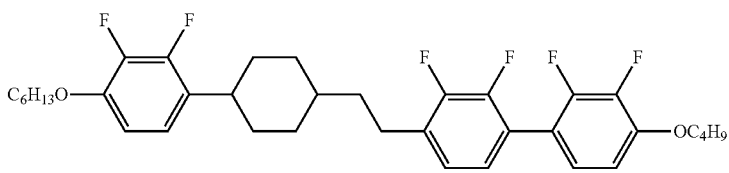 |
| 269 | 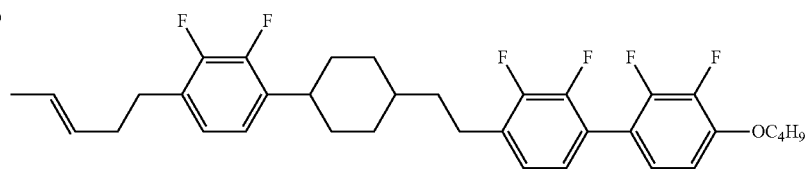 |
| 270 | 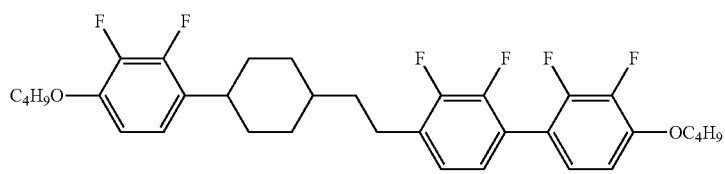 |
| 271 | 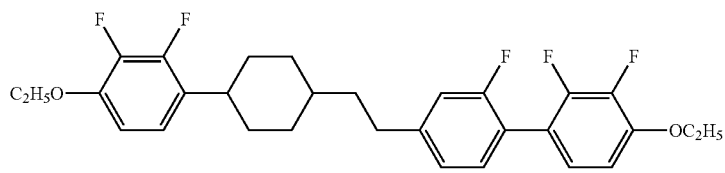 |

-continued
| No. | |
|---|---|
| 272 | 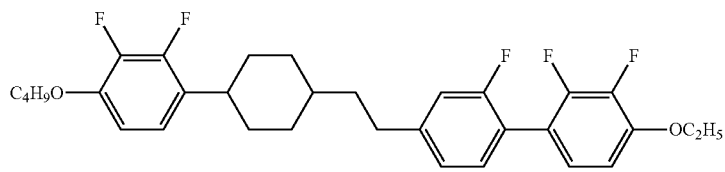 |
| 273 | 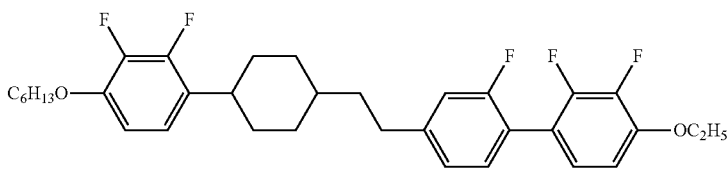 |
| 274 | 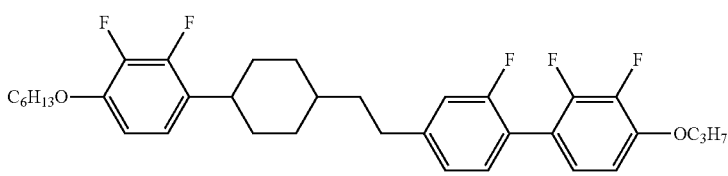 |
| 275 | 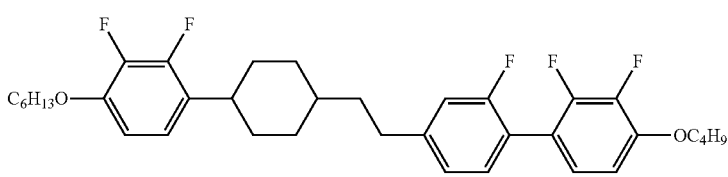 |
| 276 | 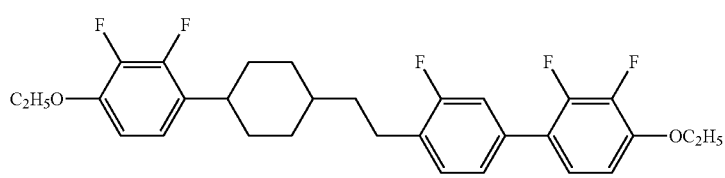 |
| 277 | 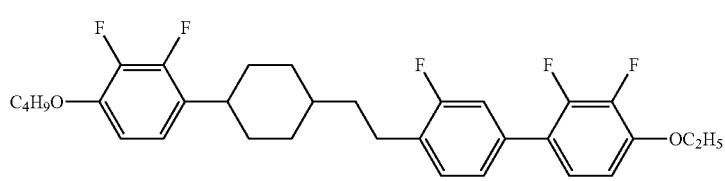 |
| 278 | 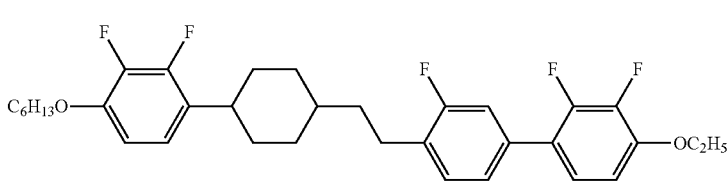 |
| 279 | 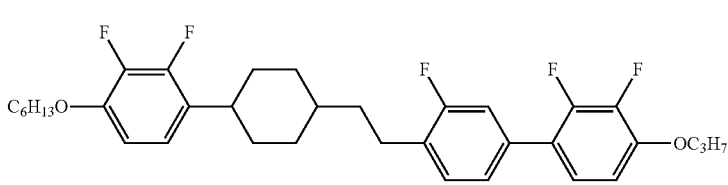 |
| 280 | 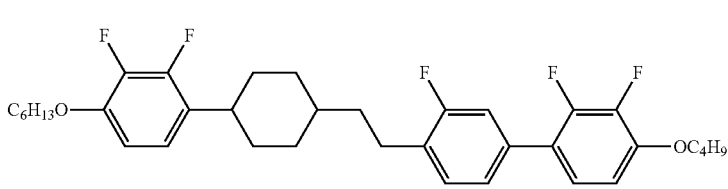 |

-continued
| No. | |
|---|---|
| 281 | 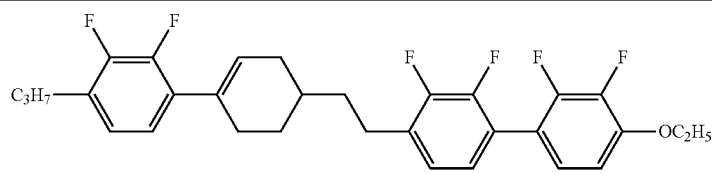 |
| 282 | 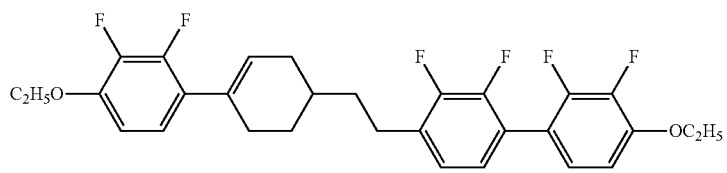 |
| 283 | 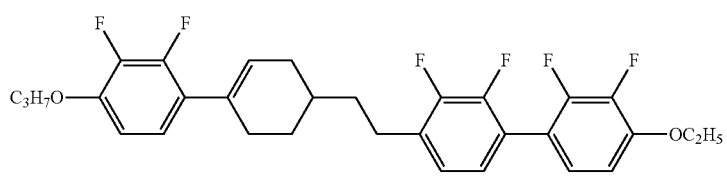 |
| 284 | 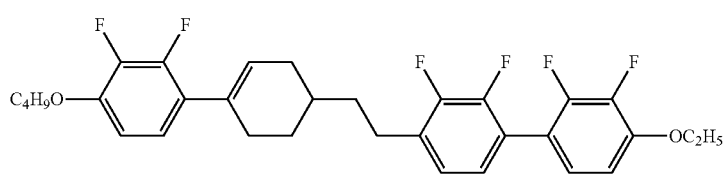 |
| 285 | 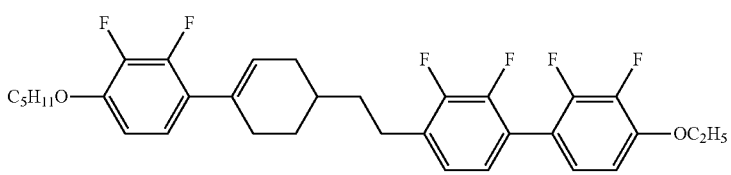 |
| 286 | 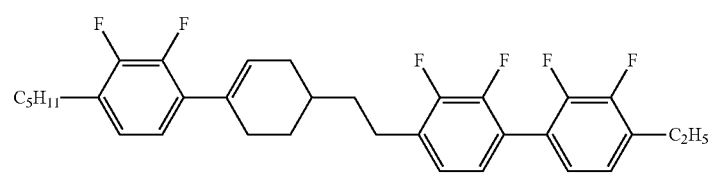 |
| 287 | 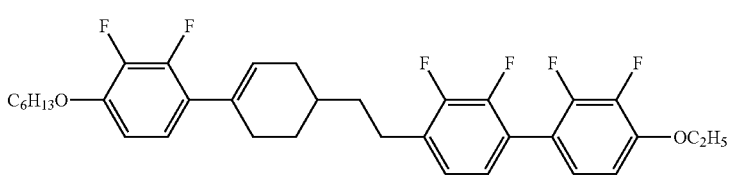 |
| 288 | 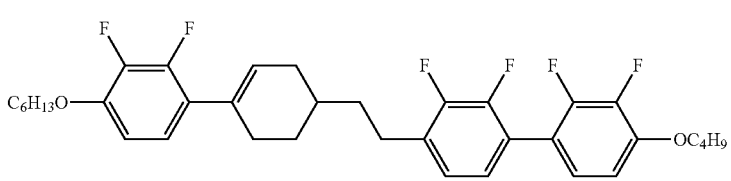 |
| 289 | 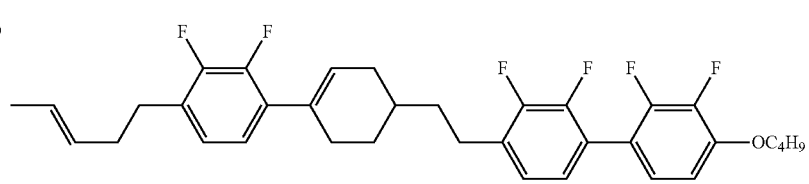 |

| No. | |
|---|---|
| 290 | 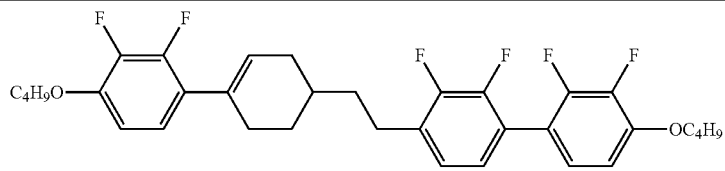 |
| 291 | 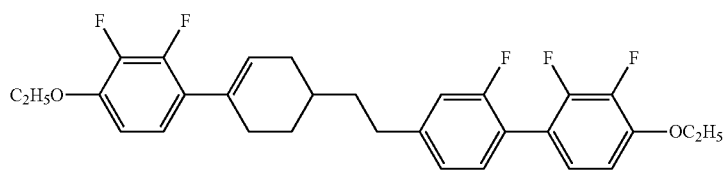 |
| 292 | 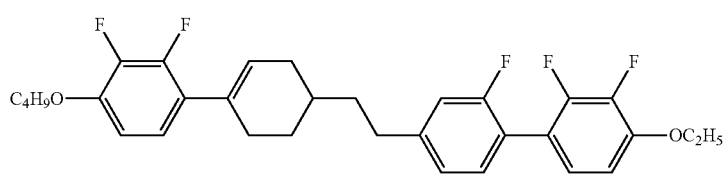 |
| 293 | 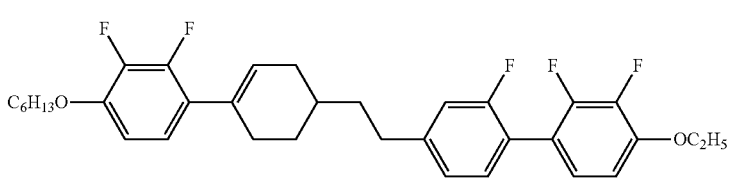 |
| 294 | 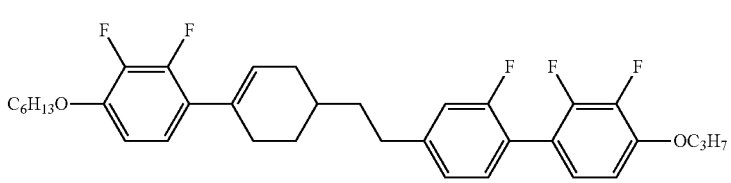 |
| 295 | 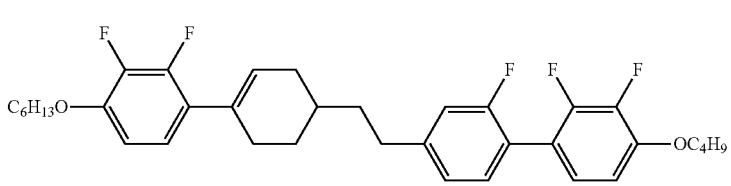 |
| 296 | 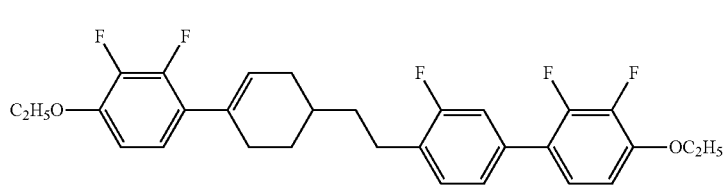 |
| 297 | 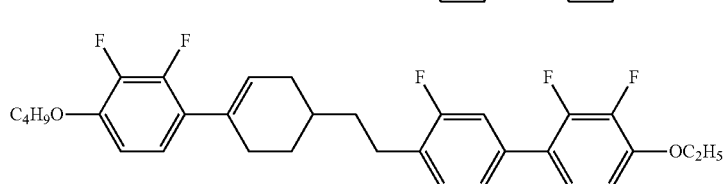 |
| 298 | 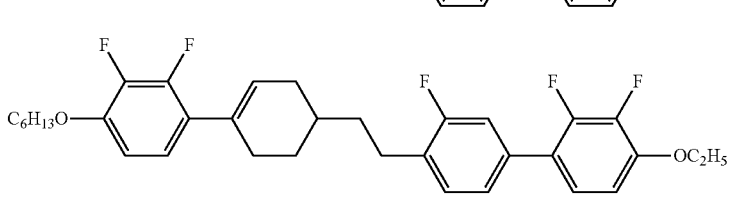 |

| No. | |
|---|---|
| 299 | 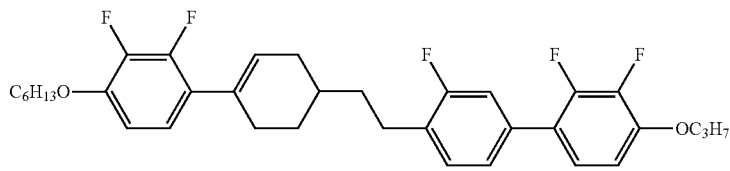 |
| 300 | 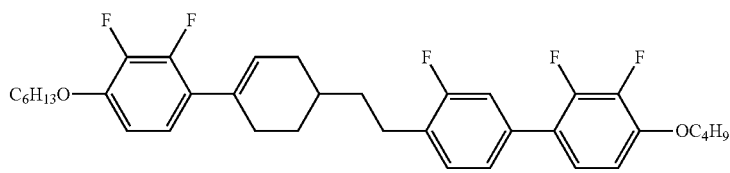 |
| 301 | 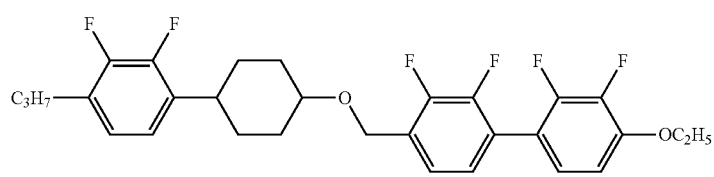 |
| 302 | 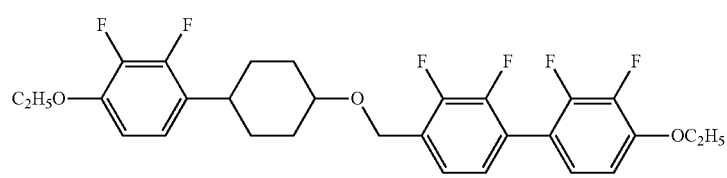 |
| 303 | 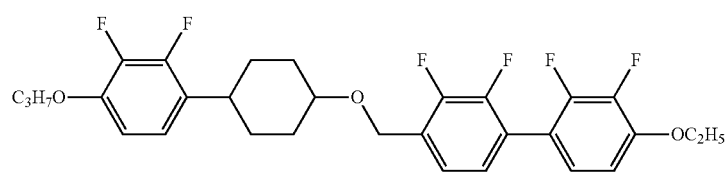 |
| 304 | 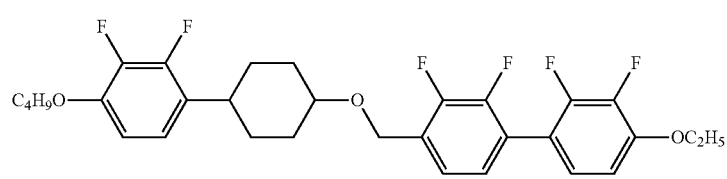 |
| 305 | 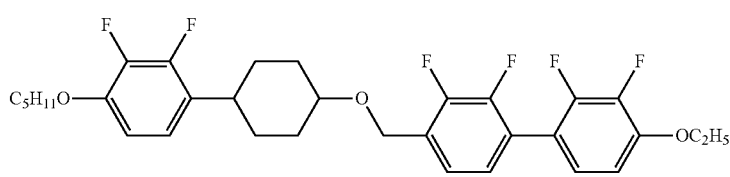 |
| 306 | 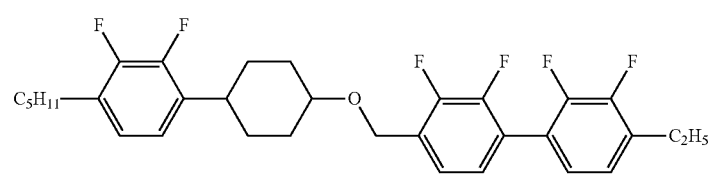 |
| 307 | 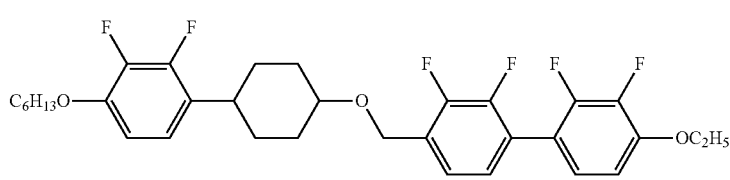 |

-continued
| No. | |
|---|---|
| 308 | 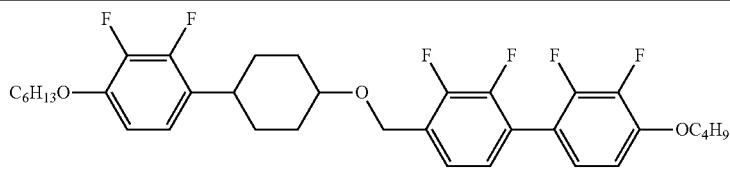 |
| 309 | 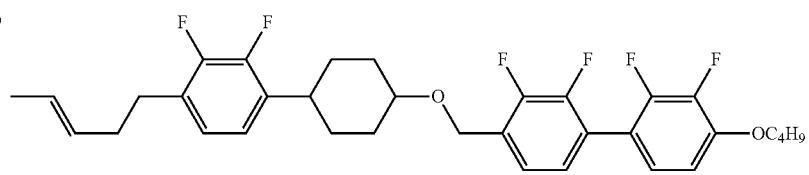 |
| 310 | 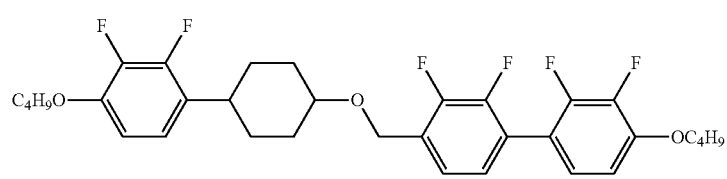 |
| 311 | 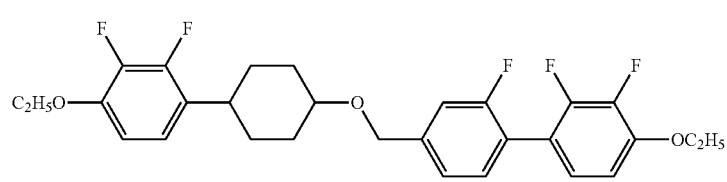 |
| 312 | 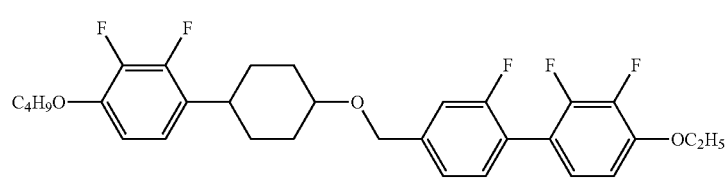 |
| 313 | 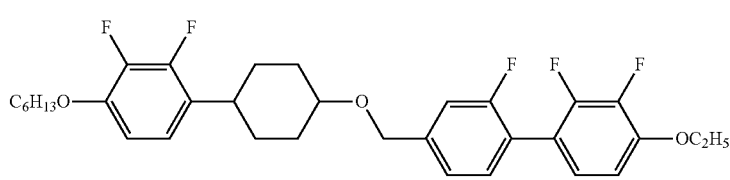 |
| 314 | 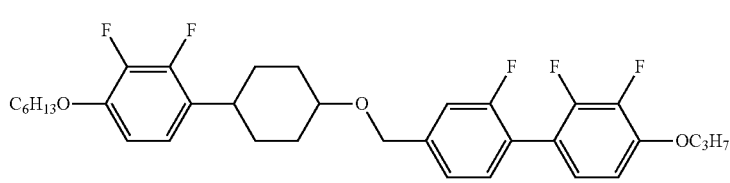 |
| 315 | 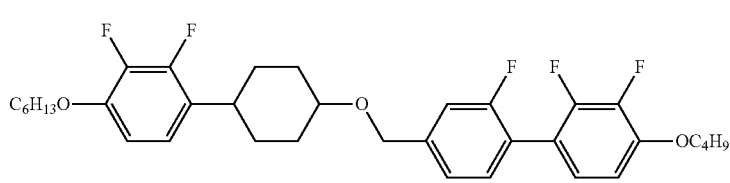 |
| 316 | 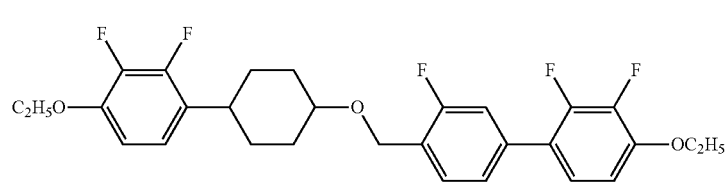 |

-continued
| No. | |
|---|---|
| 317 | 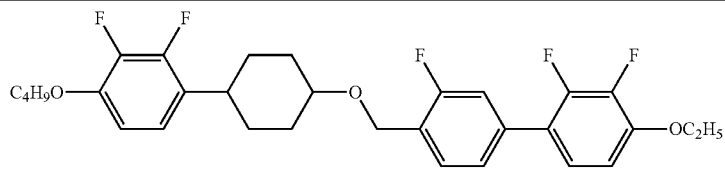 |
| 318 | 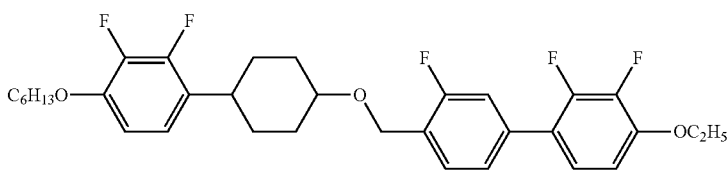 |
| 319 | 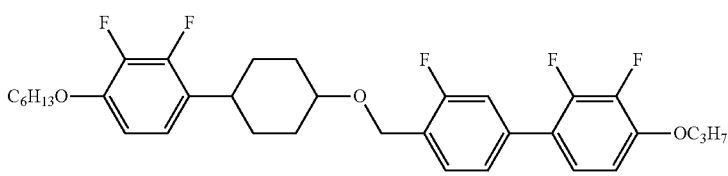 |
| 320 | 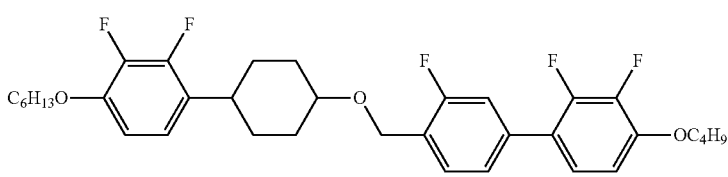 |
| 321 | 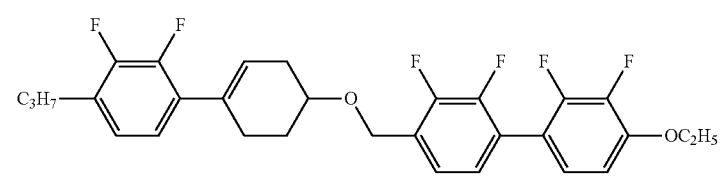 |
| 322 | 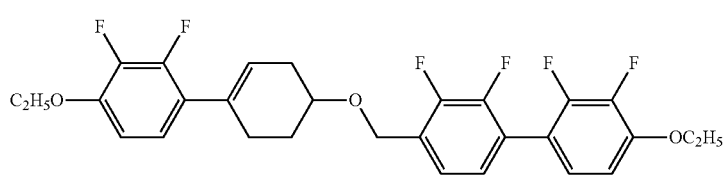 |
| 323 | 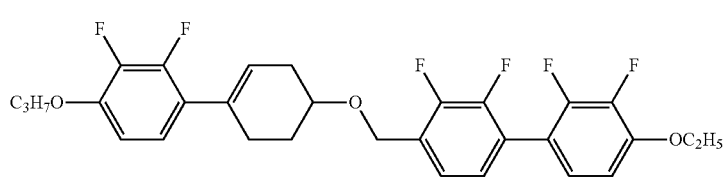 |
| 324 | 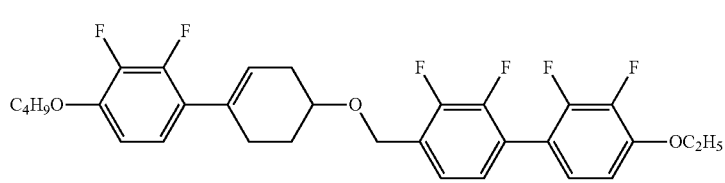 |
| 325 | 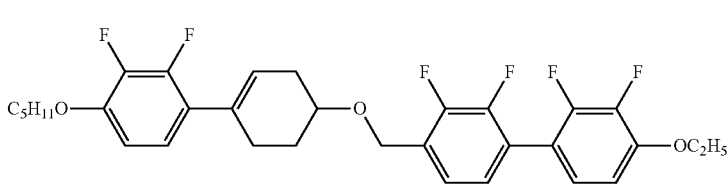 |

-continued
| No. | |
|---|---|
| 326 | 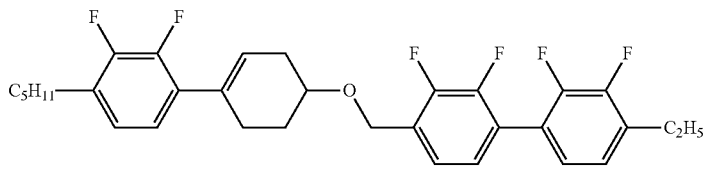 |
| 327 | 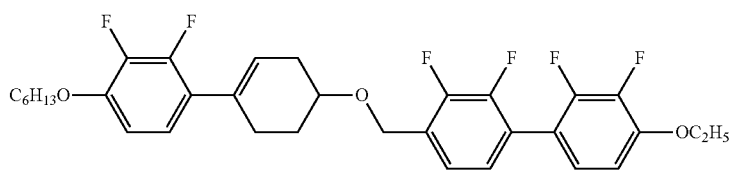 |
| 328 | 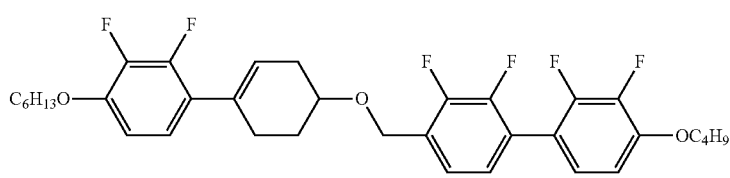 |
| 329 | 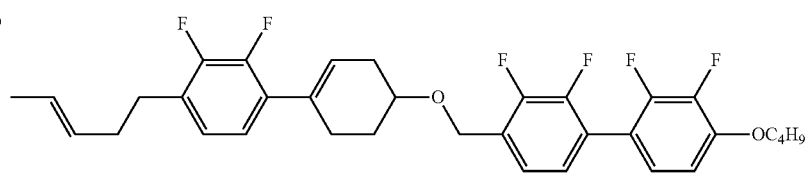 |
| 330 | 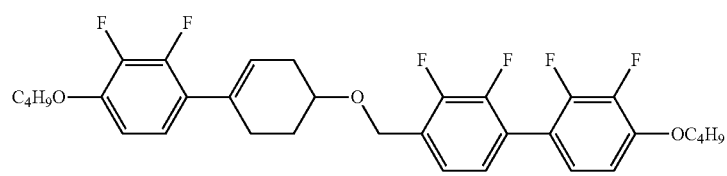 |
| 331 | 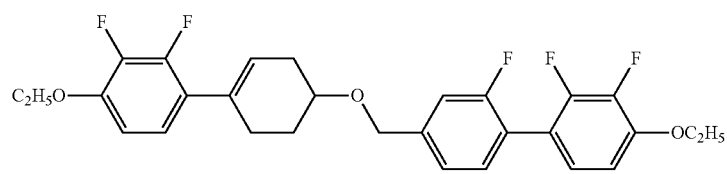 |
| 332 | 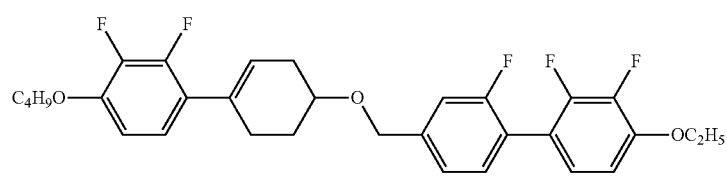 |
| 333 | 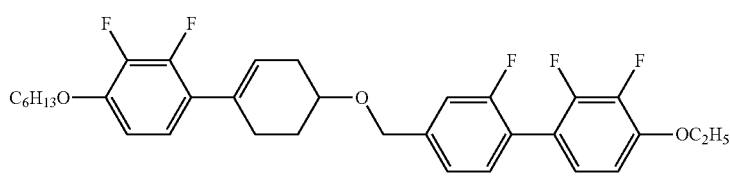 |
| 334 | 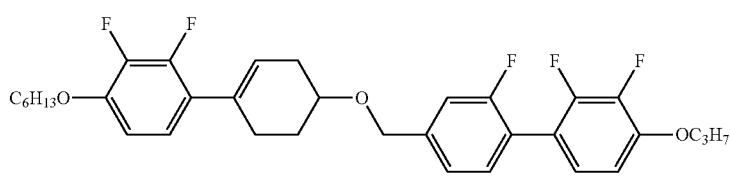 |

-continued
| No. | |
|---|---|
| 335 | 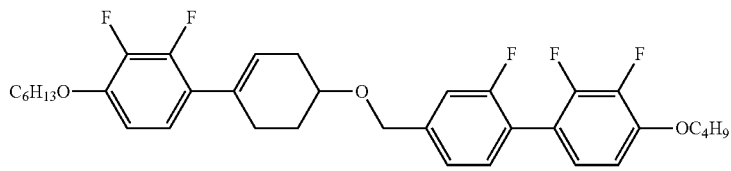 |
| 336 | 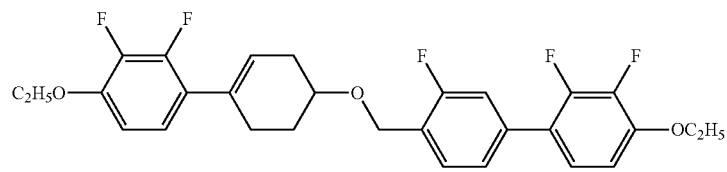 |
| 337 | 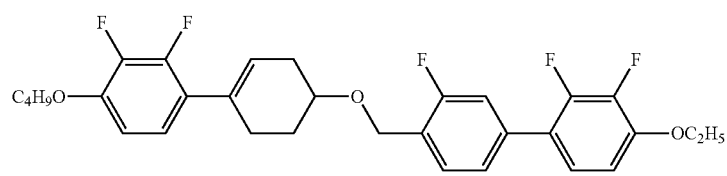 |
| 338 | 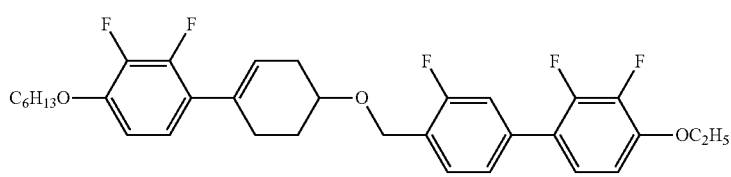 |
| 339 | 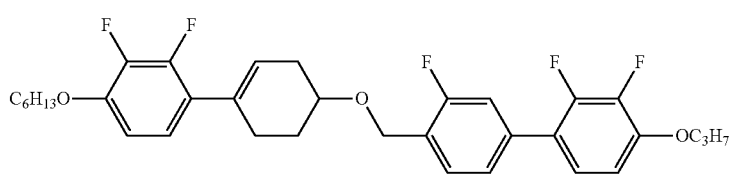 |
| 340 | 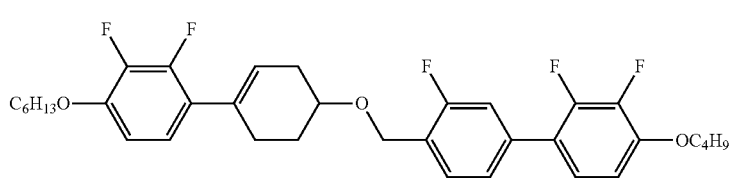 |
| 341 | 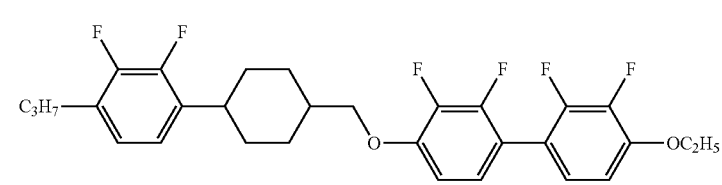 |
| 342 | 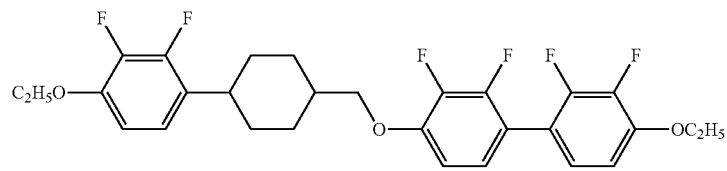 |
| 343 | 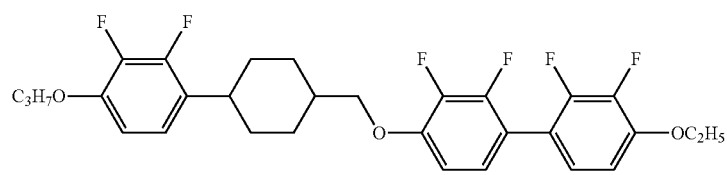 |

| No. | |
|---|---|
| 344 | 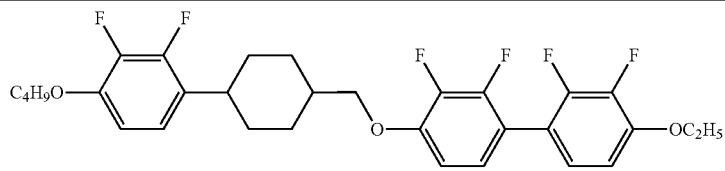 |
| 345 | 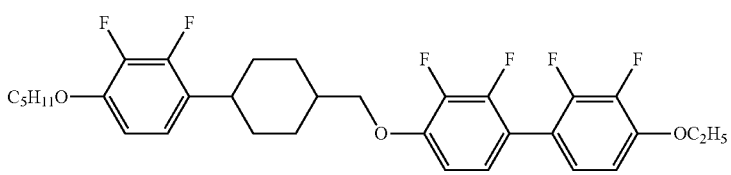 |
| 346 | 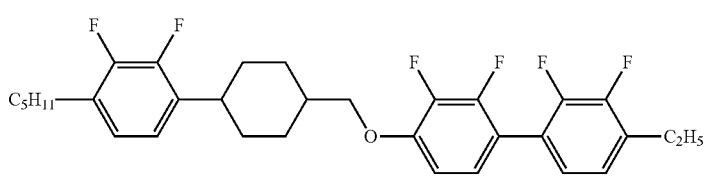 |
| 347 | 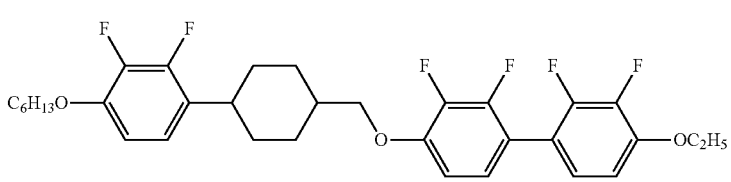 |
| 348 | 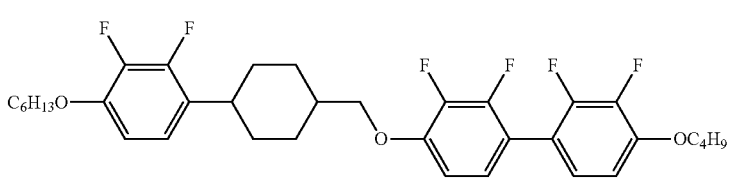 |
| 349 | 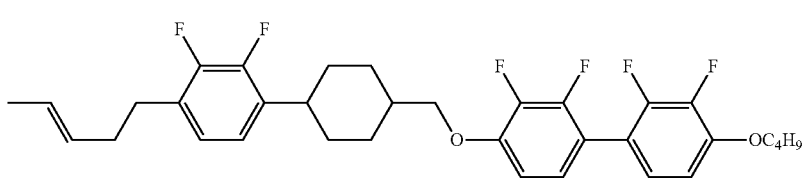 |
| 350 | 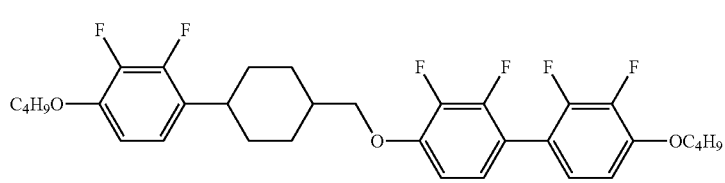 |
| 351 | 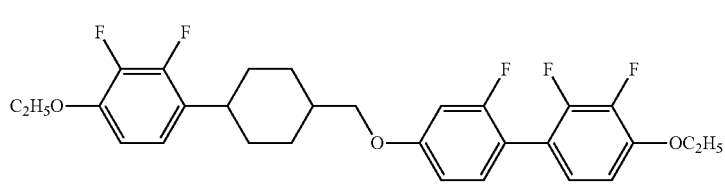 |
| 352 | 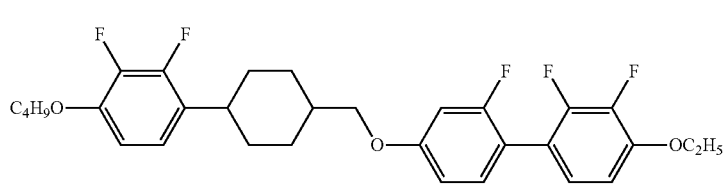 |

| No. | |
|---|---|
| 353 | 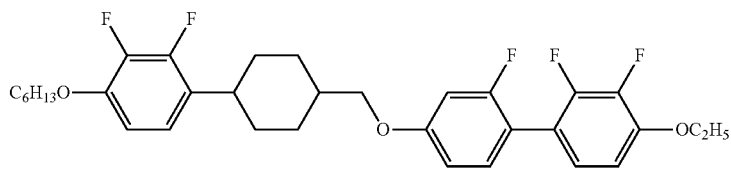 |
| 354 | 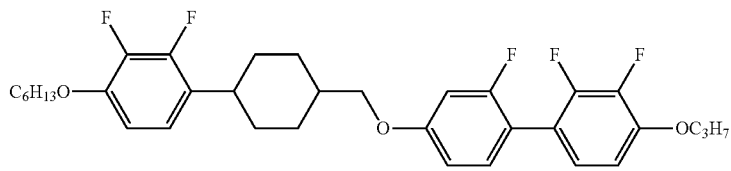 |
| 355 | 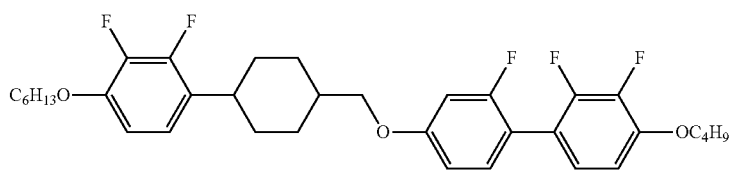 |
| 356 | 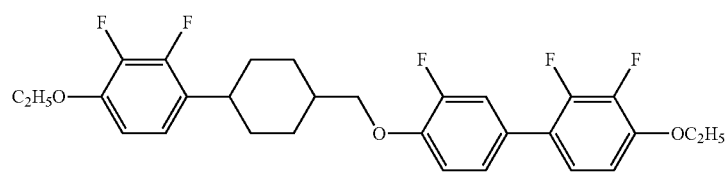 |
| 357 | 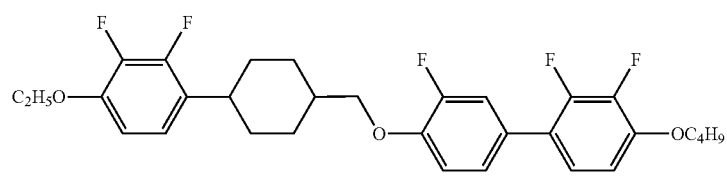 C 119.0N 204.1 I<br>$T_{NI}$; 181.6° C., Δ ε; -7.95; Δ n; 0.190 |
| 358 | 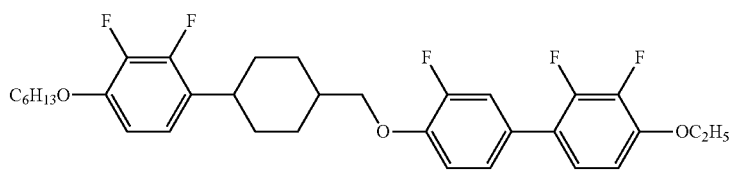 |
| 359 | 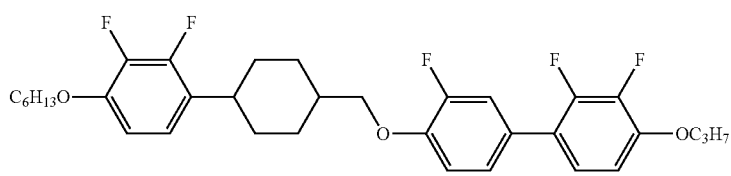 |
| 360 | 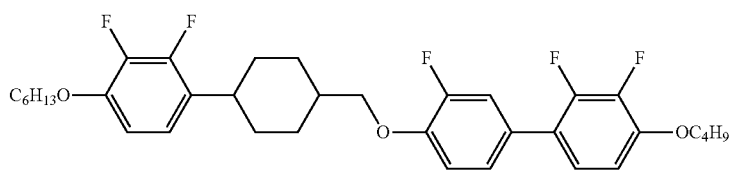 |

| No. | |
|---|---|
| 361 | 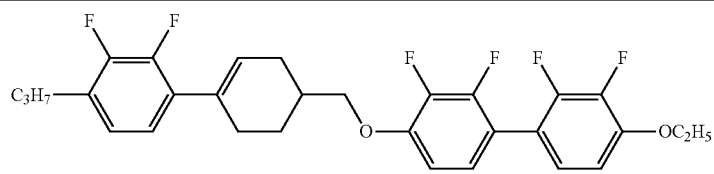 |
| 362 | 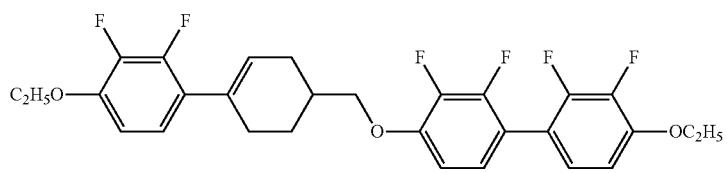 |
| 363 | 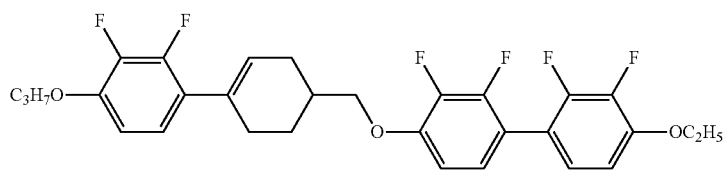 |
| 364 | 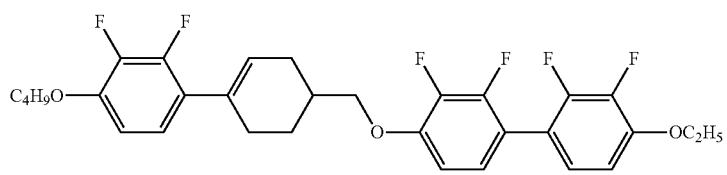 |
| 365 | 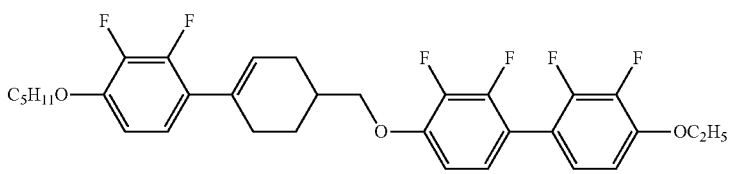 |
| 366 | 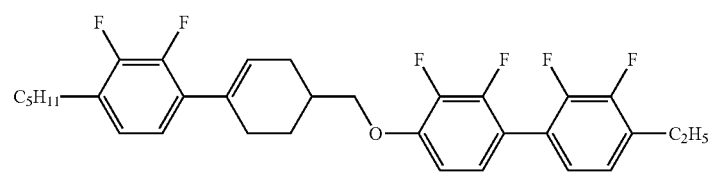 |
| 367 | 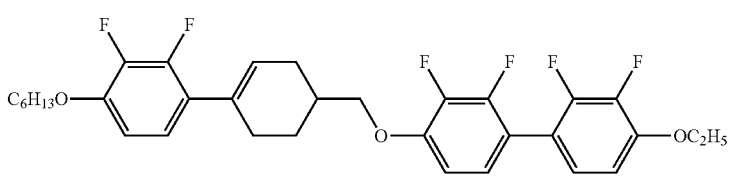 |
| 368 | 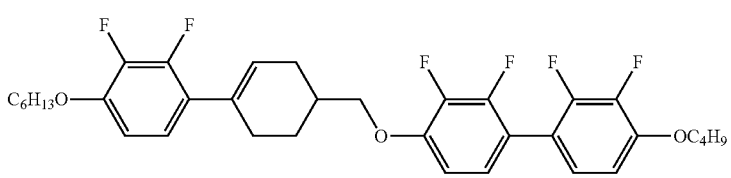 |
| 369 | 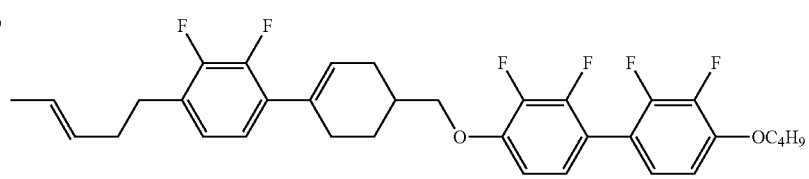 |

-continued
| No. | |
|---|---|
| 370 | 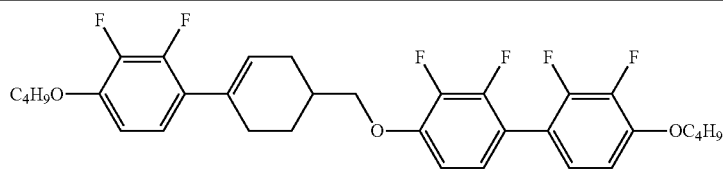 |
| 371 | 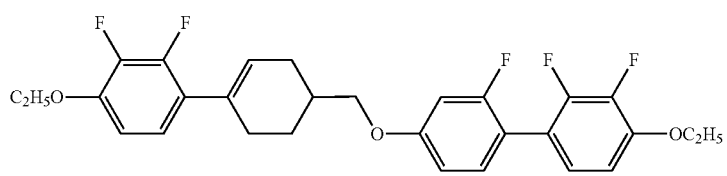 |
| 372 | 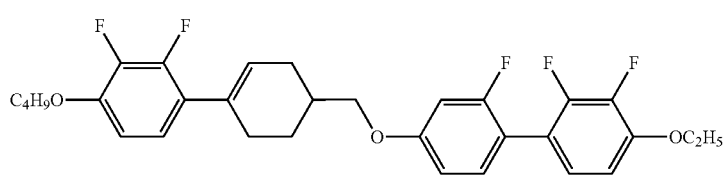 |
| 373 | 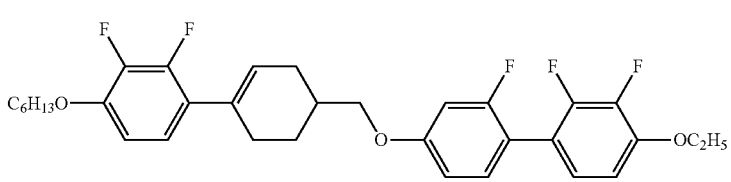 |
| 374 | 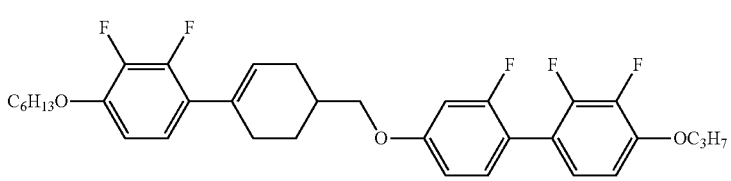 |
| 375 | 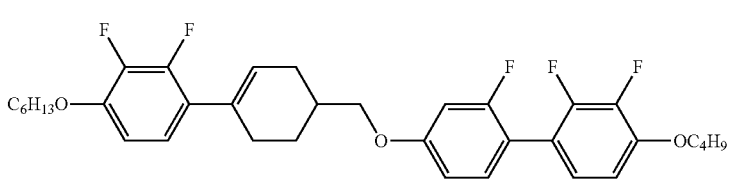 |
| 376 | 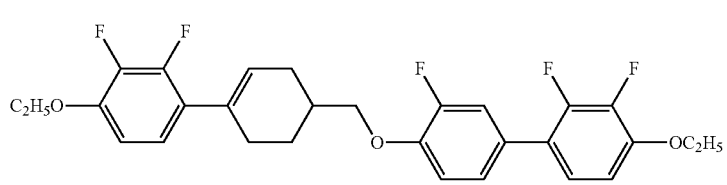 |
| 377 | 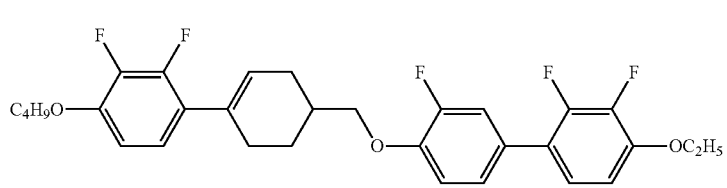 |
| 378 | 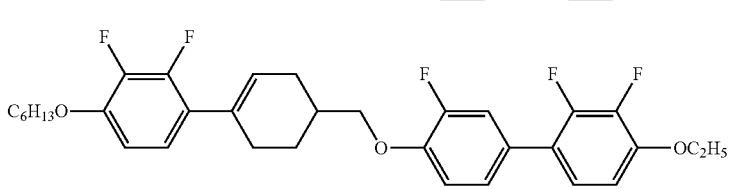 |

-continued
| No. | |
|---|---|
| 379 | 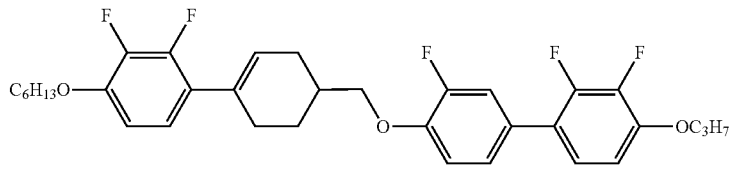 |
| 380 | 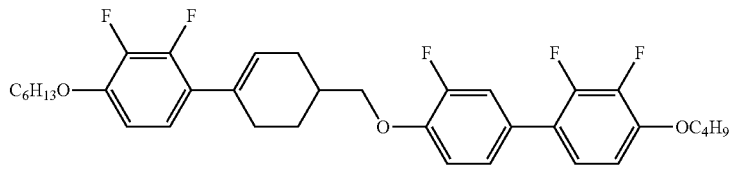 |
| 381 | 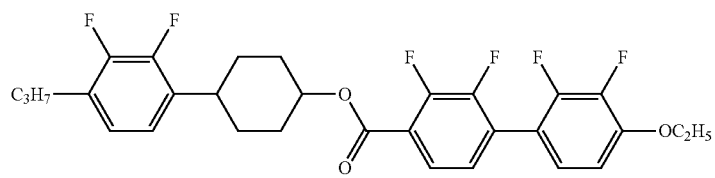 |
| 382 | 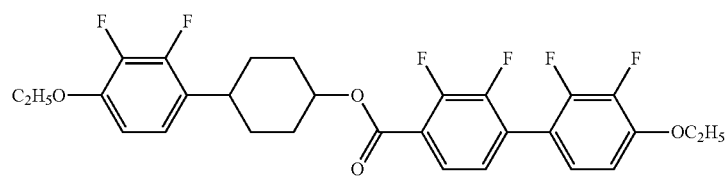 |
| 383 | 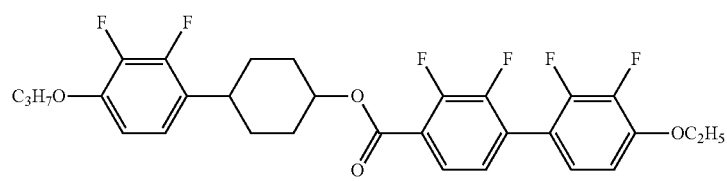 |
| 384 | 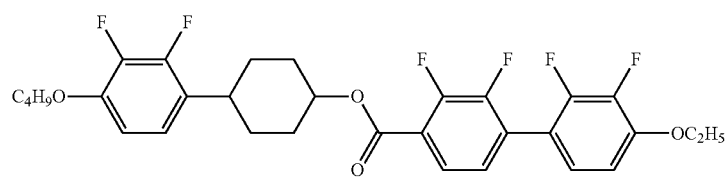 |
| 385 | 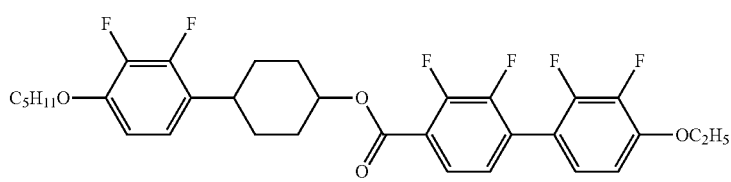 |
| 386 | 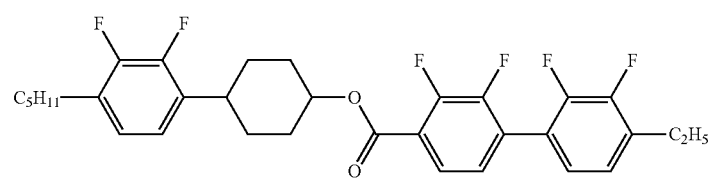 |

-continued
| No. | |
|---|---|
| 387 | 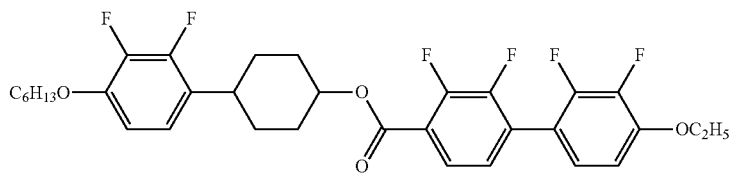 |
| 388 | 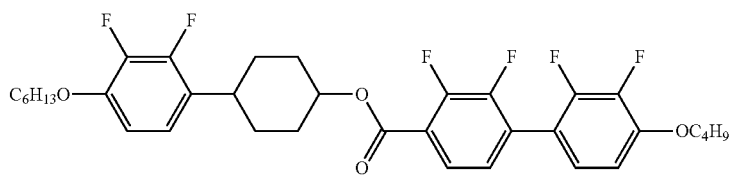 |
| 389 | 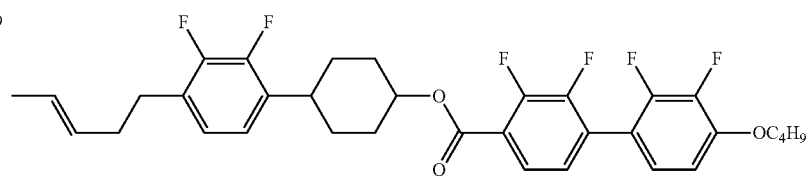 |
| 390 | 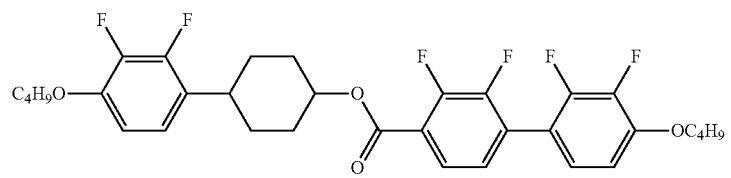 |
| 391 | 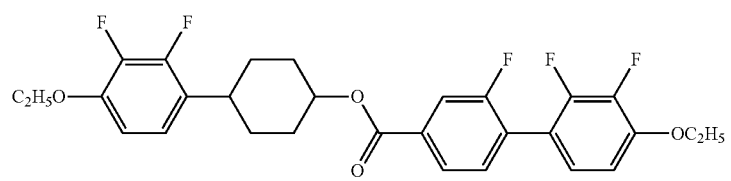 |
| 392 | 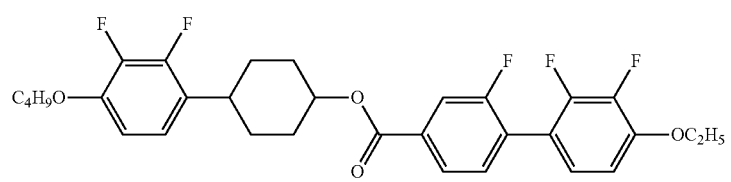 |
| 393 | 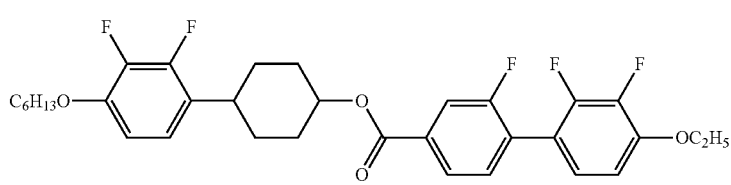 |
| 394 | 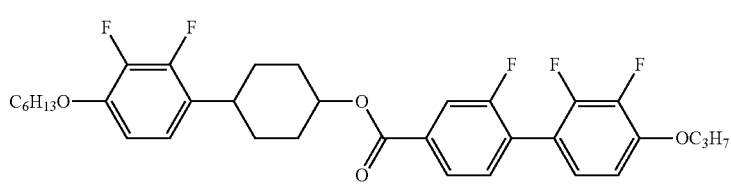 |

-continued
| No. | |
|---|---|
| 395 | 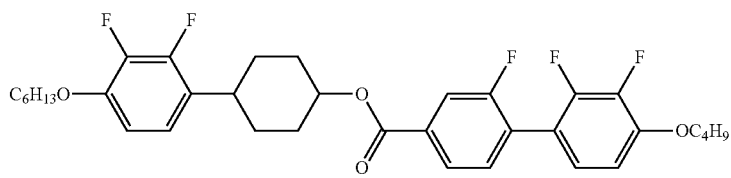 |
| 396 | 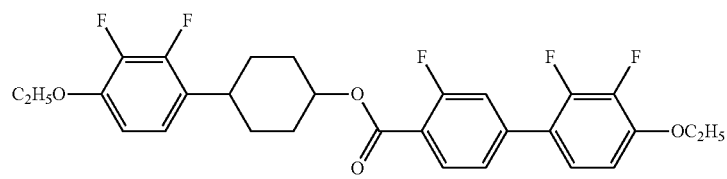 |
| 397 | 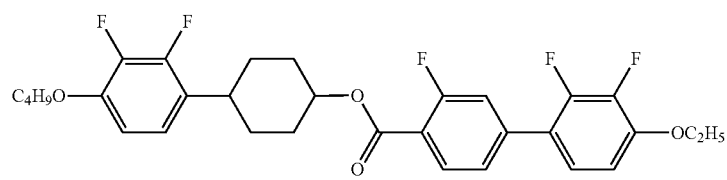 |
| 398 | 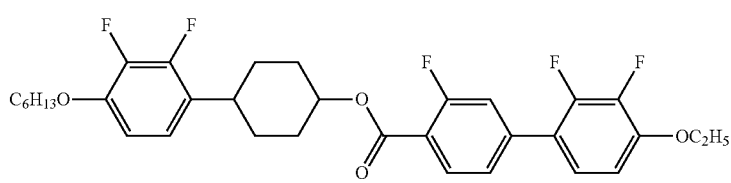 |
| 399 | 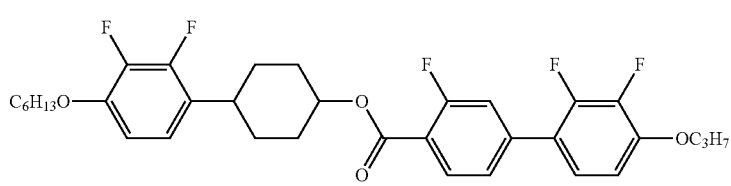 |
| 400 | 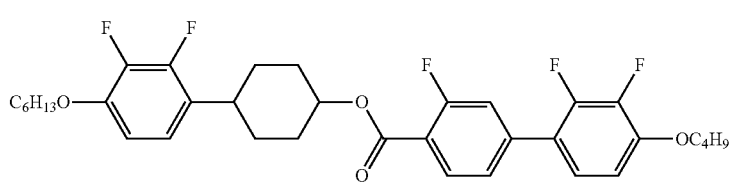 |
| 401 | 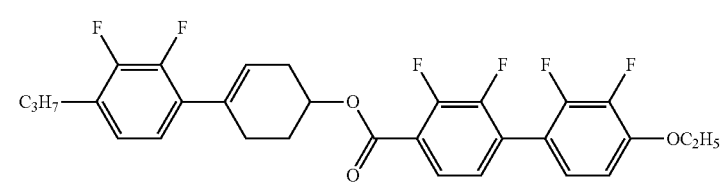 |
| 402 | 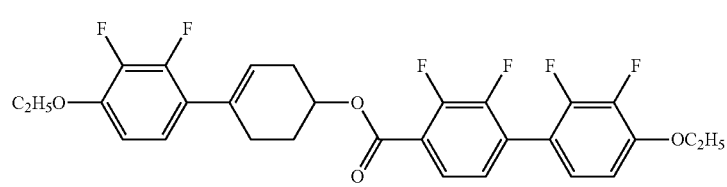 |

-continued
| No. | |
|---|---|
| 403 | 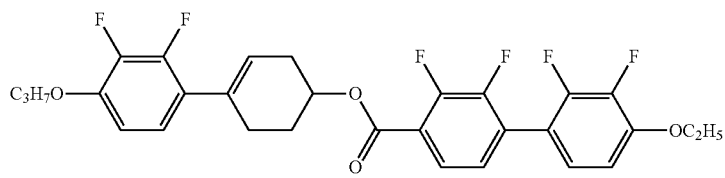 |
| 404 | 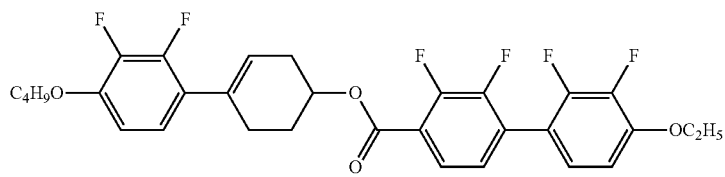 |
| 405 | 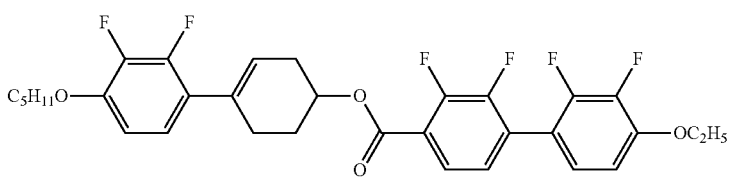 |
| 406 | 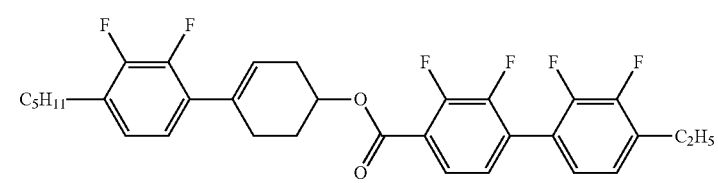 |
| 407 | 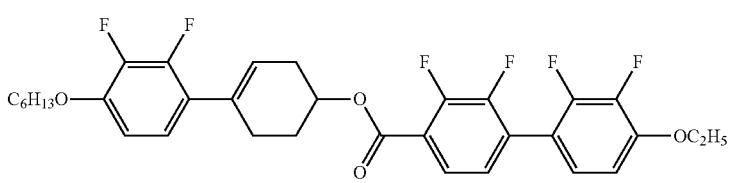 |
| 408 | 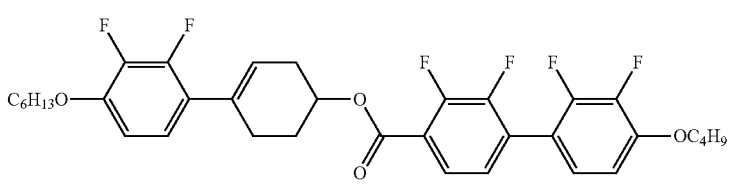 |
| 409 | 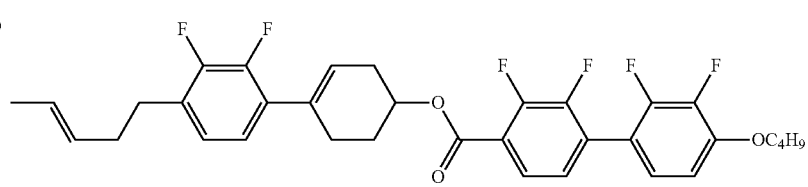 |
| 410 | 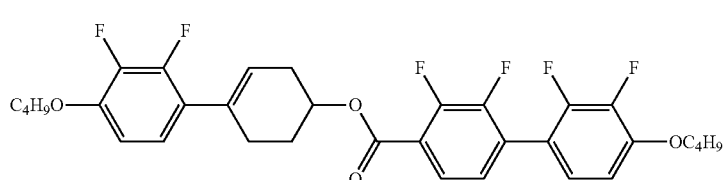 |

-continued
| No. | |
|---|---|
| 411 | 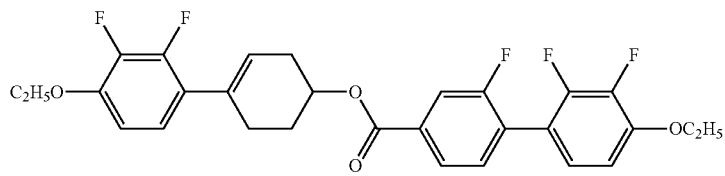 |
| 412 | 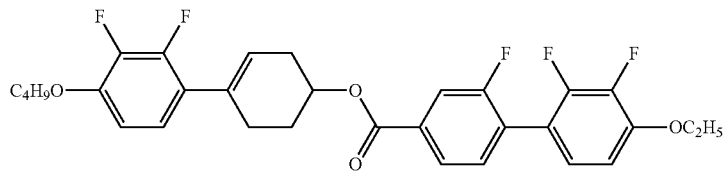 |
| 413 | 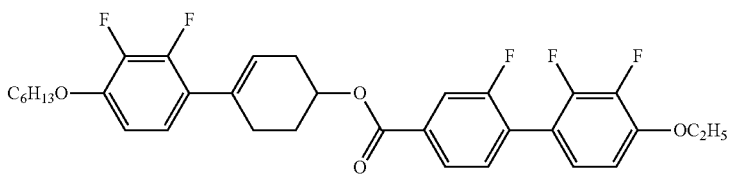 |
| 414 | 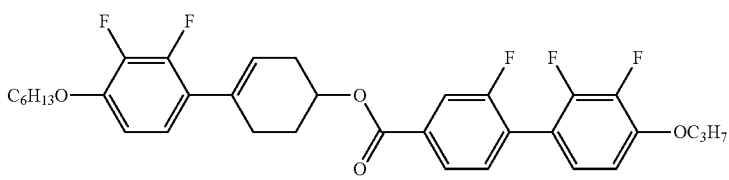 |
| 415 | 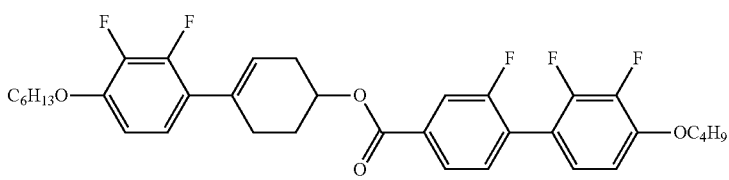 |
| 416 | 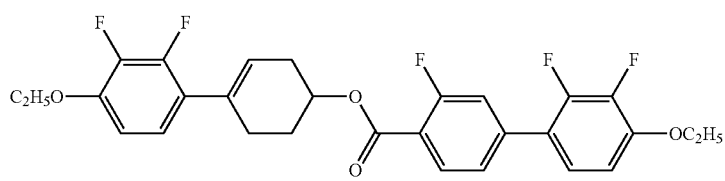 |
| 417 | 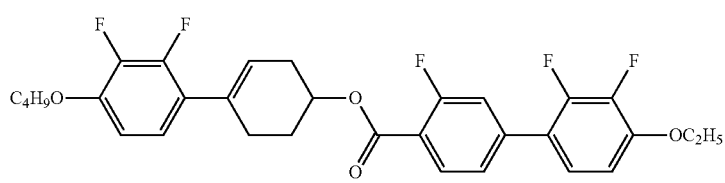 |
| 418 | 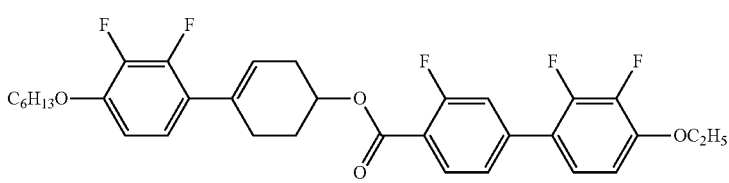 |

-continued
| No. | |
|---|---|
| 419 | 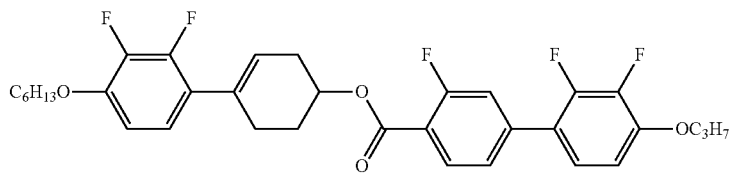 |
| 420 | 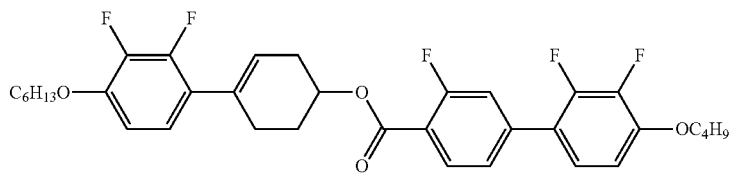 |
| 421 | 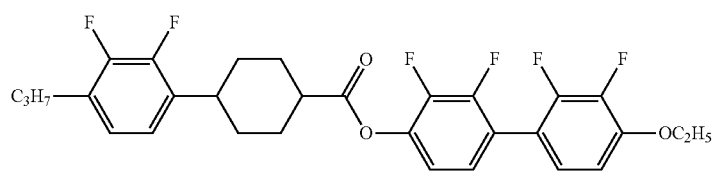 |
| 422 | 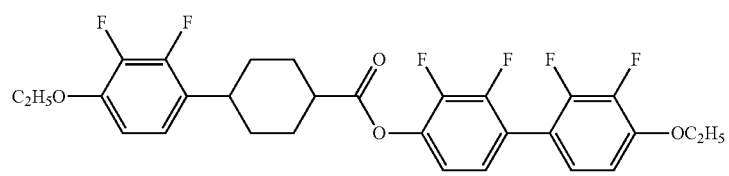 |
| 423 | 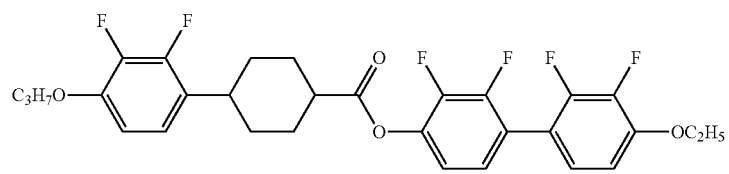 |
| 424 | 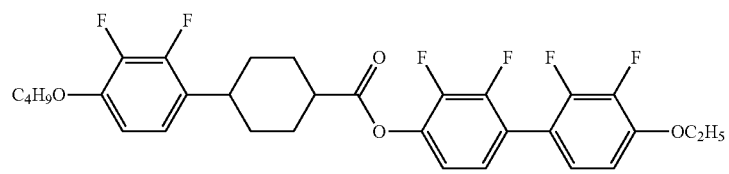 |
| 425 | 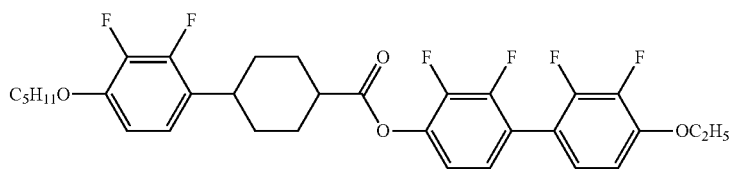 |
| 426 | 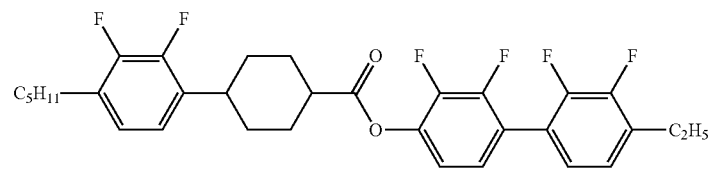 |
| 427 | 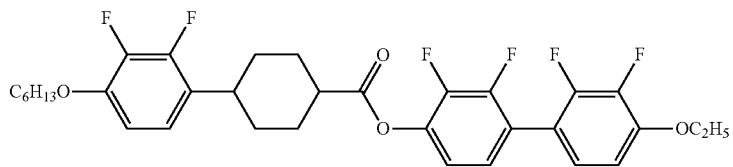 |

| No. | |
|---|---|
| 428 | 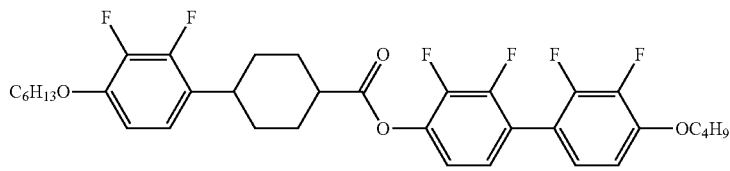 |
| 429 | 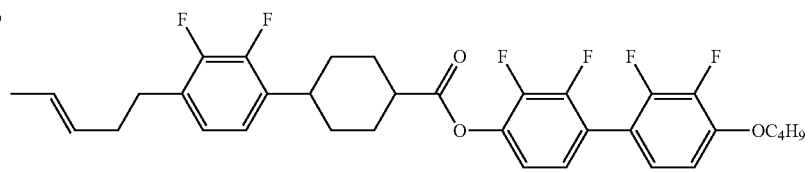 |
| 430 | 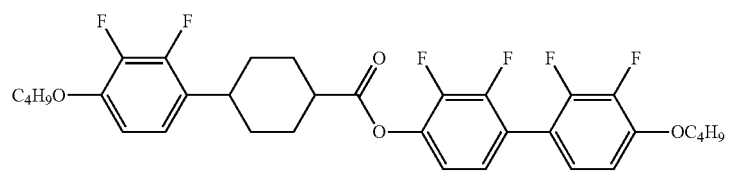 |
| 431 | 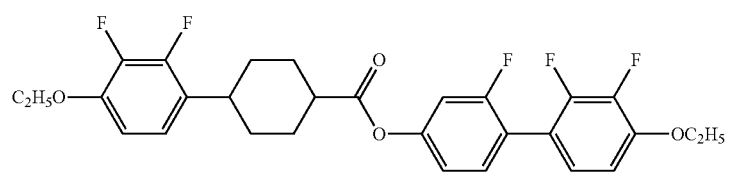 |
| 432 | 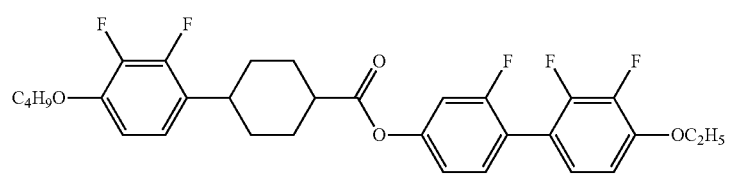 |
| 433 | 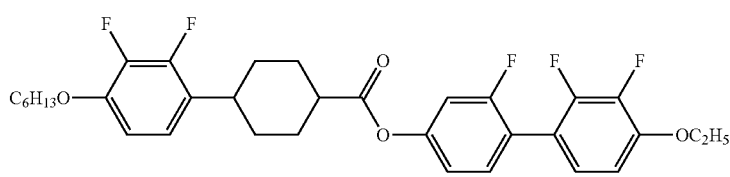 |
| 434 | 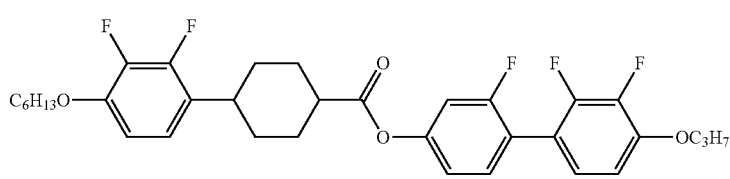 |
| 435 | 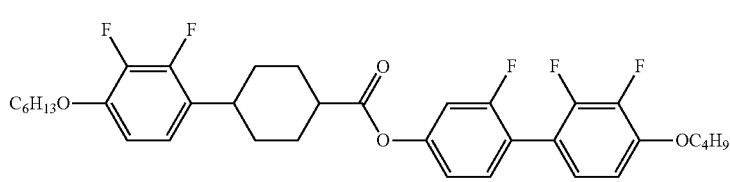 |
| 436 | 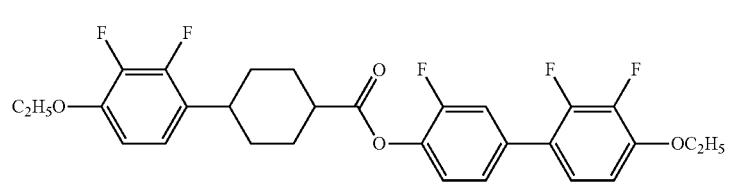 |

| No. | |
|---|---|
| 437 | 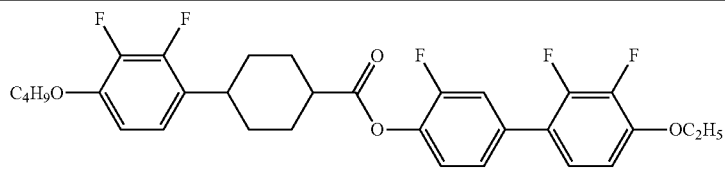 |
| 438 | 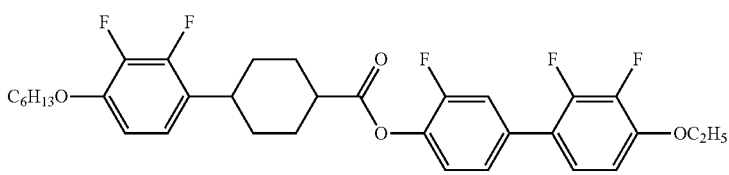 |
| 439 | 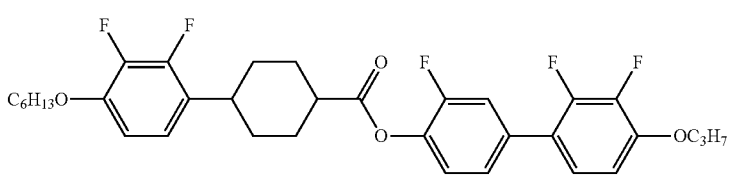 |
| 440 | 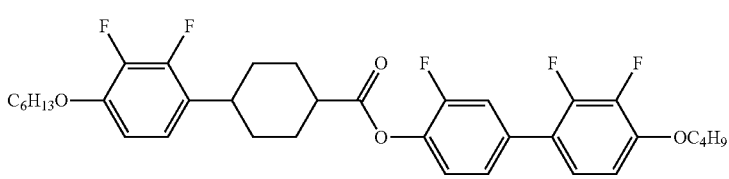 |
| 441 | 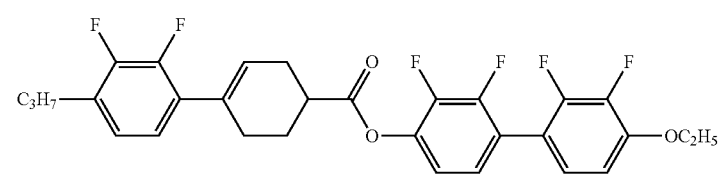 |
| 442 | 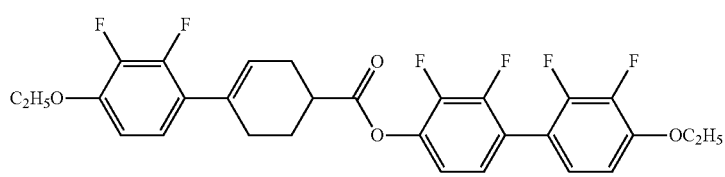 |
| 443 | 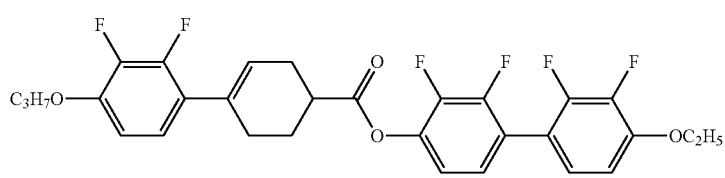 |
| 444 | 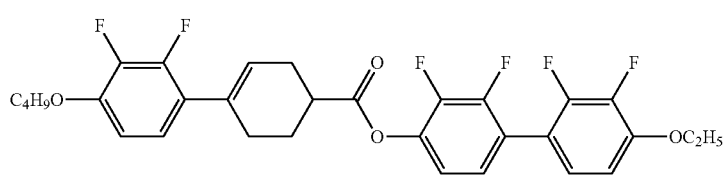 |
| 445 | 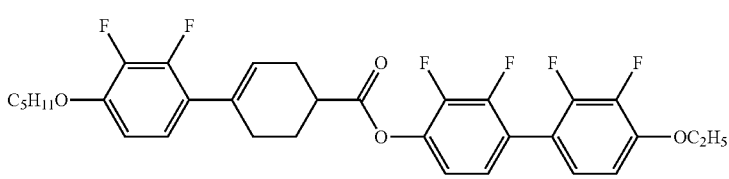 |

-continued
| No. | |
|---|---|
| 446 | 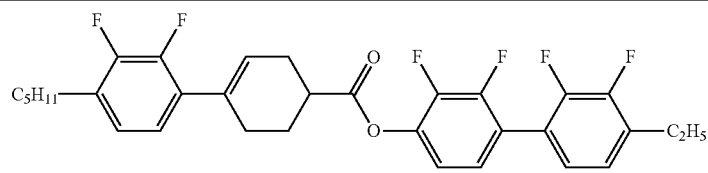 |
| 447 | 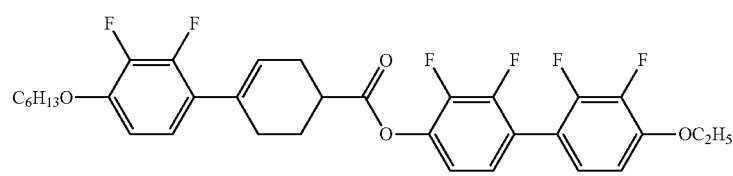 |
| 448 | 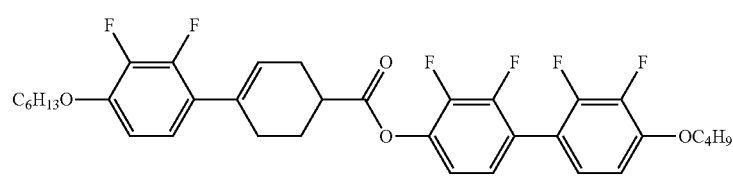 |
| 449 | 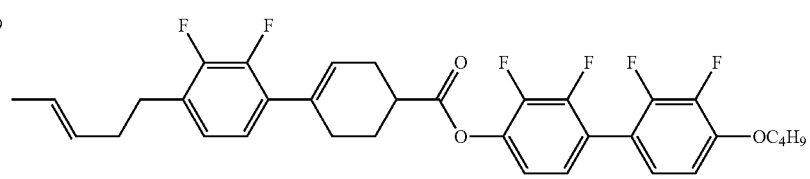 |
| 450 | 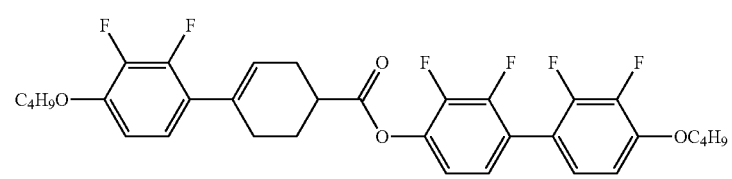 |
| 451 | 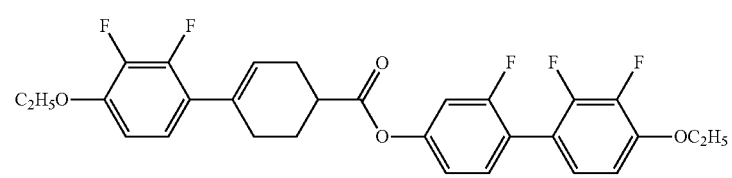 |
| 452 | 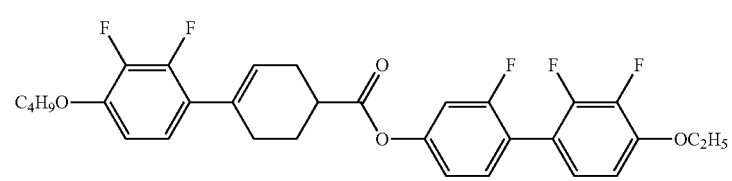 |
| 453 | 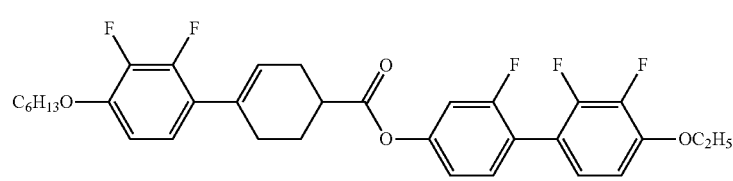 |
| 454 | 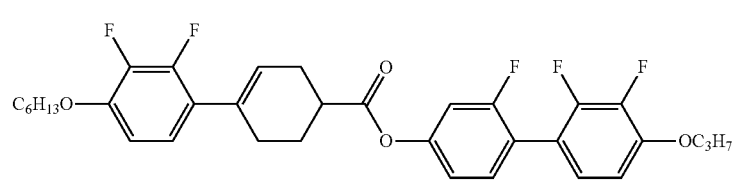 |

-continued
| No. | |
|---|---|
| 455 | 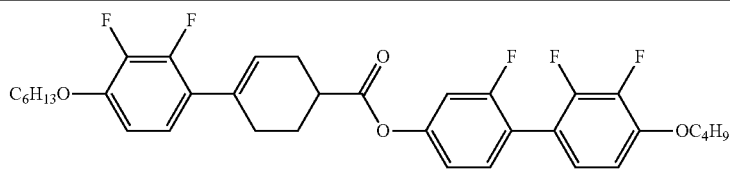 |
| 456 | 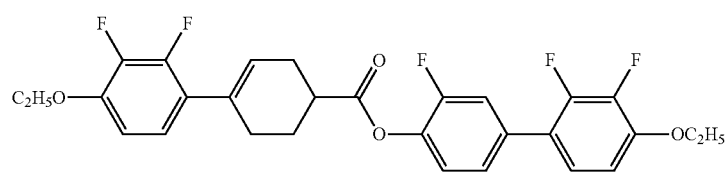 |
| 457 | 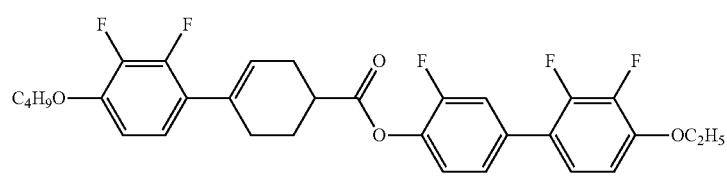 |
| 458 | 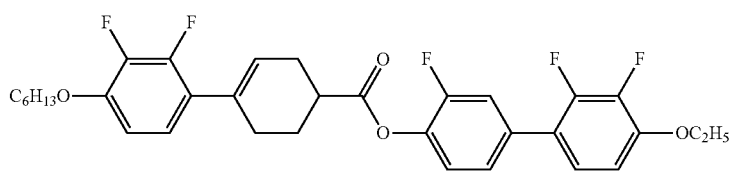 |
| 459 | 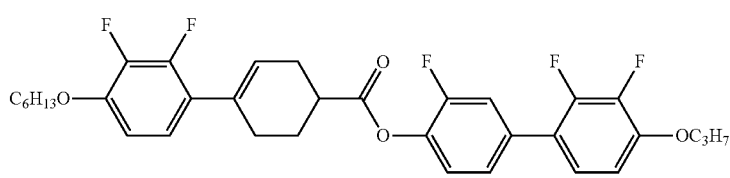 |
| 460 | 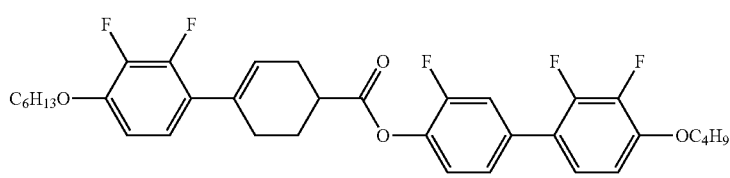 |
| 461 | 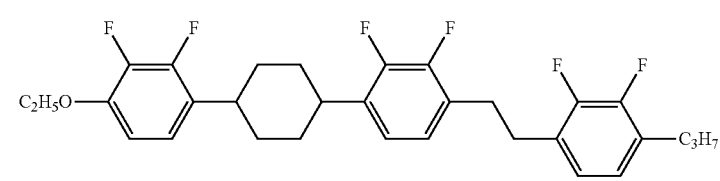 |
| 462 | 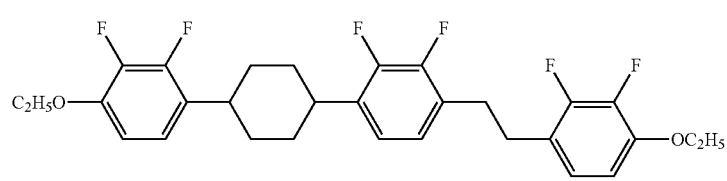 |
| 463 | 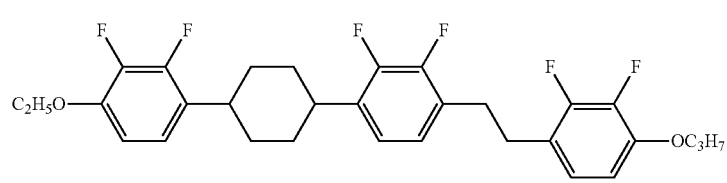 |

| No. | |
|---|---|
| 464 | 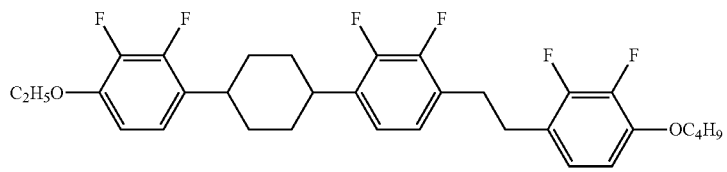 |
| 465 | 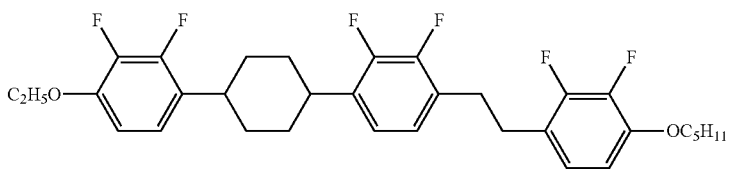 |
| 466 | 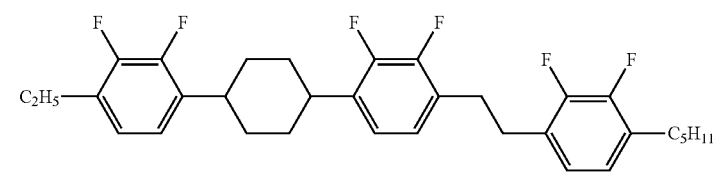 |
| 467 | 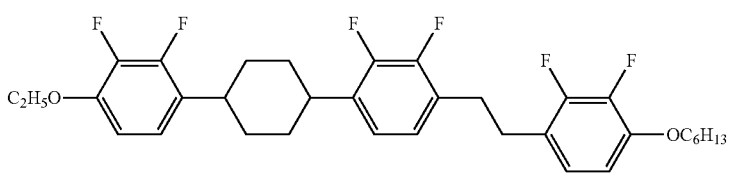 |
| 468 | 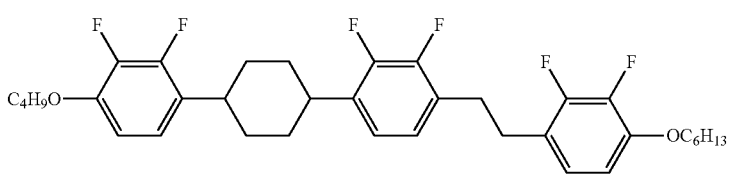 |
| 469 | 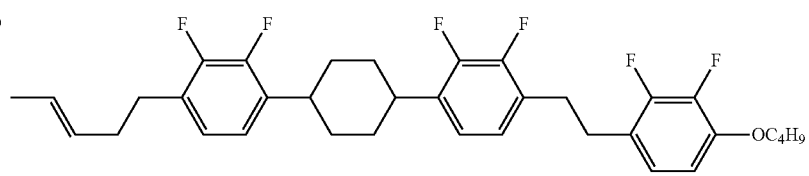 |
| 470 | 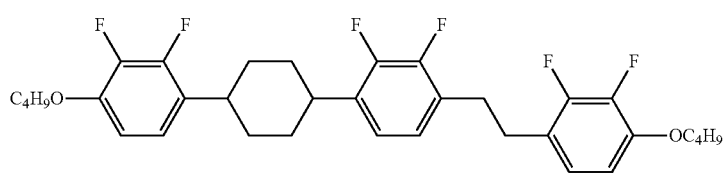 |
| 471 | 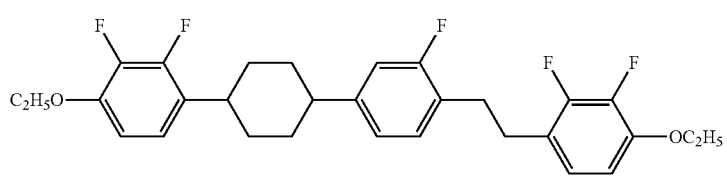 |
| 472 | 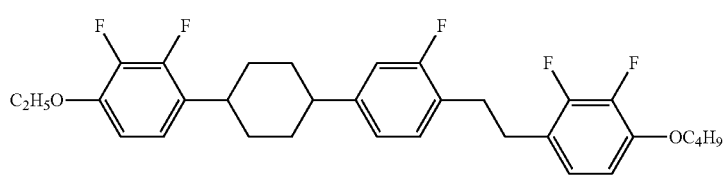 |

| No. | |
|---|---|
| 473 | 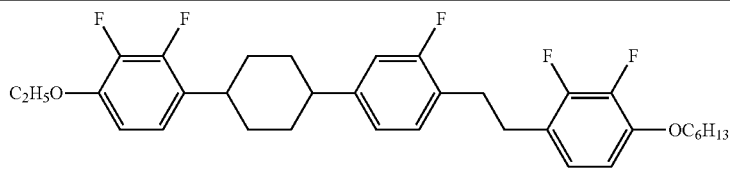 |
| 474 | 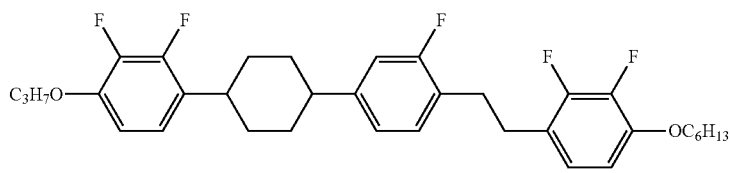 |
| 475 | 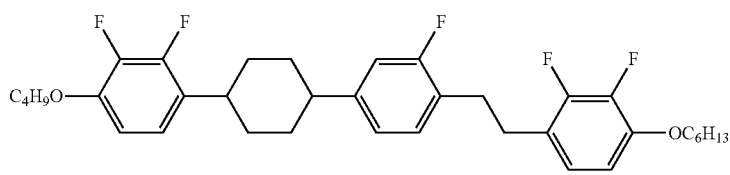 |
| 476 | 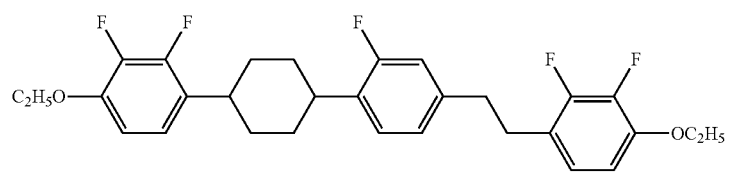 |
| 477 | 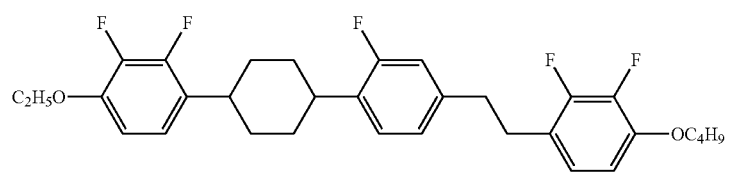 |
| 478 | 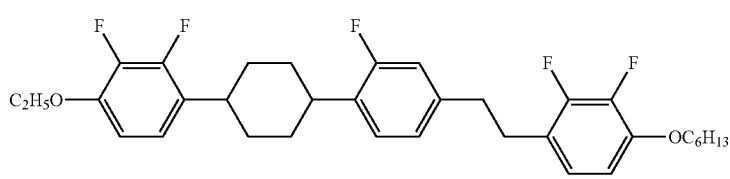 |
| 479 | 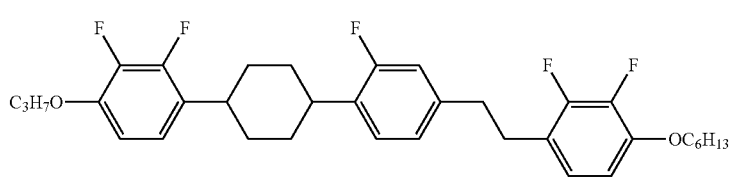 |
| 480 | 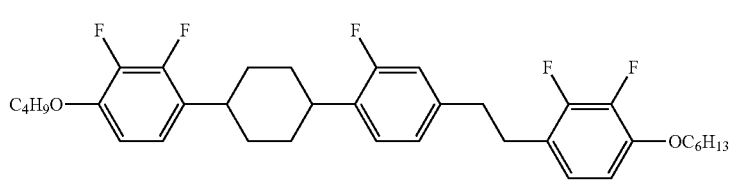 |
| 481 | 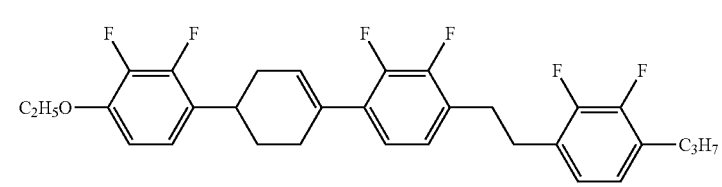 |

-continued
| No. | |
|---|---|
| 482 | 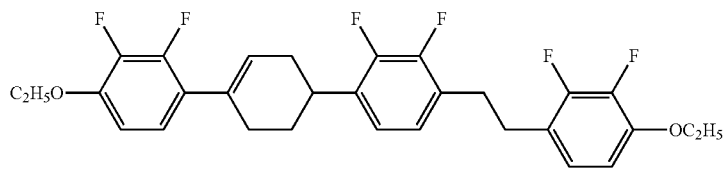 |
| 483 | 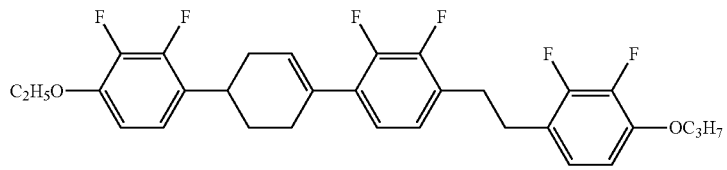 |
| 484 | 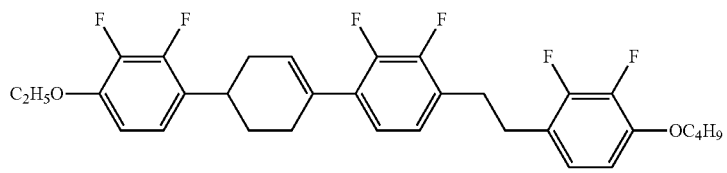 |
| 485 | 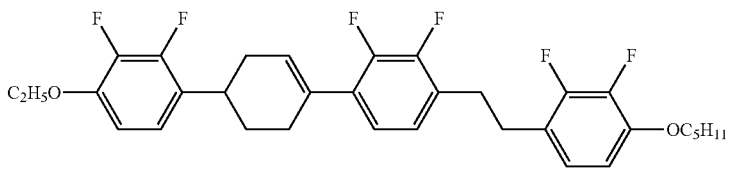 |
| 486 | 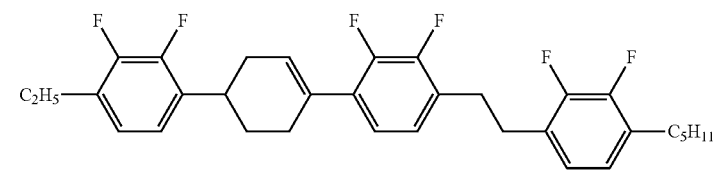 |
| 487 | 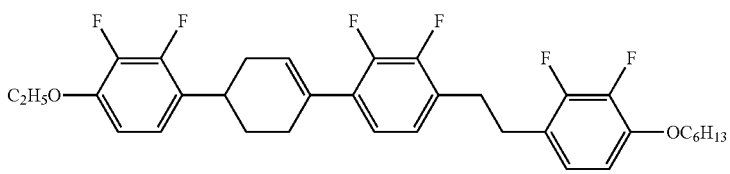<br>C 81.8N 148.1 I<br>$T_{NI}$; 133.9° C., Δ ε; -9.04, Δ n; 0.174 |
| 488 | 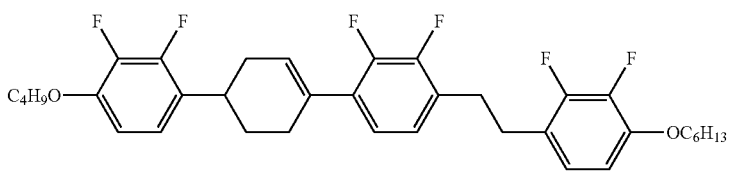 |
| 489 | 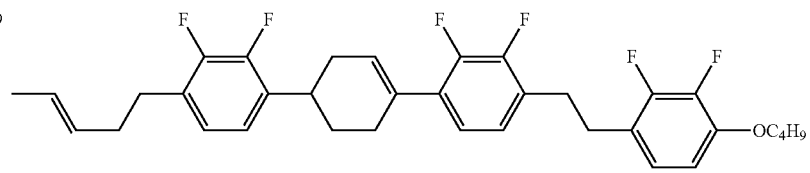 |

| No. | |
|---|---|
| 490 | 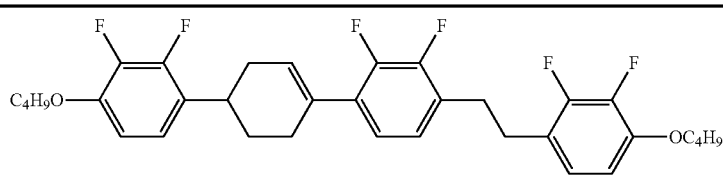 |
| 491 | 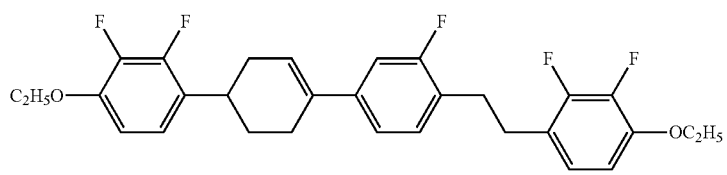 |
| 492 | 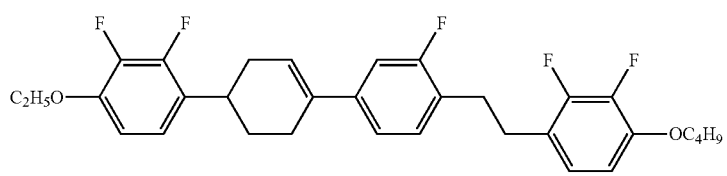 |
| 493 | 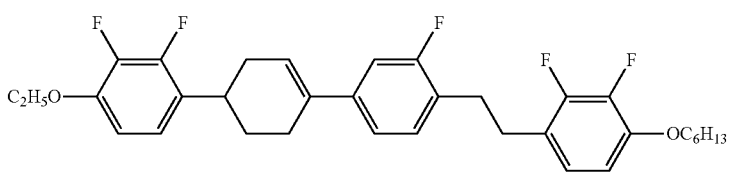 |
| 494 | 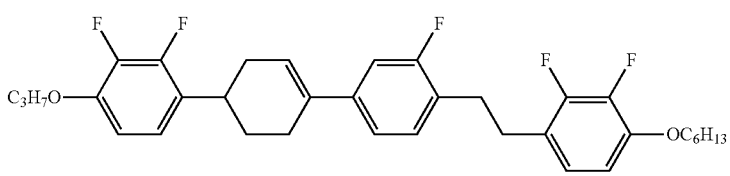 |
| 495 | 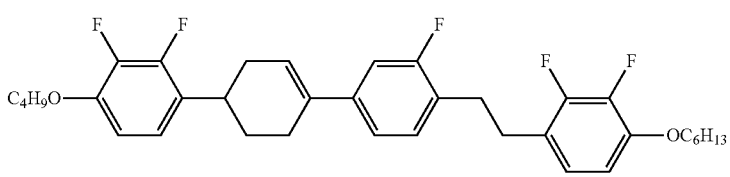 |
| 496 | 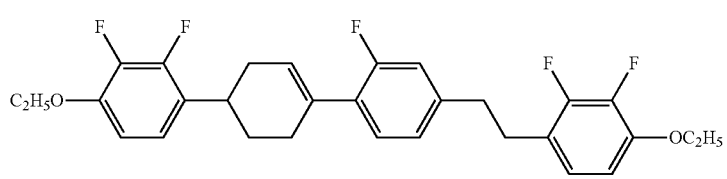 |
| 497 | 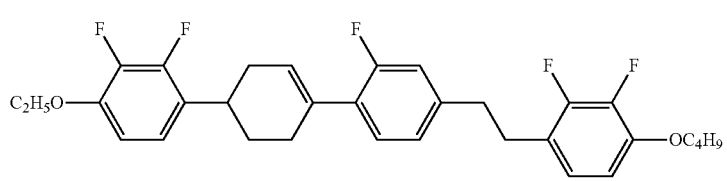 |
| 498 | 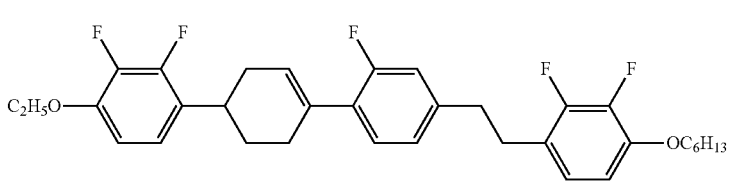 |

-continued
| No. | |
|---|---|
| 499 | 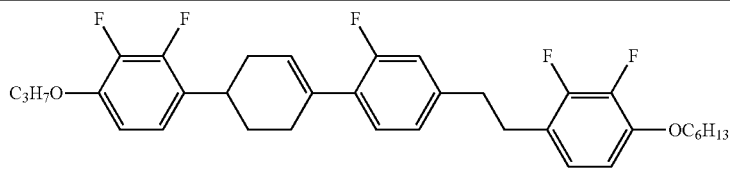 |
| 500 | 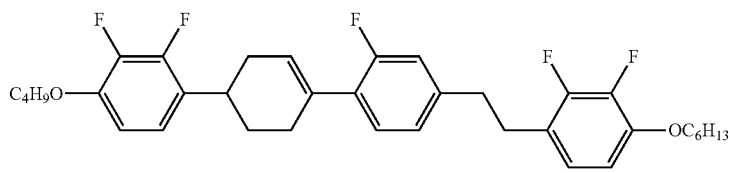 |
| 501 | 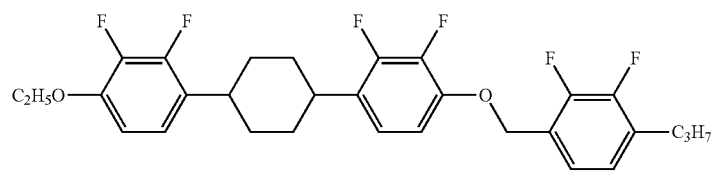 |
| 502 | 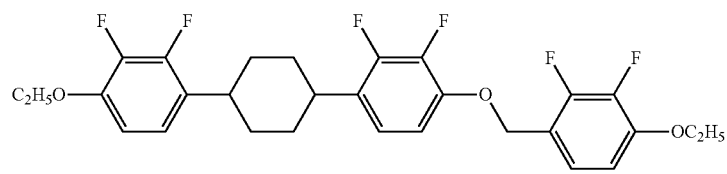 |
| 503 | 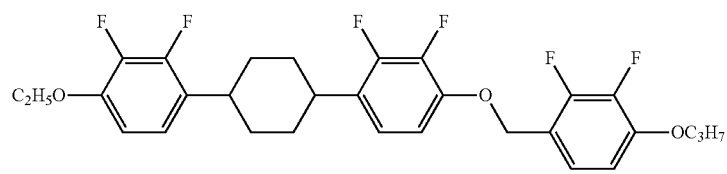 |
| 504 | 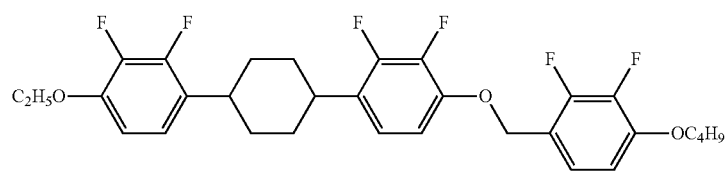 |
| 505 | 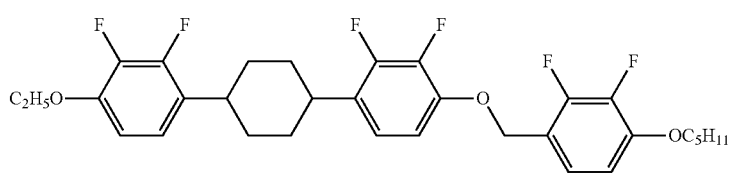 |
| 506 | 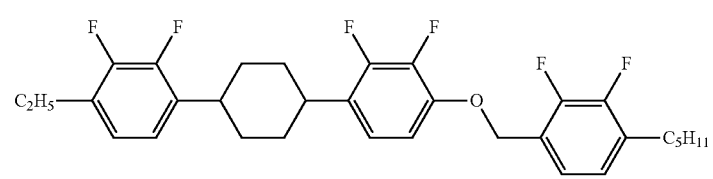 |
| 507 | 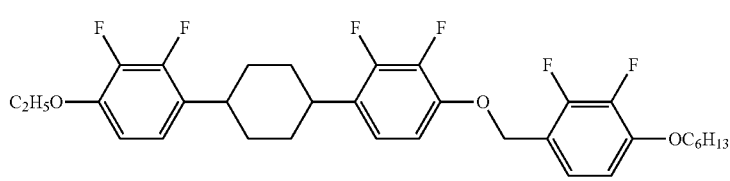 |

-continued
| No. | |
|---|---|
| 508 | 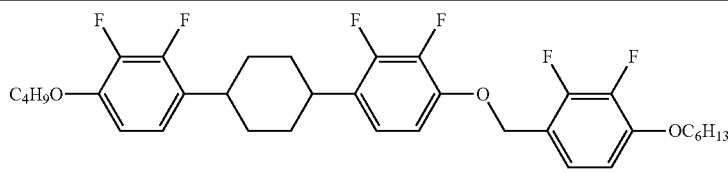 |
| 509 | 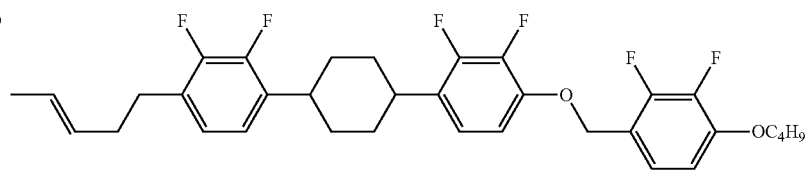 |
| 510 | 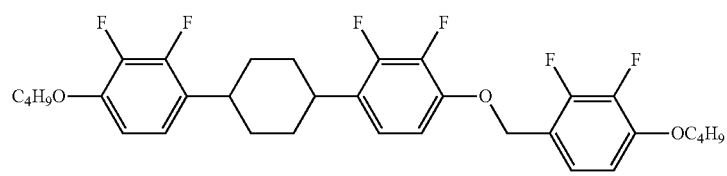 |
| 511 | 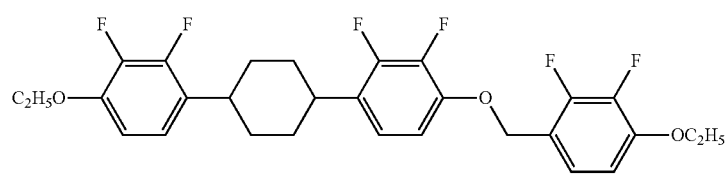 |
| 512 | 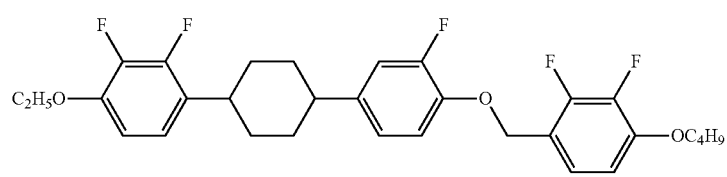 |
| 513 | 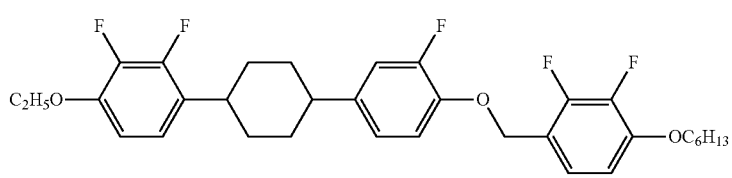 |
| 514 | 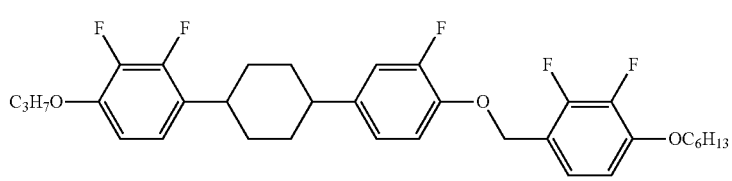 |
| 515 | 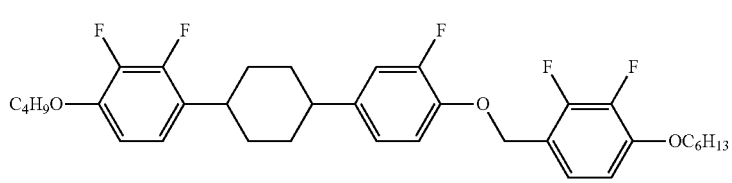 |
| 516 | 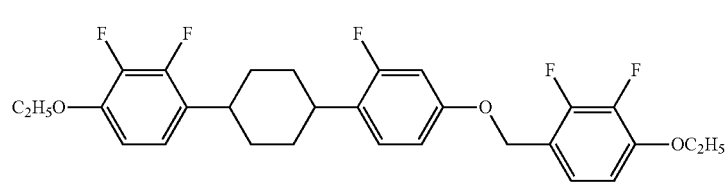 |

-continued
| No. | |
|---|---|
| 517 | 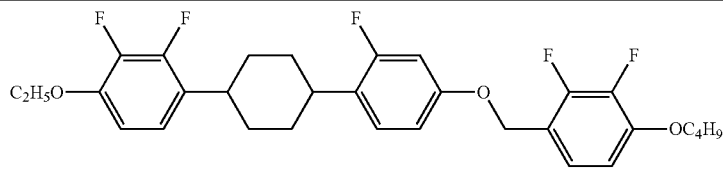 |
| 518 | 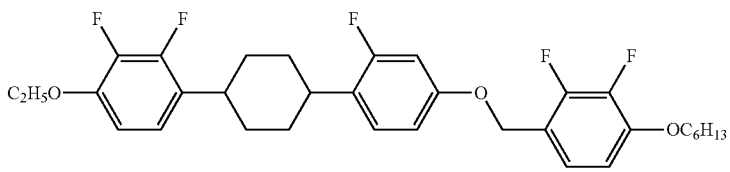 |
| 519 | 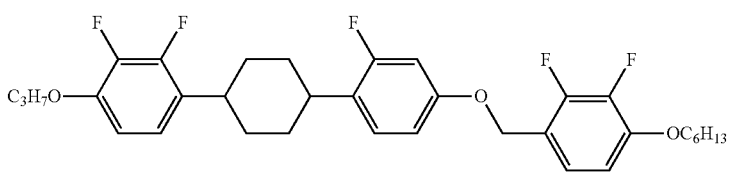 |
| 520 | 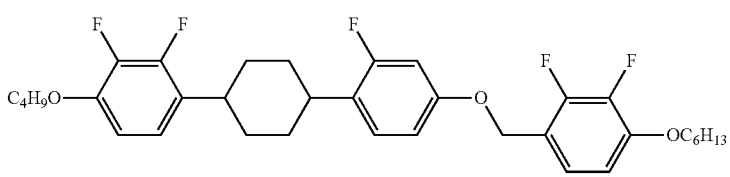 |
| 521 | 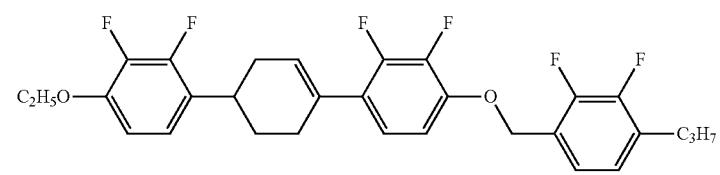 |
| 522 | 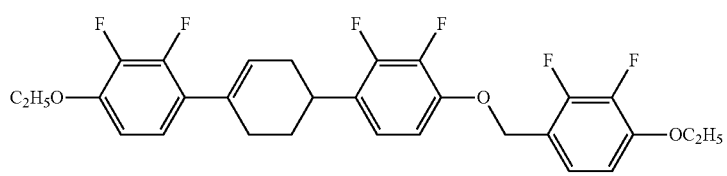 |
| 523 | 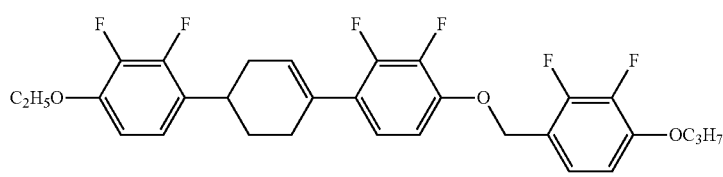 |
| 524 | 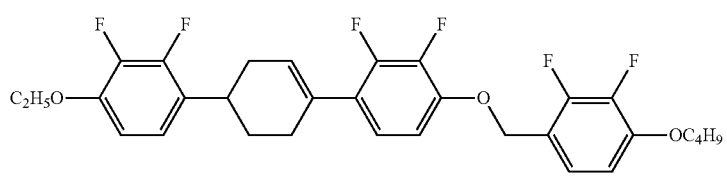 |
| 525 | 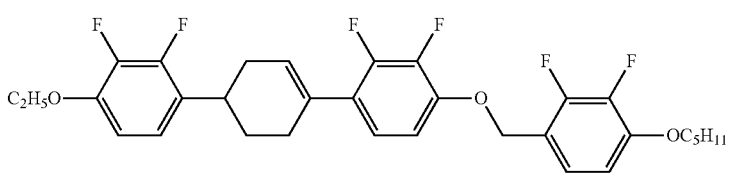 |

-continued
| No. | |
|---|---|
| 526 | 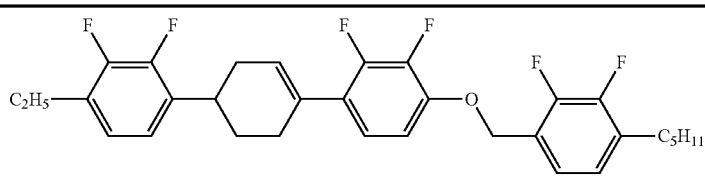 |
| 527 | 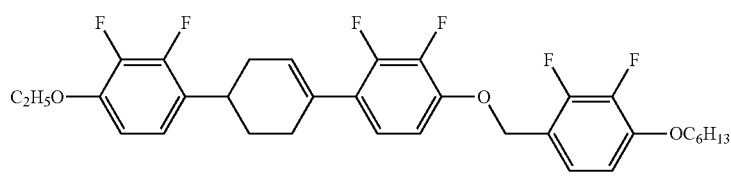 |
| 528 | 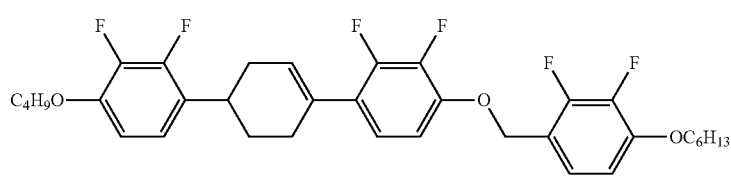 |
| 529 | 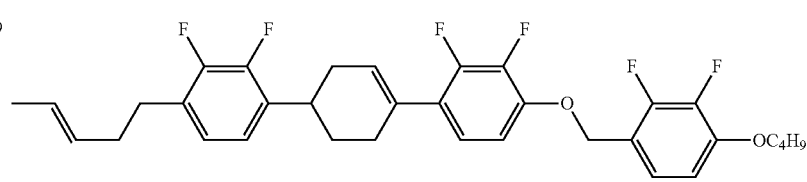 |
| 530 | 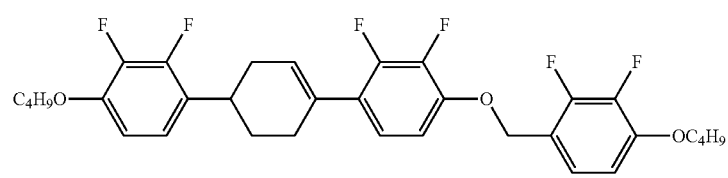 |
| 531 | 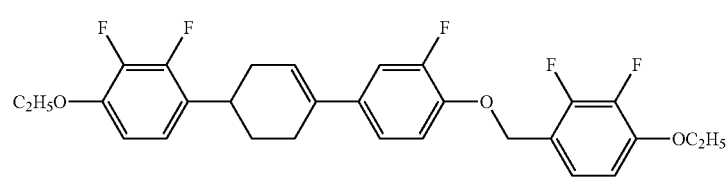 |
| 532 | 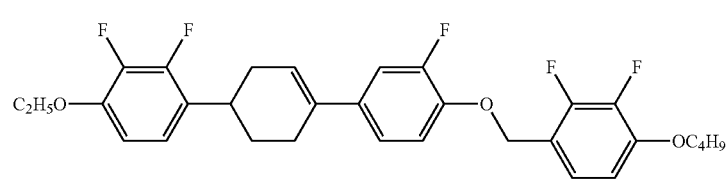 |
| 533 | 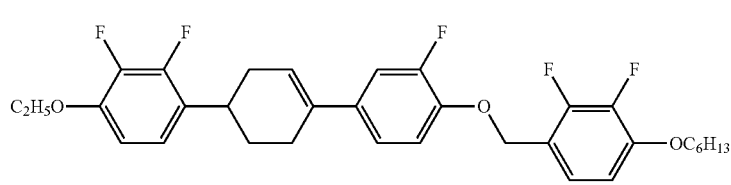 |
| 534 | 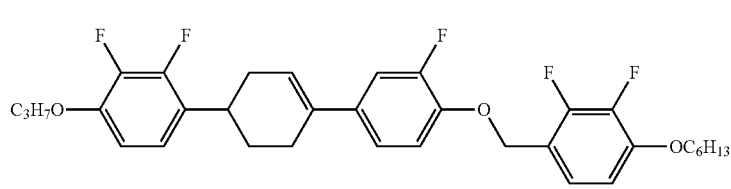 |

-continued
| No. | |
|---|---|
| 535 | 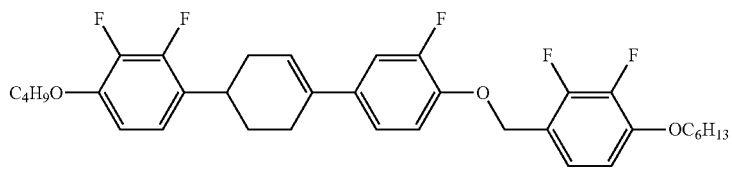 |
| 536 | 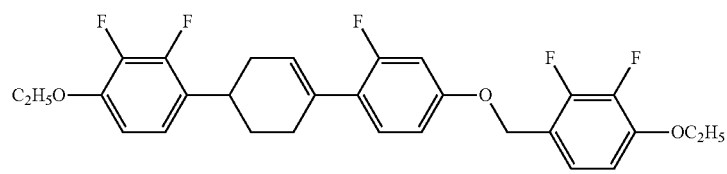 |
| 537 | 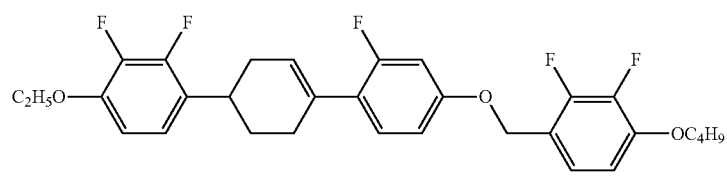 |
| 538 | 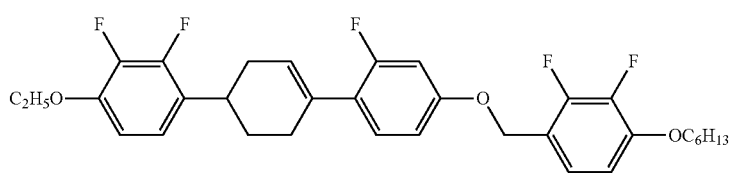 |
| 539 | 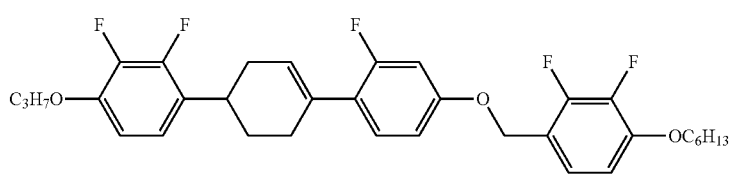 |
| 540 | 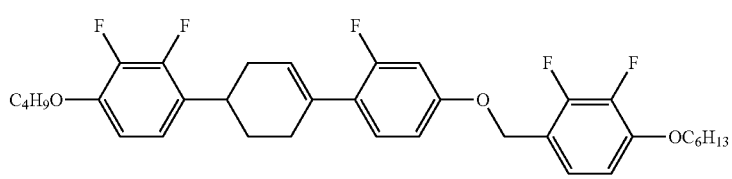 |
| 541 | 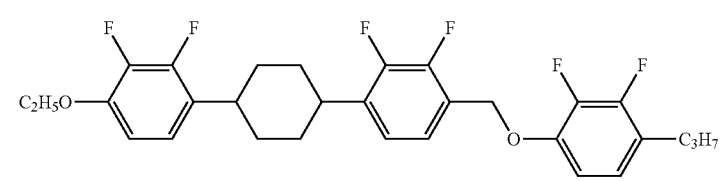 |
| 542 | 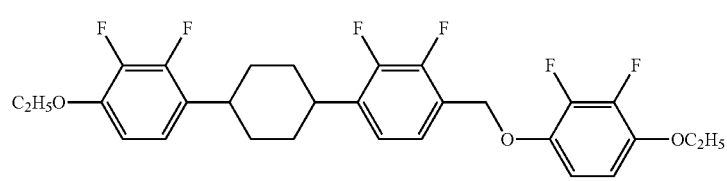 |
| 543 | 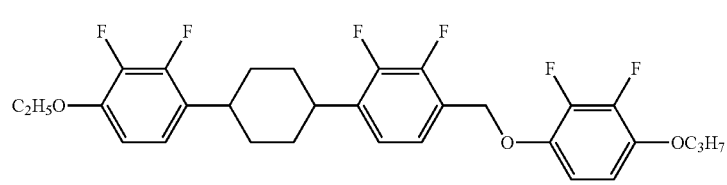 |

-continued
| No. | |
|---|---|
| 544 | 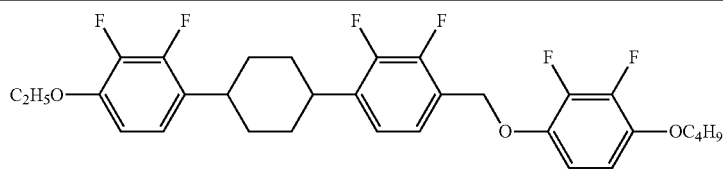 |
| 545 | 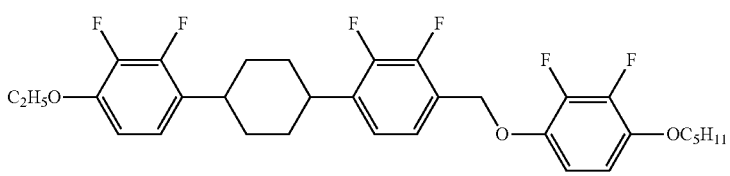 |
| 546 | 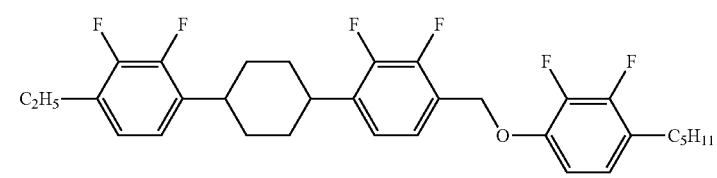 |
| 547 | 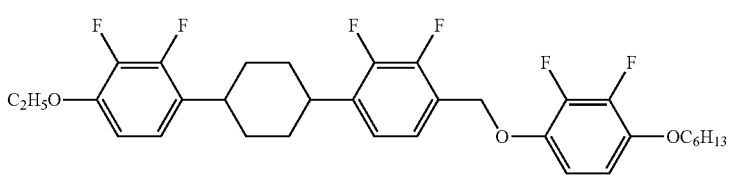 |
| 548 | 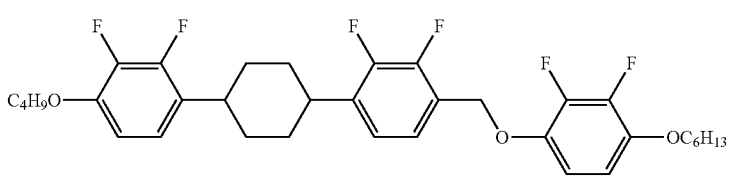 |
| 549 | 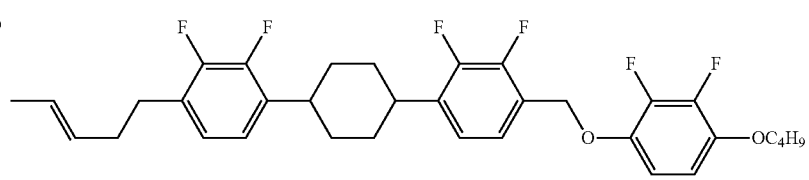 |
| 550 | 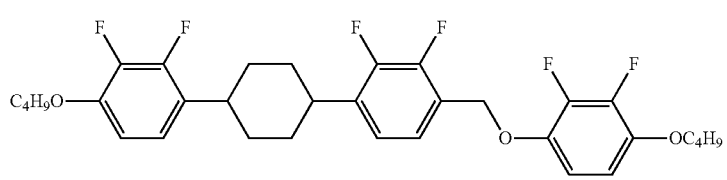 |
| 551 | 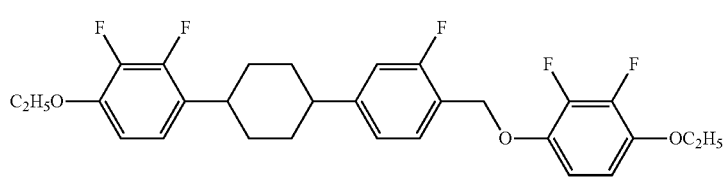 |
| 552 | 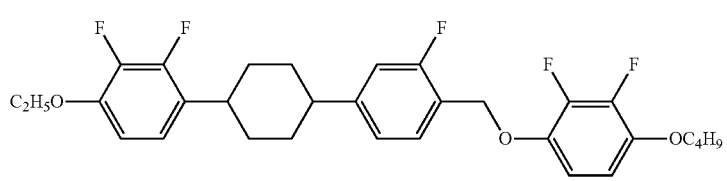 |

-continued
| No. | |
|---|---|
| 553 | 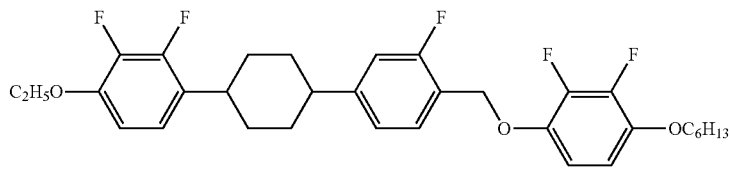 |
| 554 | 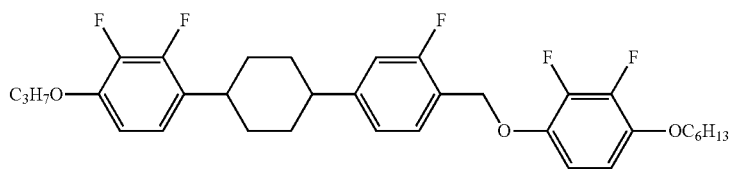 |
| 555 | 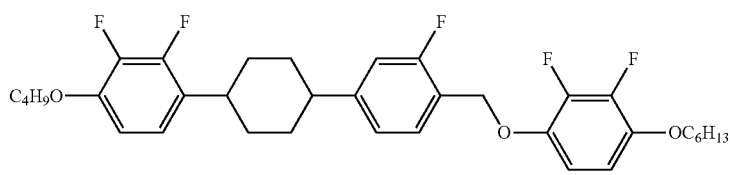 |
| 556 | 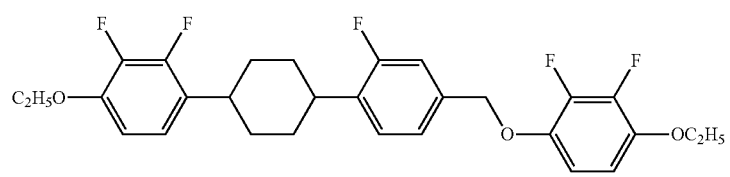 |
| 557 | 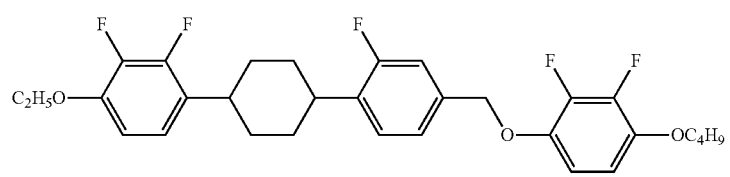 |
| 558 | 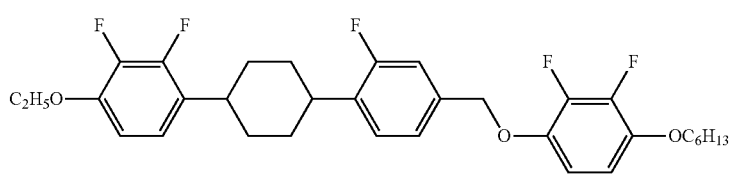 |
| 559 | 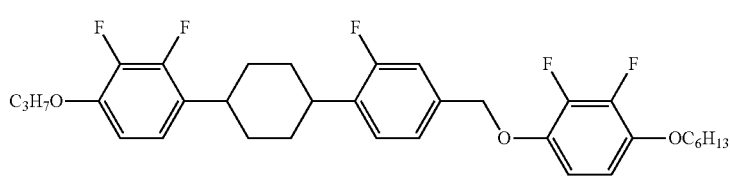 |
| 560 | 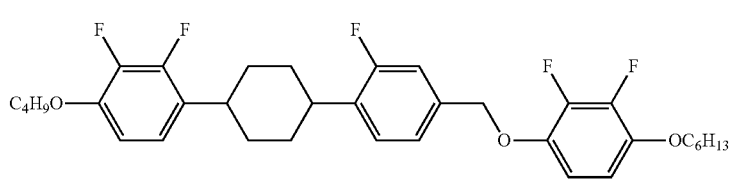 |
| 561 | 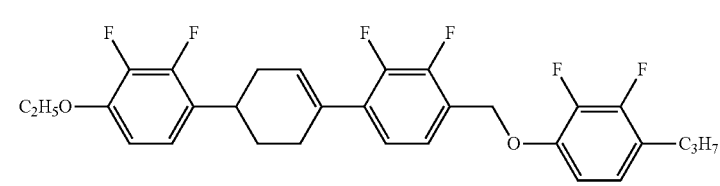 |

-continued
| No. | |
|---|---|
| 562 | 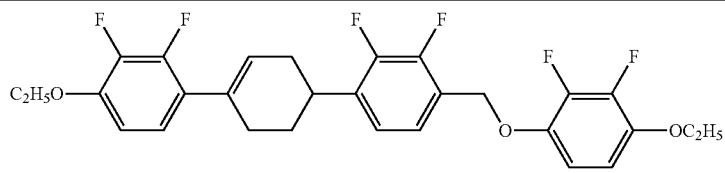 |
| 563 | 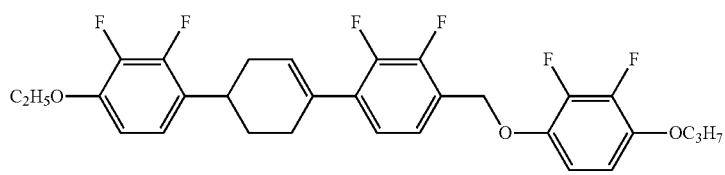 |
| 564 | 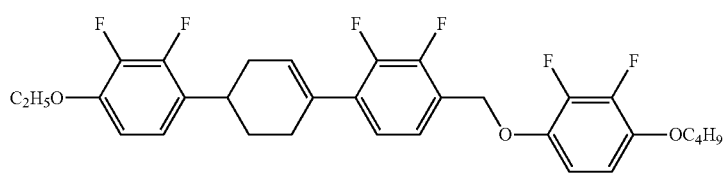 |
| 565 | 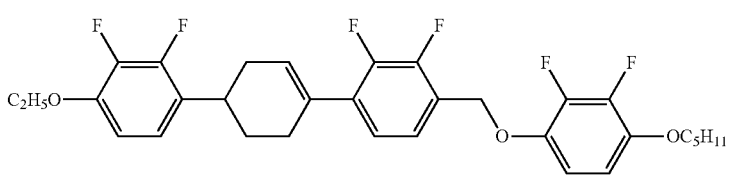 |
| 566 | 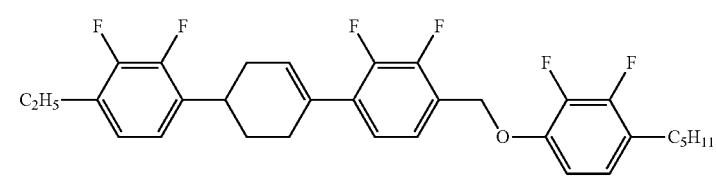 |
| 567 | 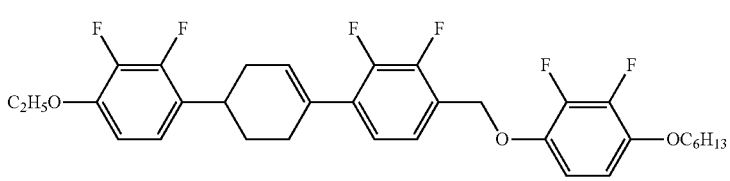 |
| 568 | 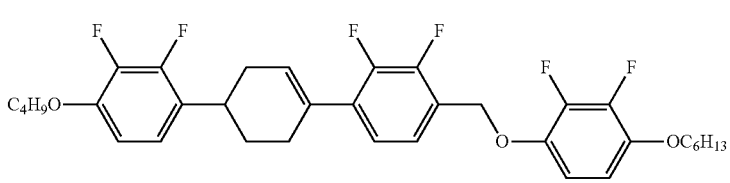 |
| 569 | 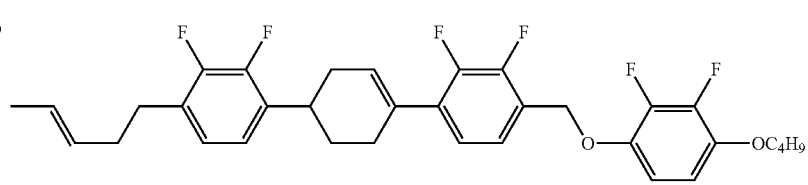 |
| 570 | 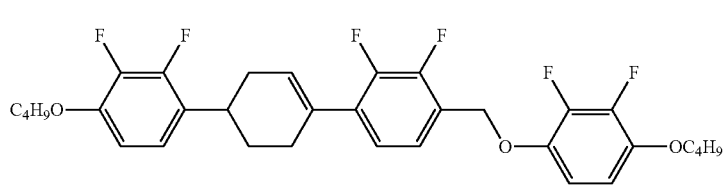 |

-continued
| No. | |
|---|---|
| 571 | 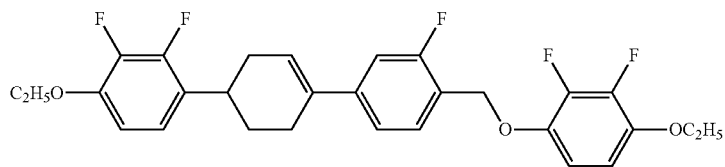 |
| 572 | 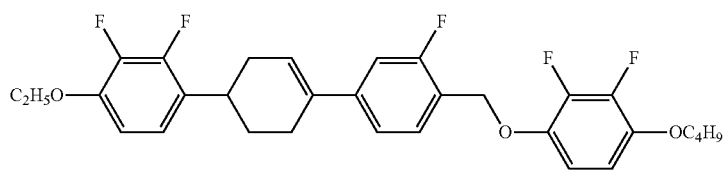 |
| 573 | 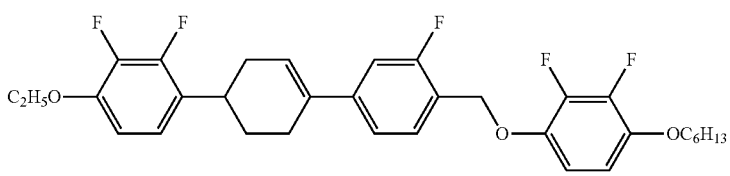 |
| 574 | 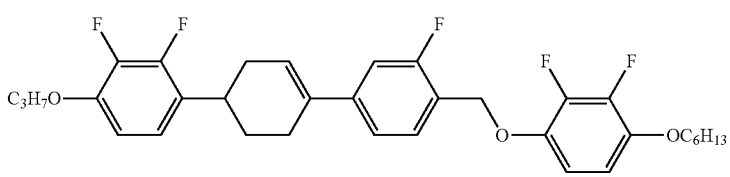 |
| 575 | 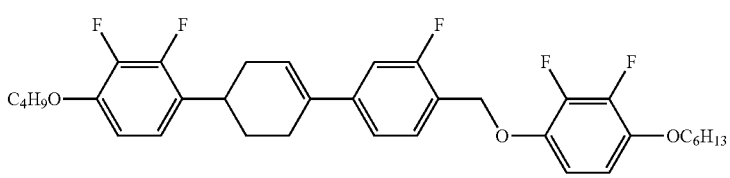 |
| 576 | 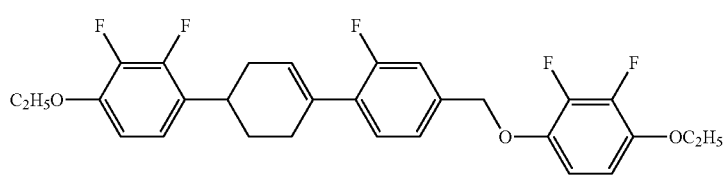 |
| 577 | 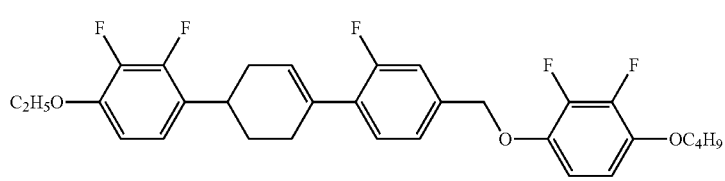 |
| 578 | 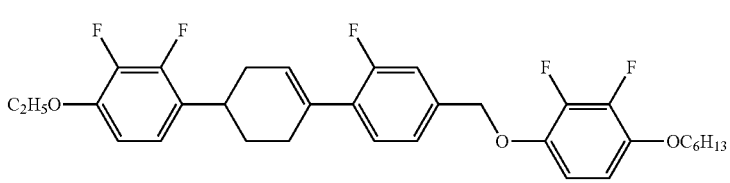 |
| 579 | 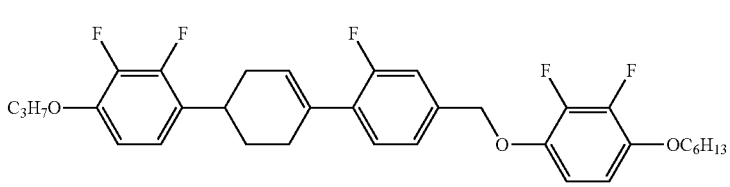 |

-continued
| No. | |
|---|---|
| 580 | 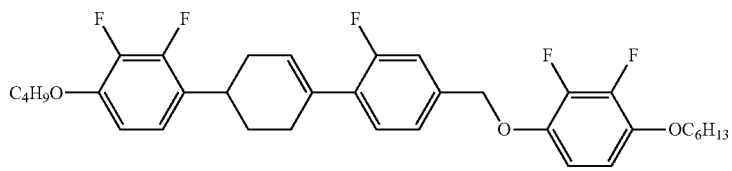 |
| 581 | 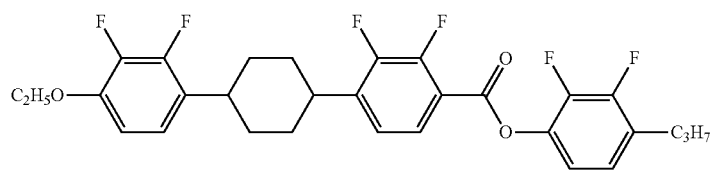 |
| 582 | 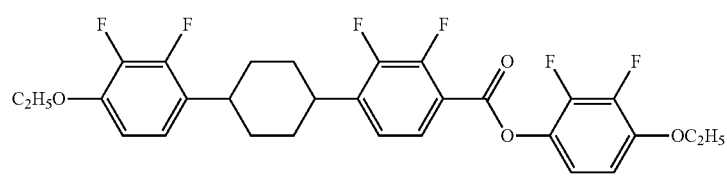 |
| 583 | 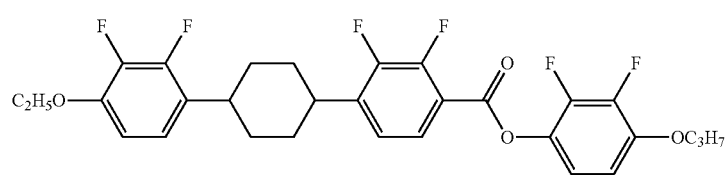 |
| 584 | 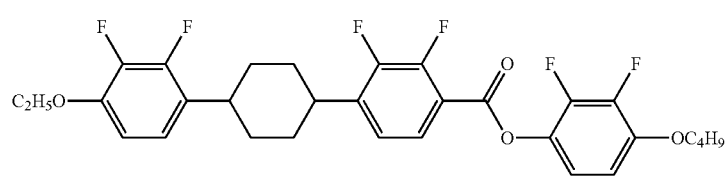 |
| 585 | 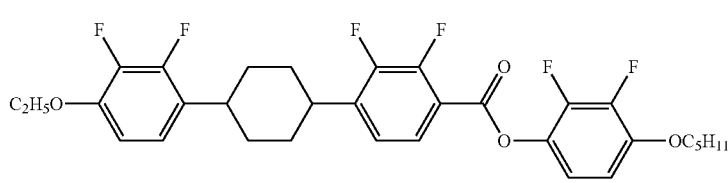 |
| 586 | 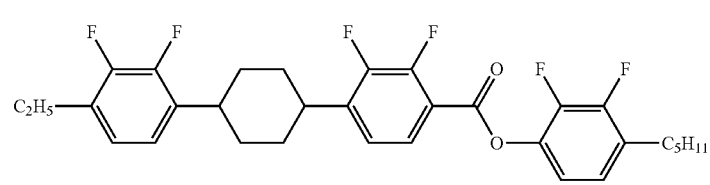 |
| 587 | 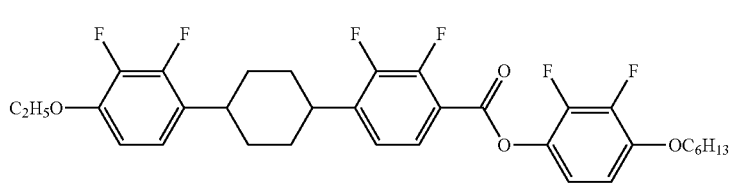 |
| 588 | 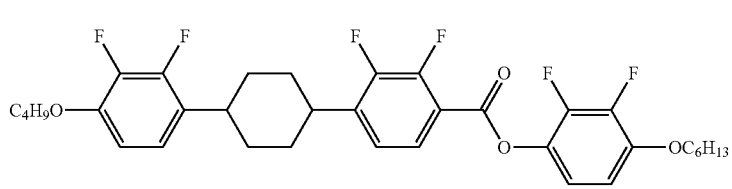 |

| No. | |
|---|---|
| 589 | 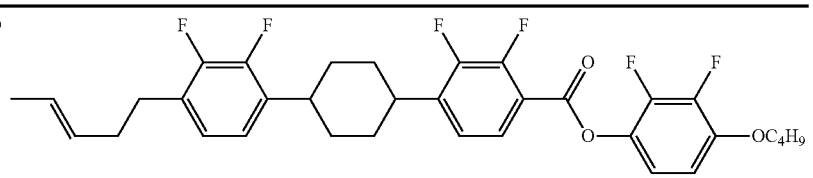 |
| 590 | 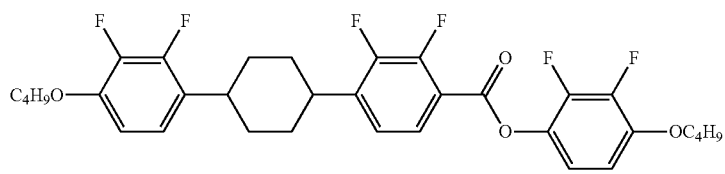 |
| 591 | 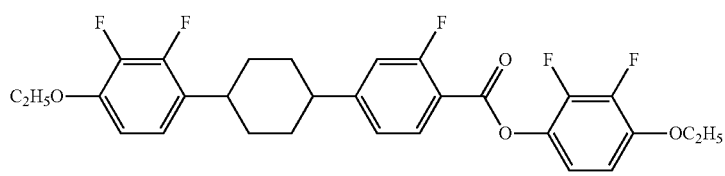 |
| 592 | 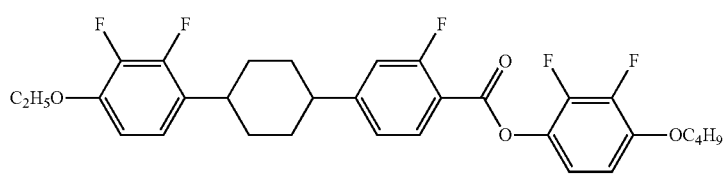 |
| 593 | 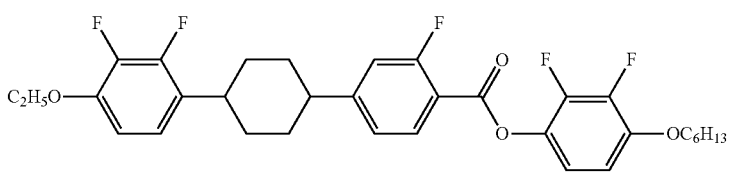 |
| 594 | 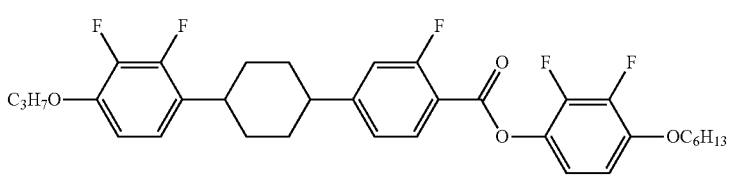 |
| 595 | 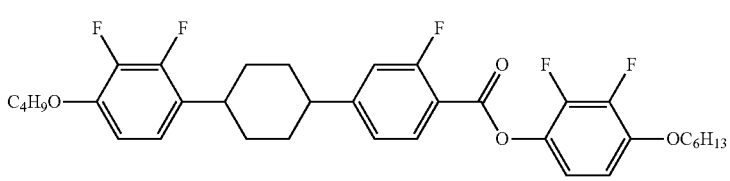 |
| 596 | 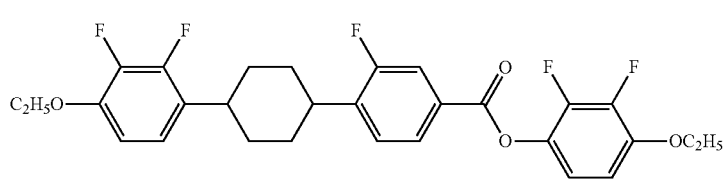 |
| 597 | 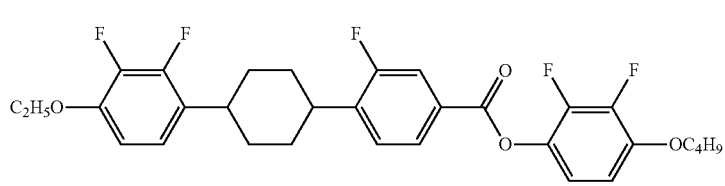 |

| No. | |
|---|---|
| 598 | 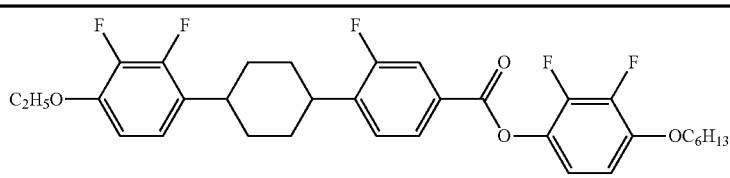 |
| 599 | 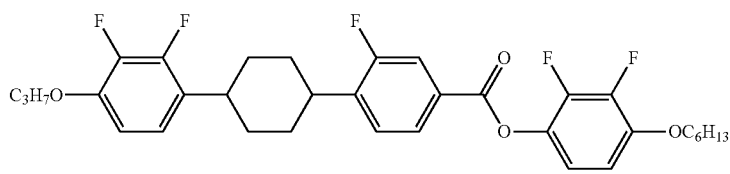 |
| 600 | 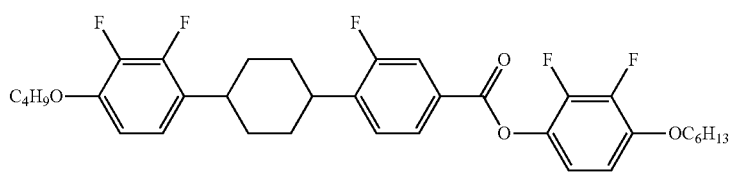 |
| 601 | 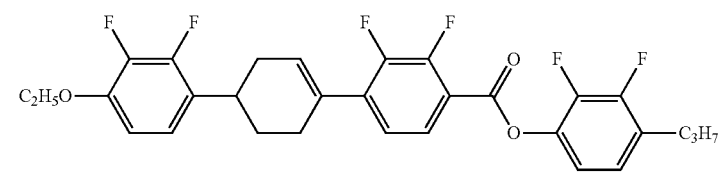 |
| 602 | 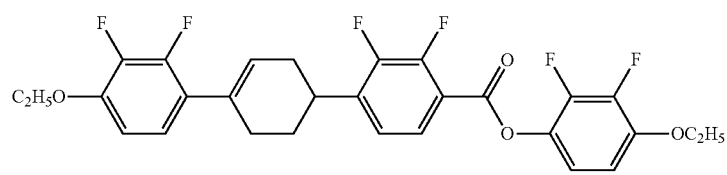 |
| 603 | 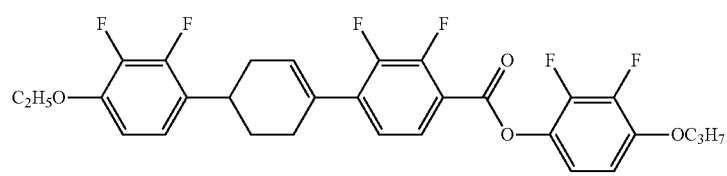 |
| 604 | 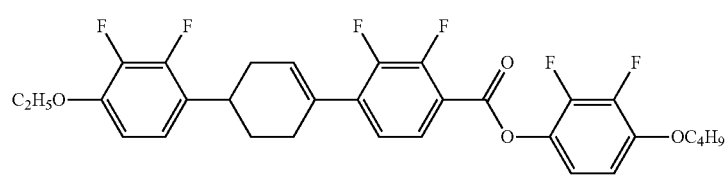 |
| 605 | 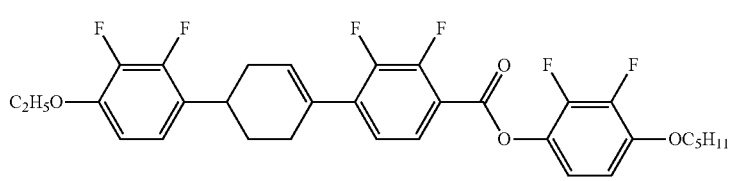 |
| 606 | 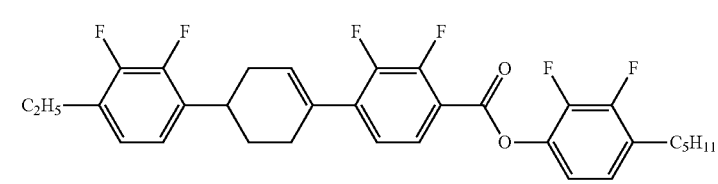 |

| No. | |
|---|---|
| 607 | 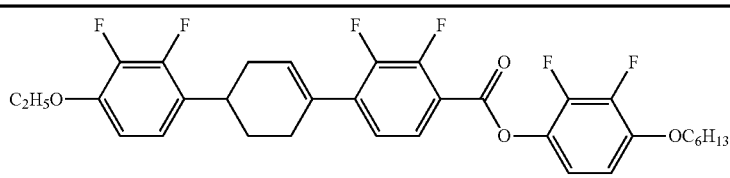 |
| 608 | 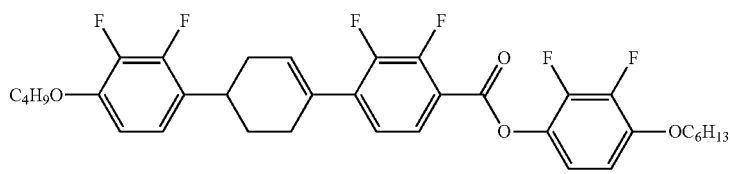 |
| 609 | 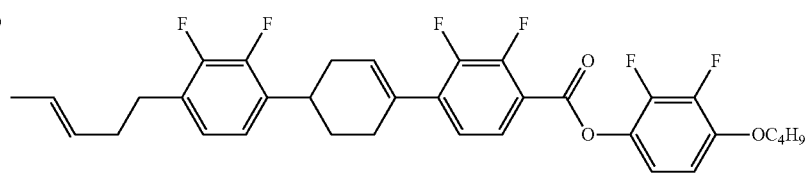 |
| 610 | 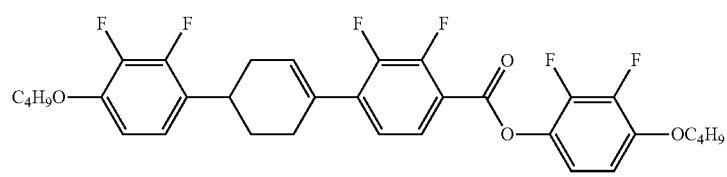 |
| 611 | 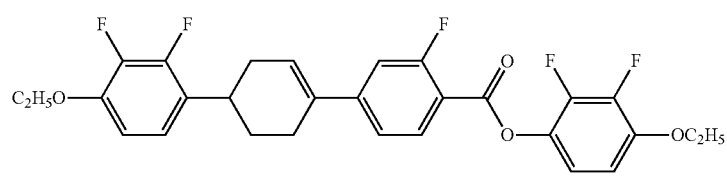 |
| 612 | 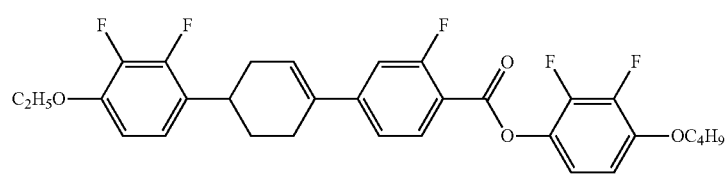 |
| 613 | 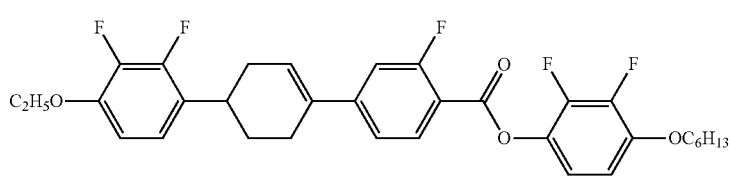 |
| 614 | 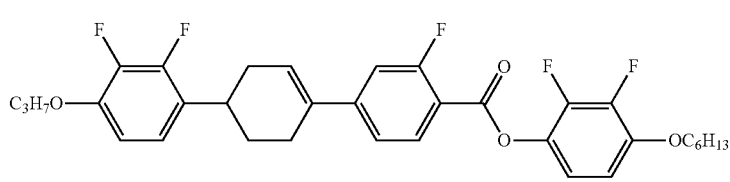 |
| 615 | 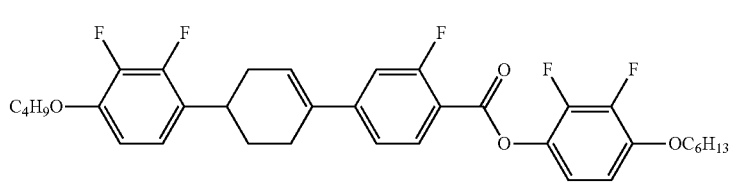 |

-continued

| No. | |
|---|---|
| 616 | (structure: C₂H₅O-[2,3-F₂-phenyl]-cyclohexene-[3-F-phenyl]-C(=O)O-[2,3-F₂-4-OC₂H₅-phenyl]) |
| 617 | (structure: C₂H₅O-[2,3-F₂-phenyl]-cyclohexene-[3-F-phenyl]-C(=O)O-[2,3-F₂-4-OC₄H₉-phenyl]) |
| 618 | (structure: C₂H₅O-[2,3-F₂-phenyl]-cyclohexene-[3-F-phenyl]-C(=O)O-[2,3-F₂-4-OC₆H₁₃-phenyl]) |
| 619 | (structure: C₃H₇O-[2,3-F₂-phenyl]-cyclohexene-[3-F-phenyl]-C(=O)O-[2,3-F₂-4-OC₆H₁₃-phenyl]) |
| 620 | (structure: C₄H₉O-[2,3-F₂-phenyl]-cyclohexene-[3-F-phenyl]-C(=O)O-[2,3-F₂-4-OC₆H₁₃-phenyl]) |
| 621 | (structure: C₂H₅O-[2,3-F₂-phenyl]-cyclohexyl-[2,3-F₂-phenyl]-O-C(=O)-[2,3-F₂-4-C₃H₇-phenyl]) |
| 622 | (structure: C₂H₅O-[2,3-F₂-phenyl]-cyclohexyl-[2,3-F₂-phenyl]-O-C(=O)-[2,3-F₂-4-OC₂H₅-phenyl]) |
| 623 | (structure: C₂H₅O-[2,3-F₂-phenyl]-cyclohexyl-[2,3-F₂-phenyl]-O-C(=O)-[2,3-F₂-4-OC₃H₇-phenyl]) |
| 624 | (structure: C₂H₅O-[2,3-F₂-phenyl]-cyclohexyl-[2,3-F₂-phenyl]-O-C(=O)-[2,3-F₂-4-OC₄H₉-phenyl]) |

-continued
| No. | |
|---|---|
| 625 | 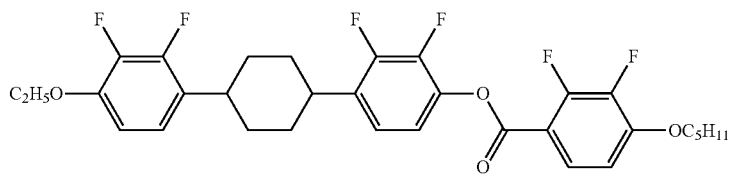 |
| 626 | 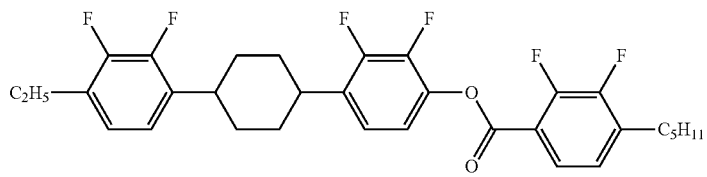 |
| 627 | 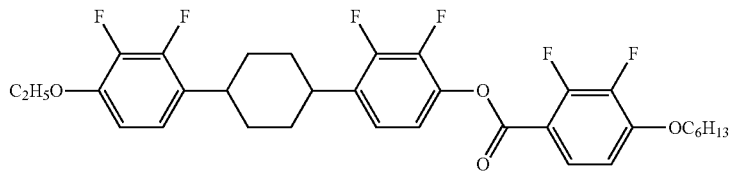 |
| 628 | 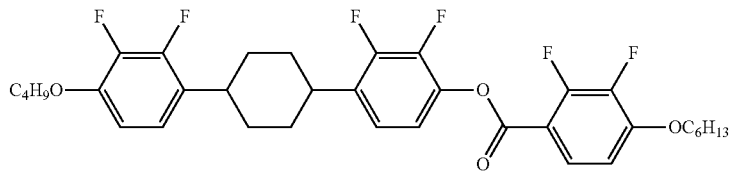 |
| 629 | 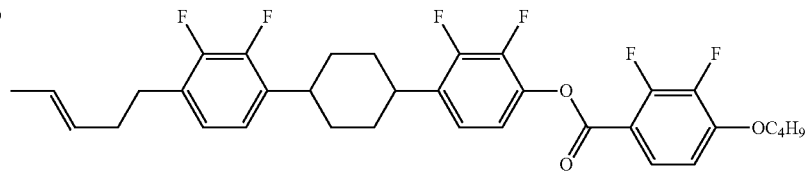 |
| 630 | 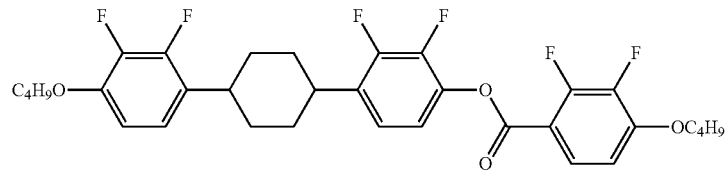 |
| 631 | 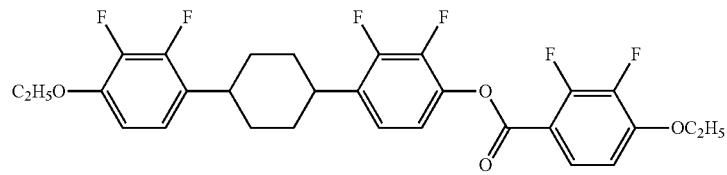 |
| 632 | 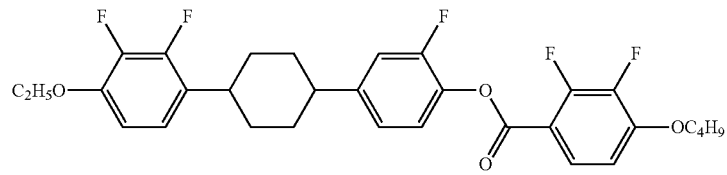 |

| No. | |
|---|---|
| 633 | 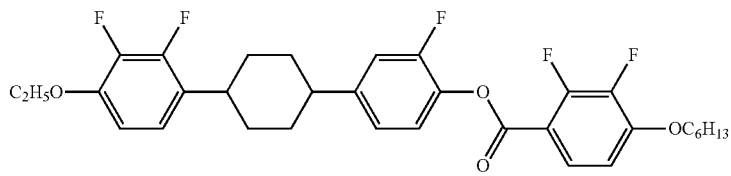 |
| 634 | 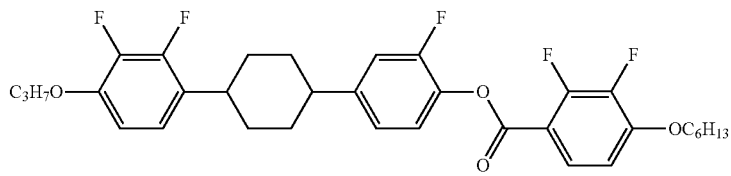 |
| 635 | 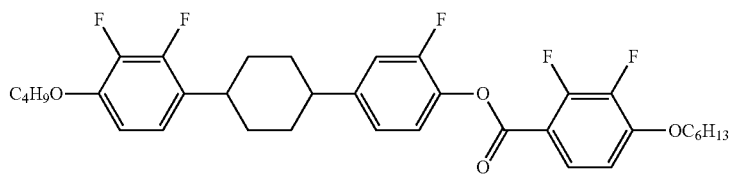 |
| 636 | 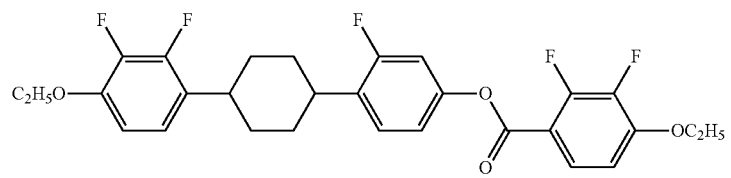 |
| 637 | 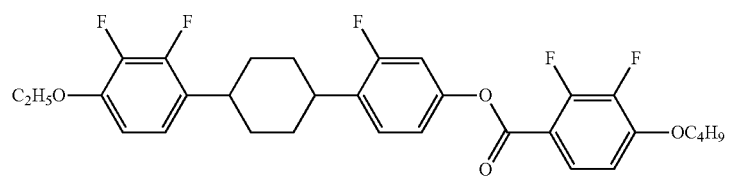 |
| 638 | 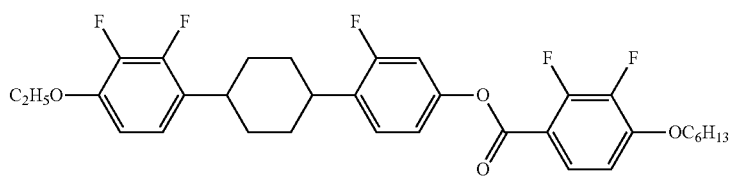 |
| 639 | 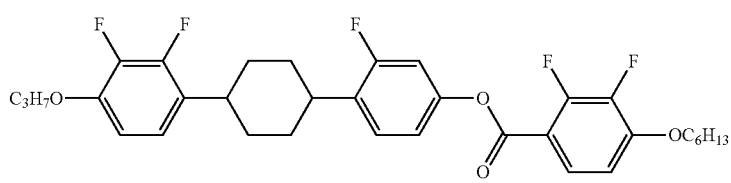 |
| 640 | 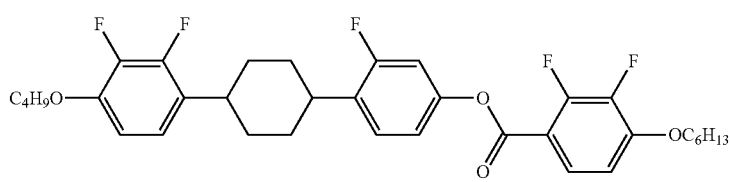 |

-continued
| No. | |
|---|---|
| 641 | 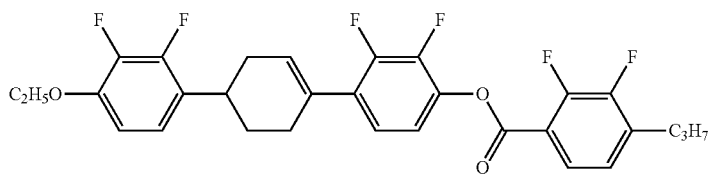 |
| 642 | 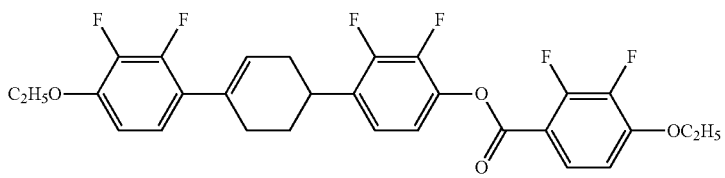 |
| 643 | 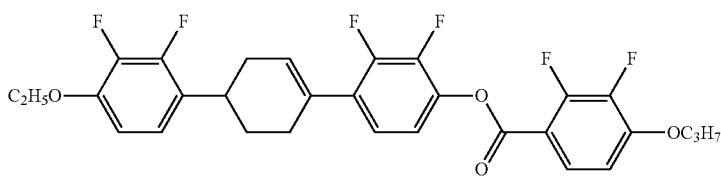 |
| 644 | 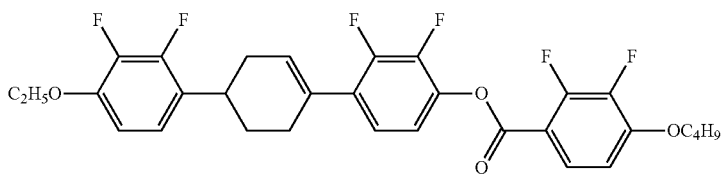 |
| 645 | 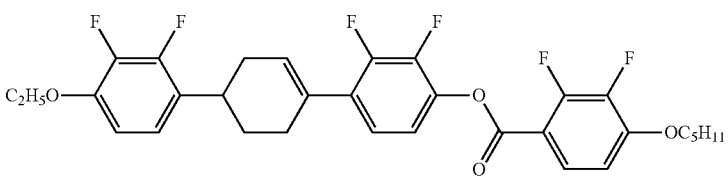 |
| 646 | 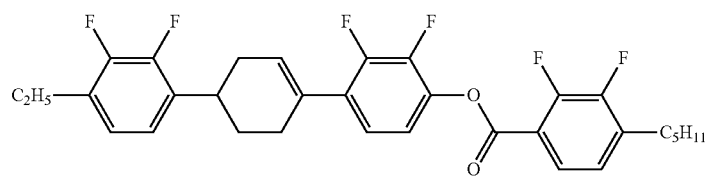 |
| 647 | 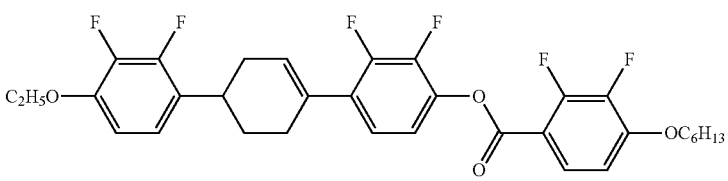 |
| 648 | 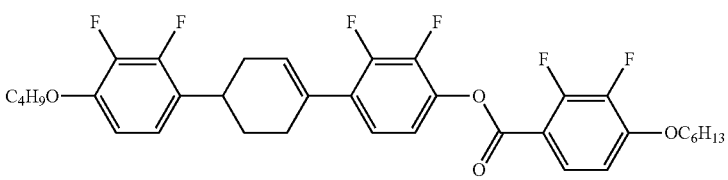 |

-continued
| No. | |
|---|---|
| 649 | 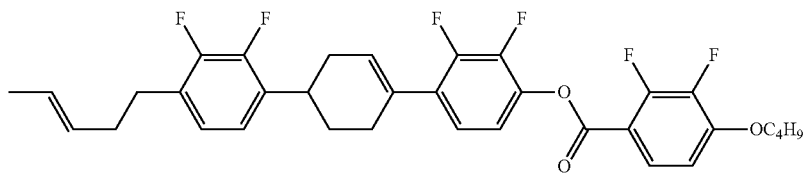 |
| 650 | 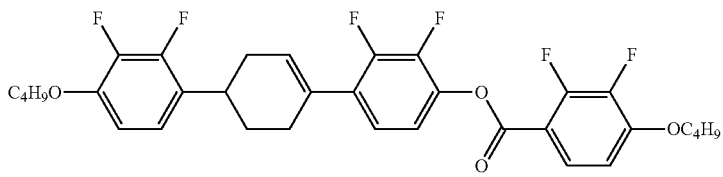 |
| 651 | 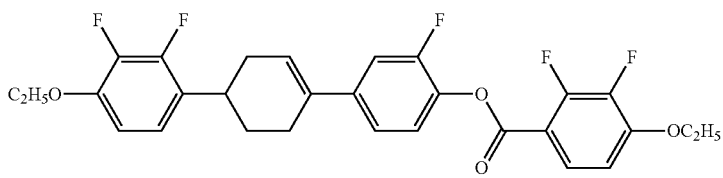 |
| 652 | 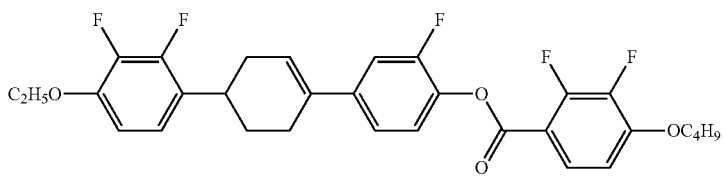 |
| 653 | 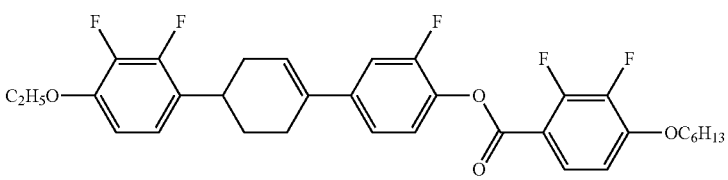 |
| 654 | 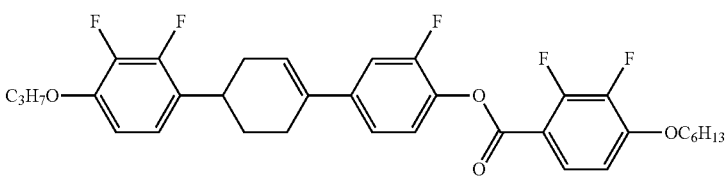 |
| 655 | 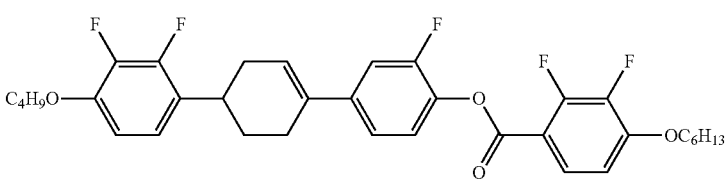 |
| 656 | 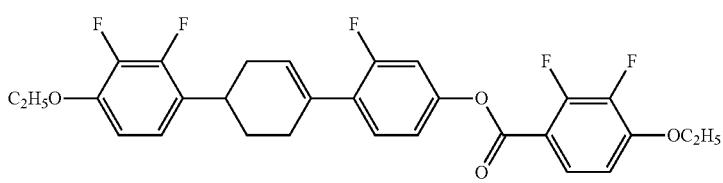 |

-continued
| No. | |
|---|---|
| 657 | 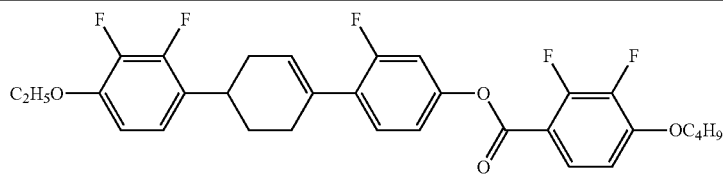 |
| 658 | 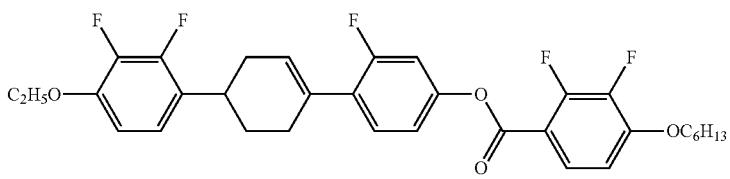 |
| 659 | 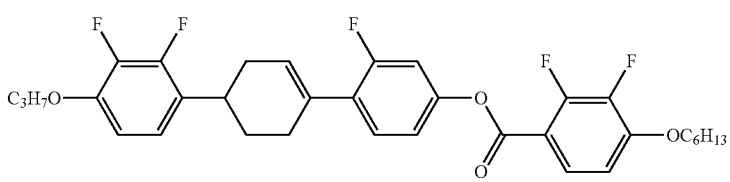 |
| 660 | 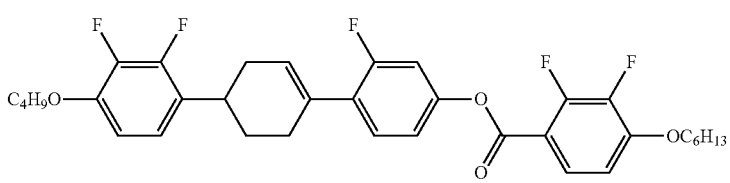 |
| 661 | 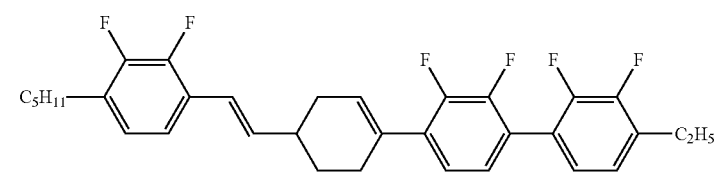 |
| 662 | 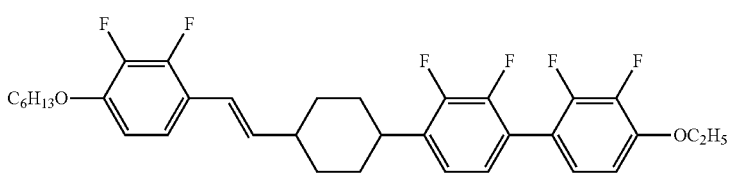 |
| 663 | 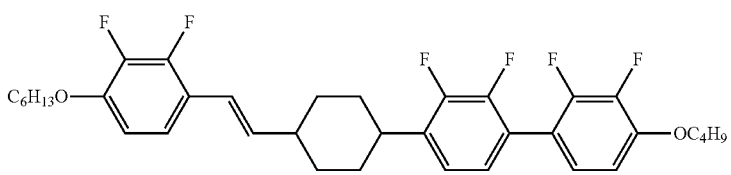 |
| 664 | 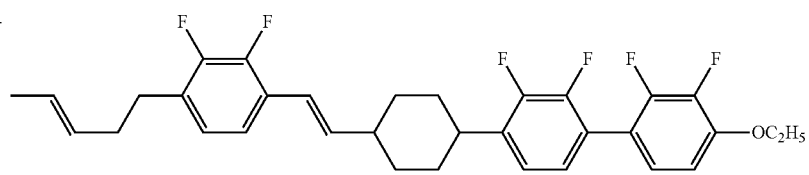 |
| 665 | 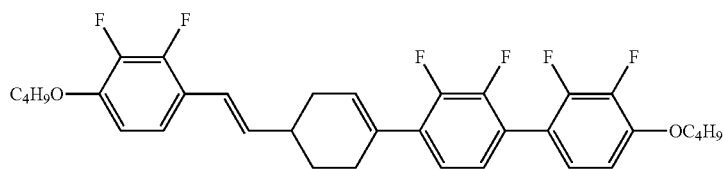 |

| No. | |
|---|---|
| 666 | 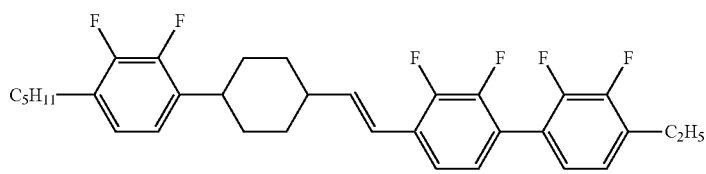 |
| 667 | 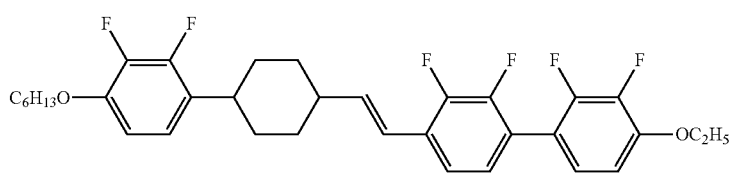 |
| 668 | 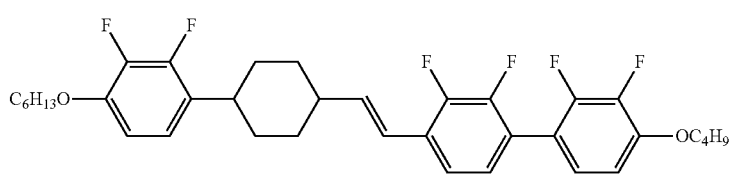 |
| 669 | 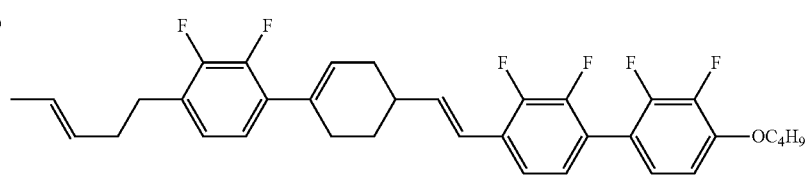 |
| 670 | 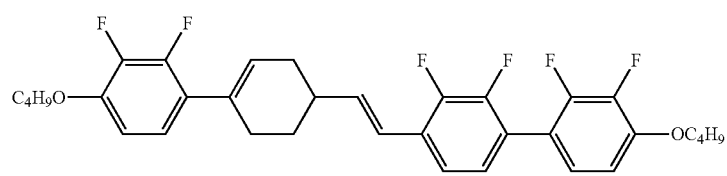 |
| 671 | 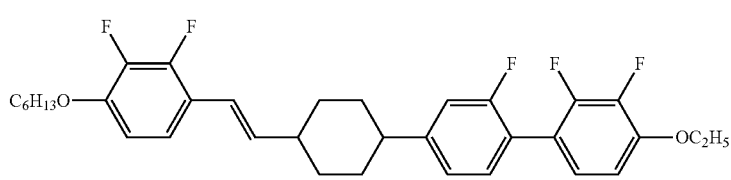 |
| 672 | 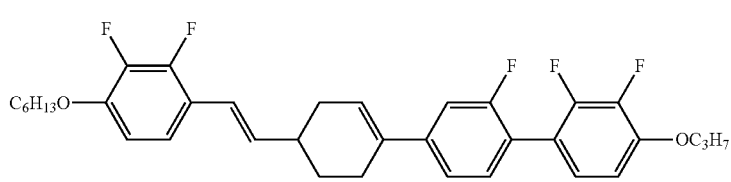 |
| 673 | 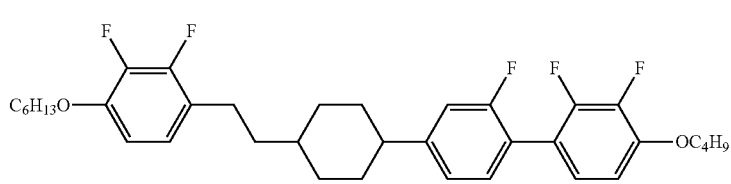 |
| 674 | 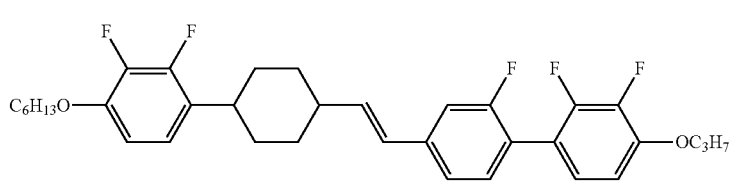 |

-continued
| No. | |
|---|---|
| 675 | 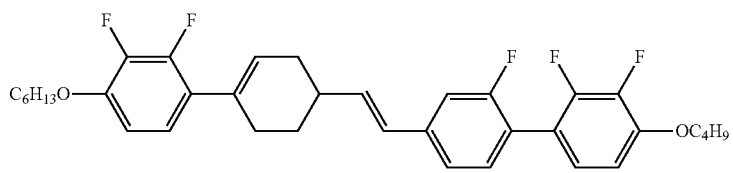 |
| 676 | 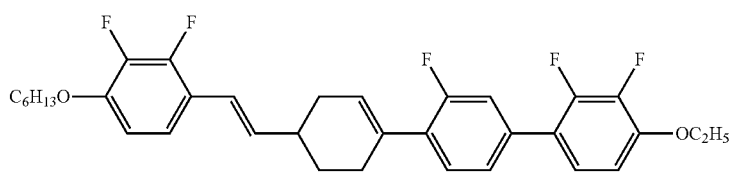 |
| 677 | 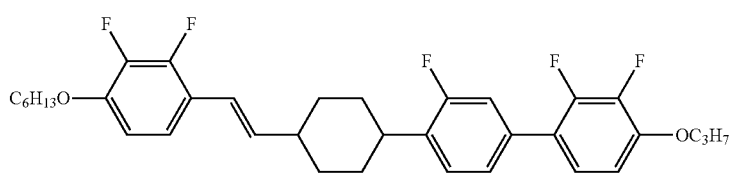 |
| 678 | 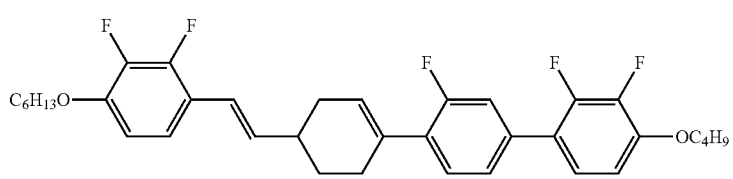 |
| 679 | 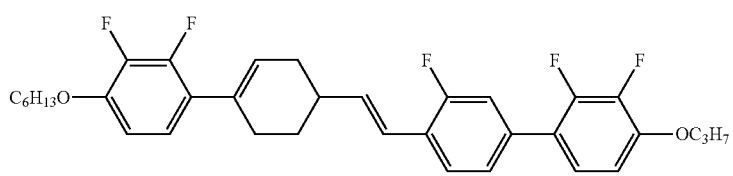 |
| 680 | 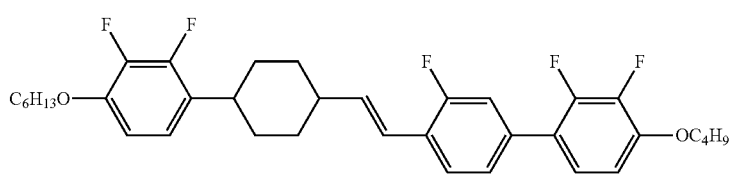 |
| 681 | 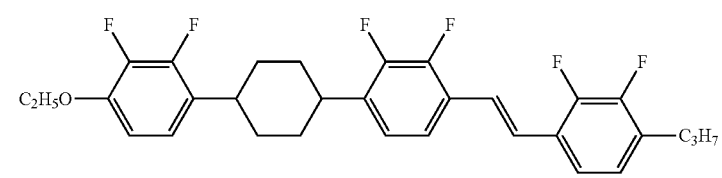 |
| 682 | 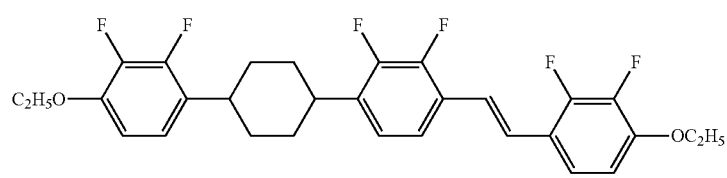 |
| 683 | 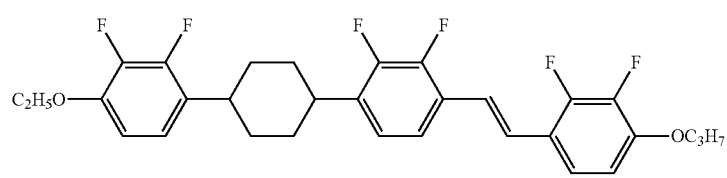 |

-continued
| No. |
|---|
| 687 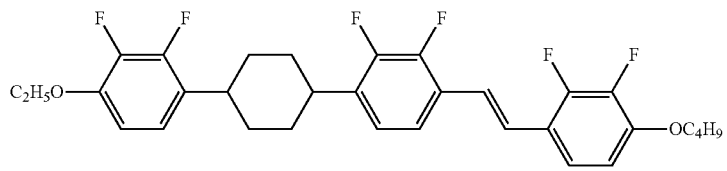 |
| 685 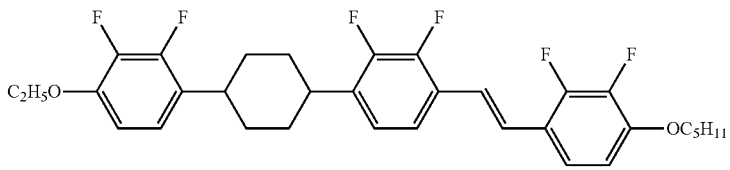 |
| 686 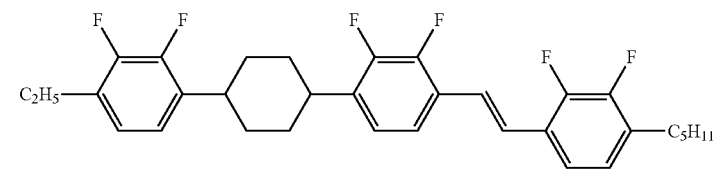 |
| 687 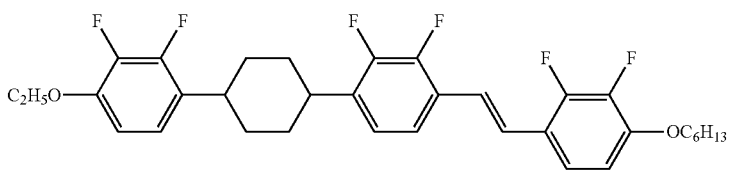 |
| 688 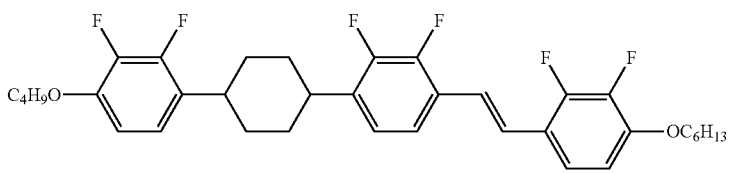 |
| 689 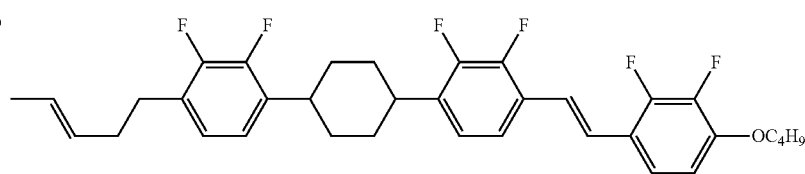 |
| 690 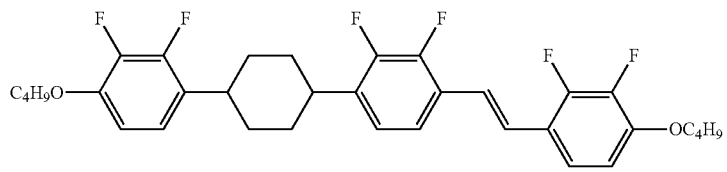 |
| 691 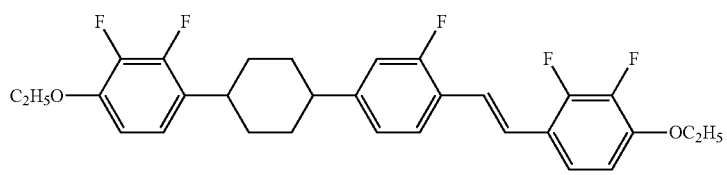 |
| 692 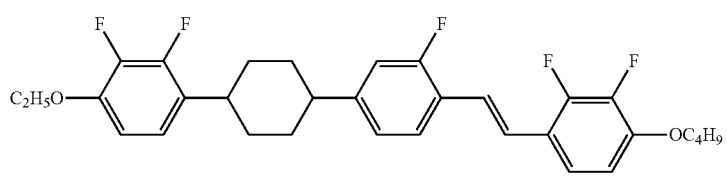 |

-continued
| No. | |
|---|---|
| 693 | 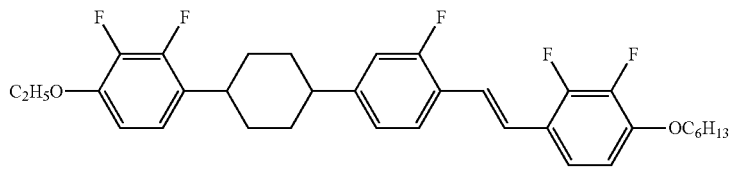 |
| 694 | 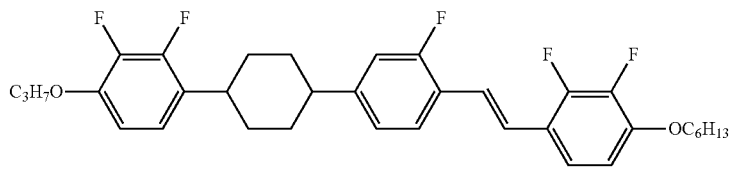 |
| 695 | 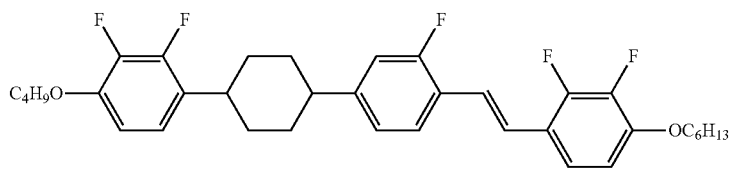 |
| 696 | 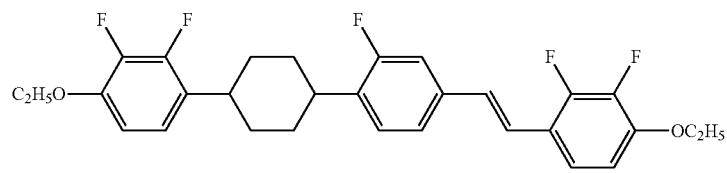 |
| 697 | 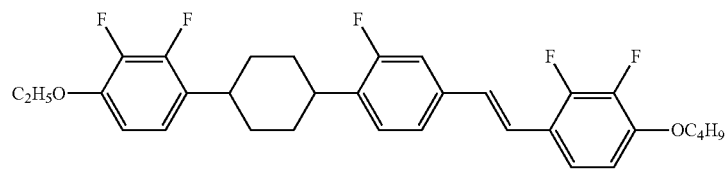 |
| 698 | 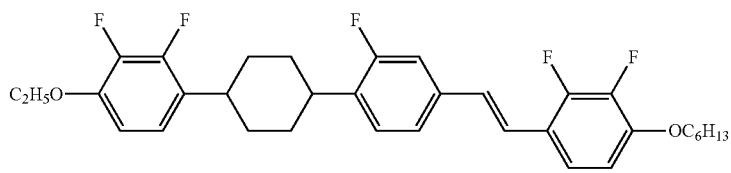 |
| 699 | 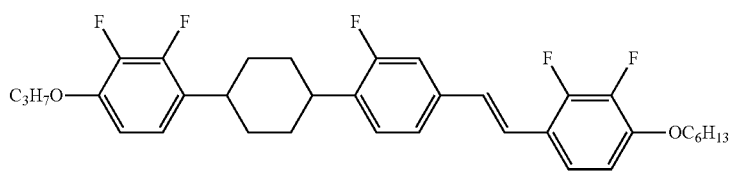 |
| 700 | 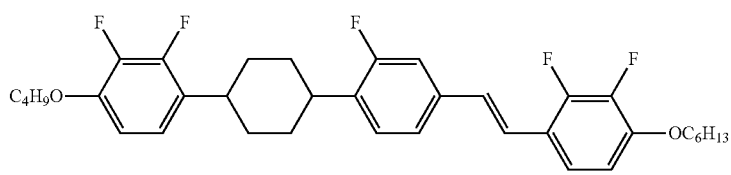 |

Comparative Example 1 trans-4-Propyl-trans-4'-(2,3-difluoroethoxyphenyl)-1,1'-bicyclohexyl (A) was prepared as a comparative example.

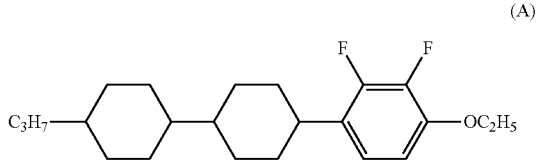

(A)

The chemical shift (δ, ppm) in $^1$H-NMR analysis was described below, and the resulting compound was identified as trans-4-propyl-trans-4'-(2,3-difluoroethoxyphenyl)-1,1'-bicyclohexyl (A). The solvent for measurement was $CDCl_3$.

Chemical shift (δ ppm): 6.82 (dd, 1H), 6.64 (dd, 1H), 4.06 (q, 2H), 2.71 (tt, 1H), 1.89-1.79 (m, 4H), 1.79-1.69 (m, 4H), 1.45-1.26 (m, 14H), 1.20-1.04 (m, 4H) and 0.90-0.79 (t, 3H).

The transition temperature of the compound (A) was as follows.

Transition temperature: C 66.9 $S_B$ 79.9 N 185.1 I.

Five compounds described above as the mother liquid crystals (i) were mixed to prepare the mother liquid crystals (i) having a nematic phase. The physical properties of the mother liquid crystals (i) were as follows.

Maximum temperature $(T_{NI})$=74.6° C.; viscosity $(\eta_{20})$=18.9 mPa·s; optical anisotropy (Δn)=0.087; and dielectric anisotropy (Δ∈)=−1.3.

The liquid crystal composition (ii) consisting of the mother liquid crystals (i) (85% by weight) and the resulting trans-4-propyl-trans-4'-(2,3-difluoroethoxyphenyl)-1,1'-bicyclohexyl (A) (15% by weight) was prepared. The extrapolated values of physical properties of the comparative compound (A) were calculated by the measurement of physical properties of the resulting liquid crystal composition (ii) and then by the extrapolation of the measured values. The values were as follows.

Maximum temperature $(T_{NI})$=158.7° C.; optical anisotropy (Δn)=0.114; and dielectric anisotropy (Δ∈)=−5.43.

Example 9

Physical Properties of the Liquid Crystal Compound (No. 27)

The liquid crystal composition (iii) consisting of the mother liquid crystals (i) (85% by weight) and 4-(trans-4-(2,3-difluoro-4-(hexyloxy)phenyl)cyclohex-1-enyl)-4'-ethoxy-2,2',3,3'-tetrafluorobiphenyl (No. 27) (15% by weight) obtained in Example 1 was prepared. The extrapolated values of physical properties of the liquid crystal compound (No. 27) were calculated by the measurement of physical properties of the resulting liquid crystal composition (iii) and then by the extrapolation of the measured values. The values were as follows.

Maximum temperature $(T_{NI})$=169.3° C.; optical anisotropy (Δn)=0.205; and dielectric anisotropy (Δ∈)=−10.55.

From these results, it was found that the liquid crystal compound (No. 27) had a high maximum temperature $(T_{NI})$, a large optical anisotropy (Δn) and a large negative dielectric anisotropy (Δ∈).

It was also found that the compound (No. 27) had a high maximum temperature $(T_{NI})$, a large optical anisotropy (Δn) and a large negative dielectric anisotropy (Δ∈) in comparison with the comparative compound (A).

Comparative Example 2 trans-4-Pentyl-trans-4"-(2,3-difluoroethoxyphenyl)-1,1',4',1"-tercyclohexyl (C) was prepared as a comparative example.

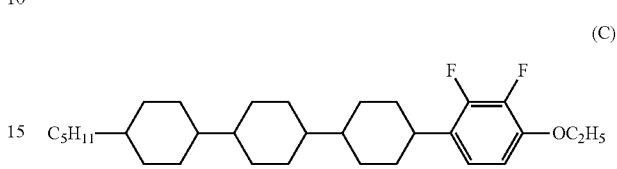

(C)

The chemical shift (δ, ppm) in $^1$H-NMR analysis was described below, and the resulting compound was identified as trans-4-pentyl-trans-4"-(2,3-difluoroethoxyphenyl)-1,1',4',1"-tercyclohexyl (C). The solvent for measurement was $CDCl_3$.

Chemical shift (δ ppm): 6.85 (td, 1H), 6.68 (td, 1H), 4.11 (q, 2H), 2.74 (tt, 1H), 1.93-1.82 (m, 4H), 1.82-1.68 (m, 8H), 1.48-1.37 (m, 4H) and 1.37-0.82 (m, 27H).

The transition temperature of the compound (C) was as follows.

Transition temperature: C 71.8 $S_B$ 298.2 N 330.7 I.

The liquid crystal composition (iv) consisting of the mother liquid crystals (i) (97% by weight) and trans-4-pentyl-trans-4"-(2,3-difluoroethoxyphenyl)-1,1',4',1"-tercyclohexyl (C) (3% by weight) prepared was prepared. The extrapolated values of physical properties of the comparative compound (C) were calculated by the measurement of physical properties of the resulting liquid crystal composition (iv) and then by the extrapolation of the measured values. The values were as follows.

Optical anisotropy (Δn)=0.137; and dielectric anisotropy (Δ∈)=−1.86.

The elastic constant $K_{33}$ of the liquid crystal composition (iv) was 11.31 pN.

Example 10

Physical Properties of the Liquid Crystal Compound (No. 13)

The liquid crystal composition (v) consisting of the mother liquid crystals (i) (95% by weight) and 4'-(trans-4-(2,3-difluoro-4-(hexyloxy)phenyl)cyclohexyl)-4-ethoxy-2,2',3-trifluorobiphenyl (No. 13) (5% by weight) obtained in Example 7 was prepared. The extrapolated values of physical properties of the liquid crystal compound (No. 13) were calculated by the measurement of physical properties of the resulting liquid crystal composition (v) and then by the extrapolation of the measured values. The values were as follows.

Optical anisotropy (Δn)=0.201; and dielectric anisotropy (Δ∈)=−8.85.

The elastic constant $K_{33}$ of the liquid crystal composition (v) was 16.00 pN.

From these results, it was found that the liquid crystal compound (No. 13) had a large optical anisotropy (Δn), a large negative dielectric anisotropy (Δ∈) and a large elastic constant $K_{33}$.

It was also found that the compound (No. 13) had a large optical anisotropy (Δn), a large negative dielectric anisotropy (Δ∈) and a large elastic constant $K_{33}$ in comparison with the comparative compound (C).

Comparative Example 3

4-Ethoxy-4'''-pentyl-2''',3''',2,3-tetrafluoro-1,1',4',1'',4'', 1'''-Quaterphenyl (F) which is similar to the compound (D) was prepared as a comparative example.

(F)

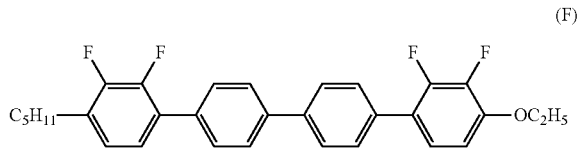

The chemical shift (δ, ppm) in ¹H-NMR analysis was described below, and the resulting compound was identified as 4-ethoxy-4'''-pentyl-2''',3''',2,3-tetrafluoro-1,1',4',1'',4'', 1'''-quaterphenyl (F). The solvent for measurement was CDCl₃.

Chemical shift (δ ppm): 7.50 (q, 4H), 7.14 (d, 2H), 7.09 (td, 1H), 6.92 (d, 1H), 6.78 (t, 1H), 4.17 (q, 2H), 2.42 (tt, 1H), 1.86 (m, 4H), 1.53-1.17 (m, 13H), 1.08-0.98 (m, 2H) and 0.89 (t, 3H).

The transition temperature of the compound (F) was as follows.

Transition temperature: C 149.8 N 306.7 I.

The liquid crystal composition (v) consisting of the mother liquid crystals (i) (95% by weight) and the resulting 4-ethoxy-4'''-pentyl-2''',3''',2,3-tetrafluoro-1,1',4',1'',4'',1'''-Quaterphenyl (F) (5% by weight) was prepared. The extrapolated values of physical properties of the comparative compound (F) were calculated by the measurement of physical properties of the resulting liquid crystal composition (v) and then by the extrapolation of the measured values. The values were as follows.

Dielectric anisotropy (Δ∈)=−6.05; and viscosity (η)=118.2 mPa·s.

The elastic constant $K_{33}$ of the liquid crystal composition (v) was 15.21 pN.

Example 11

Physical Properties of the Liquid Crystal Compound (No. 18)

The liquid crystal composition (v) consisting of the mother liquid crystals (i) (90% by weight) and the resulting 4-ethoxy-2,3-difluoro-4'-[2,3-difluoro-4-(4-pentylcyclohexyl)phenoxymethyl]-1,1'-biphenyl (No. 18) (5% by weight) in Example 7 was prepared. The extrapolated values of physical properties of the liquid crystal compound (No.) were calculated by the measurement of physical properties of the resulting liquid crystal composition (v) and then by the extrapolation of the measured values. The values were as follows.

Dielectric anisotropy (Δ∈)=−7.31; and viscosity (η)=105.3 mPa·s.

The elastic constant $K_{33}$ of the liquid crystal composition (v) was 16.03 pN.

From these results, it was found that the liquid crystal compound (No. 18) had a low melting point, a small viscosity (η) and a large negative dielectric anisotropy (Δ∈).

It was also found that the compound (No. 18) had a large negative dielectric anisotropy (Δ∈), a low melting point, a small viscosity (η) and a large elastic constant $K_{33}$ in comparison with the comparative compound (F).

Comparative Example 4

4-Ethoxy-2,3,2'',3''-tetrafluoro-4''-(2,3-difluoro-4-pentylphenylethyl)-1,1''-terphenyl (G) which is similar to the compound (E) was prepared as a comparative example.

(G)

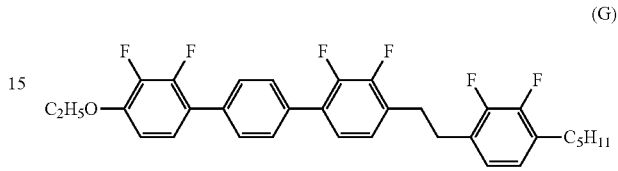

The chemical shift (δ, ppm) in ¹H-NMR analysis was described below, and the resulting compound was identified as 4-ethoxy-2,3,2'',3''-tetrafluoro-4''-(2,3-difluoro-4-pentylphenylethyl)-1,1''-terphenyl (G). The solvent for measurement was CDCl₃.

Chemical shift (δ ppm): 7.60 (m, 4H), 7.15 (m, 2H), 6.97 (m, 1H), 6.83 (m, 3H), 4.18 (q, 2H), 2.99 (m, 2H), 2.62 (t, 2H), 1.64-1.55 (m, 5H), 1.49 (t, 3H), 1.33 (m, 3H) and 0.90 (t, 3H).

The transition temperature of the compound (G) was as follows.

Transition temperature: C 136.5 N 201.0 I.

The liquid crystal composition (vi) consisting of the mother liquid crystals (i) 97% by weight and the resulting 4-ethoxy-2,3,2'',3''-tetrafluoro-4''-(2,3-difluoro-4-pentylphenylethyl)-1,1''-terphenyl (G) (3% by weight) was prepared. The extrapolated values of physical properties of the comparative compound (G) were calculated by the measurement of physical properties of the resulting liquid crystal composition (vi) and then by the extrapolation of the measured values. The values were as follows.

Maximum temperature ($T_{NI}$)=154.6° C.; and dielectric anisotropy (Δ∈)=−6.73.

The elastic constant $K_{33}$ of the liquid crystal composition (vi) was 14.57 pN.

Example 12

Physical Properties of the Liquid Crystal Compound (No. 107)

The liquid crystal composition (vii) consisting of the mother liquid crystals (i) (90% by weight) and trans-4-(4-((2, 3-difluoro-4-(hexyloxy)phenoxy)methyl)cyclohexyl)-4'-ethoxy-2,2',3,3'-tetrafluorobiphenyl (No. 107) (10% by weight) obtained in Example 5 was prepared. The extrapolated values of physical properties of the liquid crystal compound (No. 107) were calculated by the measurement of physical properties of the resulting liquid crystal composition (vii) and then by the extrapolation of the measured values. The values were as follows.

Maximum temperature ($T_{NI}$)=165.6° C.; and dielectric anisotropy (Δ∈)=−9.26.

The elastic constant $K_{33}$ of the liquid crystal composition (vii) was 16.1 pN.

From these results, it was found that the liquid crystal compound (No. 107) had a low melting point, a high maximum temperature ($T_{NI}$) and a large negative dielectric anisotropy (Δ∈).

It was also found that the liquid crystal compound (No. 107) had a high maximum temperature ($T_{NI}$), a large negative dielectric anisotropy ($\Delta\varepsilon$), a low melting point, a small viscosity ($\eta$) and a large elastic constant $K_{33}$ in comparison with the comparative compound (G).

Examples of the Liquid Crystal Composition

Hereinafter, the liquid crystal compositions obtained by means of the invention will be explained in detail by way of examples. Liquid crystal compounds used in the examples are expressed as symbols according to the notations in Table below. In the table, 1,4-cyclohexylene has a trans-configuration. The ratio (percentage) of each compound means a weight percentage (% by weight) based on the total weight of the liquid crystal composition, unless otherwise indicated. The values of characteristics of the resulting liquid crystal composition are shown in the last part of each example.

The number next to the name of a liquid crystal compound in each example indicate the formula number of the liquid crystal compound used for the first to third components of the invention described above. When only the symbol "-" is given instead of the formula number, it means another compound, which is different from these components.

The notations using symbols for compounds are shown below.

TABLE

Method of Description of Compounds using Symbols
R—(A$_1$)—Z$_1$—...—Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |

| 2) Right-terminal Group —R' | Symbol |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —CH=$CF_2$ | —VFF |
| —$COOCH_3$ | -EMe |
| —CN | —C |
| —F | —F |
| —Cl | —CL |
| —$OCF_3$ | —OCF3 |
| —$CF_3$ | —CF3 |

| 3) Bonding Group —Zn— | Symbol |
|---|---|
| —$C_nH_{2n}$— | n |
| —COO— | E |
| —CH=CH— | V |
| —$CH_2O$— | 1O |
| —$CF_2O$— | X |
| —C≡C— | T |

| 4) Ring Structure —An— | Symbol |
|---|---|
|  | H |
| 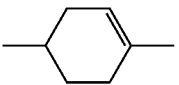 | Ch |
| 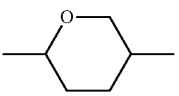 | Dh |
| 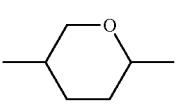 | dh |

TABLE-continued
Method of Description of Compounds using Symbols
R—(A$_1$)—Z$_1$—...—Z$_n$—(A$_n$)—R'
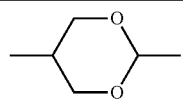 G
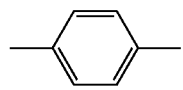 B
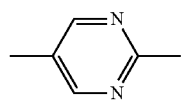 Py
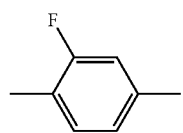 B(2F)
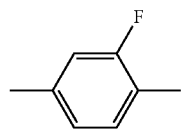 B(F)
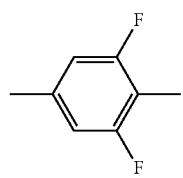 B(F,F)
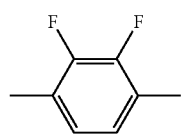 B(2F,3F)
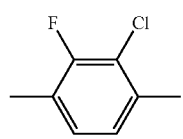 B(2F,3CL)
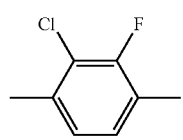 B(2Cl,3F)
5) Examples of Description
Example 1. 6O—WChB(2F,3F)B(2F,3F)—O2
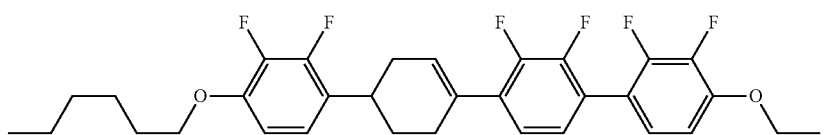 [SMILES: CCCCCCOc1ccc(C2CC=C(c3ccc(-c4ccc(OCC)c(F)c4F)c(F)c3F)CC2)c(F)c1F]

TABLE-continued

Method of Description of Compounds using Symbols
R—(A₁)—Z₁—...—Zₙ—(Aₙ)—R'

Example 2. 6O—B(2F,3F)HB(2F,3F)B(2F,3F)—O2

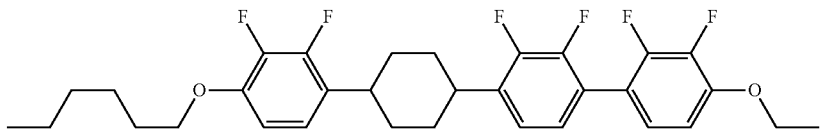 [SMILES: CCCCCCOc1ccc(C2CCC(c3ccc(-c4ccc(OCC)c(F)c4F)c(F)c3F)CC2)c(F)c1F]

Example 3. 3-HHB-3

Example 4. 5-HBB(2F,3CL)—O2

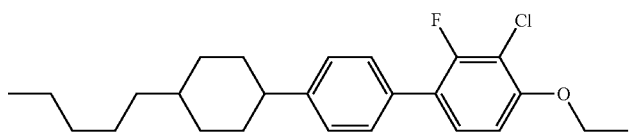 [SMILES: CCCCCC1CCC(c2ccc(-c3ccc(OCC)c(Cl)c3F)cc2)CC1]

Characteristics were measured according to the following methods. Most are methods described in the Standards of Electronic Industries Association of Japan, EIAJ•ED-2521 A, or the methods with some modifications.

(1) Maximum Temperature of a Nematic Phase (NI; ° C.)

A sample was placed on a hot plate in a melting point apparatus equipped with a polarizing microscope and was heated at the rate of 1° C. per minute. The temperature was measured when part of the sample began to change from a nematic phase to an isotropic liquid. Hereinafter, a higher limit of the temperature range of a nematic phase may be abbreviated to "the maximum temperature."

(2) Minimum Temperature of a Nematic Phase (Tc; ° C.)

A sample having a nematic phase was in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., Tc was expressed as ≤−20° C. Hereinafter, a lower limit of the temperature range of a nematic phase may be abbreviated to "the minimum temperature."

(3) Optical Anisotropy (Δn; Measured at 25° C.)

Measurement was carried out by use of an Abbe refractometer with a polarizing plate mounted on the ocular, using light at a wavelength of 589 nanometers. The surface of the main prism was rubbed in one direction, and then a sample was placed on the main prism. The refractive index (n∥) was measured when the direction of polarized light was parallel to that of the rubbing. The refractive index (n⊥) was measured when the direction of polarized light was perpendicular to that of the rubbing. The value of optical anisotropy was calculated from the equation: $\Delta n = n_\parallel - n_\perp$.

(4) Viscosity (Bulk Viscosity; η; Measured at 20° C.; mPa·s)

An E-type viscometer was used for measurement.

(5) Dielectric Anisotropy (Δ∈; Measured at 25° C.)

An ethanol (20 mL) solution of octadecyltriethoxysilane (0.16 mL) was applied to well-washed glass substrates. The glass substrates were rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film obtained on the glass substrates, a TN device in which the distance between the two glass substrates was 9 micrometers and the twist angle was 80 degrees was assembled.

A sample (a liquid crystal composition, or a mixture of a liquid crystal compound and mother liquid crystals) was put in the resulting VA device, a voltage of 0.5 V (1 kHz, sine waves) was applied to the sample, and then the dielectric constant (∈∥) in the major axis direction of the liquid crystal molecules was measured.

The sample (a liquid crystal composition, a liquid crystal composition) was put in the resulting TN device, a voltage of 0.5 V (1 kHz, sine waves) was applied to the sample, and then the dielectric constant (∈⊥) in the minor axis direction of the liquid crystal molecules was measured. The value of the dielectric anisotropy was calculated from the equation: $\Delta \in = \in_\parallel - \in_\perp$. A composition in which this value is negative has negative dielectric anisotropy.

(6) Voltage Holding Ratio (VHR; Measured at 25° C. and 100° C.; %)

A TN device was prepared by putting a sample in a cell having a polyimide alignment film, where the distance between the two glass substrates (cell gap) was 6 micrometers. The TN device was charged at 25° C. by applying pulse voltage (60 microseconds at 5V). The waveforms of the voltage applied to the TN device were observed with a cathode ray oscilloscope and the area between the voltage curve and the axis of abscissa in a unit period (16.7 milliseconds) was measured. An area was similarly measured based on the waveform of the applied voltage after the TN device had been removed. The value of the voltage holding ratio (%) was calculated from the value of (voltage holding ratio)=(value of the area in the presence of a TN device)/(value of the area in the absence of a TN device)×100.

The voltage holding ratio thus obtained was referred to as "VHR-1." Then, the TN device was heated at 100° C. for 250 hours. After the TN device had been allowed to return to 25° C., the voltage holding ratio was measured by a method similar to that described above. The voltage holding ratio obtained after the heating test was referred to as "VHR-2." The heating test means an acceleration test and was used as a test corresponding to a long-term durability test for the TN device.

Example 13

| | | |
|---|---|---|
| 6O—B(2F,3F)ChB(2F,3F)B(2F,3F)—O2 | (No. 27) | 4% |
| 6O—B(2F,3F)HB(2F,3F)B(2F,3F)—O2 | (No. 7) | 4% |
| 3-HH—O1 | (12-1) | 8% |
| 5-HH—O1 | (12-1) | 4% |
| 3-HH-4 | (12-1) | 5% |
| 3-HB(2F,3F)—O2 | (6-1) | 15% |
| 5-HB(2F,3F)—O2 | (6-1) | 14% |
| 2-HHB(2F,3F)-1 | (7-1) | 5% |
| 3-HHB(2F,3F)-1 | (7-1) | 7% |
| 3-HHB(2F,3F)—O2 | (7-1) | 14% |
| 5-HHB(2F,3F)—O2 | (7-1) | 20% |

NI = 74.4° C.; Δn = 0.086; η = 31.5 mPa·s; Δε = −4.6.

Example 14

| | | |
|---|---|---|
| 6O—B(2F,3F)ChB(F)B(2F,3F)—O2 | (No. 33) | 4% |
| 6O—B(2F,3F)HB(F)B(2F,3F)—O2 | (No. 13) | 4% |
| 3-HB—O1 | (12-5) | 10% |
| 3-HH-4 | (12-1) | 5% |
| 3-HB—V | (12-5) | 5% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 13% |
| 5-HHB(2F,3F)—O2 | (7-1) | 5% |
| 3-HHB-1 | (13-1) | 6% |

NI = 90.1° C.; Δn = 0.096; η = 44.0 mPa·s; Δε = −3.6.

Example 15

| | | |
|---|---|---|
| 6O—B(2F,3F)ChB(2F)B(2F,3F)—O2 | (No. 38) | 3% |
| 6O—B(2F,3F)HB(2F)B(2F,3F)—O2 | (No. 18) | 3% |
| 3-HB—O1 | (12-5) | 15% |
| 3-HH-4 | (12-1) | 5% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 13% |
| 5-HHB(2F,3F)—O2 | (7-1) | 7% |
| 6-HEB(2F,3F)—O2 | (6-6) | 6% |

NI = 83.1° C.; Δn = 0.093; η = 38.3 mPa·s; Δε = −3.8.

Example 16

| | | |
|---|---|---|
| 6O—B(2F,3F)O1HB(2F,3F)B(2F,3F)—O2 | (No. 107) | 4% |
| 2O—B(2F,3F)ChB(2F,3F)2B(2F,3F)—O6 | (No. 487) | 4% |
| 3-HH-4 | (12-1) | 4% |
| 3-HH—V | (12-1) | 4% |
| 3-H2B(2F,3F)—O2 | (6-4) | 22% |
| 5-H2B(2F,3F)—O2 | (6-4) | 22% |
| 5-HHB(2F,3CL)—O2 | (7-12) | 2% |
| 3-HBB(2F,3F)—O2 | (7-7) | 9% |
| 5-HBB(2F,3F)—O2 | (7-7) | 8% |
| V—HHB-1 | (13-1) | 6% |
| 3-HHB-3 | (13-1) | 6% |
| 3-HHEBH-3 | (14-6) | 3% |
| 3-HHEBH-4 | (14-6) | 3% |
| 3-HHEBH-5 | (14-6) | 3% |

NI = 93.3° C.; Δn = 0.104; η = 33.0 mPa·s; Δε = −4.3.

Example 17

| | | |
|---|---|---|
| 6O—B(2F,3F)H2B(2F,3F)B(2F,3F)—O2 | (No. 267) | 3% |
| 6O—B(2F,3F)2HB(2F,3F)B(2F,3F)—O2 | (No. 67) | 3% |
| 3-HH-4 | (12-1) | 12% |
| 3-HH-5 | (12-1) | 4% |
| 3-HH—V | (12-1) | 6% |
| 3-HB—O2 | (12-5) | 12% |
| 3-H2B(2F,3F)—O2 | (6-4) | 15% |
| 5-H2B(2F,3F)—O2 | (6-4) | 15% |
| 3-HHB(2F,3CL)—O2 | (7-12) | 5% |
| 3-HBB(2F,3F)—O2 | (7-7) | 6% |
| 5-HBB(2F,3F)—O2 | (7-7) | 9% |
| 3-HHB-1 | (13-1) | 3% |
| 3-HHB-3 | (13-1) | 4% |
| 3-HHB—O1 | (13-1) | 3% |

NI = 76.3° C.; Δn = 0.093; η = 22.7 mPa·s; Δε = −4.2.

The helical pitch was 60.3 micrometers, when 0.25 part of the compound (Op-05) was added to 100 parts of the preceding composition.

Example 18

| | | |
|---|---|---|
| 6O—B(2F,3F)ChB(2F,3F)B(2F,3F)—O2 | (No. 27) | 3% |
| 6O—B(2F,3F)ChB(F)B(2F,3F)—O2 | (No. 33) | 3% |
| 3-HB—O1 | (12-5) | 10% |
| 3-HH-4 | (12-1) | 5% |
| 3-HH—V1 | (12-1) | 5% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 7% |
| 5-HHB(2F,3F)—O2 | (7-1) | 13% |
| 3-HHB-1 | (13-1) | 6% |

NI = 90.7° C.; Δn = 0.096; Δε = −3.7; η = 40.4 mPa·s.

Example 19

| | | |
|---|---|---|
| 6O—B(2F,3F)HB(2F,3F)B(2F,3F)—O2 | (No. 7) | 4% |
| 6O—B(2F,3F)HB(F)B(2F,3F)—O2 | (No. 13) | 3% |
| 2-BEB(F)—C | (5-14) | 5% |

-continued

| | | |
|---|---|---|
| 3-BEB(F)—C | (5-14) | 4% |
| 4-BEB(F)—C | (5-14) | 12% |
| 1V2-BEB(F,F)—C | (5-15) | 11% |
| 3-HB—O2 | (12-5) | 10% |
| 3-HH-4 | (12-1) | 3% |
| 3-HHB—F | (3-1) | 3% |
| 3-HHB-1 | (13-1) | 8% |
| 3-HHB—O1 | (13-1) | 4% |
| 3-HBEB—F | (3-37) | 4% |
| 3-HHEB—F | (3-10) | 7% |
| 5-HHEB—F | (3-10) | 5% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

NI = 96.1° C.; Δn = 0.145; Δε = 24.0; η = 45.0 mPa · s.

Example 20

| | | |
|---|---|---|
| 6O—B(2F,3F)ChB(2F)B(2F,3F)—O2 | (No. 38) | 4% |
| 6O—B(2F,3F)HB(2F,3F)—O2 | (No. 18) | 4% |
| 6O—B(2F,3F)O1HB(2F,3F)B(2F,3F)—O2 | (No. 107) | 4% |
| 1V2-BEB(F,F)—C | (5-15) | 6% |
| 3-HB—C | (5-1) | 12% |
| 2-BTB-1 | (12-10) | 10% |
| 5-HH—VFF | (—) | 30% |
| 3-HHB-1 | (13-1) | 4% |
| VFF—HHB-1 | (—) | 8% |
| VFF2-HHB-1 | (—) | 5% |
| 3-H2BTB-2 | (13-17) | 5% |
| 3-H2BTB-3 | (13-17) | 4% |
| 3-H2BTB-4 | (13-17) | 4% |

NI = 91.7° C.; Δn = 0.139; Δε = 4.5; η = 24.1 mPa · s.

Example 21

| | | |
|---|---|---|
| 6O—B(2F,3F)O1HB(2F,3F)B(2F,3F)—O2 | (No. 107) | 4% |
| 2O—B(2F,3F)ChB(2F,3F)2B(2F,3F)—O6 | (No. 487) | 4% |
| 2-HB—C | (5-1) | 5% |
| 3-HB—C | (5-1) | 12% |
| 3-HB—O2 | (12-5) | 11% |
| 2-BTB-1 | (12-10) | 3% |
| 3-HHB—F | (3-1) | 4% |
| 3-HHB-1 | (13-1) | 8% |
| 3-HHB—O1 | (13-1) | 5% |
| 3-HHB-3 | (13-1) | 14% |
| 5-HHEB—F | (3-10) | 4% |
| 2-HHB(F)—F | (3-2) | 7% |
| 3-HHB(F)—F | (3-2) | 7% |
| 5-HHB(F)—F | (3-2) | 7% |
| 3-HHB(F,F)—F | (3-3) | 5% |

NI = 102.1° C.; Δn = 0.105; Δε = 3.7; η = 24.4 mPa · s.

Example 22

| | | |
|---|---|---|
| 6O—B(2F,3F)H2B(2F,3F)B(2F,3F)—O2 | (No. 267) | 3% |
| 6O—B(2F,3F)2HB(2F,3F)B(2F,3F)—O2 | (No. 67) | 3% |
| 5-HB—CL | (2-2) | 13% |
| 3-HH-4 | (12-1) | 12% |
| 3-HH-5 | (12-1) | 4% |
| 3-HHB—F | (3-1) | 4% |
| 3-HHB—CL | (3-1) | 3% |

-continued

| | | |
|---|---|---|
| 4-HHB—CL | (3-1) | 4% |
| 3-HHB(F)—F | (3-2) | 10% |
| 4-HHB(F)—F | (3-2) | 9% |
| 5-HHB(F)—F | (3-2) | 9% |
| 7-HHB(F)—F | (3-2) | 8% |
| 5-HBB(F)—F | (3-23) | 4% |
| 1O1-HBBH-5 | (14-1) | 3% |
| 3-HHBB(F,F)—F | (4-6) | 2% |
| 5-HHBB(F,F)—F | (4-6) | 3% |
| 3-HH2BB(F,F)—F | (4-15) | 3% |
| 4-HH2BB(F,F)—F | (4-15) | 3% |

NI = 119.4° C.; Δn = 0.095; Δε = 2.7; η = 24.3 mPa · s.

Example 23

| | | |
|---|---|---|
| 6O—B(2F,3F)H2B(2F,3F)B(2F,3F)—O2 | (No. 267) | 4% |
| 6O—B(2F,3F)2HB(2F,3F)B(2F,3F)—O2 | (No. 67) | 4% |
| 5-HB—CL | (2-2) | 3% |
| 7-HB(F)—F | (2-3) | 7% |
| 3-HH-4 | (12-1) | 9% |
| 3-HH-EMe | (12-2) | 23% |
| 3-HHEB—F | (3-10) | 5% |
| 5-HHEB—F | (3-10) | 8% |
| 3-HHEB(F,F)—F | (3-12) | 10% |
| 4-HGB(F,F)—F | (3-103) | 5% |
| 5-HGB(F,F)—F | (3-103) | 6% |
| 2-H2GB(F,F)—F | (3-106) | 4% |
| 3-H2GB(F,F)—F | (3-106) | 5% |
| 5-GHB(F,F)—F | (3-109) | 7% |

NI = 83.4° C.; Δn = 0.072; Δε = 4.4; η = 26.5 mPa · s.

What is claimed is:
1. A compound represented by formula (1-1):

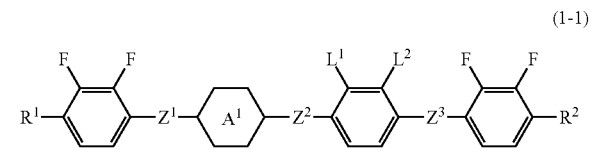

(1-1)

wherein $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
the ring $A^1$ is trans-1,4-cyclohexylene, 1,4-cyclohexenylene, 1,3-dioxane-2,5-diyl, pyrimidine-2,5-diyl or pyridine-2,5-diyl;
$L^1$ and $L^2$ are independently hydrogen or fluorine, and at least one of them is fluorine; and
$Z^1$, $Z^2$ and $Z^3$ are independently a single bond, —(CH$_2$)$_2$—, —CH=CH—, —C≡C—, —CH$_2$O—, —OCH$_2$—, —COO— or —OCO—.

2. The compound according to claim 1, wherein the compound is represented by formula (1-2):

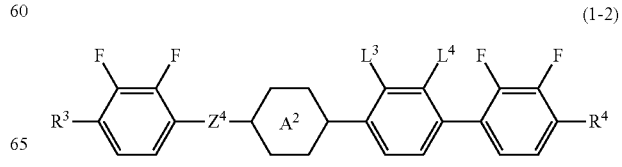

(1-2)

wherein $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^2$ is trans-1,4-cyclohexylene or 1,4-cyclohexenylene;

$L^3$ and $L^4$ are independently hydrogen or fluorine, and at least one of them is fluorine; and $Z^4$ is a single bond, $-(CH_2)_2-$, $-CH=CH-$, $-CH_2O-$, $-OCH_2-$, $-COO-$ or $-OCO-$.

3. The compound according to claim 1, wherein the compound is represented by formula (1-3):

(1-3)

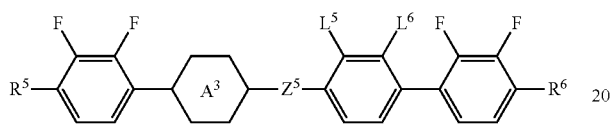

wherein $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^3$ is trans-1,4-cyclohexylene or 1,4-cyclohexenylene;

$L^5$ and $L^6$ are independently hydrogen or fluorine, and at least one of them is fluorine; and $Z^5$ is $-(CH_2)_2-$, $-CH=CH-$, $-CH_2O-$, $-OCH_2-$, $-COO-$ or $-OCO-$.

4. The compound according to claim 1, wherein the compound is represented by formula (1-4):

(1-4)

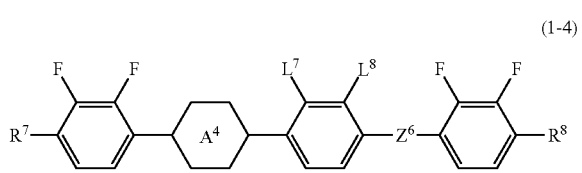

wherein $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

the ring $A^4$ is trans-1,4-cyclohexylene or 1,4-cyclohexenylene;

$L^7$ and $L^8$ are independently hydrogen or fluorine, and at least one of them is fluorine; and $Z^6$ is $-(CH_2)_2-$, $-CH=CH-$, $-CH_2O-$, $-OCH_2-$, $-COO-$ or $-OCO-$.

5. The compound according to claim 2, wherein the compound is represented by any one of formulas (1-5) and (1-6):

(1-5)

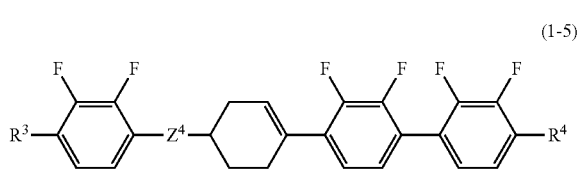

(1-6)

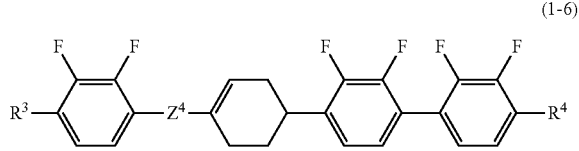

wherein $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, $-(CH_2)_2-$, $-CH_2O-$, $-OCH_2-$, $-COO-$ or $-OCO-$.

6. The compound according to claim 3, wherein the compound is represented by formula (1-7):

(1-7)

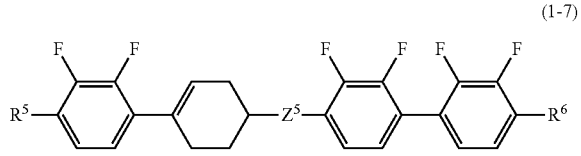

wherein $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is $-(CH_2)_2-$, $-CH_2O-$, $-OCH_2-$, $-COO-$ or $-OCO-$.

7. The compound according to claim 4, wherein the compound is represented by any one of formulas (1-8) and (1-9):

(1-8)

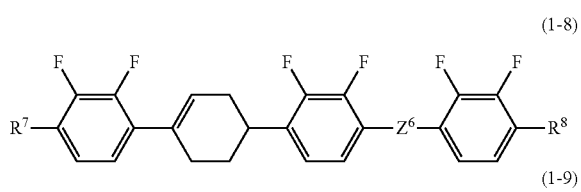

(1-9)

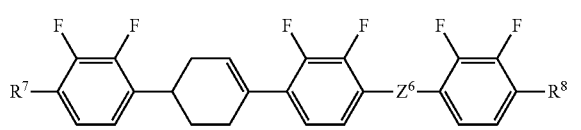

wherein $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is $-(CH_2)_2-$, $-CH_2O-$, $-OCH_2-$, $-COO-$ or $-OCO-$.

8. The compound according to claim 2, wherein the compound is represented by formula (1-10):

(1-10)

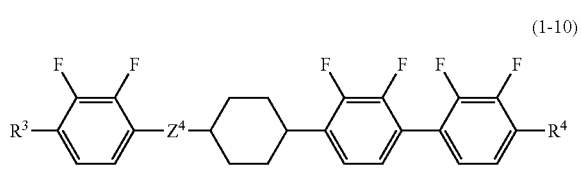

wherein $R^3$ and $R^4$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^4$ is a single bond, —$(CH_2)_2$—, —$CH_2O$—, —$OCH_2$—, —COO— or —OCO—.

9. The compound according to claim 3, wherein the compound is represented by formula (1-11):

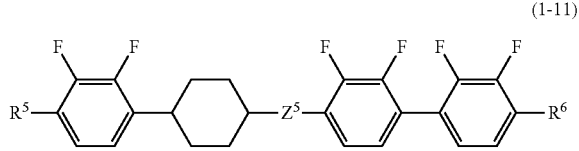
(1-11)

wherein $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ is —$(CH_2)_2$—, —$CH_2O$—, —$OCH_2$—, —COO— or —OCO—.

10. The compound according to claim 4, wherein the compound is represented by formula (1-12):

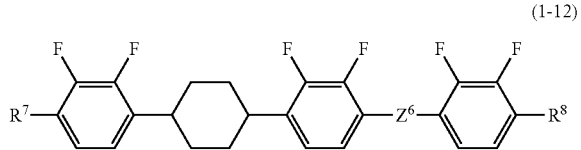
(1-12)

wherein $R^7$ and $R^8$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^6$ is —$(CH_2)_2$—, —$CH_2O$—, —$OCH_2$—, —COO— or —OCO—.

11. A liquid crystal composition comprising a compound according to claim 1.

12. The liquid crystal composition according to claim 11, further comprising at least one compound selected from the group of compounds represented by formulas (2), (3) and (4):

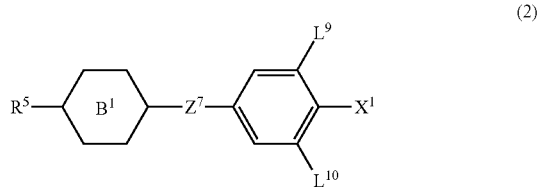
(2)

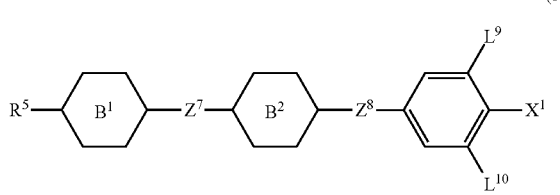
(3)

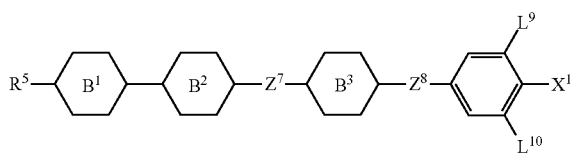
(4)

wherein $R^9$ is independently alkyl having 1 to 10 carbons or alkenyl having 2 to 10 carbons, and in the alkyl and the alkenyl, arbitrary hydrogen may be replaced by fluorine, and arbitrary —$CH_2$— may be replaced by —O—;

$X^1$ is fluorine, halogen, —$OCF_3$, —$OCHF_2$, —$CF_3$, —$CHF_2$, —$CH_2F$, —$OCF_2CHF_2$ or —$OCF_2CHFCF_3$;

the ring $B^1$, the ring $B^2$ and the ring $B^3$ are independently 1,4-cyclohexylene, 1,3-dioxane-2,5-diyl, pyrimidine-2,5-diyl, 1-pyran-2,5-diyl, 1,4-phenylene, 2-fluoro-1,4-phenylene, 3-fluoro-1,4-phenylene or 3,5-difluoro-1,4-phenylene;

$Z^7$ and $Z^8$ are independently —$(CH_2)_2$—, —$(CH_2)_4$—, —COO—, —$OCF_2$—, —CH=CH—, —C≡C—, —$CH_2O$— or a single bond; and $L^9$ and $L^{10}$ are independently hydrogen or fluorine.

13. The liquid crystal composition according to claim 11, further comprising at least one compound selected from the group of compounds represented by formula (5):

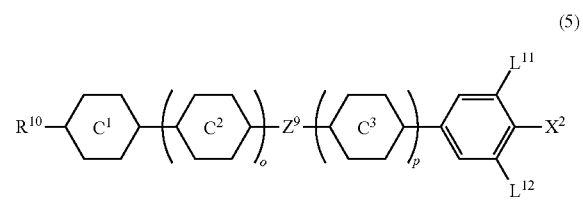
(5)

wherein $R^{10}$ is alkyl having 1 to 10 carbons or alkenyl having 2 to 10 carbons, and in the alkyl and the alkenyl, arbitrary hydrogen may be replaced by fluorine, and arbitrary —$CH_2$— may be replaced by —O—;

$X^2$ is or —C≡C—C≡N;

the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

$Z^9$ is —$(CH_2)_2$—, —COO—, —$CF_2O$—, —$OCF_2$—, —C≡C—, —$CH_2O$— or a single bond;

$L^{11}$ and $L^{12}$ are independently hydrogen or fluorine; and o is 0, 1 or 2, p is 0 or 1, and the sum of o; and p is 0, 1, 2 or 3.

14. The liquid crystal composition according to claim 11, further comprising at least one compound selected from the group of compounds represented by formulas (6), (7), (8), (9), (10) and (11):

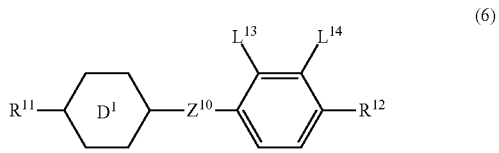
(6)

-continued

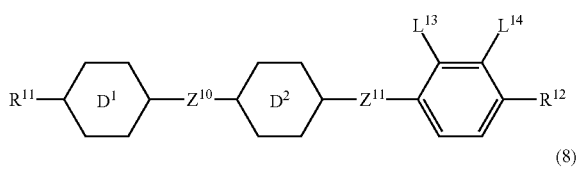
(7)

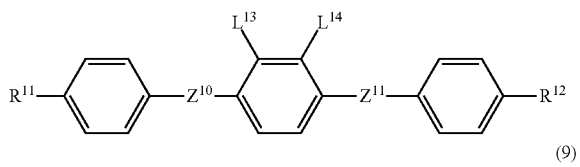
(8)

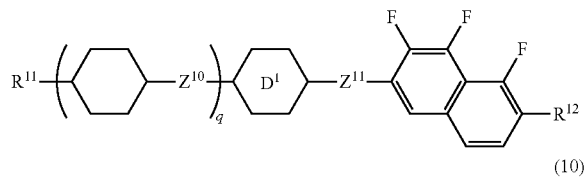
(9)

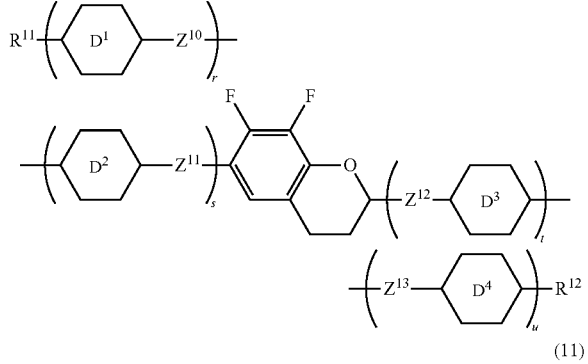
(10)
(11)

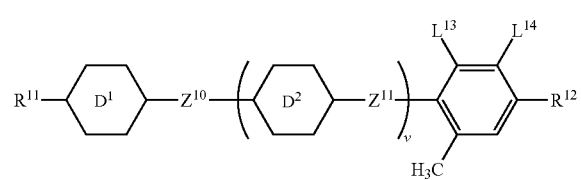

wherein $R^{11}$ and $R^{12}$ are independently alkyl having 1 to 10 carbons or alkenyl having 2 to 10 carbons, and in the alkyl and the alkenyl, arbitrary hydrogen may be replaced by fluorine, and arbitrary —CH$_2$— may be replaced by —O—;

the ring $D^1$, the ring $D^2$, the ring $D^3$ and the ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene;

$Z^{10}$, $Z^{11}$, $Z^{12}$ an $Z^{13}$ are independently —(CH$_2$)$_2$—, —COO—, —CH$_2$O—, —OCF$_2$—, —OCF$_2$(CH$_2$)$_2$— or a single bond;

$L^{13}$ and $L^{14}$ are independently fluorine or halogen; and q, r, s, t, u and v are independently 0 or 1, and the sum of r, s, t and u is 1 or 2.

15. The liquid crystal composition according to claim 11, further comprising at least one compound selected from the group of compounds represented by formulas (12), (13) and (14):

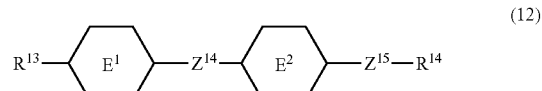
(12)

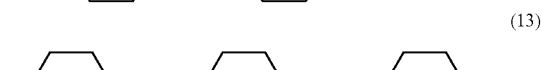
(13)

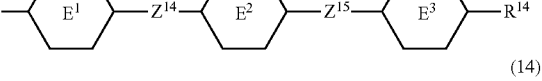
(14)

wherein $R^{13}$ and $R^{14}$ are independently alkyl having 1 to 10 carbons or alkenyl having 2 to 10 carbons, and in the alkyl and the alkenyl, arbitrary —CH$_2$— may be replaced by —O—;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and and $Z^{15}$ are independently —C≡C—, —COO—, —(CH$_2$)$_2$—, —CH=CH— or a single bond.

16. The liquid crystal composition according to claim 12, further comprising at least one compound selected from the group of compounds represented by formula (5).

17. The liquid crystal composition according to claim 14, further comprising at least one compound selected from the group of compounds represented by formulas (12), (13) and (14).

18. The liquid crystal composition according to claim 11, further comprising at least one optically active compound and/or at least one polymerizable compound.

19. The liquid crystal composition according to claim 11, further comprising at least one antioxidant and/or at least one ultraviolet light absorber.

20. A liquid crystal display device comprising the liquid crystal composition according to claim 11.

* * * * *